(12) United States Patent
Weitzner et al.

(10) Patent No.: US 11,344,185 B2
(45) Date of Patent: May 31, 2022

(54) GUIDE TUBE SYSTEMS AND METHODS

(71) Applicant: Boston Scientific Scimed, Inc., Maple Grove, MN (US)

(72) Inventors: Barry Weitzner, Acton, MA (US); Paul J. Smith, Smithfield, RI (US); John B. Golden, Norton, MA (US); Brian J. Intoccia, Westminster, CO (US); Naroun Suon, Lawrence, MA (US); Katie Krueger, Rochester Hills, MI (US); Brian Tinkham, Scituate, MA (US); Michal Weisman, Winchester, MA (US); Brett A. Krueger, Rochester Hills, MI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 356 days.

(21) Appl. No.: 16/378,074

(22) Filed: Apr. 8, 2019

(65) Prior Publication Data

US 2019/0231466 A1 Aug. 1, 2019

Related U.S. Application Data

(63) Continuation of application No. 14/665,197, filed on Mar. 23, 2015, now Pat. No. 10,299,874, which is a
(Continued)

(51) Int. Cl.
*A61B 1/00* (2006.01)
*A61B 1/018* (2006.01)
(Continued)

(52) U.S. Cl.
CPC ...... *A61B 1/00154* (2013.01); *A61B 1/00087* (2013.01); *A61B 1/00147* (2013.01);
(Continued)

(58) Field of Classification Search
CPC ......... A61B 34/74; A61B 34/70; A61B 34/71; A61B 1/00147; A61B 1/018; A61B 2090/0811; A61B 2017/00323
See application file for complete search history.

(56) References Cited

U.S. PATENT DOCUMENTS 3,485,234 A 12/1969 Stevens
3,605,725 A 9/1971 Bentov
(Continued)

FOREIGN PATENT DOCUMENTS

DE 1972151 U 11/1967
EP 0640319 A1 1/1995
(Continued)

OTHER PUBLICATIONS

English abstract of JP 2001-277177 (2 pages).
(Continued)

*Primary Examiner* — Bradley J Osinski
(74) *Attorney, Agent, or Firm* — Bookoff McAndrews, PLLC

(57) ABSTRACT

Disclosed herein are various systems and methods for guiding, supporting, and/or housing instruments. One exemplary system includes a guide tube having a manipulation section and mated with rails carrying instrument control members. Moving the rails with respect to the guide tube, or another point of reference, can control movement of the manipulation section.

20 Claims, 138 Drawing Sheets

Related U.S. Application Data continuation of application No. 11/946,812, filed on Nov. 28, 2007, now Pat. No. 9,084,621.

(60) Provisional application No. 60/909,219, filed on Mar. 30, 2007, provisional application No. 60/872,155, filed on Dec. 1, 2006.

(51) Int. Cl.

| | | |
|---|---|---|
| *A61B 1/04* | (2006.01) | |
| *A61B 34/00* | (2016.01) | |
| *A61B 90/00* | (2016.01) | |
| *A61B 34/10* | (2016.01) | |
| *A61B 1/005* | (2006.01) | |
| *A61B 90/11* | (2016.01) | |
| *A61B 10/06* | (2006.01) | |
| *A61B 17/04* | (2006.01) | |
| *A61B 17/29* | (2006.01) | |
| *A61B 17/00* | (2006.01) | |
| *A61B 17/34* | (2006.01) | |
| *A61B 17/02* | (2006.01) | |
| *A61B 1/12* | (2006.01) | |
| *A61B 17/32* | (2006.01) | |
| *A61B 1/313* | (2006.01) | |

(52) U.S. Cl.
CPC .......... *A61B 1/00165* (2013.01); *A61B 1/018* (2013.01); *A61B 1/04* (2013.01); *A61B 1/0014* (2013.01); *A61B 1/00039* (2013.01); *A61B 1/0052* (2013.01); *A61B 1/0057* (2013.01); *A61B 1/00183* (2013.01); *A61B 1/12* (2013.01); *A61B 1/3132* (2013.01); *A61B 10/06* (2013.01); *A61B 17/00234* (2013.01); *A61B 17/0218* (2013.01); *A61B 17/0469* (2013.01); *A61B 17/29* (2013.01); *A61B 17/320016* (2013.01); *A61B 34/10* (2016.02); *A61B 34/70* (2016.02); *A61B 34/71* (2016.02); *A61B 34/74* (2016.02); *A61B 90/11* (2016.02); *A61B 2017/003* (2013.01); *A61B 2017/0034* (2013.01); *A61B 2017/00212* (2013.01); *A61B 2017/00287* (2013.01); *A61B 2017/00323* (2013.01); *A61B 2017/00331* (2013.01); *A61B 2017/00353* (2013.01); *A61B 2017/00362* (2013.01); *A61B 2017/00398* (2013.01); *A61B 2017/00469* (2013.01); *A61B 2017/00876* (2013.01); *A61B 2017/2905* (2013.01); *A61B 2017/2906* (2013.01); *A61B 2017/2931* (2013.01); *A61B 2017/3445* (2013.01); *A61B 2017/3447* (2013.01); *A61B 2090/0811* (2016.02); *A61B 2090/374* (2016.02)

(56) References Cited

U.S. PATENT DOCUMENTS

| | | | |
|---|---|---|---|
| 3,924,608 A | 12/1975 | Mitsui | |
| 3,949,757 A | 4/1976 | Sabel | |
| 4,499,895 A | 2/1985 | Takayama | |
| 4,503,842 A | 3/1985 | Takayama | |
| 4,539,976 A | 9/1985 | Sharpe | |
| 4,688,555 A | 8/1987 | Wardle | |
| 4,696,544 A | 9/1987 | Costella | |
| 4,826,087 A | 5/1989 | Chinery | |
| 4,854,301 A | 8/1989 | Nakajima | |
| 5,007,406 A | 4/1991 | Takahashi et al. | |
| 5,025,778 A | 6/1991 | Silverstein et al. | |
| 5,120,323 A | 6/1992 | Shockey et al. | |
| 5,159,446 A | 10/1992 | Hibino et al. | |
| 5,188,591 A | 2/1993 | Dorsey, III | |
| 5,196,928 A | 3/1993 | Karasawa et al. | |
| 5,234,443 A | 8/1993 | Phan et al. | |
| 5,250,054 A | 10/1993 | Li | |
| 5,254,088 A | 10/1993 | Lundquist et al. | |
| 5,284,130 A | 2/1994 | Rattiff | |
| 5,325,845 A | 7/1994 | Adair | |
| 5,337,731 A | 8/1994 | Takahashi et al. | |
| 5,354,279 A | 10/1994 | Hofling | |
| 5,368,015 A | 11/1994 | Wilk | |
| 5,383,852 A | 1/1995 | Stevens-Wright | |
| 5,395,367 A | 3/1995 | Wilk | |
| 5,402,793 A | 4/1995 | Gruner et al. | |
| 5,423,848 A | 6/1995 | Washizuka et al. | |
| 5,441,483 A * | 8/1995 | Avitall ............... | A61B 18/1492 604/95.05 |
| 5,462,527 A | 10/1995 | Steven-Wright et al. | |
| 5,477,856 A | 12/1995 | Lundquist | |
| 5,480,406 A | 1/1996 | Nolan et al. | |
| 5,501,654 A | 3/1996 | Failla et al. | |
| 5,607,435 A | 3/1997 | Sachdeva et al. | |
| 5,636,634 A | 6/1997 | Kordis et al. | |
| 5,643,294 A | 7/1997 | Tovey et al. | |
| 5,681,331 A | 10/1997 | de la Torre et al. | |
| 5,749,828 A | 5/1998 | Solomon et al. | |
| 5,797,928 A | 8/1998 | Kogasaka | |
| 5,813,813 A | 9/1998 | Daum et al. | |
| 5,827,323 A | 10/1998 | Klieman et al. | |
| 5,863,286 A | 1/1999 | Yabe et al. | |
| 5,916,146 A | 6/1999 | Allotta et al. | |
| 5,931,849 A | 8/1999 | Desvignes et al. | |
| 5,976,121 A | 11/1999 | Matern et al. | |
| 5,984,939 A | 11/1999 | Yoon | |
| 6,001,114 A | 12/1999 | Ouchi | |
| 6,007,482 A | 12/1999 | Madni et al. | |
| 6,017,322 A | 1/2000 | Snoke et al. | |
| 6,059,719 A | 5/2000 | Yamamoto et al. | |
| 6,066,090 A | 5/2000 | Yoon | |
| 6,093,195 A | 7/2000 | Ouchi | |
| 6,126,665 A | 10/2000 | Yoon | |
| 6,143,006 A | 11/2000 | Chan | |
| 6,156,027 A | 12/2000 | West | |
| 6,270,508 B1 | 8/2001 | Klieman et al. | |
| 6,325,808 B1 * | 12/2001 | Bernard ............. | A61B 17/0469 318/568.11 |
| 6,352,503 B1 * | 3/2002 | Matsui ............... | A61B 17/1285 600/104 |
| 6,390,973 B1 * | 5/2002 | Ouchi ................ | A61B 1/00098 600/104 |
| 6,451,027 B1 | 9/2002 | Cooper et al. | |
| 6,527,753 B2 | 3/2003 | Sekine et al. | |
| 6,638,268 B2 | 10/2003 | Niazi | |
| 6,648,816 B2 | 11/2003 | Irion et al. | |
| 6,656,111 B2 | 12/2003 | Fujii et al. | |
| 6,740,030 B2 | 5/2004 | Martone | |
| 6,743,227 B2 | 6/2004 | Serraj et al. | |
| 6,755,812 B2 | 6/2004 | Peterson et al. | |
| 6,817,974 B2 | 11/2004 | Cooper et al. | |
| 6,833,912 B2 | 12/2004 | Lei et al. | |
| 6,837,849 B2 | 1/2005 | Ogura et al. | |
| 6,843,793 B2 | 1/2005 | Brock et al. | |
| 6,858,024 B1 | 2/2005 | Berg et al. | |
| 6,899,673 B2 | 5/2005 | Ogura et al. | |
| 6,899,973 B2 | 5/2005 | Nakanishi et al. | |
| 6,991,602 B2 | 1/2006 | Nakazawa et al. | |
| 7,029,435 B2 | 4/2006 | Nakao | |
| 7,090,683 B2 | 8/2006 | Brock et al. | |
| 7,153,314 B2 | 12/2006 | Laufer et al. | |
| 7,156,857 B2 | 1/2007 | Pasricha et al. | |
| 7,199,790 B2 | 4/2007 | Rosenberg et al. | |
| 7,537,550 B1 | 5/2009 | Krull | |
| 7,608,083 B2 | 10/2009 | Lee et al. | |
| 7,803,137 B2 | 9/2010 | Stefanchik et al. | |
| 7,833,156 B2 | 11/2010 | Williams et al. | |
| 7,871,371 B2 | 1/2011 | Komiya et al. | |
| 8,579,902 B2 | 11/2013 | Bleich et al. | |
| 9,084,621 B2 | 7/2015 | Weizner et al. | |
| 2001/0049497 A1 | 12/2001 | Kalloo et al. | |
| 2002/0068868 A1 | 6/2002 | Thompson et al. | |
| 2002/0128633 A1 | 9/2002 | Brock et al. | |

(56) References Cited

U.S. PATENT DOCUMENTS

| | | |
|---|---|---|
| 2002/0138082 A1 | 9/2002 | Brock et al. |
| 2002/0161281 A1 | 10/2002 | Jaffe et al. |
| 2002/0177750 A1 | 11/2002 | Pilvisto |
| 2002/0183758 A1 | 12/2002 | Middleton et al. |
| 2003/0004460 A1 | 1/2003 | Bedell |
| 2003/0050649 A1 | 3/2003 | Brock et al. |
| 2003/0092965 A1 | 5/2003 | Konomura et al. |
| 2003/0135091 A1 | 7/2003 | Nakazawa et al. |
| 2004/0019359 A1 | 1/2004 | Worley et al. |
| 2004/0034365 A1 | 2/2004 | Lentz et al. |
| 2004/0059191 A1 | 3/2004 | Krupa et al. |
| 2004/0073088 A1 | 4/2004 | Friedman et al. |
| 2004/0122360 A1 | 6/2004 | Waldhauser |
| 2004/0138525 A1 | 7/2004 | Saadat et al. |
| 2004/0138529 A1 | 7/2004 | Willshire et al. |
| 2004/0176751 A1 | 9/2004 | Weitzner et al. |
| 2004/0181140 A1 | 9/2004 | Falwell et al. |
| 2004/0193016 A1 | 9/2004 | Root et al. |
| 2004/0230097 A1 | 11/2004 | Stefanchik et al. |
| 2004/0236316 A1 | 11/2004 | Danitz et al. |
| 2004/0260245 A1 | 12/2004 | Clem et al. |
| 2004/0267090 A1 | 12/2004 | Ueno et al. |
| 2005/0033355 A1 | 2/2005 | Frank et al. |
| 2005/0054899 A1 | 3/2005 | Miyake |
| 2005/0075538 A1 | 4/2005 | Banik et al. |
| 2005/0085691 A1 | 4/2005 | Nakao |
| 2005/0090709 A1 | 4/2005 | Okada et al. |
| 2005/0096694 A1 | 5/2005 | Lee |
| 2005/0113640 A1 | 5/2005 | Saadat et al. |
| 2005/0117118 A1 | 6/2005 | Miller et al. |
| 2005/0119522 A1 | 6/2005 | Okada |
| 2005/0119524 A1 | 6/2005 | Sekine et al. |
| 2005/0119525 A1 | 6/2005 | Takemoto |
| 2005/0165277 A1 | 7/2005 | Carrillo et al. |
| 2005/0182292 A1 | 8/2005 | Suzuki |
| 2005/0203382 A1 | 9/2005 | Govari et al. |
| 2005/0222495 A1 | 10/2005 | Okada et al. |
| 2005/0228224 A1 | 10/2005 | Okada et al. |
| 2005/0234293 A1 | 10/2005 | Yamamoto et al. |
| 2005/0240078 A1 | 10/2005 | Kwon et al. |
| 2005/0250990 A1 | 11/2005 | Le et al. |
| 2005/0251091 A1 | 11/2005 | Saadat et al. |
| 2005/0267335 A1 | 12/2005 | Okada et al. |
| 2005/0272975 A1 | 12/2005 | McWeeney et al. |
| 2005/0277945 A1 | 12/2005 | Saadat et al. |
| 2005/0288549 A1 | 12/2005 | Mathis |
| 2006/0020287 A1 | 1/2006 | Lee et al. |
| 2006/0079873 A1 | 4/2006 | Scopton et al. |
| 2006/0089626 A1 | 4/2006 | Vlegele et al. |
| 2006/0095074 A1 | 5/2006 | Lee et al. |
| 2006/0142897 A1 | 6/2006 | Green |
| 2006/0149129 A1 | 7/2006 | Watts et al. |
| 2006/0155247 A1 | 7/2006 | Lampropoulos |
| 2006/0178560 A1 | 8/2006 | Saadat et al. |
| 2006/0178562 A1 | 8/2006 | Saadat et al. |
| 2006/0206006 A1 | 9/2006 | Schara et al. |
| 2006/0252993 A1* | 11/2006 | Freed ............... A61M 25/0147 600/146 |
| 2006/0258955 A1 | 11/2006 | Hoffman et al. |
| 2006/0264705 A1 | 11/2006 | Adams et al. |
| 2007/0010800 A1 | 1/2007 | Weitzner et al. |
| 2007/0010801 A1 | 1/2007 | Chen et al. |
| 2007/0021737 A1 | 1/2007 | Lee |
| 2007/0049435 A1 | 3/2007 | Jinno et al. |
| 2007/0051631 A1 | 3/2007 | Hartnack et al. |
| 2007/0088340 A1 | 4/2007 | Brock et al. |
| 2007/0100201 A1 | 5/2007 | Komiya et al. |
| 2007/0100254 A1 | 5/2007 | Murakami et al. |
| 2007/0129605 A1 | 6/2007 | Schaaf |
| 2007/0135803 A1 | 6/2007 | Belson |
| 2007/0156225 A1 | 7/2007 | George et al. |
| 2007/0167679 A1 | 7/2007 | Miyamoto et al. |
| 2007/0167680 A1 | 7/2007 | Miyamoto et al. |
| 2007/0219411 A1 | 9/2007 | Dejima et al. |
| 2007/0225554 A1 | 9/2007 | Maseda et al. |
| 2007/0225562 A1 | 9/2007 | Spivey et al. |
| 2007/0249896 A1 | 10/2007 | Goldfarb et al. |
| 2007/0249897 A1 | 10/2007 | Miyamoto et al. |
| 2007/0255100 A1 | 11/2007 | Barlow et al. |
| 2007/0255291 A1 | 11/2007 | Brock et al. |
| 2007/0270752 A1 | 11/2007 | LaBombard |
| 2007/0282371 A1 | 12/2007 | Lee et al. |
| 2007/0287992 A1 | 12/2007 | Diolaiti et al. |
| 2008/0045803 A1 | 2/2008 | Williams et al. |
| 2008/0051629 A1 | 2/2008 | Sugiyama et al. |
| 2008/0051631 A1 | 2/2008 | Dejima et al. |
| 2008/0172038 A1 | 7/2008 | Dollar et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0221391 A1 | 9/2008 | Weitzner et al. |
| 2008/0243176 A1 | 10/2008 | Weitzner et al. |
| 2008/0287862 A1 | 11/2008 | Weitzner et al. |
| 2012/0165829 A1 | 6/2012 | Chen et al. |
| 2015/0238180 A1 | 8/2015 | Weizner et al. |

FOREIGN PATENT DOCUMENTS

| | | |
|---|---|---|
| EP | 1582138 A2 | 9/2008 |
| JP | 08-224241 | 9/1996 |
| JP | 10-118072 | 5/1998 |
| JP | 10-262983 | 10/1998 |
| JP | 11-099124 | 4/1999 |
| JP | 11-104063 | 4/1999 |
| JP | 11-276489 | 10/1999 |
| JP | 2000-037390 | 2/2000 |
| JP | 2001-104315 | 4/2001 |
| JP | 2001-161631 | 6/2001 |
| JP | 2001-277177 | 10/2001 |
| JP | 2002-287613 | 10/2002 |
| JP | 2002-291765 | 10/2002 |
| JP | 2002-330924 | 11/2002 |
| JP | 2003-111769 | 4/2003 |
| JP | 2004-041572 | 2/2004 |
| JP | 2004-154164 | 6/2004 |
| JP | 2004-173963 | 6/2004 |
| JP | 2004-180781 | 7/2004 |
| JP | 2005-058400 | 3/2005 |
| JP | 2005-081058 | 3/2005 |
| JP | 2005-103140 | 4/2005 |
| JP | 2005-296412 | 10/2005 |
| JP | 2006149844 A | 6/2006 |
| JP | 2009-537233 | 10/2009 |
| WO | WO 94/21179 | 9/1994 |
| WO | WO 97/12557 | 4/1997 |
| WO | WO 97/32528 | 9/1997 |
| WO | WO 02/07611 | 1/2002 |
| WO | WO 2006/110275 A2 | 10/2006 |
| WO | WO 2006/111966 A2 | 10/2006 |
| WO | WO 2007/033379 A2 | 3/2007 |
| WO | WO 2008/070556 A1 | 6/2008 |

OTHER PUBLICATIONS

English abstract of JP 2002-287613 (2 pages).
English abstract of JP 2002-291765 (2 pages).
English abstract of JP 2003-111769 (1 page).
English abstract of JP 2004-173963 (1 page).
English abstract of JP 2004-180781 (2 pages).
English translation of JP 2005-103140 (40 pages).
English abstract of JP 2005-296412 (1 page).
English translation of JP 08-224241 (15 pages).
English abstract of JP 10-262983 (2 pages).
English abstract of JP 11-099124 (2 pages).
International Search Report for PCT/US2007/086079 (published as WO 2008/070556), dated May 9, 2008.

* cited by examiner

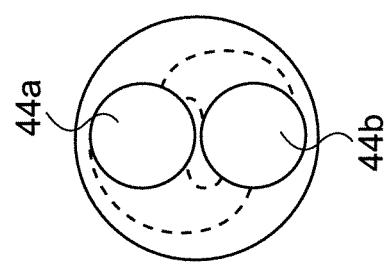
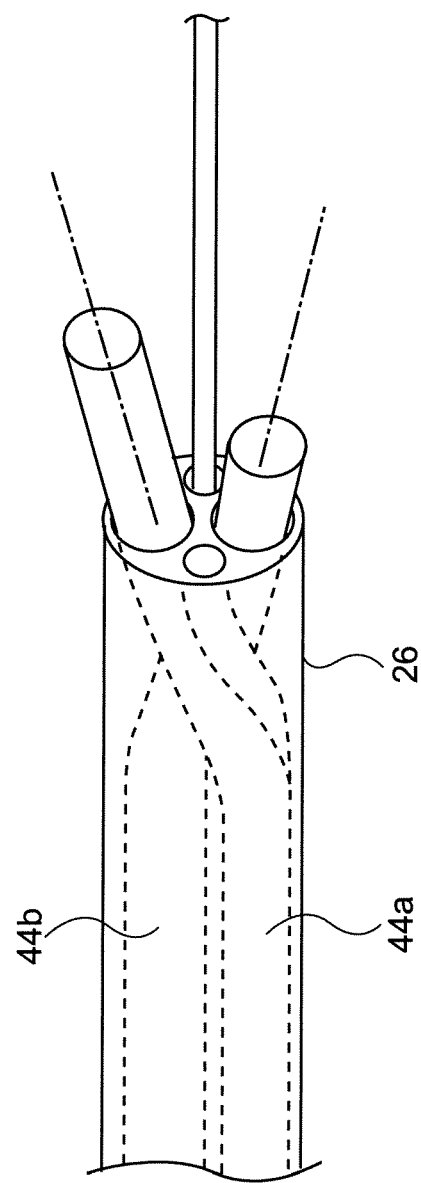
FIG. 9B
FIG. 9A

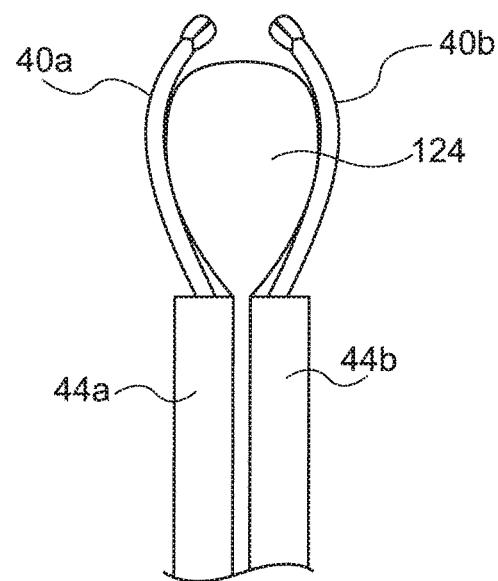
FIG. 14
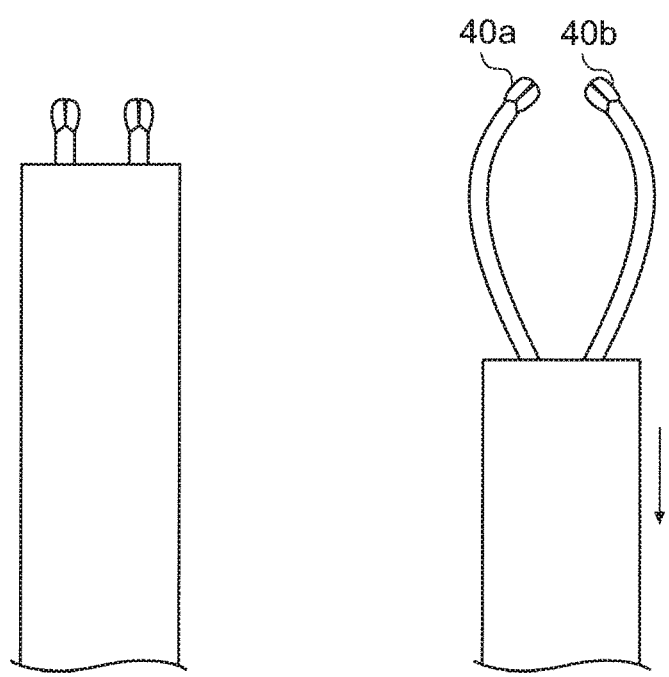
FIG. 15A  FIG. 15B

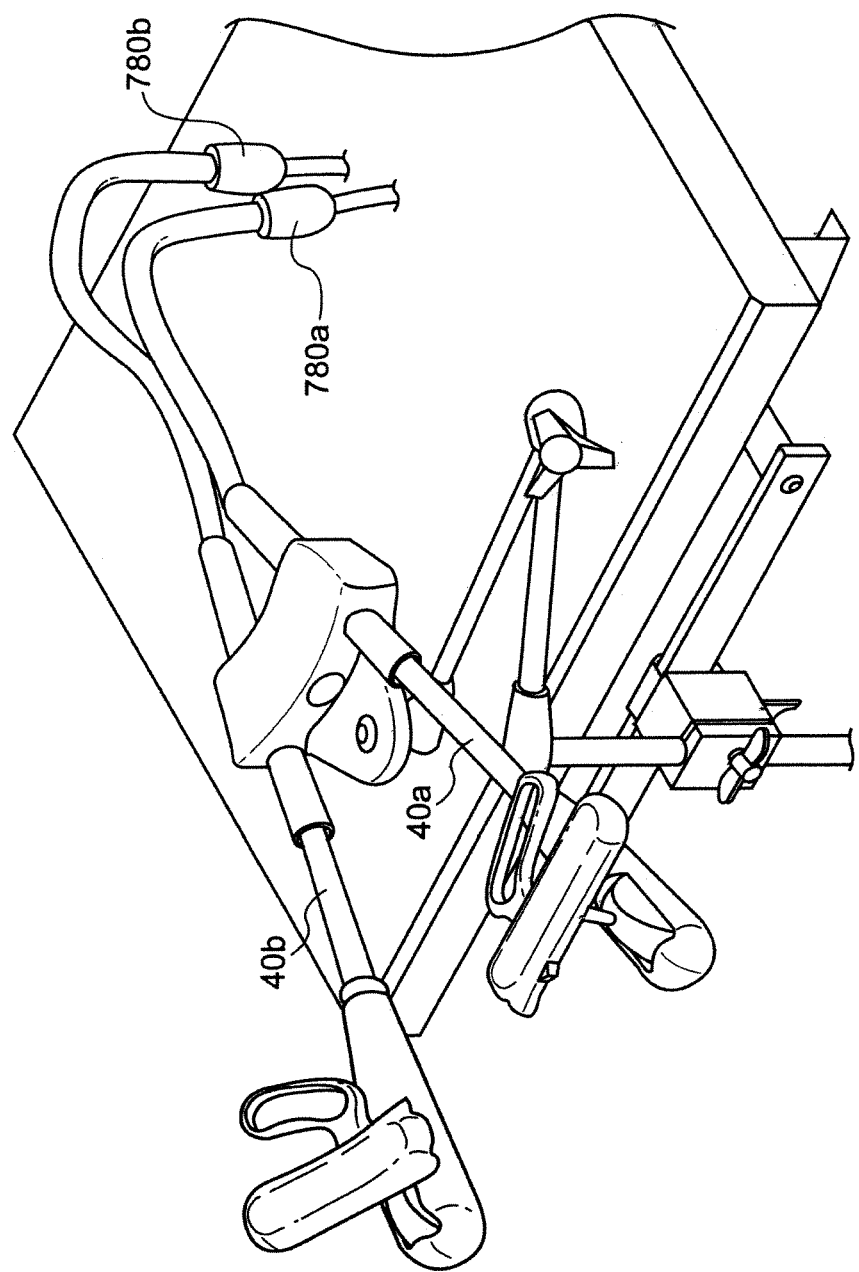

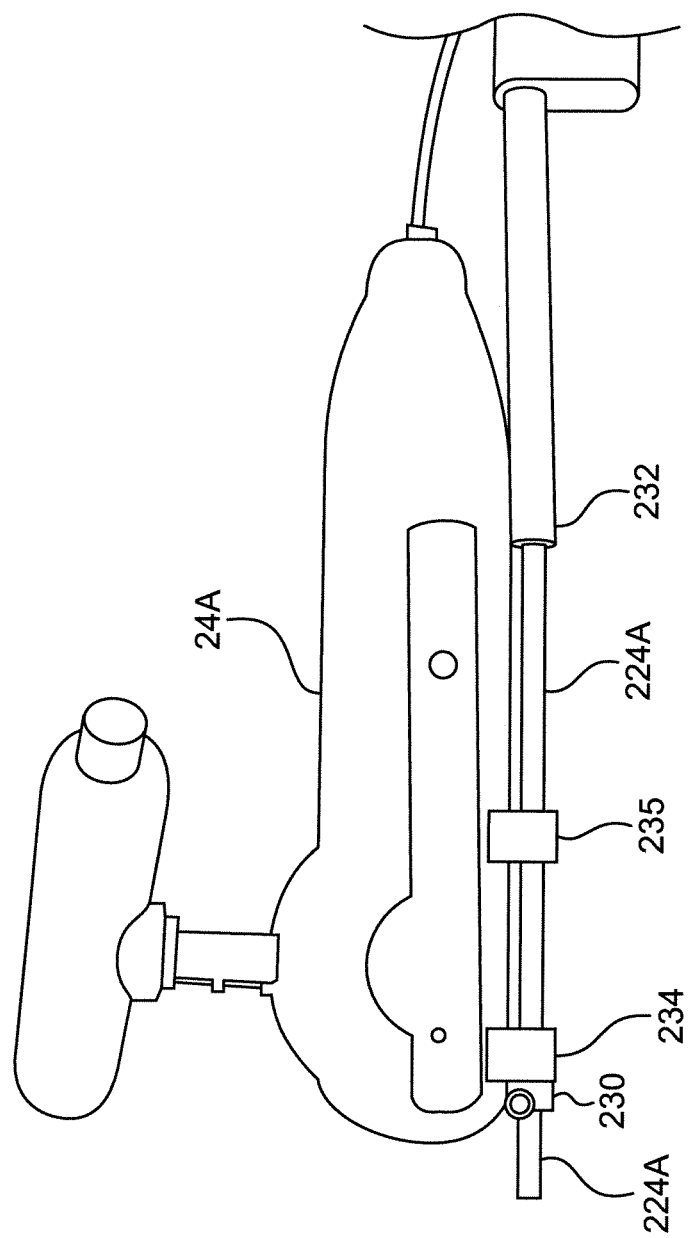

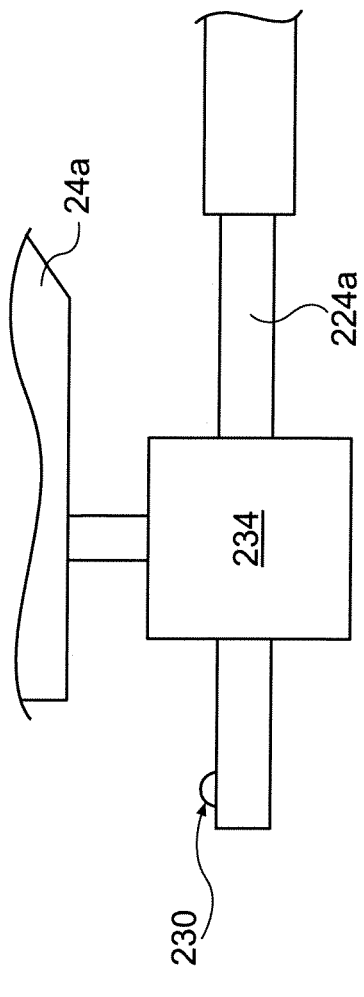
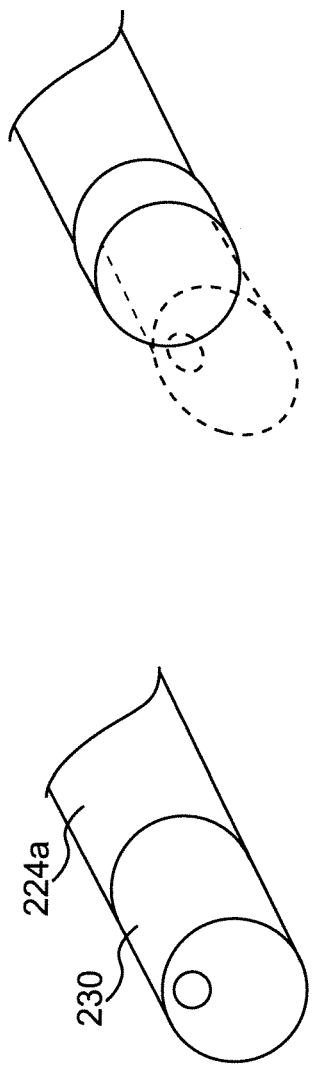

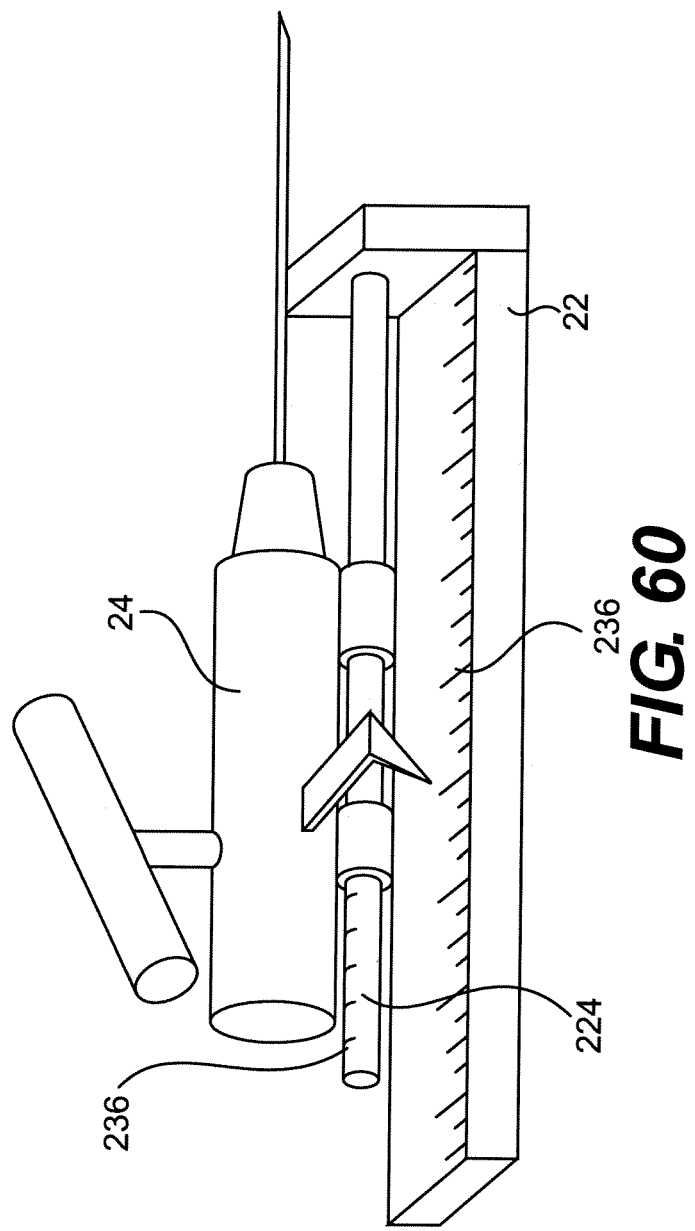

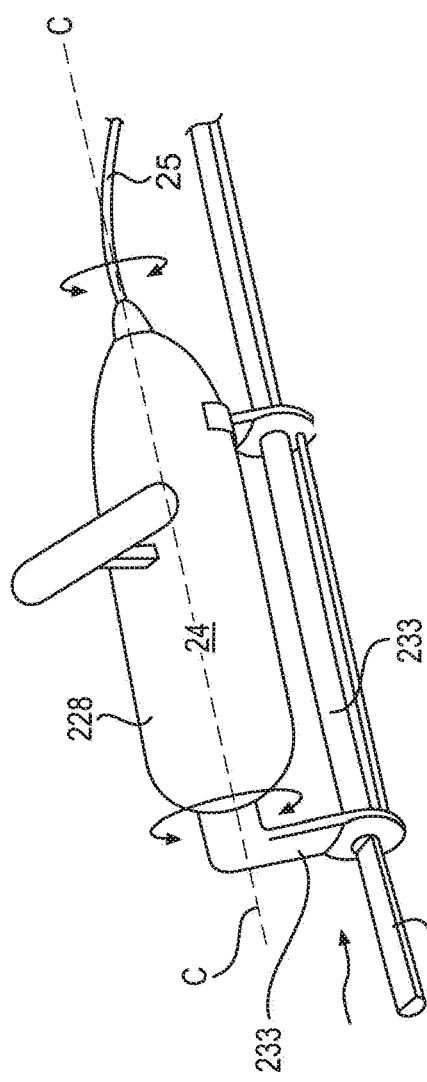
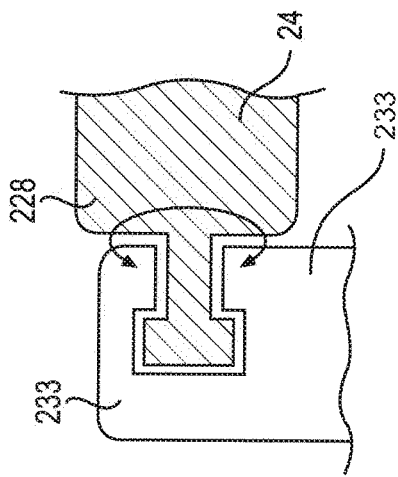
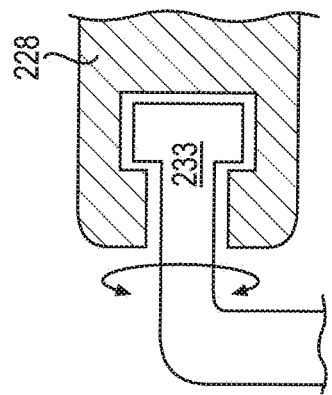
FIG. 62A
FIG. 62B
FIG. 62C

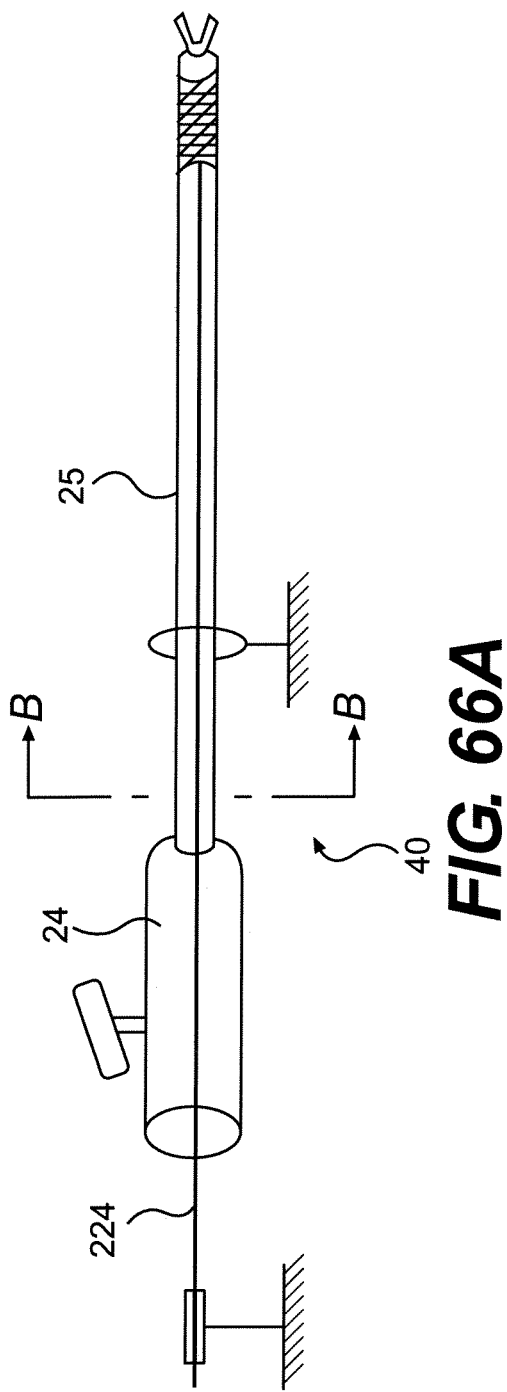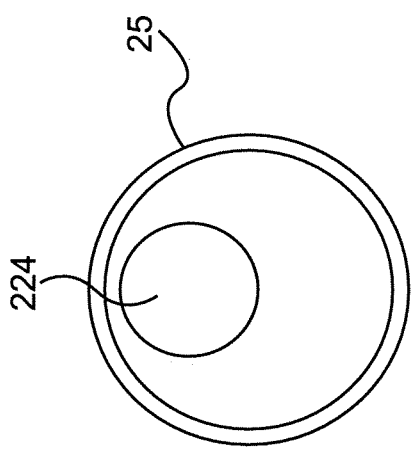
FIG. 66A
FIG. 66B

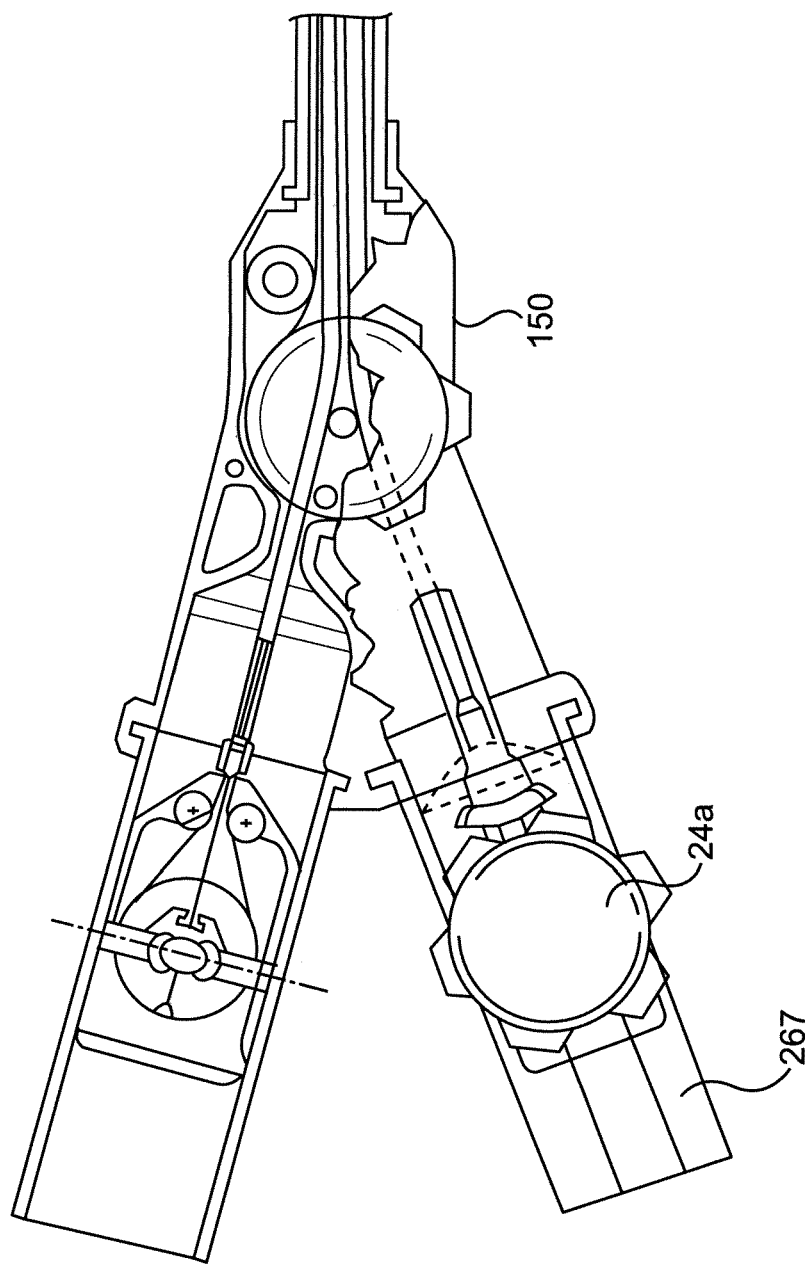

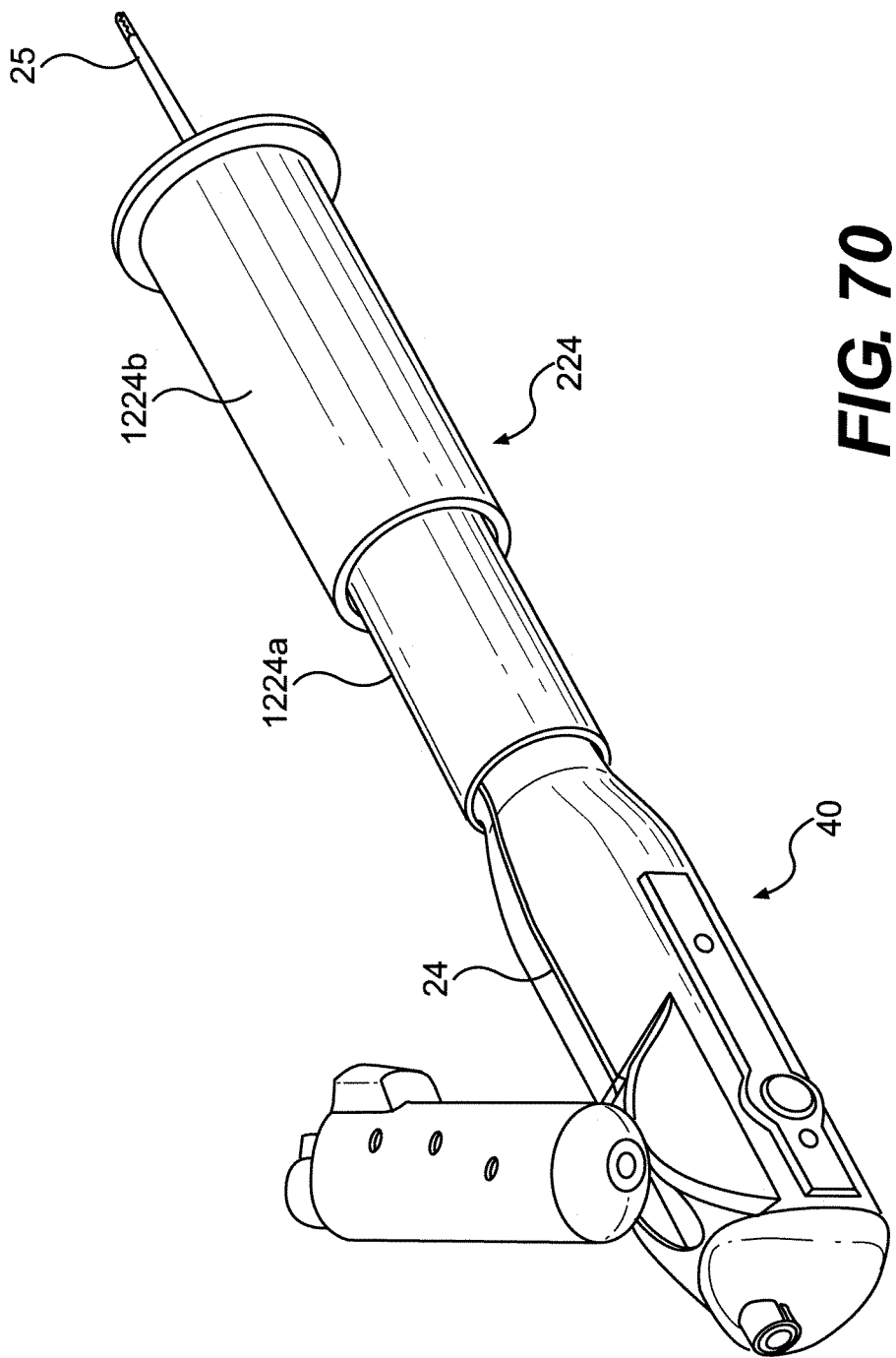

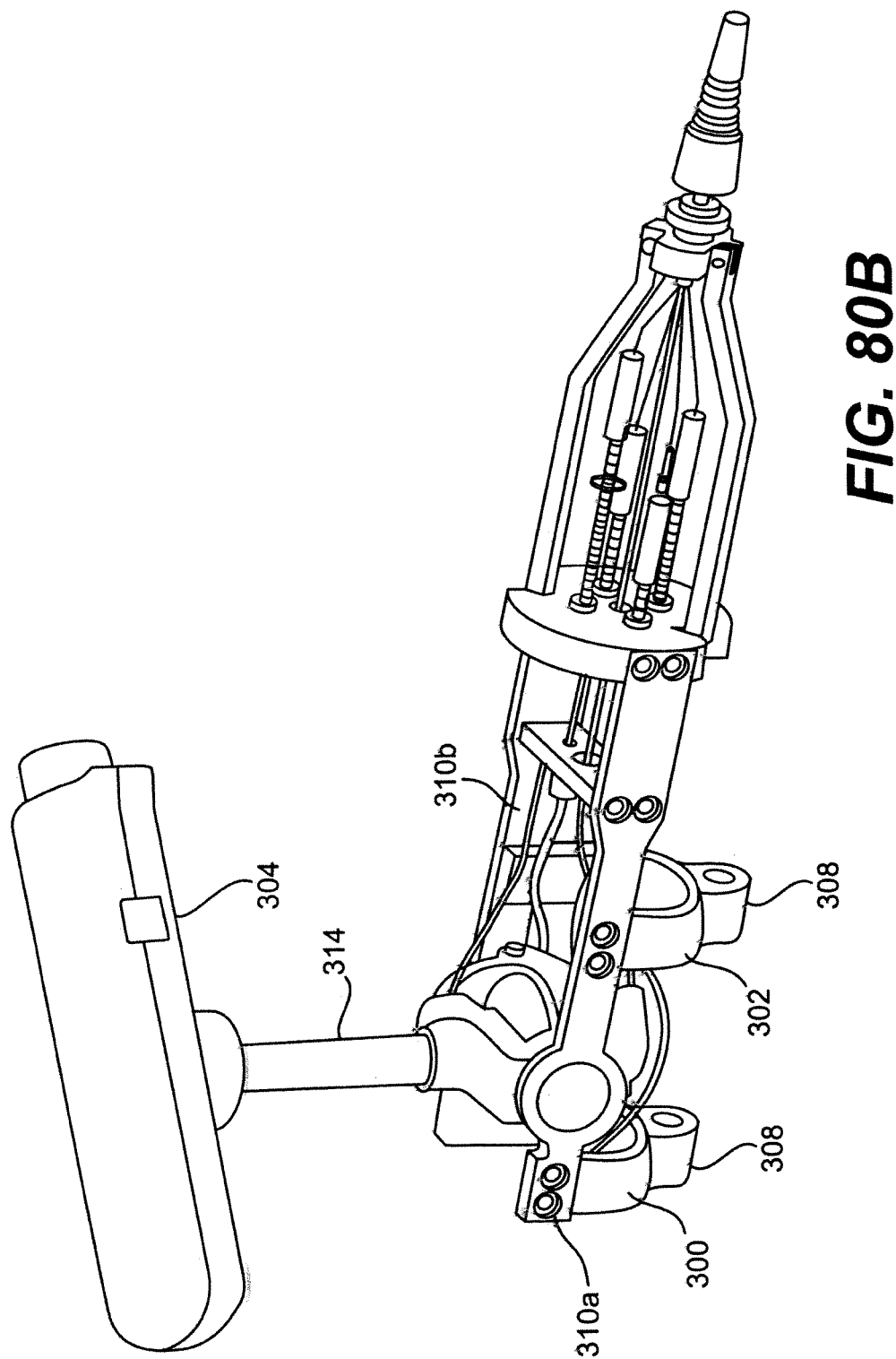

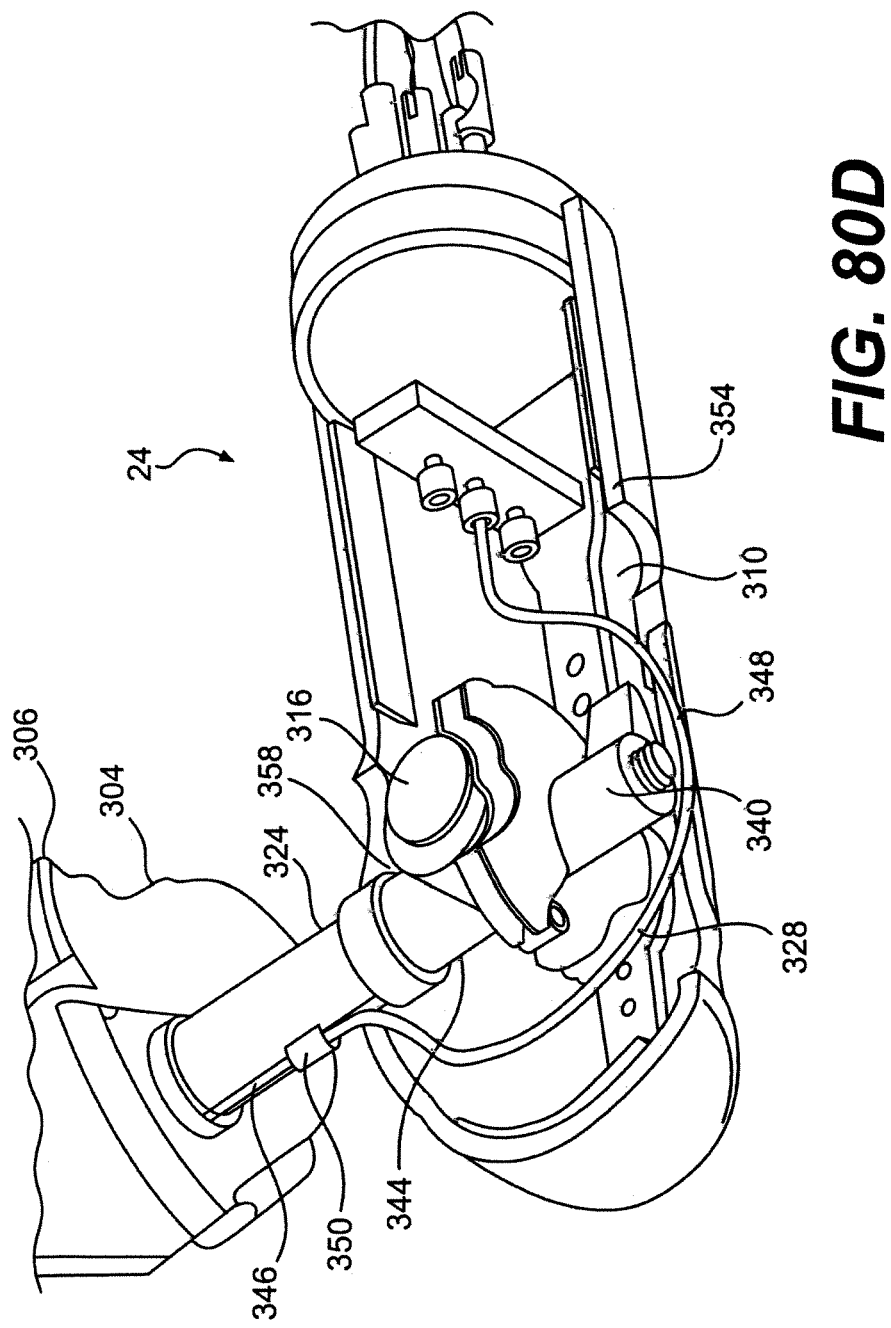

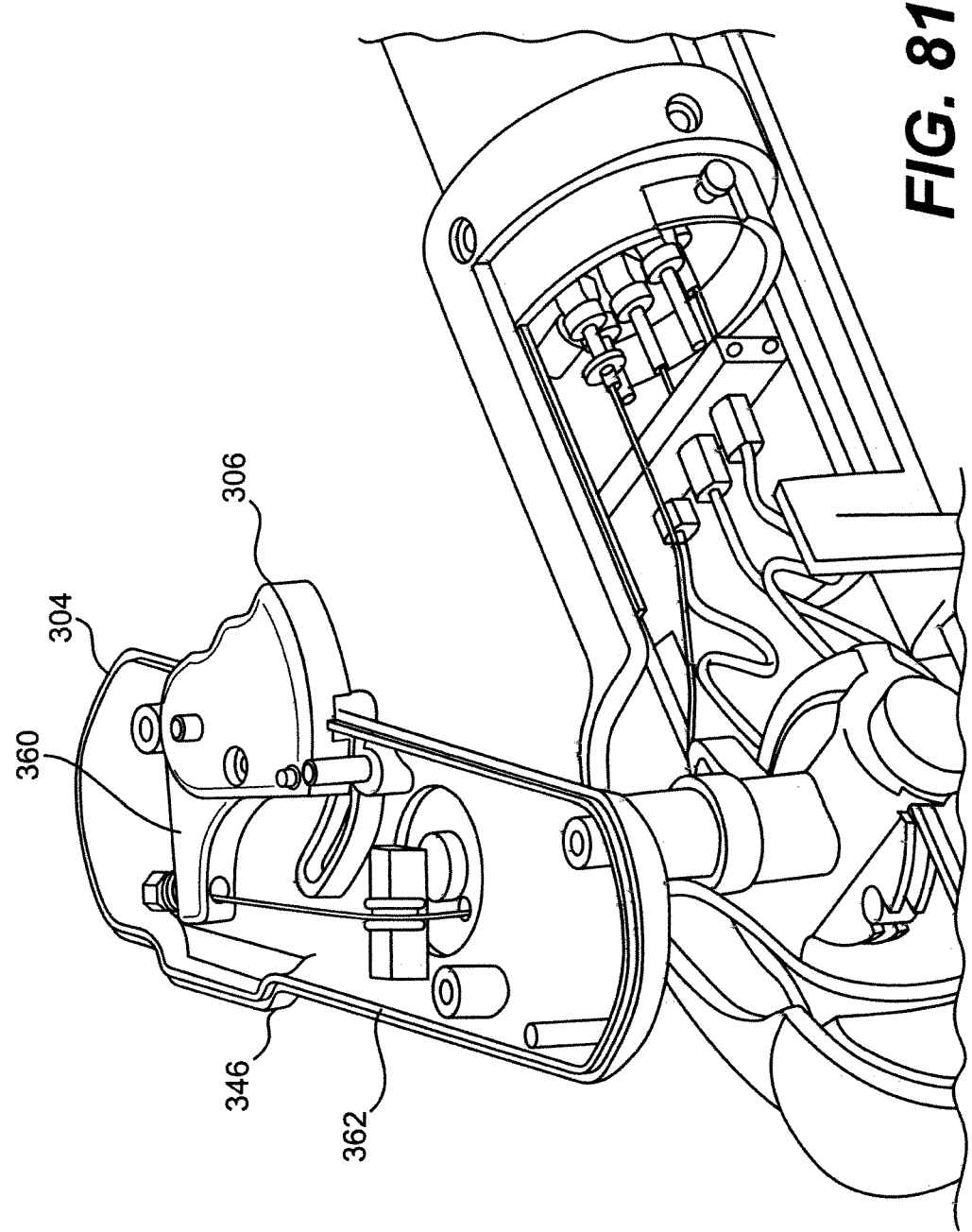

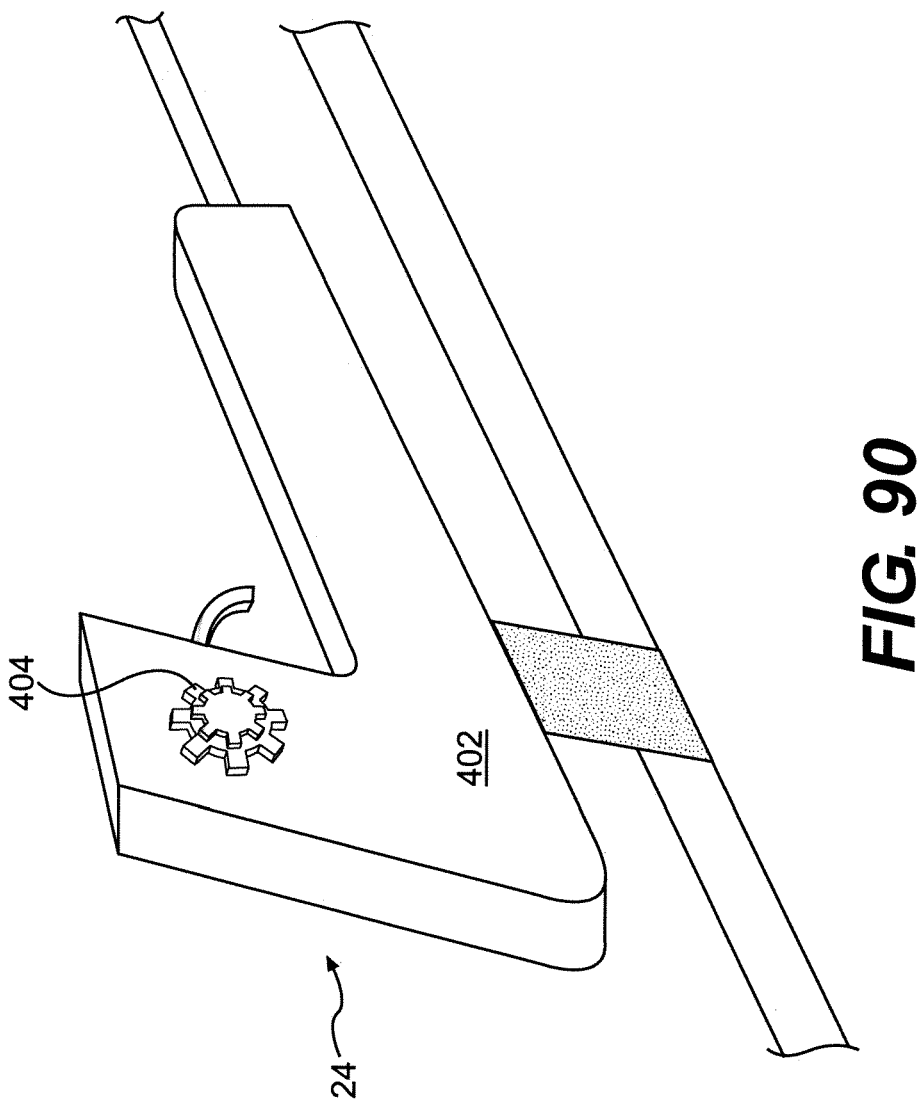

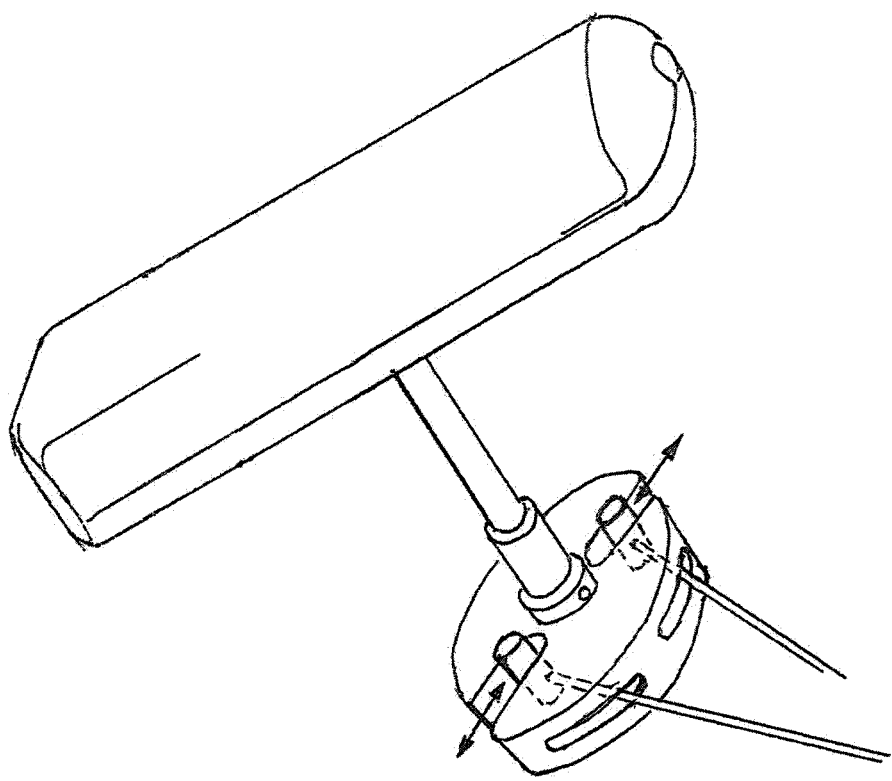
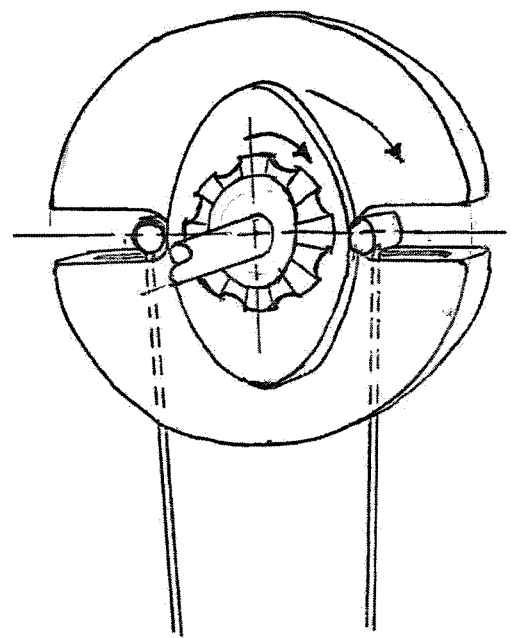
FIG. 99

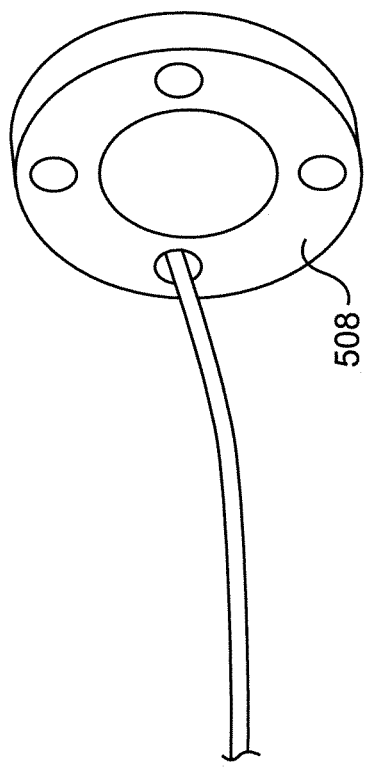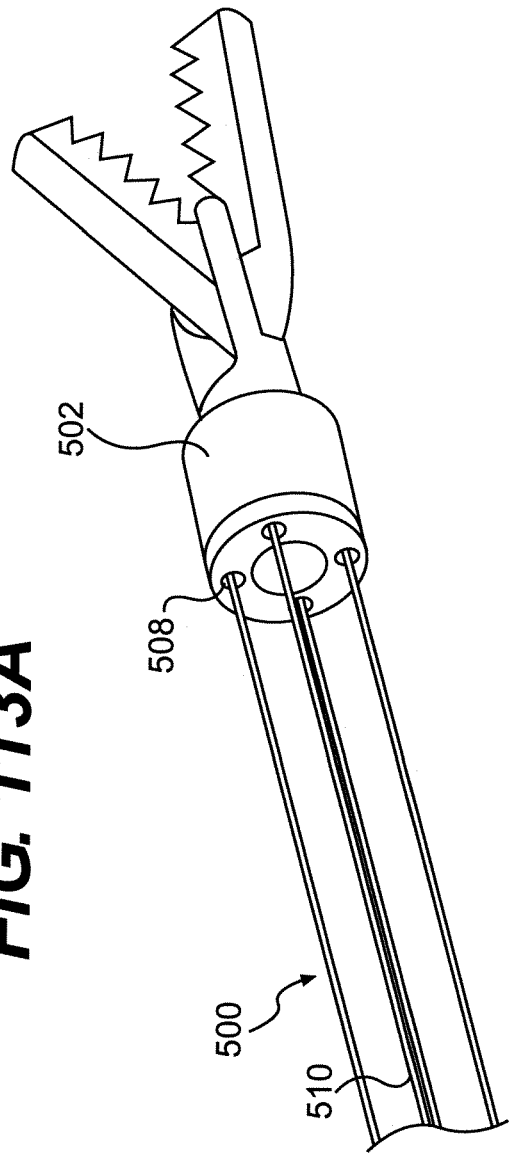
FIG. 113A
FIG. 113B

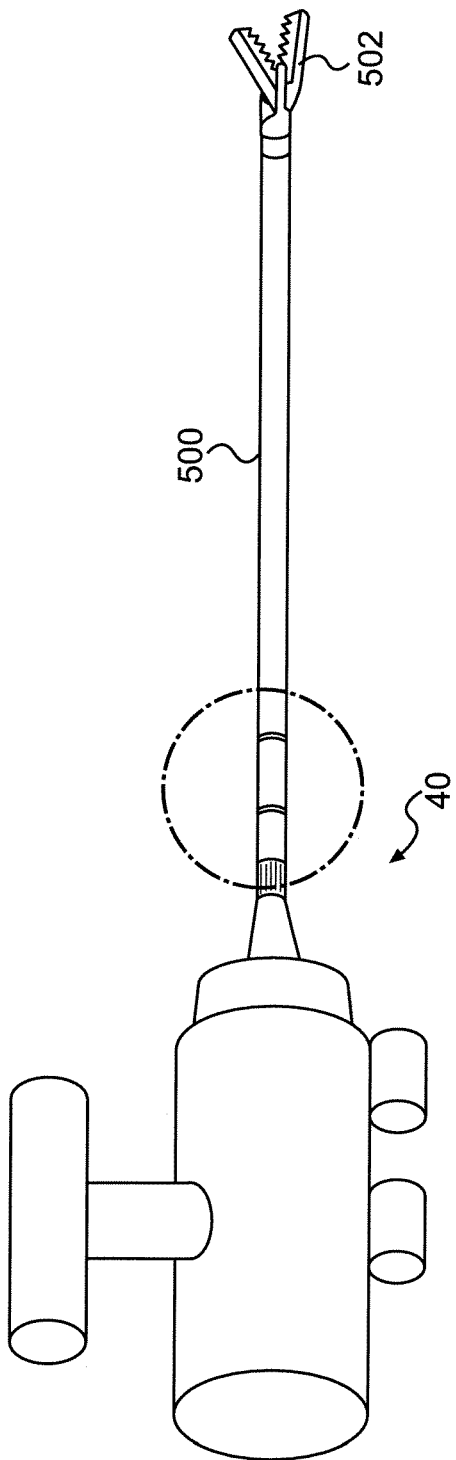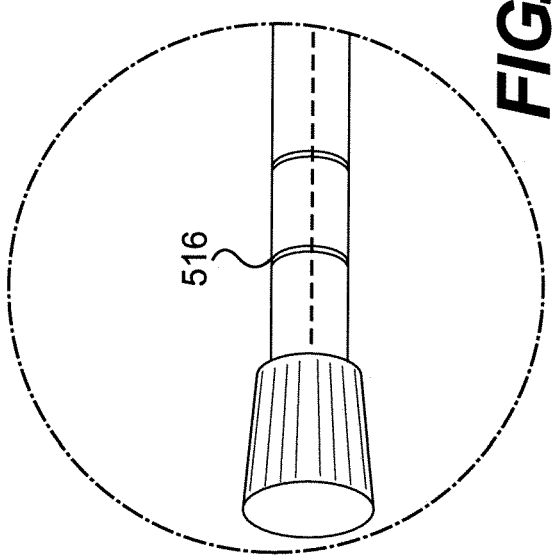
FIG. 119A
FIG. 119B

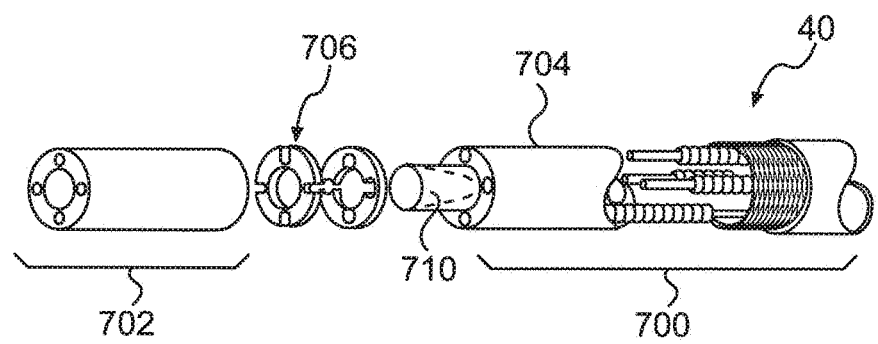
FIG. 120A
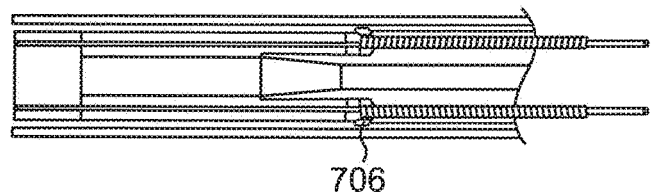
FIG. 120B
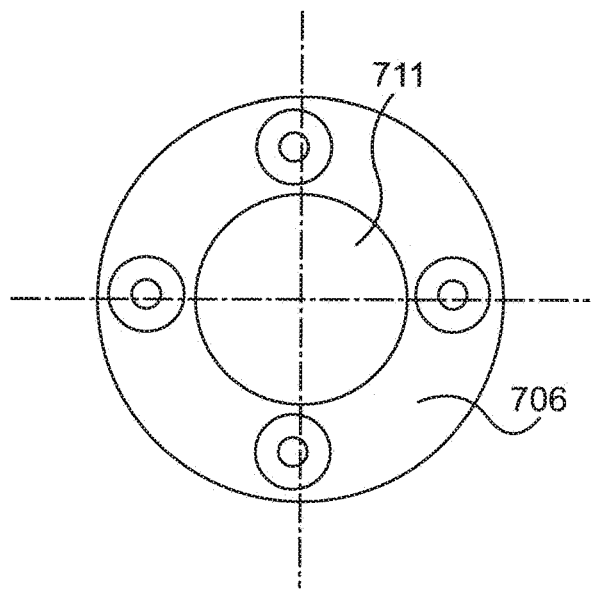 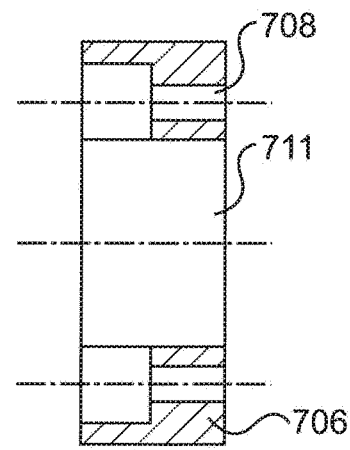
FIG. 121A  FIG. 121B

GUIDE TUBE SYSTEMS AND METHODS

CROSS-REFERENCE TO RELATED APPLICATIONS

This application is a continuation of U.S. application Ser. No. 14/665,197, filed on Mar. 23, 2015, which is a continuation of U.S. application Ser. No. 11/946,812, filed on Nov. 28, 2007, now U.S. Pat. No. 9,084,621, which claims priority to U.S. Provisional Application No. 60/872,155 entitled "Systems and Methods For Intraluminal Surgery" filed Dec. 1, 2006 and to U.S. Provisional Application No. 60/909,219 entitled "Direct Drive Endoscopy Systems and Methods" filed Mar. 30, 2007, all of which are incorporated herein by reference.

BACKGROUND OF THE INVENTION

Minimally invasive surgical tools, such as endoscopic and laparoscopic devices, can provide surgical access to surgical sites while minimizing patient trauma. Although the growing capabilities of such therapeutic devices allow physicians to perform an increasing variety of surgeries through traditional minimally invasive routes, further refinements may allow surgical access through even less invasive routes. Currently some robotic systems have been proposed to allow surgical access via a natural orifice. The user interface is remote from surgical tools and/or end effectors. Unfortunately, these systems are generally expensive and complicated. In addition, they fail to provide the tactile user feedback which traditional devices can provide.

Accordingly, there is room for further refinement to conventional minimally invasive surgical devices and a need to develop new surgical systems.

SUMMARY OF THE INVENTION

Described herein are various systems and methods for driving tools. The tools, in one aspect, can be driven via user input forces that are delivered to a distal working area. The tools and/or other elements of the various systems described below, in response to user input forces, can move in multiple degrees of freedom. The systems described herein can also facilitate control of those multiple degrees of freedom. For example, multiple degrees of freedom can be actuated with only one hand.

In one embodiment, a system is provided which includes a guide tube for. The guide tube can include at least one channel therein for delivering a surgical instrument. In one aspect, multiple surgical instruments can be delivered through one or more channels in the guide tube. The guide tube can provide at least one degree of freedom to the system, and in another embodiment, can provide multiple degrees of freedom.

In one aspect, the guide tube can receive a flexible endoscope, or other visualization means, to allow visualization of a surgical site. In another aspect, the guide tube can receive tools for tissue repair, evaluation, and/or resection. The endoscope, guide tube, and/or tools can provide additional degrees of freedom to the system. For example, the tools can provide at least one, and in an other aspect, two or more, degrees of freedoms via a hand control.

In another aspect, the guide tube, tools, and/or optical device can work with a support frame. The frame, for example, can mate with the tools and assist with controlling additional degrees of freedom. In addition, the frame can provide a reference with respect to a patient.

Further described herein is a method of accessing a surgical site. In one embodiment, a guide tube can be directed through a natural orifice to a surgical site. An optical device and at least one surgical tool can be delivered to the surgical site through a channel in the guide tube. A user can then view and manipulate a tissue mass via the optical device and the at least one surgical tool. In one aspect, the user can interact with one or more controllers mated to a support frame as part of actuating the at least one surgical tool.

It is to be understood that both the foregoing general description and the following detailed description are exemplary and are not restrictive of the invention, as claimed.

BRIEF DESCRIPTION OF THE DRAWINGS

The accompanying drawings, which are incorporated in and constitute a part of this specification, illustrate exemplary embodiments of the invention and together with the description, serve to explain the principles of the invention.

FIG. 9A a transparent view of one exemplary embodiment of a guide tube described herein.

FIG. 9B is a transparent front view of the guide tube of FIG. 9A.

FIG. 14 is a side view of the distal end of one exemplary embodiment of a system described herein.

FIG. 15A is a side view of the distal end of one exemplary embodiment of a system described herein.

FIG. 15B is a side view of the distal end of one exemplary embodiment of a system described herein.

FIGS. 42A, 42B, and 42C are perspective views of various exemplary embodiments of a system described herein for laparoscopic procedures.

FIG. 55 is a side view of one exemplary embodiment of tool and rail for use with a system described herein.

FIGS. 57, 58A, and 58B illustrate various exemplary quick-disconnects for use with a system described herein.

FIGS. 60 and 61 are perspective views of exemplary features of tools and rails described herein.

FIG. 62A is a perspective view of one exemplary embodiment of a control member and rail described herein.

FIGS. 62B and 62C are cross-sectional view of exemplary features of a control member described herein.

FIG. 66A is a partially transparent view of one exemplary embodiment of a rail and tool described herein.

FIG. 66B is a cross-sectional view along B-B of FIG. 66A.

FIG. 68B is a perspective view of another exemplary embodiment of a control member and rail described herein.

FIG. 70 is a perspective view of another exemplary embodiment of a control member and rail described herein.

FIGS. 80B, 80C, 80D, 80E, 81, 82A, 82B, 83A, 83B, and 84 are various partially disassembled views of the tool of FIG. 80A.

FIGS. 90, 91, 92, 93, 94, 95, and 96 are various perspective views of exemplary handles for use with a control member described herein.

FIGS. 99, 100, and 101 are perspective views of exemplary control mechanisms described herein.

FIGS. 113A and 113B are perspective views of various exemplary elements of a tool described herein.

FIGS. 119A and 119B are perspective views of an exemplary embodiment of a tool described herein.

FIG. 120A is a disassembled view of one exemplary embodiment of a tools described herein.

FIG. 120B is a cross-sectional view of the tool of FIG. 120A.

FIGS. 121A and 121B are front and cross-sectional views of an exemplary element of the tool of FIG. 102A.

FIGS. 123A, 123B, 123C, and 123D are cross-sectional view of exemplary embodiments of a tool described herein.

Figure 124:
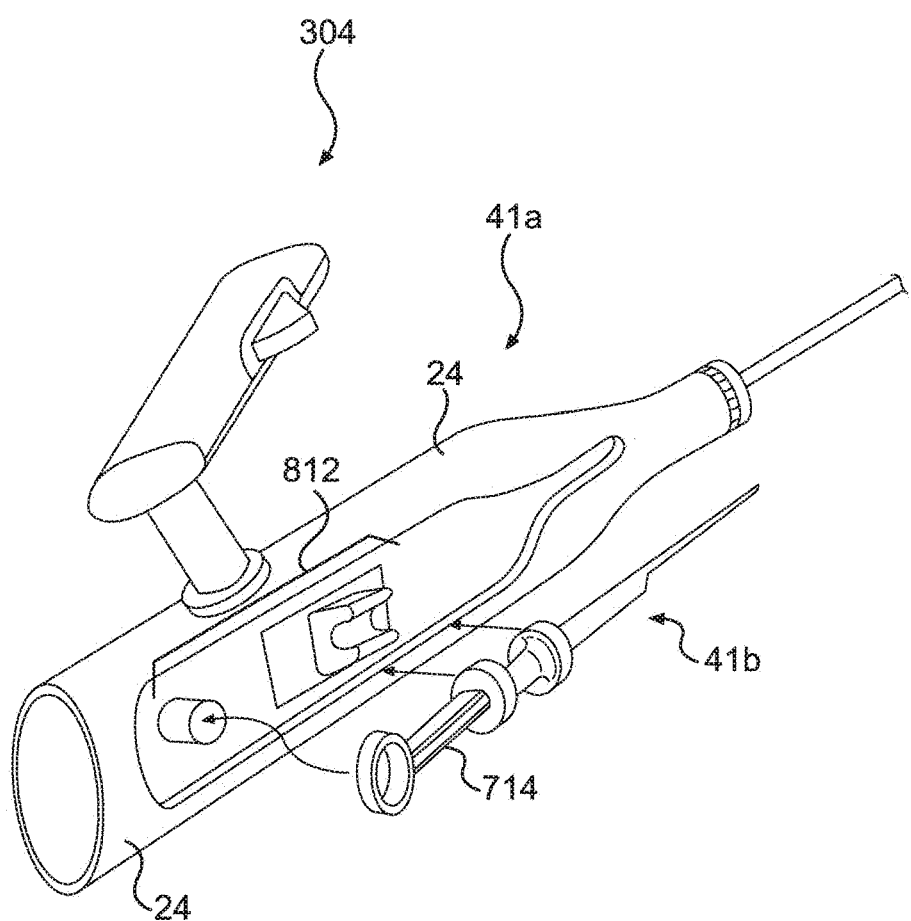

FIG. 124 is a perspective view of one exemplary embodiment of a tool described herein.

Figure 125A:
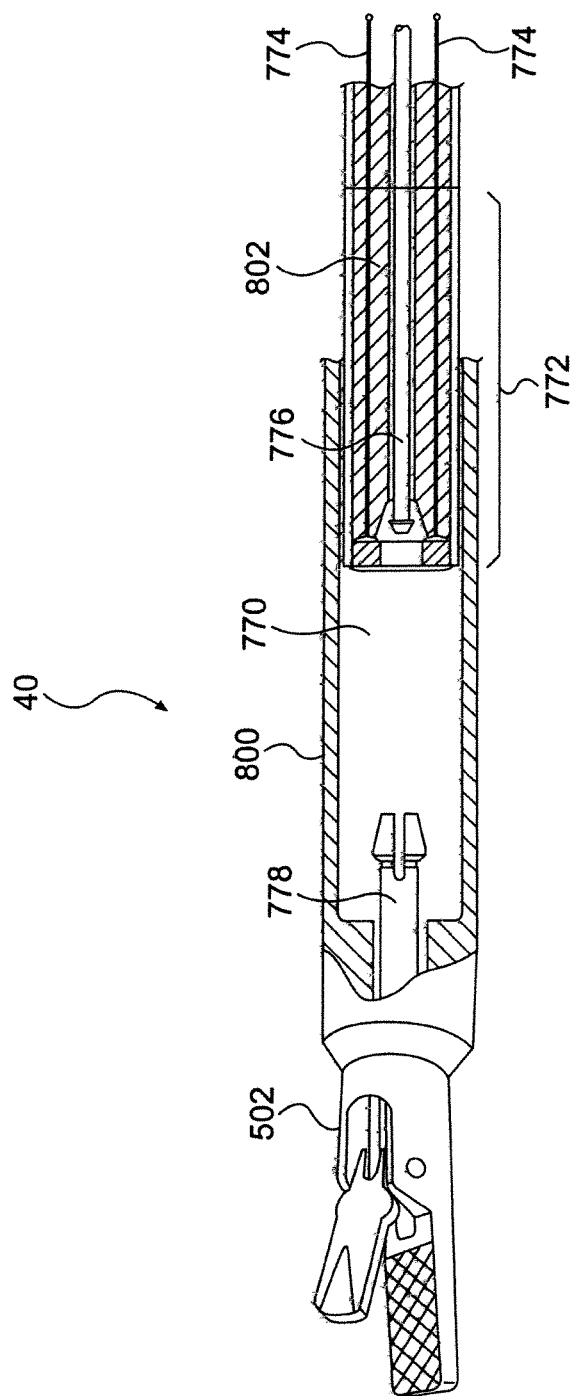
Figure 125B:
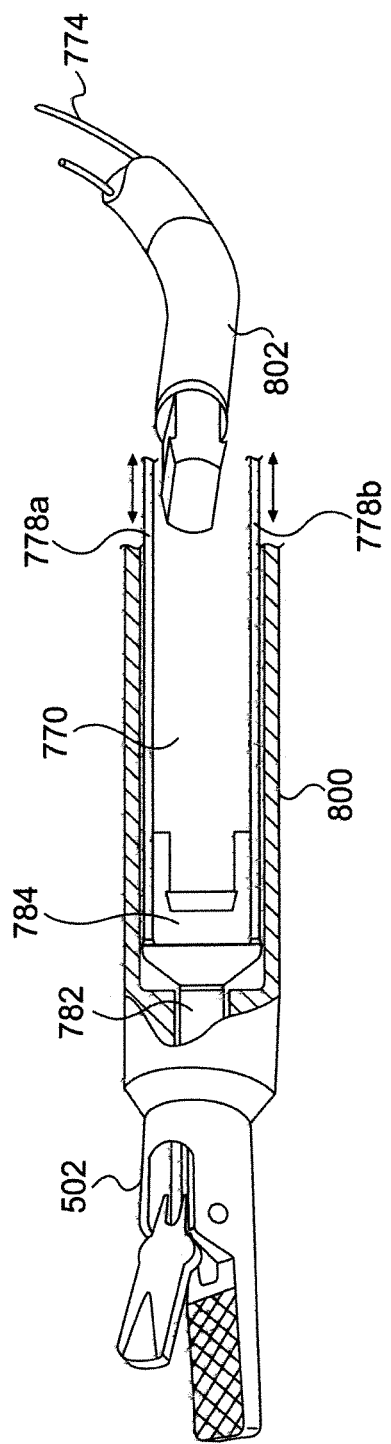
Figure 125C:
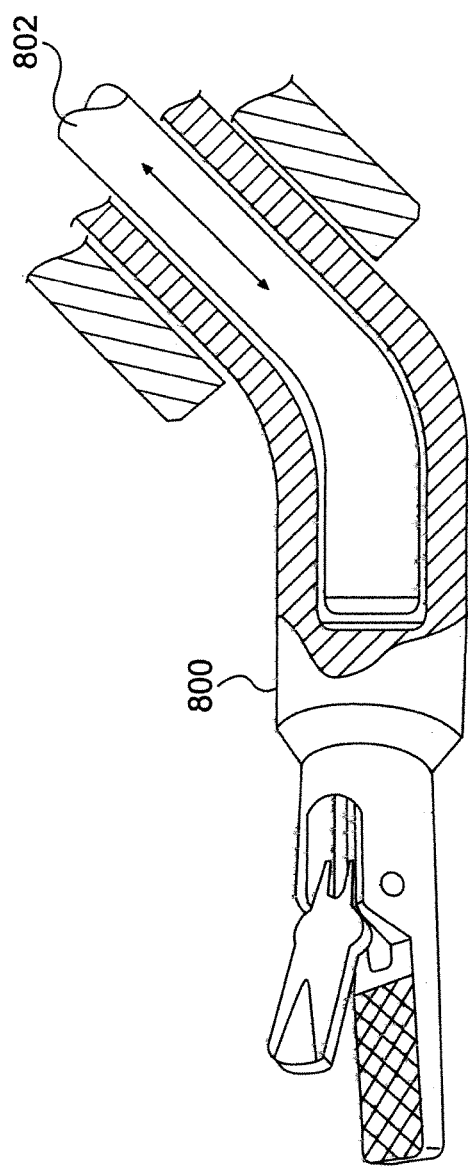

FIGS. 125A, 125B, and 125C are partial cross-sectional views of exemplary embodiments of a two-part tool described herein.

FIGS. 126, 127, 128, 129, and 130 are side views of exemplary embodiments of disposable elements of tools described herein.

FIGS. 131A, 131B, 131C, 131D, 131E, 131F, 131G, 131H, 131I, and 131J are perspective views of exemplary steps of knot tying using a system described herein.

DETAILED DESCRIPTION

Disclosed herein are systems and methods for performing surgery at a distance via medical instruments directly connected to user controls. In one aspect, the system is adapted for trans-oral, trans-anal, trans-vaginal, trans-urethral, trans-nasal, transluminal, laparoscopic, thoracoscopic, orthopedic, through the ear, and/or percutaneous access.

Various exemplary components of the system are described below in more detail. However, generally, the system can include at least one instrument directly connected to a user control. The system can permit a user to control at least two degrees of freedom via a controller that can be manipulated with a single hand. In another aspect, the single-hand controller can control three, four, or more than four degrees of freedom. In yet another aspect, at least two controllers, each configured for single-hand control, are provided. Each controller can provide at least two degrees of freedom, three degrees of freedom, four degrees of freedom, or more than four degrees of freedom. In order to allow the user to manipulate the multiple degrees of freedom, the systems can include a structure that provides a frame of reference between the user, the instruments, the controllers, and/or the patient. This structure can be provided by a variety of different components as described below.

The following disclosure is broken into several sections, including a description of a guide tube for housing a portion of an instrument or instruments, a frame, rails which can facilitate instrument movement, a controller for manipulating the instrument or instruments, and the instruments themselves. It should be appreciated that the systems described and claimed herein can include any or all of the various disclosed components and the various embodiments of those components. In addition, a single structure can define and/or perform the function of elements described in two separate sections of the disclosure. For example, the frame or guide tube can define a rail. A portion of the disclosure is directed to exemplary systems (e.g., FIG. 1), but it should be understood that this invention is not limited to those exemplary systems.

In addition, while the discussion of systems and methods below may generally refer to "surgical tools," "surgery," or a "surgical site" for convenience, the described systems and their methods of use are not limited to tissue resection and/or repair. In particular, the described systems can be used for inspection and diagnosis in addition, or as an alternative, to surgery. Moreover, the systems describe herein can perform non-medical applications such as in the inspection and/or repair of machinery.

Figure 1:
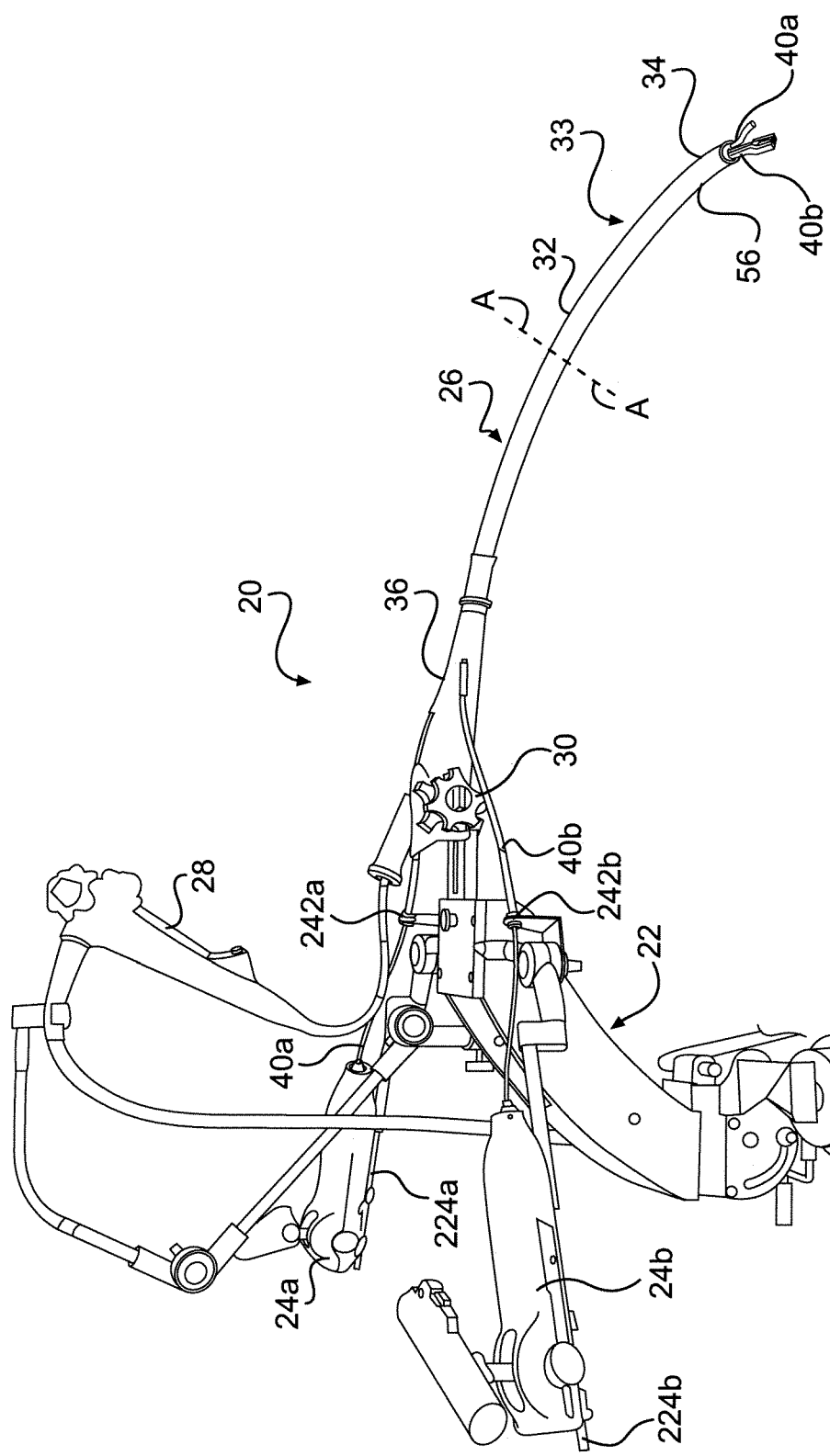
FIG. 1 is a perspective view of one embodiment of a system described herein.

FIG. 1 provides a perspective view of one embodiment of a system 20 for performing intraluminal and/or transluminal surgery through a natural orifice. The system includes a frame 22 for supporting control members 24a, 24b, of tools 40a, 40b, and a guide tube 26 for housing the elongate body of tools 40a, 40b, and/or an optical device 28. When the guide tube 26 is inserted into a patient, control members 24a, 24b allow a surgeon to manipulate surgical tools 40a, 40b which extend to a surgical site positioned adjacent to the distal end 34 of guide tube 26. As will be described in more detail below, frame 22 can have a variety of configurations depending on patient location, spacing, ergonomics, physician preference, and/or the availability of an operating table frame.

The Guide Tube

Guide tube 26 can have an elongate body 32 extending from the frame and configured for insertion through a natural orifice and/or incision to a surgical site within a patient. While the guide tube is shown in FIG. 1 as mated with frame 22, guide tube 26 can be used without frame 22 during a portion or all of a surgical procedure. In one aspect, guide tube 26 includes a distal articulating end 34 that is controlled by proximal guide tube controls 30. A proximal end 36 of the guide tube can include at least one aperture for receipt of surgical instruments, such as, for example, tools 40a, 40b and/or optical device 28 (together generally referred to herein as "surgical instruments"). Between proximal end 36 and distal end 34 of guide tube 26, elongate body 32 can include a mid-portion 33. In one embodiment, mid-portion 33 is generally flexible and non-articulating. In another embodiment, at least a portion of the guide tube is rigid. For example, a portion or the whole of guide tube 26 can be rigid.

In one embodiment, as discussed below, guide tube 26 can provide system 20 with one, two, or more than two degrees of freedom. For example, guide tube 26 can be articulated with controls 30 to move at least a portion of guide tube 26 (e.g., distal end 34) up/down and/or side-to-side. Additional degrees of freedom, provided for example, via rotation, translational movement of the guide tube with respect to the frame, and/or additional articulation or bending sections, are also contemplated.

The outer surface of elongate body 32 of guide tube 26 can include a layer of lubricous material to facilitate insertion of guide tube 26 through a body lumen or surgical insertion. The interior of elongate body 32 can include at least one channel adapted to guide at least one elongate surgical instrument to a surgical site. In another aspect, the body can have two channels, three channels, or more than three channels. In one aspect, the guide tube includes multiple channels comprising a main channel for receipt of an optical device, such as an endoscope, and working channels for receipt of articulating surgical tools. The number of channels and their particular configuration can be varied depending on the intended use of the system and the resultant number and type of surgical instruments required during a procedure. For example, the guide tube can include a single channel adapted to receive multiple instruments or multiple channels for multiple instruments.

Figure 2B:
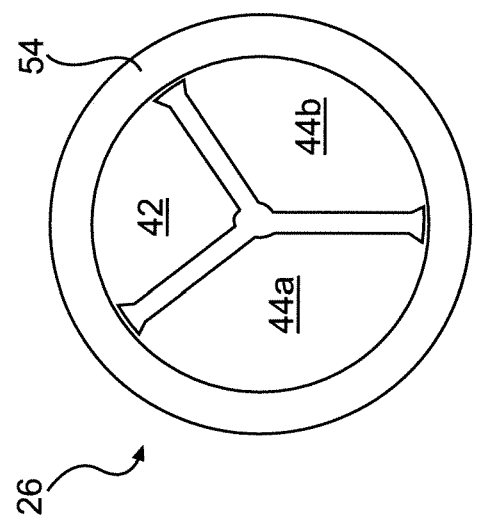
FIG. 2B is another embodiment of a cross-sectional view of FIG. 1 along A-A.
Figure 2A:
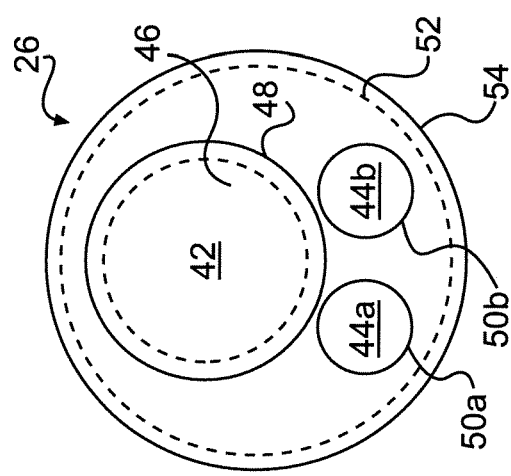
FIG. 2A is a cross-sectional view of FIG. 1 along A-A.

FIGS. 2A and 2B illustrate exemplary cross-sectional views of the mid-portion of elongate body 32 (taken along line A-A in FIG. 1) that includes main channel 42 and working channels 44a, 44b. While three channels are illustrated, fewer channels (e.g., one or two) or more channels (e.g., four or more) are also contemplated. In addition, while main channel 42 is described as the largest channel, in terms of cross-sectional width, the working channels 44a, 44b can be a larger or smaller size than main channel 43. Moreover, use of the word "channel" does not require that the optical devices and/or surgical instruments traversing the guide tube be distinct or stand alone devices. For example, in one embodiment, the system includes an optical device and/or surgical instrument formed integrally with the guide tube. In still another embodiment, the optical devices and/or instruments described herein can, themselves, define the guide tube. For example, the optical device can define the guide tube and include channels for instruments.

Regardless, in the exemplary illustrated embodiment of FIG. 2A, main channel 42 can be defined by at least one elongate lumen that extends, at least partially, between proximal and distal ends 36, 34 of guide tube 26. Similarly, working channels 44a, 44b can be defined by separate lumens, with main and working channels housed in an outer lumen. Alternatively, as illustrated in FIG. 2B, at least one of channels 42, 44a, 44b, can be defined by a divider that extend along at least a portion of guide tube 26. For example, all three channels 42, 44a, 44b can share a common sheath or outer jacket 54. One skilled in the art will appreciate that the divider can be defined by a portion of the guide tube and/or by a separate element that is mated with the guide tube and/or instruments (an example of which is described in more detail with respect to FIGS. 7A through 7C).

Referring now to FIG. 2A, in one aspect, main channel 42 comprises an inner tubular body 46 and an outer tubular body 48. Both the inner and outer tubular bodies can comprise flexible materials. In one aspect, inner tubular body 46 has a lubricous inner surface. For example, inner tubular body 46 can be formed from a low friction material such as a fluoropolymer (e.g., polytetrafluoroethylene). Alternatively, inner tubular body can defined by a coating of low friction material.

In order to improve the flexible characteristics of the inner tubular body, the inner tubular body can have a configuration that reduces the risk of kinking or narrowing the tubular body and/or that increases the bend angle of the guide tube. In one aspect, the inner tubular body is spiral cut to provide open sections of inner tubular body 46. For example, the spiral cut tube can result in windings with open sections between the windings, such that the windings can move toward and away from each other when the guide tube bends. One skilled in the art will appreciate that the materials and construction of the inner tubular body can be chosen to meet the desired flexibility of the guide tube. In addition, the inner tubular body can include different materials and/or configurations along the length of the guide tube to provide varying flexibility along the length of the guide tube.

Where the inner tubular body has a spiral cut or "open" configuration, the main channel can further be defined by outer tubular body 48. The outer tubular body of the main channel can provide structure to the spiral cut inner tubular body and limit the amount of play between the windings of the spiral cut tubular body. The outer tubular body can be formed from a variety of flexible materials including polymers and/or metals. In addition, outer tubular body 48 can include reinforcing materials to further strengthen the main channel, such as, for example, a mesh and/or braid. In one aspect, the wall of the outer tubular body of the main channel does not have any perforations or openings to the adjacent environment. For example, the outer tubular body can be impervious and provide a fluid barrier.

The working channels 44a, 44b can have a similar or different configuration from the main channel and from each other, including, for example, one, two, or more than two coaxial tubular bodies. In addition, working channels 44a, 44b can extend for all or a part of the length of the guide tube. In one aspect, the working channels include a lubricious material that coats or defines a working channel tubular body. As shown in FIG. 2A, the working channels 44a, 44b, in one embodiment, includes single tubular bodies 50a, 50b formed of a fluoropolymer. In addition, the working channel tubular bodies 50a, 50b can include reinforcing materials 51 (FIG. 3A), such as, for example, a mesh, spiral, and/or braid. Regardless of the configuration of the channels 44a, 44b, the inner walls of the working channel bodies 50a, 50b can be lubricous. For example, a lubricous coating, film, paste, or fluid and/or secondary material (liner) can be use to facilitate insertion of a tool or optical device through the channels. Additionally, or alternatively, the inner and/or outer surfaces of the guide tube can have raised surface features, such as, for example ribs, to reduce friction.

In another embodiment, one or more of the channels (e.g., main and/or working channels) can be formed from walls comprising a loose or stretchable material (not illustrated), such as an accordion-type material having folds and/or a loose bag type-liner. The folds in the walls of the channel allow longitudinal expansion and contraction of portions of the channel. The loose material can have a partially folded configuration such that when the channel bends, the folds open to allow expansion of a portion of the channel wall. In another aspect, the walls of one or more of the channels are configured to allow stretching or expanding.

In still another embodiment, a single member defines two or more of the channels (e.g., main and/or working channels). For example, working channels 44a, 44b, can be defined by co-extruded lumens. Alternatively, or additionally, the multiple layers than define a channel (e.g., inner and outer tubular bodies 46, 48) could be co-extruded.

Figure 3A:
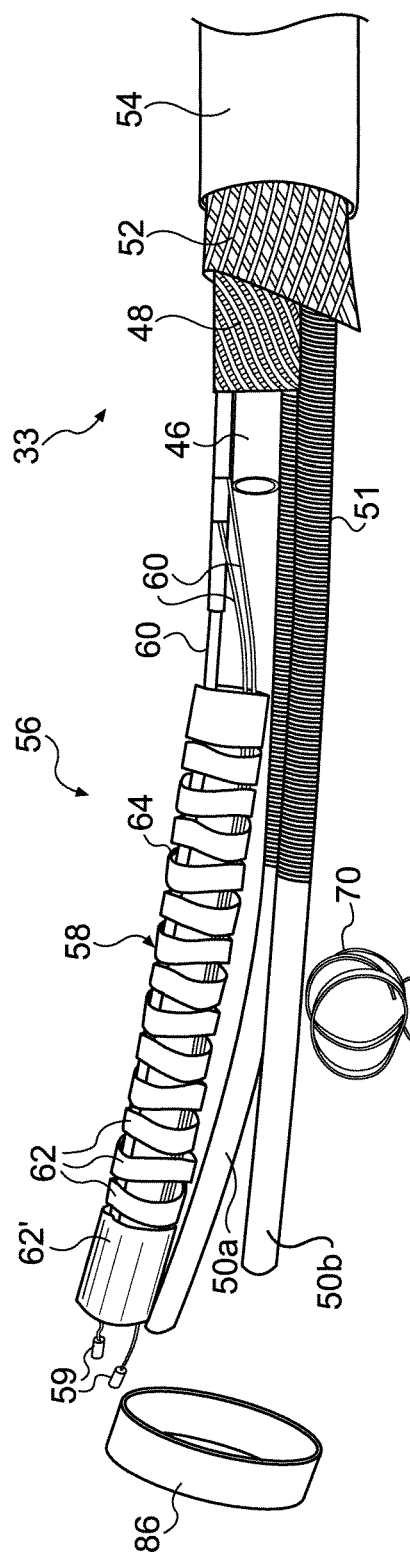
FIG. 3A is a disassembled view of a portion of the system of FIG. 1.

With respect to FIG. 3A, In one aspect, the working and main channels are not fixedly mated to one another. Instead, a mesh, spiral, jacket, and/or filament braid 52 can cinch the channels together and keep the channels bundled together. Depending on the desired rigidity of the mid-portion of the guide tube, the mesh density, rigidity, and materials of braid 52 can be varied. In an alternative aspect, filaments, bands, or other place holders can be positioned around two or more of the channels to limit transverse movement of the channels away from one another. In still another aspect, the guide tube does not includes any connection between the channels.

The guide tube can further include an outer jacket 54 surrounding the channels. The outer jacket can work with, or take the place of, filament braid 52 and assist with bundling the main and working channels together. In one aspect, the outer jacket is formed of a continuous, fluid impermeable material that acts as a barrier against the intrusion of biological material into the guide tube. In use, as mentioned above, the guide tube can be inserted through a body orifice and the outer jacket can provide a barrier to bacteria found along a body pathway. In one aspect, the outer jacket is formed of an elastomeric and/or polymeric material such as, for example, PTFE, EPTFE, silicon, urethane, and/or vinyl.

In addition to protecting the inner channels, the outer jacket can have a lubricous outer surface to assist with insertion of the guide tube. The lubricous surface can minimize tissue trauma and help to ease the device through a body lumen.

In one aspect, the guide tube can include variable stiffness along its length. For example, the material properties of the various layers of guide tube 26 can be varied to control the stiffness of the guide tube. In addition, or alternatively, stiffeners can be located in areas in which increased stiffness is desired. One skilled in the art will appreciate the degree of stiffness can be chosen depending on the intended use of system 20. In addition, the stiffness of guide tube 26 can be controlled by the user. For example, the guide tube can have a locking configuration. Once the guide tube is positioned within a patient, the user can lock the guide tube in position.

In addition, while the guide tube channels are illustrated as enclosed and protected from the environment surrounding the guide tube, in one alternative aspect, at least one of the guide tube channels can have an open configuration. For example, the main channel can be defined by an open or split wall lumen such that a instrument can be inserted into the guide channel through the sidewall of the guide tube. Instead of inserting the instrument through the proximal opening of the guide tube, the optical device can be inserted into the working channel through the sidewall of the guide tube. In one such aspect, a snap-fit or interference fit can hold the instrument in the main channel.

Distal to the mid-portion 33 of elongate body 32, the guide tube can include an articulation portion 56 (FIG. 1). In one aspect, the articulation portion provides at least one degree of freedom, and in another aspect, provides more than one degree of freedom (e.g., two, three, or more than three degrees of freedom) to system 20. In particular, the distal end of the guide tube can be moved side-to-side and/or up/down by the proximal controls 30. In another aspect, the guide tube can additionally, or alternatively, move longitudinally and/or rotate. Articulation, regardless of the number of degrees of freedom, can be controlled in a variety ways and is discussed in more detail below.

In one aspect, the main channel is adapted to articulate while the working channels are mated to the main channel and move with the main channel. In other words, the working channels are not directly articulated. However, in another aspect, all the channels can be directly articulated together or independently depending on the intended use of system 20. Another embodiment includes a single lumen that articulates and is configured to receive multiple instruments or multiple channel bodies. For example, the guide tube can include one working channel for receiving multiple instruments.

Figure 3B:
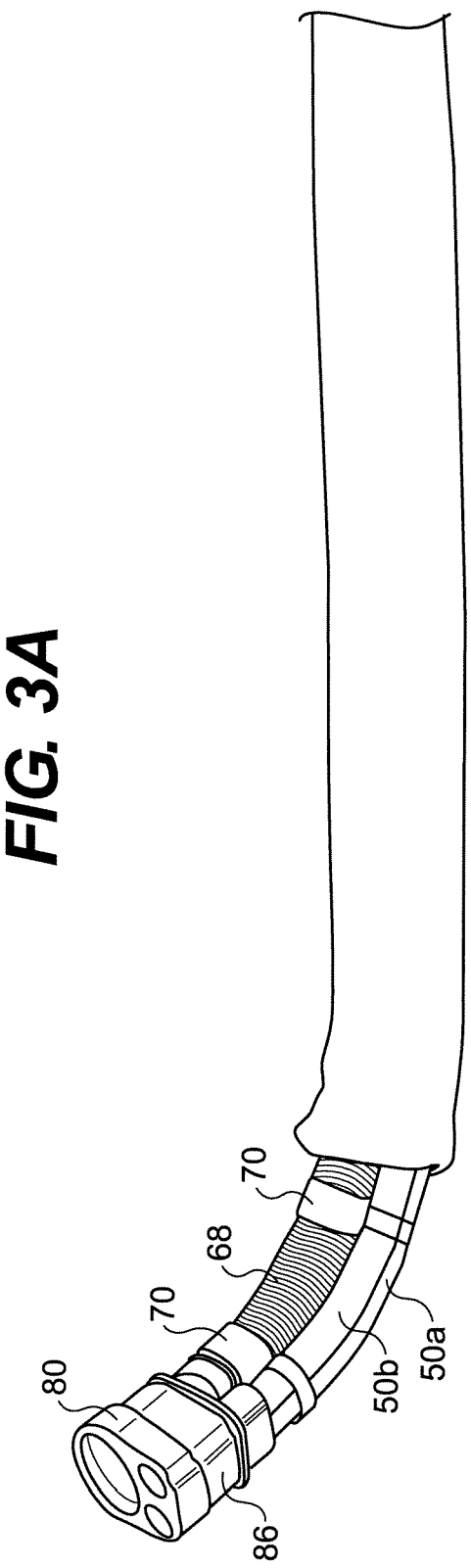
FIG. 3B is a cut-away view of a portion of the system of FIG. 1.
Figure 4A:
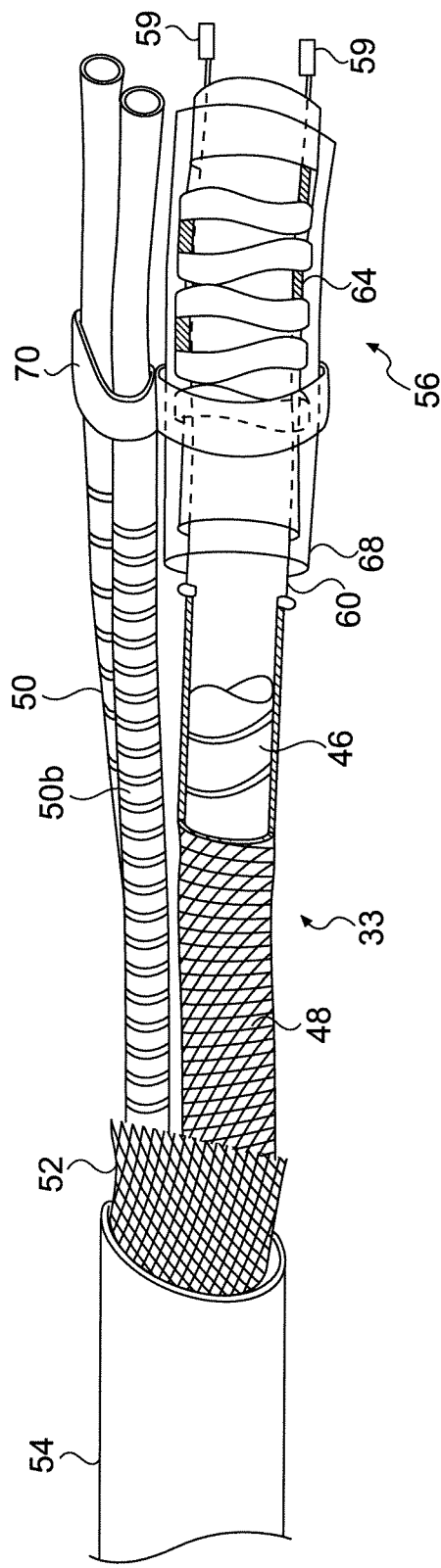
FIG. 4A is a cut-away view of a portion of the system of FIG. 1.
Figure 4B:
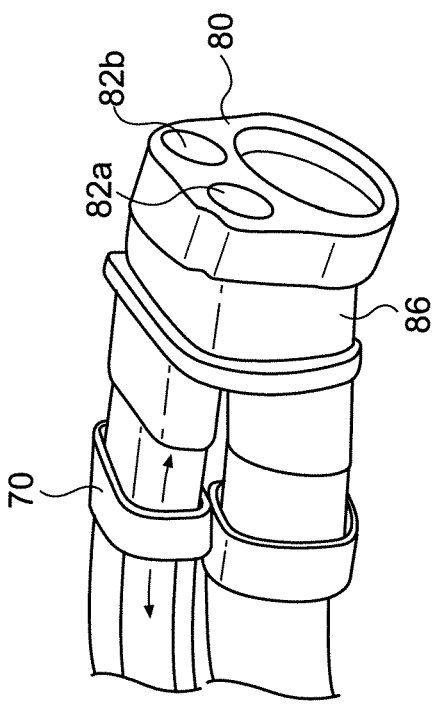
FIG. 4B is a cut-away view of a portion of the system of FIG. 1.

FIGS. 3A through 4B illustrate one embodiment of the transition between mid-portion 33 and articulation portion 56. FIGS. 3A and 3B illustrate a disassembled view and partially disassembled (outer sheath removed) view of the articulation portion of the exemplary guide tube, while FIG. 4A illustrates a partially transparent view of the articulation portion with various layers removed. FIG. 4B illustrates the distal-most end of the articulation portion with outer sheath 54 removed. As shown in FIGS. 3A through 4A, the working channel bodies 50a, 50b extend through the articulation portion 56 of guide tube 26, while the inner and outer tubular bodies 46, 48 end at articulation portion 56. The main channel 42 in the articulation portion 56 of guide tube 26 can be defined by an articulation body member 58 having an inner lumen. In addition, the working channel bodies in the articulation section can have a different configuration from the working channel bodies in the mid-portion of the guide tube. For example, in the mid-portion 33 of guide tube 26, working channel bodies 50a, 50b can include a reinforcing braid or winding 51. Conversely, as shown in FIGS. 3A, 3B and 4A, the working channel bodies 50a, 50b do not include a reinforcing braid or winding 51 in the articulation portion 56.

A variety of control mechanisms can be used to manipulate the articulation portion, including, for example, push-pull strands, leaf springs, cables, oversheaths, ribbons, electroactive materials, and/or fluid actuation.

In one embodiment, strands 60 extend from the proximal portion of the guide tube to the articulation body member 58 to control the articulation body member. Strands 60 can comprise one or more filaments formed of a flexible material including, for example, a variety of wires and cables. In one aspect, strands 60 include an inner filament positioned within an outer casing. For example, strands 60 can be defined by bowden cables which reduce power losses along the length of the guide tube.

As shown in FIGS. 3A and 4A, four strands 60 can extend to the articulation portion 56 and provide two degrees of freedom guide tube 26. When tensioned, the strands can bend the articulation body 58 by moving a series of articulation segments 62. The articulation segments 62 together define the articulation body 58 and the main channel 42 in the articulation portion 56 of the guide tube 26. In one aspect, springs 64 connect the articulation segments 62 and allow the articulation segments to move relative to one another. Strands 60 extend across the articulation portion and mate with a distal articulation segment 62'. When a strand is tensioned, the articulation segments 62 move relative to one another along at least part of the articulation portion 56 of the guide tube to allow articulation portion 56 to bend.

Strands 60 can mate with articulation body member 58 in a variety of ways. In one aspect, the ends of the strands are welded to the inner surface of the articulation body member 58. Alternatively, as shown in FIGS. 3A and 4A, the distal end of the strands can include terminals 59 which mechanically engage loops attached to, or formed on, the inner surface of the articulation body member. Terminals 59 can have a larger outer diameter than the inner diameter of the loops, such that the terminals cannot be pulled proximally through the loops.

Figure 5B:
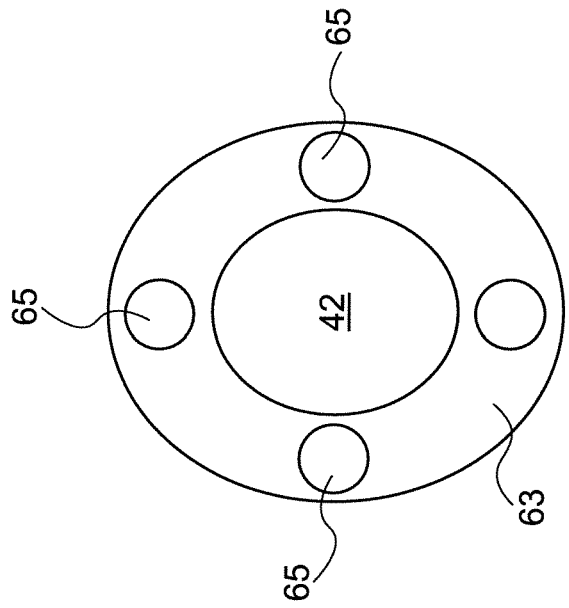
FIG. 5B is a front view of another embodiment of the element of FIG. 5A.
Figure 5A:
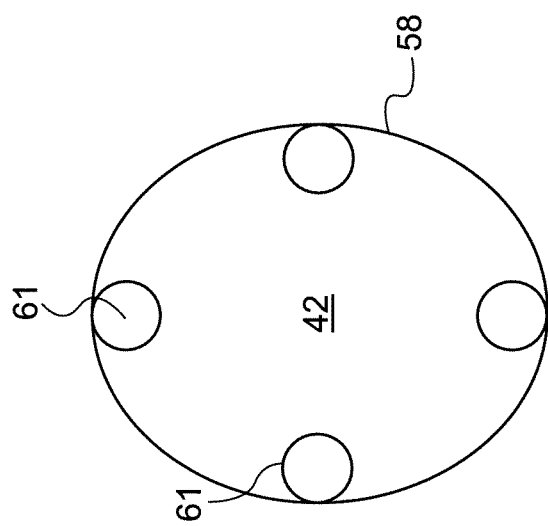
FIG. 5A is a front view of one exemplary element of the system described herein.

FIG. 5A illustrates loops 61 welded to the interior of guide tube 26 proximate to the distal end of the guide tube (i.e., proximate to the distal end of articulating body member 58) for mating with the distal ends of strands 60. In another aspect, shown in FIG. 5B, guide tube 26 can include a mating plate 63 having apertures 65 for receiving strands 60 and preventing the passage of terminals 59. Mating plate 63 can define the location and spacing apertures 65, which can eliminate the difficult process of carefully spacing, aligning, and mating individual loops to the inner surface of the articulation body member. In addition, mating plate 63 can include one or more apertures for the passage of channels 42 and/or 44a, 44b. In one aspect, mating plate 63 is mated to the distal end of articulation body member 58 via welding, adhering, mechanical interlock, and/or frictional engagement.

The mating plate can also serve to align and space a surgical instrument (e.g., an optical device), extending through the articulation section 56, from the walls of the articulation section and/or from another instrument. In one aspect, the working channel aperture 42 within the mating plate can align the a surgical instrument with the center of the articulation section. In addition, or alternatively, the location of the working channel aperture can space an optical device passing therethough from the inner surface of the articulation section. The mating plate can inhibit contact between a surgical instrument and the inner surfaces of the articulation section (e.g., springs).

To prevent articulation segments 62 from binding, pinching, and/or piercing the outer jacket 54, an articulation body member mesh or braid 68 (FIGS. 3B, and 4A) can extend over the articulation body member 58. The articulation body member mesh or braid 68 can be the same or different from the mesh or braid 52 found in the mid-portion 33 of elongate body 32. As shown in FIGS. 3B and 4A, the articulation body member mesh or braid 68 extends over articulation body member 58, but not over the adjacent working channel bodies 50a, 50b. Alternatively, the mesh or braid 58 can enclose more than one channel.

The degree to which the articulation portion bends can be varied by adjusting the shape of the articulation segments and/or the distance between the articulation segments. In one aspect, the articulation portion can bend up to about at least 180 degrees to allow retroflexing. For example, in a trans-oral approach to a gall bladder or liver, a surgeon may wish to turn in a cranial direction to look toward the diaphragm. Other procedures may require less bend, such as, for example, a bend of at least about 45 degrees from the longitudinal axis of the guide tube. Exemplary configurations of guide tube 26 with feature for directing surgical instruments along an increased bend, including retro-flexing, are described below. In addition, or alternatively, the guide tube can include multiple bending sections and/or can be adapted to lock in position or increase in stiffness.

As the articulation portion 56 bends, the articulation body member 58 and the working channel bodies 50 bend over different arcs. As a result, the working channel bodies 50a, 50b can move or side longitudinally relative to the articulation body member 58. In order to keep the articulation body member 58 and the working channel bodies 50 bundled, the articulation body member and the working channel bodies 50 can be held together with a place holder that allows relative longitudinal movement, while restricting relative transverse movement of the channels. In one aspect, as shown in FIGS. 3A through 4B, the place holder can include a rigid strap 70 extending around the articulation body member 58 and the working channel bodies 50. Strap 70 can inhibit relative transverse movement of the articulation body member and the working channel bodies while allowing the articulation body member and the working channel bodies to move longitudinally with respect to one another. In one aspect, the articulation portion 56 includes multiple place holders, such as multiple straps, along its length. One skilled in the art will appreciate that the place holder could be defined by a variety of elements that maintain the cross-sectional relationship of the channels.

Figure 6A:
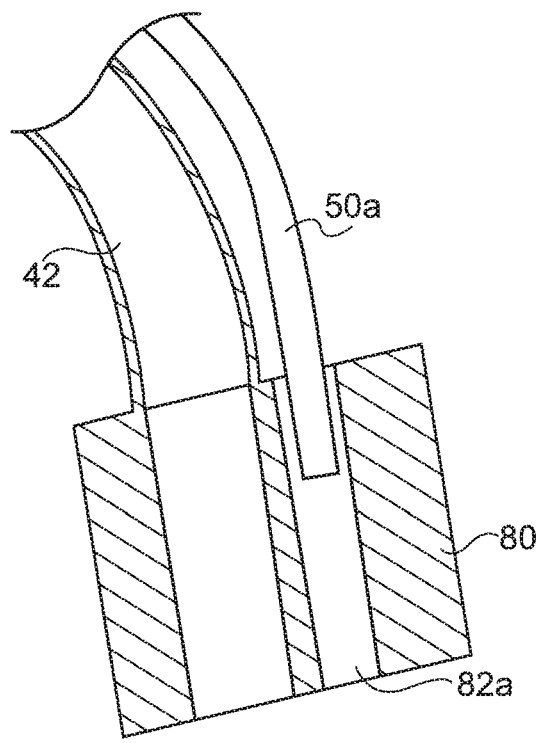
FIG. 6A is a cross-sectional view of one exemplary embodiment of an end cap described herein.
Figure 6B:
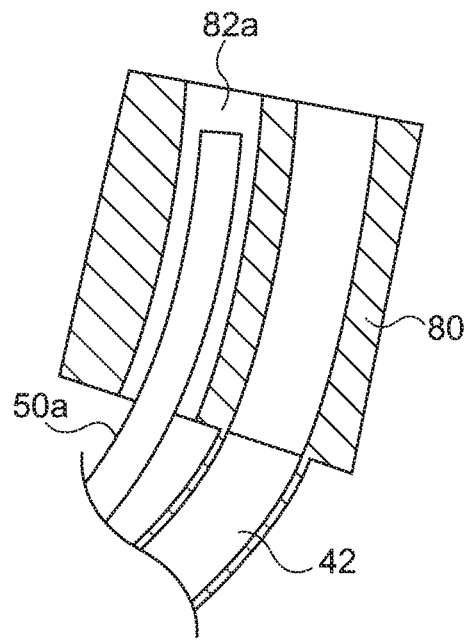
FIG. 6B is another cross-section view of the end cap of FIG. 6A.

At the distal end of the guide tube, system 20 can include an end cap 80 (FIGS. 3B and 4B) that provides openings through which surgical tools can pass from the channels of the guide tube into a working space within a patient. As mentioned above, when the articulation portion bends, the articulation body member (defining the main channel) and the working channel bodies (defining the working channels) move relative to one another. In one aspect, the articulation body member 58 is fixedly mated to the end cap, while the working channel bodies 50 are allowed to move longitudinally within end cap 80. For example, the end cap can provide a space for the distal ends of the working channel bodies 50 to move relative to the articulation body member 58 and the end cap 80. FIGS. 6A and 6B illustrate cross-sectional views of end cap 80 with the articulation portion mated with the end cap and a working passageway 82a that receive working channel body 50a (Working channel body 50b and working passageway 82b are hidden in FIGS. 6A and 6B. The second working passageway 82b is illustrated in FIG. 4B). As shown in FIG. 6A, as the articulation portion bends in the direction of the main channel 42, working body 50a withdraws from end cap 80. Conversely, as shown in FIG. 6B, as the articulation portion bends toward the working channels, working channel body 50*b* move into the end cap relative to the main channel.

In another embodiment, at least one channel (e.g., the working channel bodies) in the articulation section of the guide tube can be formed of a loose or stretchable material. For example, the wall of bodies 50*a*, 50*b* can be formed from a loose or stretchable material (not illustrated), such as an accordion-type material having folds or billows. The loose material can allow longitudinal expansion and/or contraction to reduce or eliminate the impact of relative longitudinal movement of the channels in the articulation section.

The end cap can be mated to one or more of the articulation segments 62 and/or mating plate 63. For example, end cap 80 and articulation body member 58 can mate via welding, adhering, mechanical interlock, and/or frictional engagement. Conversely, the working channel bodies 50*a*, 50*b* can move freely within the working passageways 82*a*, 82*b* within end cap 80. To prevent working channel bodies 50*a*, 50*b* from backing out of the proximal opening of passageways 82*a*, 82*b*, passageways 82*a*, 82*b* can have a sufficient length such that working channels bodies remain within the end cap passageways even when the articulation portion is at its full bend limit. In addition, while two passageways 82*a*, 82*b* are disclosed for two working channel bodies 50*a*, 50*b*, in another aspect, a single passageway could receive two or more working channel bodies.

In another aspect, end cap 80 and or working channel tubular bodies 50*a*, 50*b* can be configured to prevent the distal ends of the working channel bodies 50*a*, 50*b* from exiting the proximal and/or distal openings of working passageways 82*a*, 82*b*. For example, the distal ends of the working channel bodies 50*a*, 50*b* can have an outer diameter that is larger than the inner diameter of the proximal and/or distal openings to the working passageways 82*a*, 82*b* in end cap 80. In another aspect, the working channel bodies can include stops (not illustrated) to prevent the working channel bodies from fully withdrawing from the proximal end of end cap 80. For example, the working channel tubular bodies can include a stop formed of resilient material that can be compressed to insert the distal ends of the working channel bodies into the end cap. Once inserted, the stop can expand such that the stop has a larger diameter than the proximal opening of working passageways 82*a*, 82*b* in end cap 80. One skilled in the art will appreciate that the stops can have a variety of configurations to inhibit unwanted withdrawal of the working channel tubular bodies 50*a*, 50*b* from the proximal and/or distal end of the working passageways of the end cap.

System 20 can further include a seal between the end cap and the end of the outer jacket 54. To assist with seating of the seal, as shown in FIGS. 3A, 3B, and 4B, the end cap can include a recess into which a seal 86 can sit on the outer surface of the end cap. In one aspect, the end of the articulation portion can also include surface features to facilitate seating of the seal. Seal 86 can have a variety of configurations, and in one aspect, is formed of a heat shrinkable material that sits within a recess of end cap 80 and cinches around the outer surface of end cap 80 when shrunk.

The end cap can have a variety of shapes and sizes, and in particular, the distal surface of the end cap can be blunt to facilitate insertion of the guide tube through a body lumen while minimizing tissue trauma. For example, in one aspect, the end cap can have a taper to assist with moving the guide tube through a body lumen. The end cap can be formed, at least in part, of radiological opaque material that allows a surgeon to visualize the end of the guide tube within a body lumen. For example, the end cap can include, for example, metals or radiopaque polymers. In another aspect, at least a portion of the end cap can be formed of non-radio opaque material such as for example, plastic or elastomer materials. In yet another embodiment, the end cap is formed at least in part by transparent or partially transparent material to allow a user to observe a tool within a passageway of the end cap.

In another aspect, the guide tube end cap can include a flexible or resilient material for holding the various channels of the guide tube in position with respect to one another. As the guide tube bends, the resilient material can permit elongation/compression of the channels and can maintain the orientation of the lumens with respect to one another. In one aspect, articulation portion 56 can be defined by resilient material, such as, for example, an extrusion having lumens defining the working and main channels 44*a*, 44*b*, 42. The resilient articulation section can be articulated via pull wires as described above.

In another embodiment of guide tube 26, the guide tube the main and working channels are defined by a removable channel divider. With the channel divider removed, a large instrument channel is opened for the insertion of wider or larger tools. For example, a standard endoscope can be inserted with the channel divider removed. The channel divider can then be positioned within the large instrument channel to define several smaller channels within the guide tube. In one aspect, the channel divider defines the main and/or working channels.

Figure 7A:
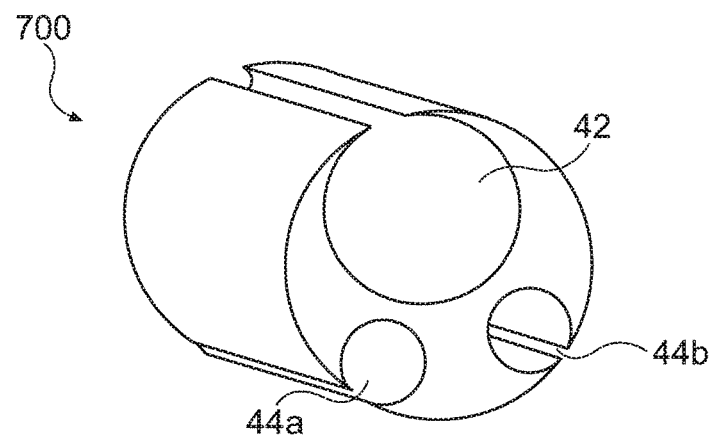
FIG. 7A is a perspective view of one exemplary embodiment of a channel divider described herein.

FIG. 7A illustrates a channel divider 700 defining main channel 42 and working channels 44*a*, 44*b*. Channel divider 700 can have an outer shape and size that generally corresponds to a lumen within the guide tube. Inserting the channel divider into the guide tube lumen can mate the channel divider and guide tube. For example, friction between the outer surface of the channel divider 700 and the inner surface of the guide tube can mate the channel divider and guide tube. In another aspect, the guide tube and/or channel divider can include mating features to lock the channel divider within the guide tube and prevent relative movement between the channel divider and guide tube.

In one aspect, the passageways within channel divider 700 are enclosed by the body of the channel divider. Alternatively, as illustrated in FIG. 7A, the passageways can have an open or split side to allow insertion of tools and/or optics through the sidewall of channel divider 700.

Figure 7B:
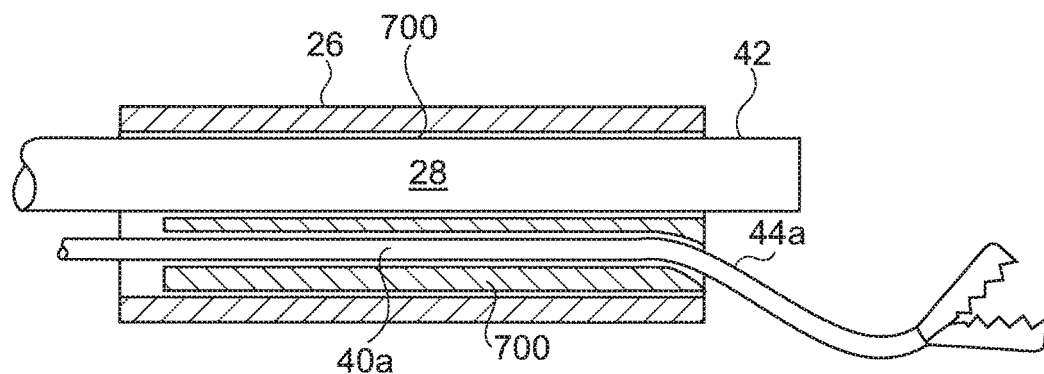
FIG. 7B is a longitudinal cross-section of the channel divider of FIG. 7A.
Figure 7C:
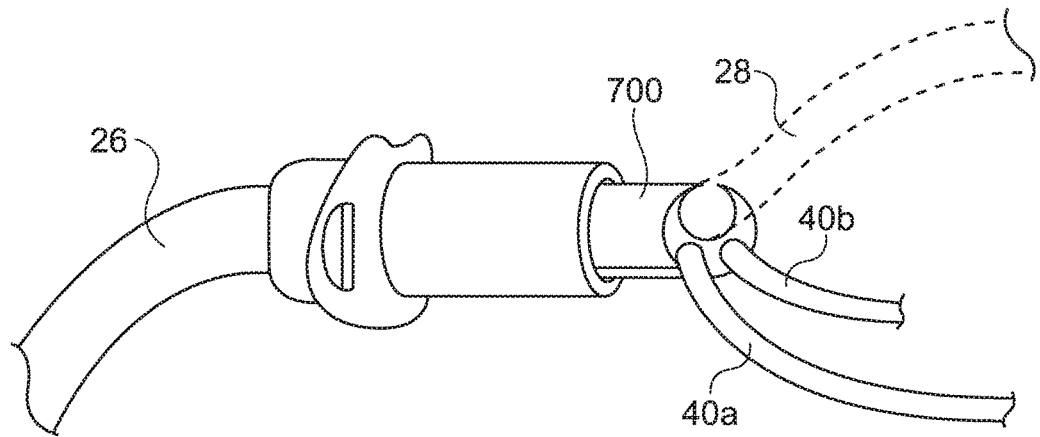
FIG. 7C is a perspective view of the channel divider of FIG. 7A positioned within a guide tube.

FIGS. 7B and 7C illustrate channel divider 700 within guide tube 26. In one embodiment, tools and/or optics can be loaded into the channel divider prior to insertion of the channel divider into the guide tube. The channel divider, with tools positioned therein, can then be inserted into the guide tube. In one aspect, channel divider 700 has a length that extends the majority of the length of the guide tube. In another aspect, multiple channel dividers can be provided.

Channel divider 700 can be formed of a variety of flexible, compressible, and/or resilient materials. Where a flexible guide tube or guide tube segment is desired, the channel divider can be formed of soft, flexible material. Conversely, where increased guide tube stiffness is desired, a harder, less flexible channel divider can be provided. In one aspect, the material properties of the channel divider vary along its length to provide varying guide tube flexibility.

Figure 7D:
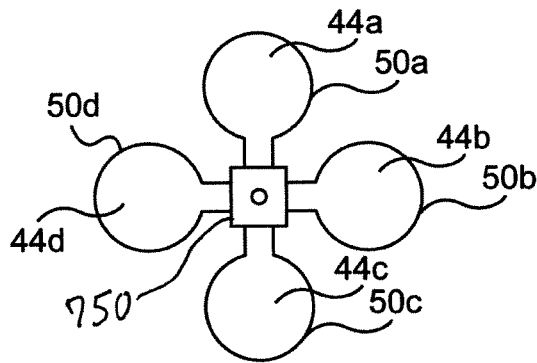
FIG. 7D is a front view of one exemplary embodiment of a guide tube described herein.
Figure 7E:
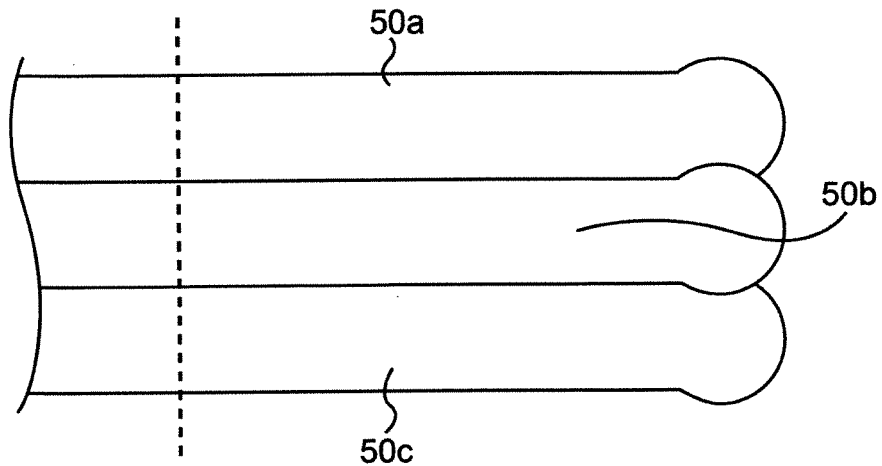
FIG. 7E is a side view of the guide tube of FIG. 7D.

In another embodiment of guide tube 26, channels (working and/or main) and/or tools can mate with a central control shaft. For example, as illustrated in FIGS. 7D and 7E, central control shaft 750 mates with working channels bodies 50*a*, 50b, 50c, and 50d defining working channels 44a, 44b, 44c, and 44d. The channel bodies can surround shaft 750 and/or attach to the outer surface of shaft 750. In one aspect, the channel bodies are exposed to the surrounding environment and not enclosed by an outer tubular body. In particular, an outer tubular body need not surround and/or constrain relative movement (e.g., relative radial movement) of the channels. Instead a central shaft or shafts 750 can mate with and hold the channel bodies in positioned with respect to one another.

Shaft 750 can also include an articulation section for steering the channels. For example, control wires can extend through or along shaft 750 to a distal articulation section. Tensioning the control wires can drive one or more degrees of freedom of shaft 750, including, for example, up/down and/or left/right movement.

In one aspect, one or more of the channel bodies 50a, 50b, 50c, and 50d fixedly mate with shaft 750. In another aspect, the channel bodies can detachably mate with shaft 750. A user can select the desired type of channel and/or the number of channels and attach the channel bodies to shaft 750. In still another aspect, the channel bodies can be movably mated with shaft 750. For example, the shaft can act as a guide wire. In use, a clinician can direct the shaft to the desired location and then mate the channel bodies with shaft 750. Moving the channel bodies along the shaft can delivery the channel bodies to the target area. Alternatively, the shaft and channel bodies can be delivered together and then the channel bodies can be moved relative to the central shaft to position the channels in a desired configuration.

Figure 7F:
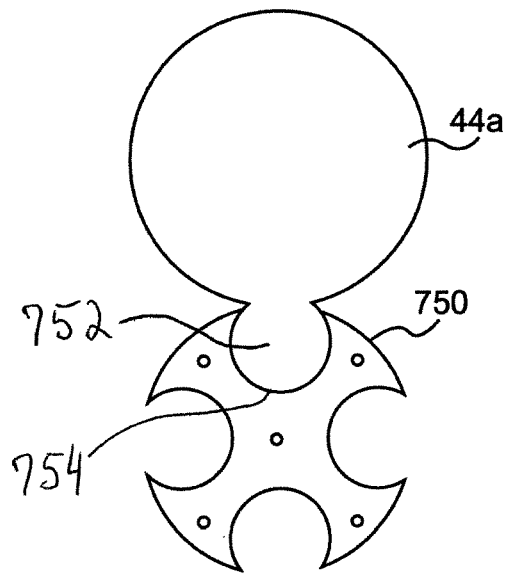
FIG. 7F is a cross-sectional view of the guide tube of FIG. 7D.

FIG. 7F illustrates a cross-section of guide tube 26 showing channel body 50a movably mated with shaft 750. In one aspect, channel body 50a includes a surface feature that mates with a surface feature of shaft 750. In the illustrated embodiment, channel body 50a includes a mating feature 752 having a curved or c-shaped outer surface corresponding to a mating feature 754 of shaft 750. In use, channel body 50a can slide along shaft 750 by slide mating feature 752 within mating feature 754. One skilled in the art will appreciate that a variety of movable mating features could be substituted for mating features 752, 754.

While guide tube 26 of FIGS. 7D through 7F is described as mating with bodies that define working or main channels, in another aspect, a tool or instrument could be substituted for one or more of the channels. For example, tool 40 and/or an optical device can be substituted for the channel bodies and directly mated with shaft 750.

In yet another aspect, shaft 750 can include a lumen or lumens defining an additional channel for delivering instruments. A first instrument or channel body can be mated with shaft 750 while another channel extends through shaft 750. Alternatively, or additionally, the shaft 750 can have a lumen for delivery or withdrawal of a liquid or gas and/or a lumen for housing a control mechanism (e.g., pull wire).

In another embodiment, channel bodies 50a, 50b, 50c, and/or 50d can articulate independently of shaft 750 at the distal end of guide tube 26. For example, the channel bodies can be detached from shaft 750 and independently moved via, for example, control wires and/or pre-shaped materials. In addition, or alternatively, the guide tube can include various structures for causing the channels, instruments within the channels, and/or the instruments themselves to angle away from one another (e.g., diverge).

Further described herein are methods and device for providing tool divergence and/or convergence for the various embodiments of system 20 described herein. In one aspect, the working and/or main channels have an angled configuration relative to the longitudinal axis of the guide tube such that surgical tools diverge or converge as they exit the distal end of the end cap. The diverging passageways can space the distal ends of the surgical instruments from one another within a body cavity. The increased spacing between the surgical tools increases the volume of the area in which the surgical tools can work (or working with one another), referred to herein as the working volume.

Figure 8:
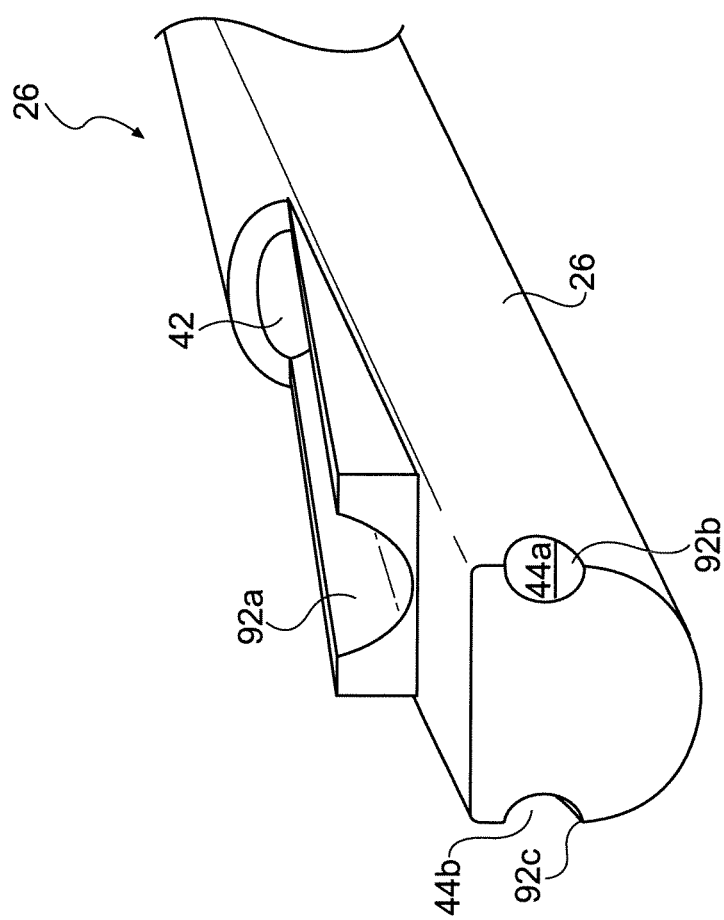
FIG. 8 is a perspective view of the distal end of one exemplary embodiment of a system described herein.

FIG. 8 illustrates one embodiment of guide tube 26 with main channel 42 having a diverging configuration. The main channel changes direction toward the distal end of the guide tube and directs instruments away from the central longitudinal axis of the guide tube. In one aspect, a ramped opening 92a can direct an optical device away from guide tube 26. The optical device can then be bent back toward the working area to provide a "birds eye" view. In one aspect, the optical device can be articulated (driven via user forces) to bend back toward the working area. In another aspect, the optical device can have a pre-bend that cause the optical device to bend toward the working area after exiting main channel 42.

In addition, or alternatively, the working channels 44a, 44b can diverge from one another or the longitudinal axis of the guide tube. In one aspect, the working channels change direction at the distal end of the guide tube and direct surgical instruments away from one another as they pass through openings 92b, 92c. The angle of openings 92a, 92b, 92c can facilitate triangulation of the tools and optical device.

In another embodiment, diverging channels within the guide tube can be provided by twisting at least two channels around one another. FIGS. 9A and 9B are partially transparent views of guide tube 26 with working channels 44a, 44b wrapping around one another to provide a spiral configuration. In one aspect, both working channels 44a, 44b have a spiral or helical shape proximate to the distal end of the guide tube. In another aspect, only one channel within the guide tube or more than two channels have a spiral or helical shape. Regardless, tools passing through wrapped channels 44a, 44b are angled away from one another as they leave the guide tube. In one aspect, working channels 44a, 44b have at least about a 90 degree turn, and in another aspect, at least about a 180 degree turn.

Figure 10A:
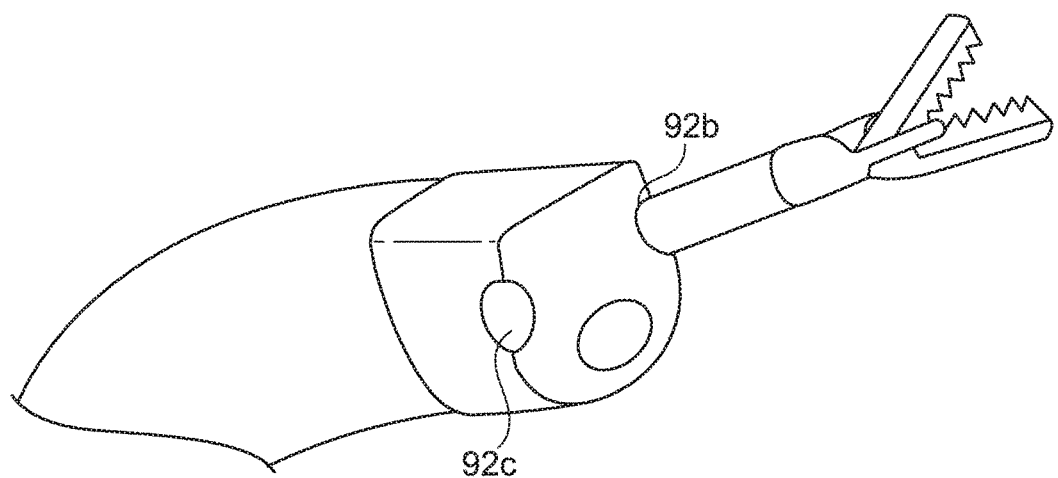
FIG. 10A is a perspective view of the distal end of one exemplary embodiment of a system described herein.
Figure 10B:
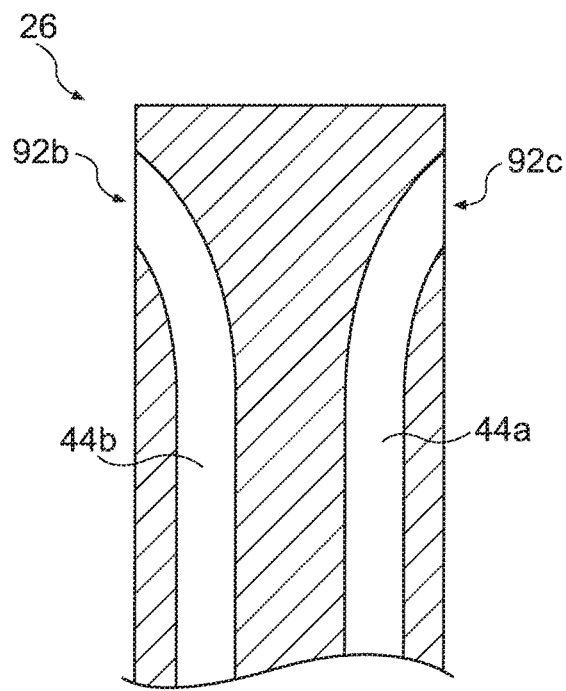
FIG. 10B is a cross-section view of the system of FIG. 10A.

In another aspect, guide tube channels can exit at a location proximal to the distal-most end of the guide tube. For example, the openings 92b, 92c through which the tools pass can be positioned proximally with respect to the distal surface of the guide tube. FIGS. 10A and 10B illustrate openings 92b and 92c positioned proximally to the distal end of the guide tube. The working channels bodies 44a, 44b extend to openings 92b, 92c in the sidewall of the guide tube 26.

The amount of convergence/divergence of the distal ends of the surgical instruments can be varied depending on the intended use. In one aspect, at least one of the passageways has an angle of at least about 7 degrees with respect to the centerline of the end cap. In another aspect, at least one of the passageways directs surgical tools at an angle of at least about 15 degrees.

Figure 11:
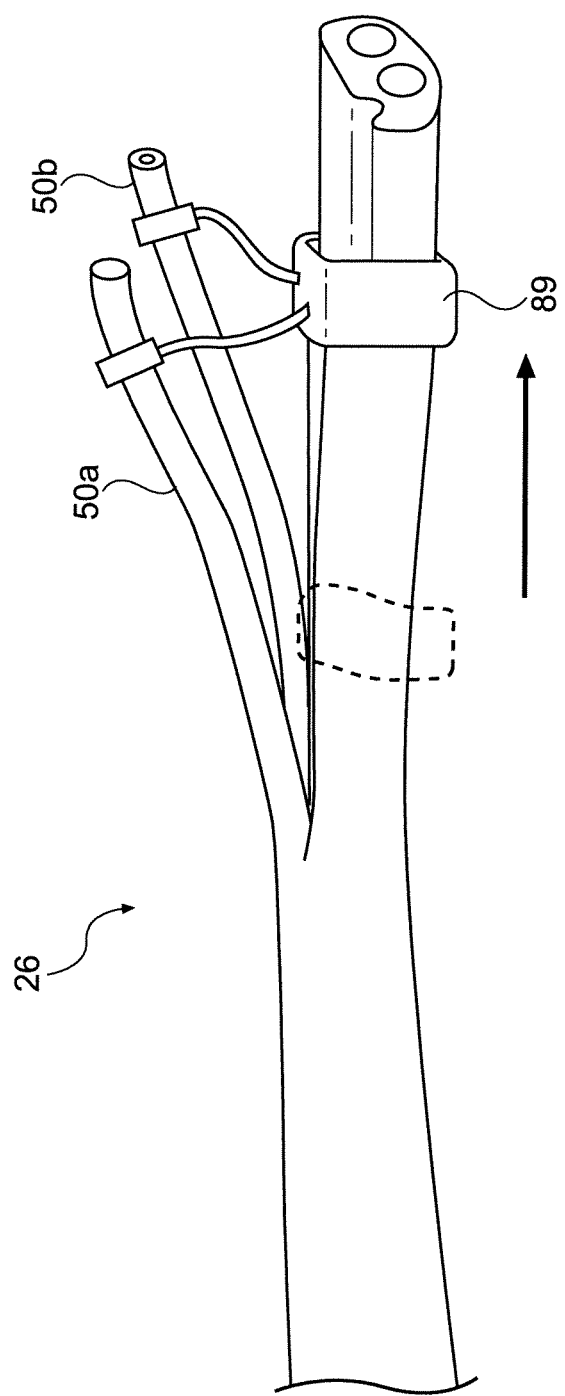
FIG. 11 is a perspective view of the distal end of one exemplary embodiment of a system described herein.

FIGS. 8 through 10B illustrate example of passive divergence. In another embodiment, guide tube 26 provides active or controllable divergence. The amount of divergence between passageways of guide tube 26 can be controlled via a diverging mechanism. For example, as illustrated in FIG. 11, a sliding ramp or collar 89 can translate relative to the main and/or working channels to adjust the angle between the passageways of the guide tube. The working and main passageways of the guide tube can be defined by detached (not connected) lumens that are each connected to collar 89. As collar 89 moves longitudinally it can increase or decrease the convergence of the passageways.

While FIG. 11 illustrates diverging the working channels to achieve divergences of tools delivered through the channels, in another aspect, the diverging mechanism can directly diverge tools. For example, the diverging mechanism can contact and/or apply force directly on the tools. In one aspect, with respect to FIG. 11, a tool can be substituted for channel 50*a* and/or 50*b* and mate with collar 89.

Figure 12:
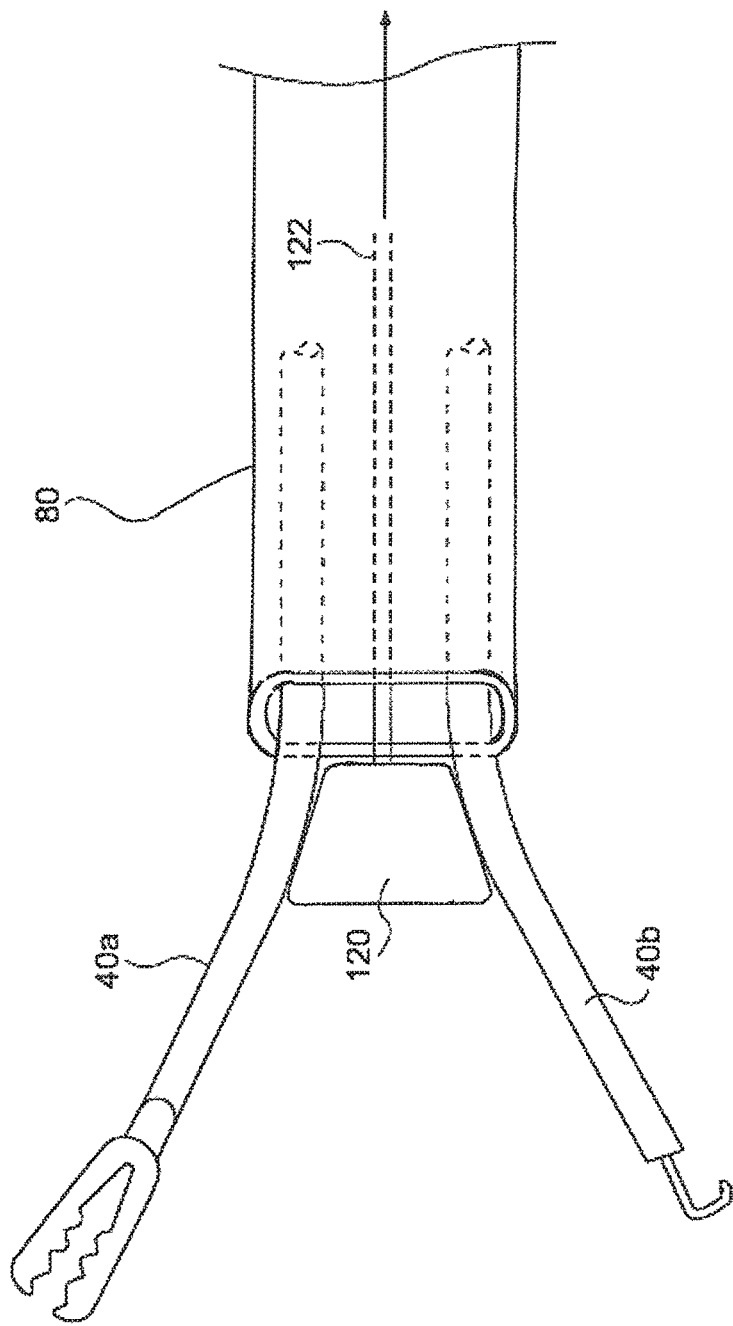
FIG. 12 is a perspective and partially transparent view of the distal end of one exemplary embodiment of a system described herein.
Figure 13:
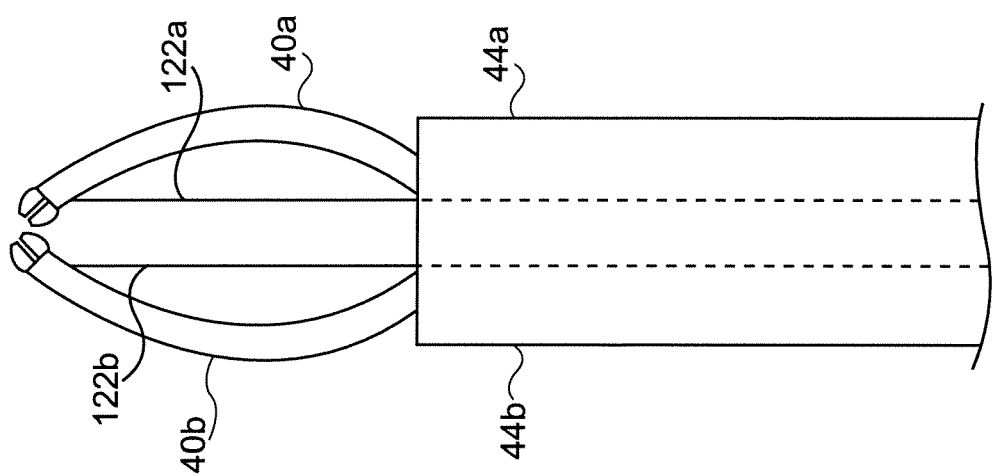
FIG. 13 is a side and partially transparent view of the distal end of one exemplary embodiment of a system described herein.
Figure 16A:
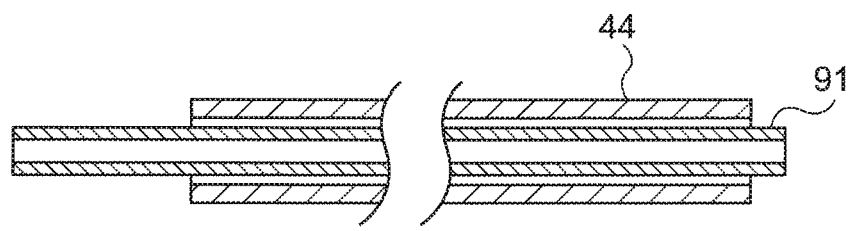
FIG. 16A is a cross-sectional view of the distal end of one exemplary embodiment of a system described herein.
Figure 16B:
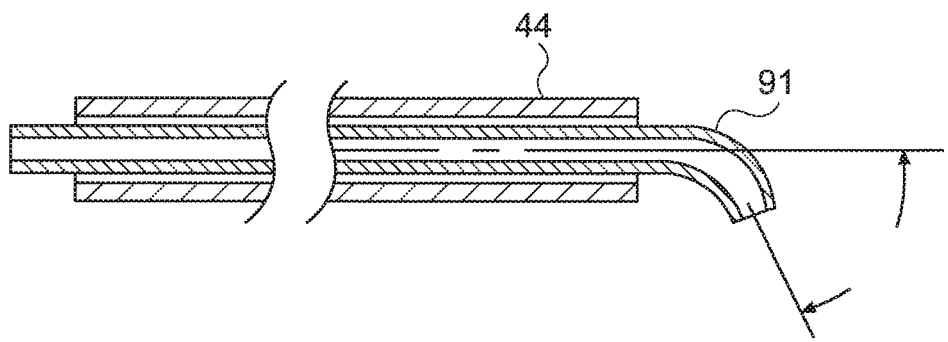
FIG. 16B is another cross-sectional view of FIG. 16A.
Figure 16C:
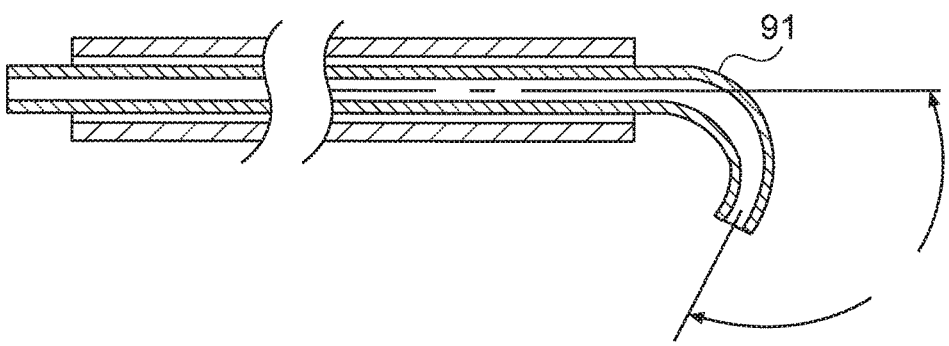
FIG. 16C is another cross-sectional view of FIG. 16A.
Figure 16D:
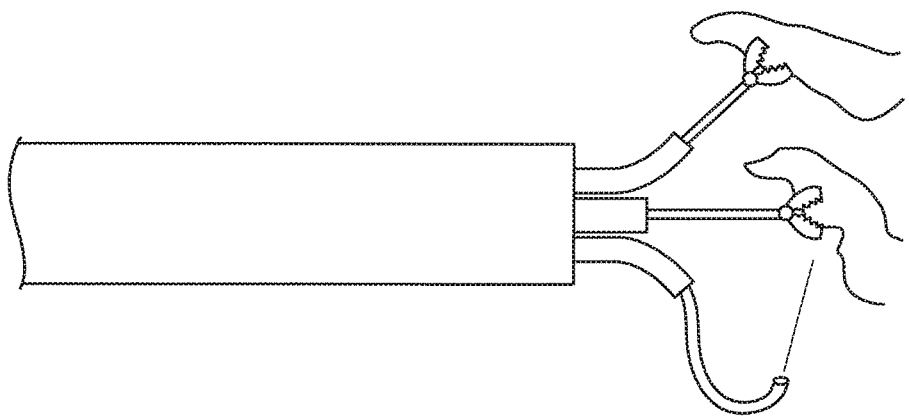
FIG. 16D is a side view of FIG. 16A.

FIG. 12 illustrates a controllable wedge 120 positioned between tools 40*a*, 40*b*. Pulling a control wire 122 can move the wedge proximally and increase the angle at which tools 40*a*, 40*b* diverge. FIG. 13 illustrates another embodiment of adjustable divergence between tools 40*a*, 40*b*. The tools can be mated with control wires 122*a*, 122*b* such that tensioning the pull wires causes the tools to bow out and increase their convergence. Tools 40*a*, 40*b* can, in one aspect, also include a bias for bending in one direction. For example, the materials of tools 40*a*, 40*b* can be selected to bias the tools to bend in one direction when pulled via control wires 122*a*, 122*b*. As an alternative, an inflatable balloon (FIG. 14) can be used to increase convergence or divergence of tools 40*a*, 40*b*. For example, a balloon 124 can be positioned between and in contact with tools 40*a*, 40*b*. When inflated, the balloon 124 can apply pressure directly on tools 40*a*, 40*b* to cause divergence. In still another embodiment, tools 40*a*, 40*b* can include a pre-bend or shape memory material (FIGS. 15A and 15B) that moves into a bent position when unconstrained by the guide tube and/or after exposure of the working channels to a trigger (e.g., body heat).

In another embodiment described herein, guide tube 26 includes channel extensions that allow increased curvature or retro-flexing. As illustrated in FIGS. 16A through 16D, guide tube 26 can include telescoping curved body 91 that when extended from the distal end of the guide tube 26, assumes a curvature of at least 45°, in another aspect, a curve of at least at 90°, and in yet another aspect, a curve of at least 150°. The curved body (or bodies) provides diverging and/or converging working channels and can thus provide one or more than one additional degree of freedom to the system.

In another embodiment, an s-curve is provided. For example, body 91 can include a first and a second preformed curves that bend in opposite directions. In another aspect, body 91 provides a first curve and a controllable instrument is extended through body 91 and bent to provide a second curved portion.

The curved bodies can have a pre-formed curvature that is constrained by a portion of system 20. In one aspect, the guide tube working channel 44 constrains curved body 91. A user can push bodies 91 out of the end of the guide tube and allows bodies 91 to bend with respect to the guide tube. In another aspect, a stiffening member can constrain the curve bodies. Withdrawing the stiffening member can allow the guide tube and/or surgical instrument to bend into a pre-curved configuration.

In one aspect, body 91 can rotate in addition to translating with respect to guide tube 26. In use, body 91 can be rotated relative to working channel 44 to direct a surgical instrument in a desired direction. In one aspect, body 91 is rotated into the desired orientation prior to insertion of guide tube 26 into a patient. In another aspect, rotation of body 91 can be controlled by a user from a proximal location.

Figure 18:
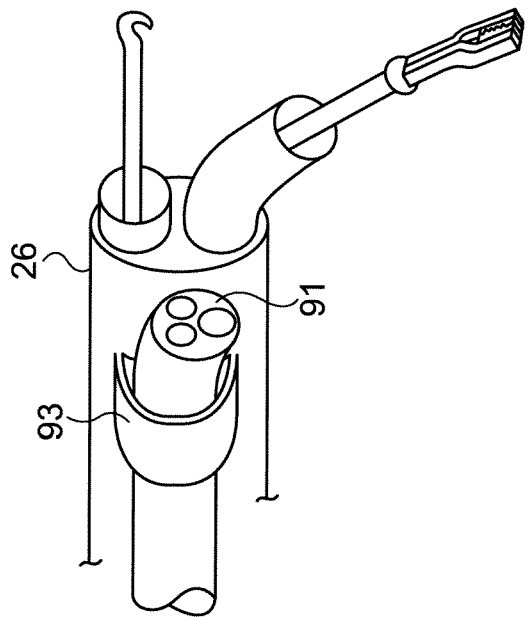
FIG. 18 is a perspective view of the distal end of another exemplary embodiment of a system described herein.
Figure 17:
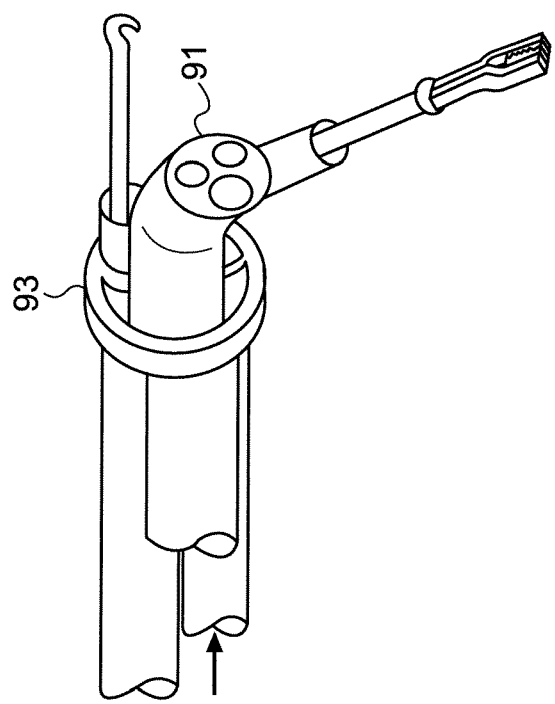
FIG. 17 is a perspective view of the distal end of one exemplary embodiment of a system described herein.

In yet another embodiment, shown in FIGS. 17 and 18, precurved body 91 can be positioned outside guide tube 26. A band 93 extending from guide tube 26 can constrain the pre-curved body until a user moves body 91 relative to the guide tube. When the distal end of the body is unconstrained by the guide tube, the pre-curved body can bend into a desired configuration. When the user completes a procedure, the user can move body 91 back into its original configuration to straighten the pre-curved body and allow withdrawal of the guide tube. Body 91 can house a variety of instruments.

Alternatively, band 93 can be moved relative to body 91 and/or guide tube 26. Moving band 93 in a proximal direction can permit body 91 to bend into a preformed curve. The band can then be moved distally to straighten body 91. In one aspect, a user can control movement of band 93 via a push/pull wire (not illustrated) that extends between a proximal controller and the distal portion of guide tube 26.

Figure 19A:
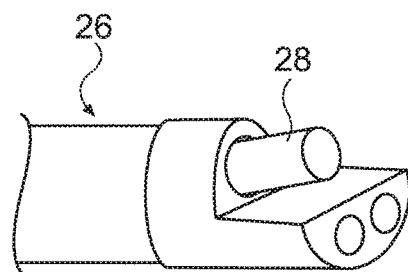
FIGS. 19A, 19B, and 19C are perspective views of the distal end of one exemplary embodiment of a system described herein.
Figure 19B:
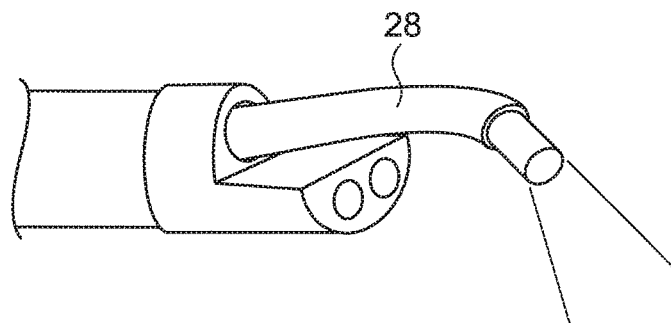
Figure 19C:
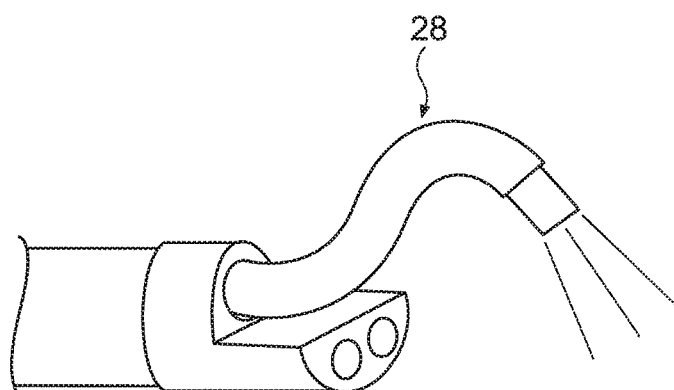

In another aspect, an optical device extending from guide tube 26 could include a prebend like that of body 91 discussed above. As illustrated in FIG. 19A through 19C, optical device 28 could include a first and second prebend spaced longitudinally from one another. As the optical device extends from the guide tube, the first and second prebend can move the optical device into an s-curve that provides a "bird's eye" view of the work space.

In another embodiment a steerable or positionable ball/socket structure can be located at the distal end of guide tube 26 for directing tools and/or optics exiting the working and/or main channels. The ball can include a passage defining a portion of the working and/or main channel. Pivoting the ball within a socket can change the direction of the channel within the ball relative to the guide tube and can direct instruments extending therethrough. Alternatively, optics can be positioned within a socket structure to allow pivoting of optics.

Figure 20:
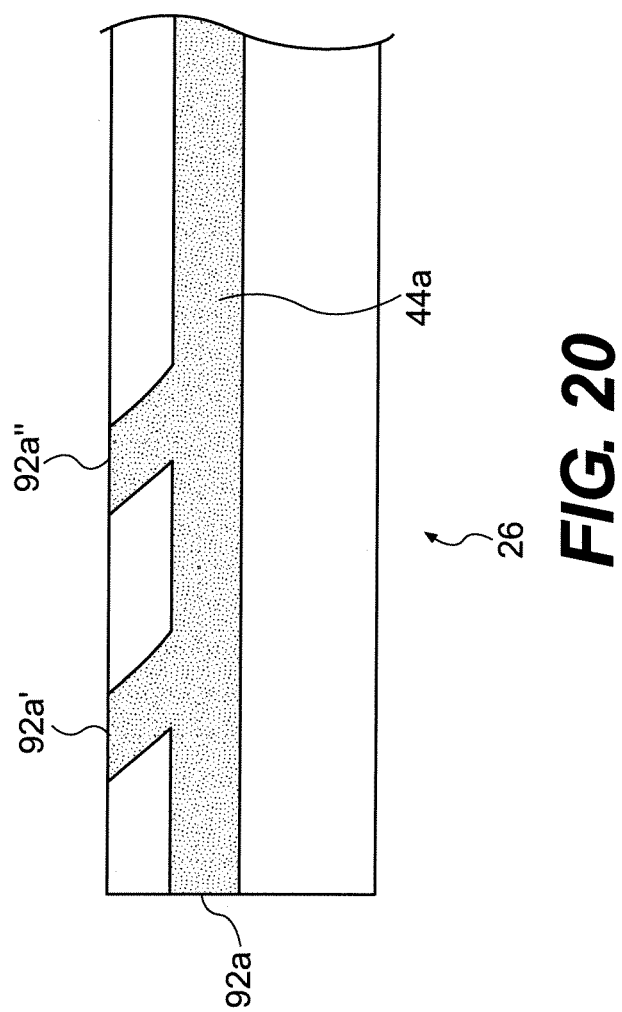
FIG. 20 is a cross-sectional view of the distal end of one exemplary embodiment of a system described herein.

FIG. 20 illustrates the use of multiple openings 92*a*, 92*a*', 92*a*" from a single channel. The user can select the desired opening to reach a desired location relative to the guide tube (rather than having to move the guide tube). In one such embodiment, the different openings have different angles such that an opening can be selected to change the angle of the instrument with respect to the guide tube. The multiple openings can extend longitudinally and/or radially around the outer surface of the guide tube.

The choice amongst several openings (e.g., 92*a*, 92*a*', 92*a*") from a single channel (e.g., working channel 44*a*) can be controlled by articulating an instrument. For example, the user can direct a instrument through a desired opening. Alternatively, or additionally, the guide tube can include articulating ramps that are controlled by a proximally located controller. The ramp associated with a desired opening can be engaged to direct the instrument through the desired opening.

Figure 21:
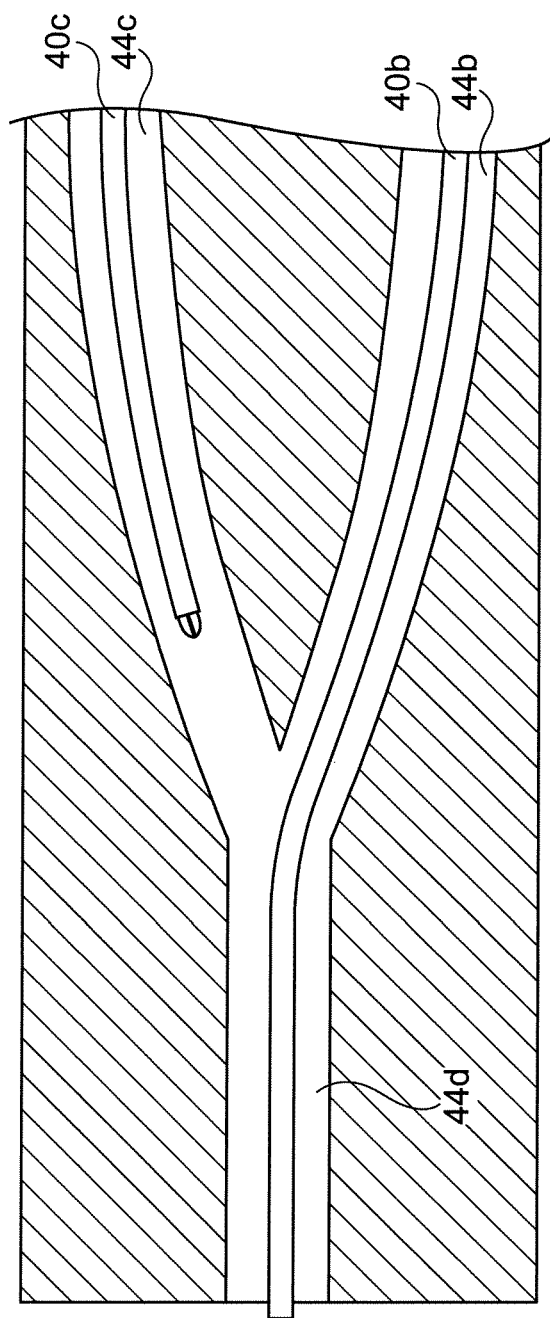
FIG. 21 is a cross-sectional view of the distal end of one exemplary embodiment of a system described herein.

In another aspect, the guide tube can include more channels than openings 92. For example, two or more channels can merge into a single channel in the distal portion of the guide tube. FIG. 21 illustrates first and second lumens 44*b*, 44*c* each containing a tool or optical device, that merge in a single lumen 44*d* at the distal end of the guide tube. As shown, tool 40*b* extends from the device while tool 40*c* remains in lumen 44*c*. If a surgeon desires to switch tools, tool 40*b* can be withdrawn into lumen 44*b*, and tool 40*c* can be advanced into 44*d* and on to the surgical site. This configuration allows surgeons to switch quickly between tools without the need to completely withdraw one tool before switching to a second tool.

The desired configuration of the surgical instruments can be achieved by articulating the instruments in addition to, or as an alternative to, converging/diverging channels. For example, a user can control the instruments after the instruments exit the distal end of the guide tube. The instruments can be bent, rotated, and/or moved longitudinally to reach a desired working area. Articulation of the instruments is discussed in more detail below.

Figure 22:
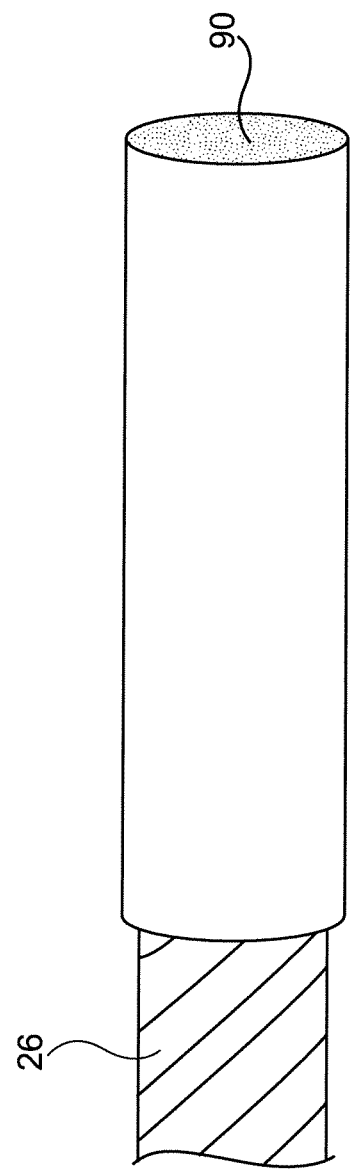
FIG. 22 is a perspective view of the distal end of one exemplary embodiment of a system described herein.
Figure 23:
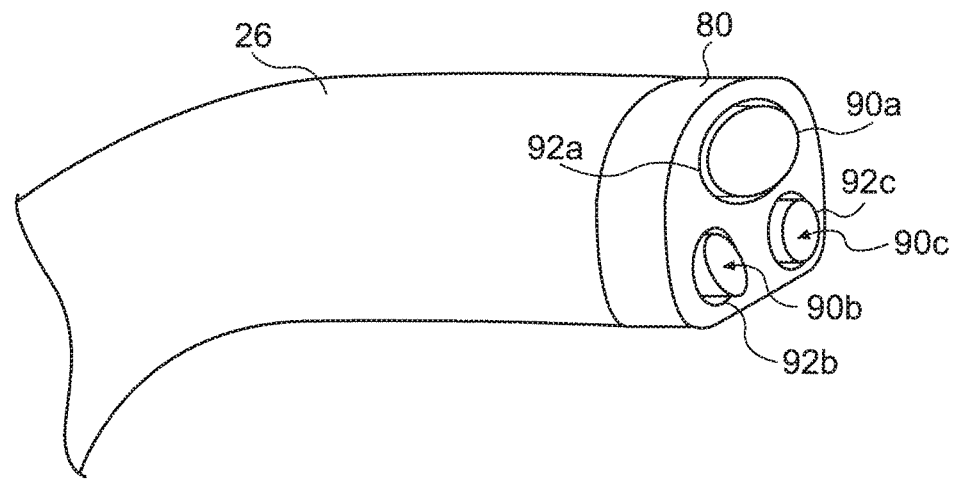
FIG. 23 is a perspective view of the distal end of one exemplary embodiment of a system described herein.

Further described herein are methods and device for preventing the ingress of materials (e.g., biomaterials) into the guide tube. In one embodiment, at least one passageway in the guide tube can include an obturator, end cover, and/or outer sleeve that can prevent or inhibit the ingress of biological materials into the at least one passageway during insertion of the guide tube into a patient. FIGS. 22 and 23 illustrate a breakable membrane 90 configured to seal the end of the end cap during introduction to prevent gas, tissue, and/or fluid from entering the guide tube. In FIG. 22, the breakable membrane 90 is formed as part of an outer sleeve, while in FIG. 23, individual membranes 90*a*, 90*b*, 90*c* cover the distal openings 92*a*, 92*b*, 92*c* of the end cap.

Figure 24:
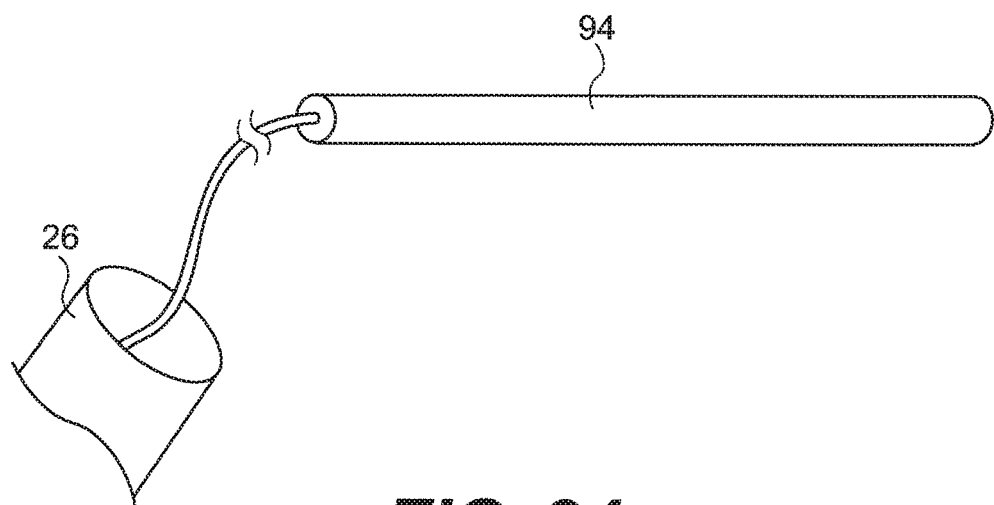
FIG. 24 is a perspective view of the distal end of one exemplary embodiment of a system described herein.
Figure 25:
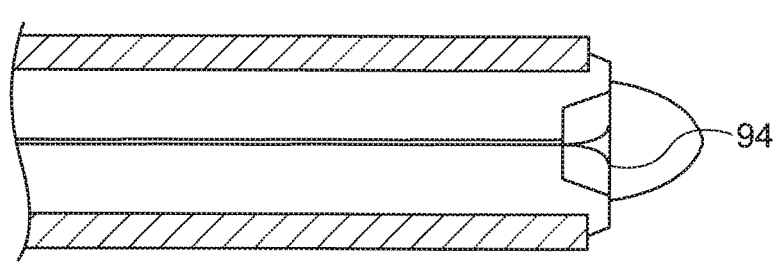
FIG. 25 is a cross-sectional view of the distal end of one exemplary embodiment of a system described herein.

FIGS. 24 and 25 illustrate obturators 94 that can be positioned within the channels of the guide tube and/or passageways of the end cap. In one aspect, the plug, obturators, sleeves, and/or membranes can be formed of a bioadsorbable or dissolvable material. In use, a physician can push the bioadsorbable material out of the end of the guide tube to open the guide tube channels. Alternatively, the bioadsorbable material can be fast dissolving and the guide tube channels can open when biofluids (e.g., blood or stomach acid) dissolve the plug, obturator, sleeve, and/or membrane. In still another embodiment, non-bioadsorbable materials are used and a clinician can withdraw the obturators through the proximal openings of the guide tube. In yet another embodiment, a user can pierce the sleeve and/or membrane to deliver an instrument through end cap 80. The use of an obturator, sleeve, and/or membrane can preserve sterility of guide tube 26 and/or inhibit the ingress of fluids during insertion of guide tube 26.

Figure 26:
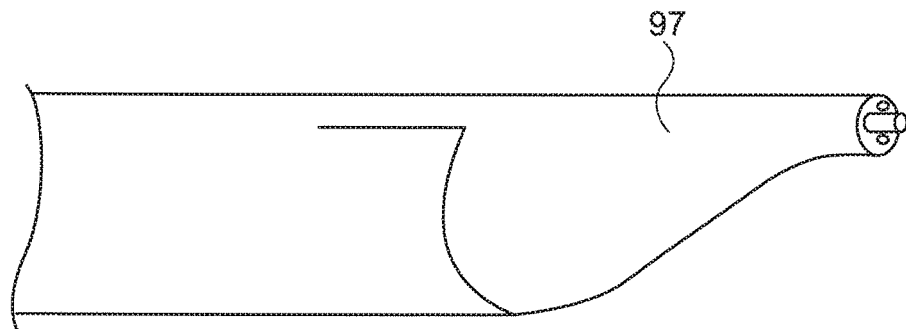
FIGS. 26 and 27 are perspective views of the distal end of one exemplary embodiment of a system described herein.
Figure 27:
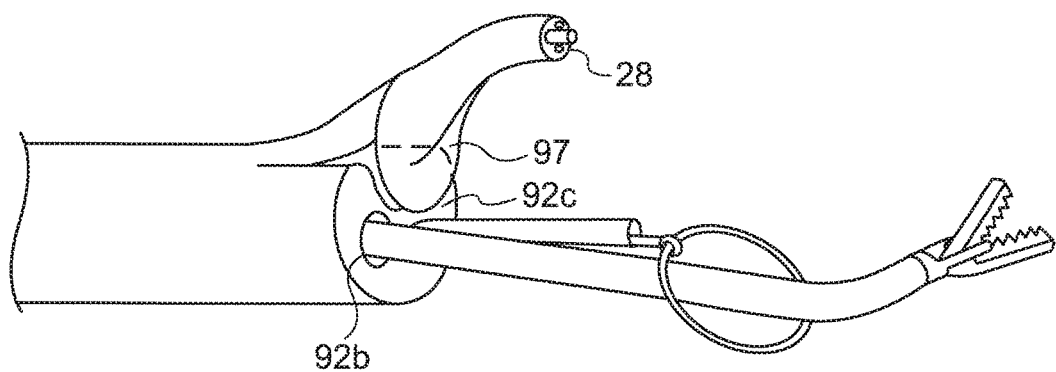

FIGS. 26 through 27 illustrate yet another exemplary embodiment of an obturator. A sleeve or cover 97 can shield at least one of the openings at the distal end of the guide tube. When the guide tube is positioned at a desired location, cover 97 can be moved to expose openings 92*b*, 92*c*. In one aspect, the cover can be controlled via a control wire extending to a proximal controller. Alternatively, as illustrated in FIGS. 26 and 27, cover 97 can be mated with one of the instruments, such as, for example, an optical device 28. To expose openings 92*b*, 92*c*, the optical device can be moved away from the distal end of the guide tube causing cover 97 to lift away from openings 92*b*, 92*c* (FIG. 27) and/or the optical device can be advanced away from the guide tube. In one aspect, the sleeve does not cover the distal-most end of the optical device, such that optics can be utilized during positioning of the guide tube. In another aspect, the sleeve, skirt, or shroud is transparent or partially transparent.

Instead of, or in addition to, closing the distal opening of guide tube 26, the pressure within the working and/or main channels can be increased to inhibit ingress of biomaterial. In one aspect, the working channels are fluidly connected with a source of pressurized gas or fluid. For example, a compressor, pump, or pressurized vessel can mate with a proximal opening to the working channels.

In another embodiment, the guide tube can store a tool or tools for use during a surgical procedure. FIGS. 28A through 35 illustrate various embodiments of a guide tube configured for the storage of a tool such as needle 100.

Figure 28A:
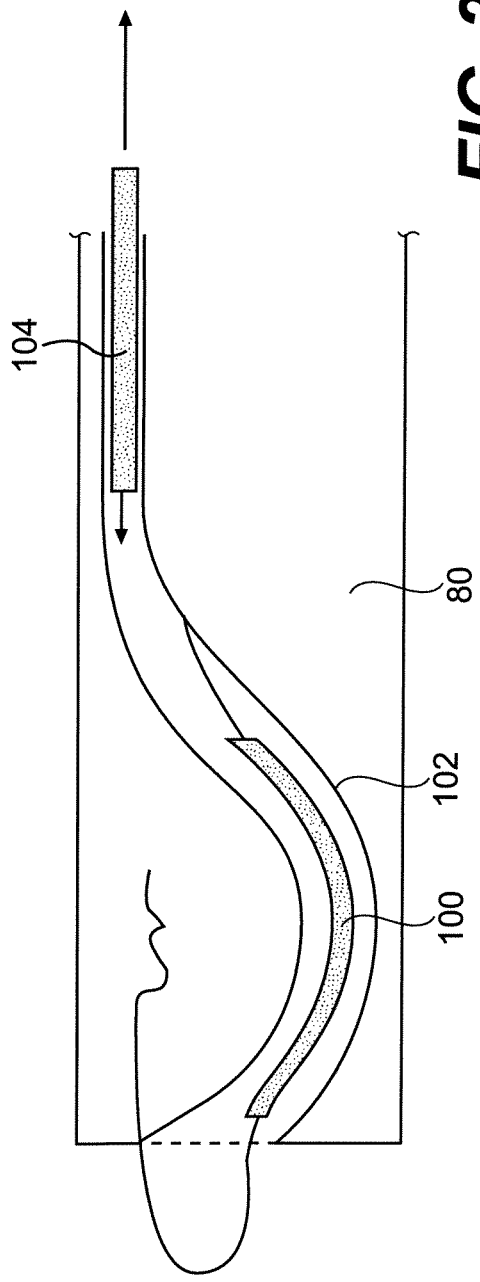
FIGS. 28A and 28B are cross-sectional views of the distal end of one exemplary embodiment of a system described herein.
Figure 28B:
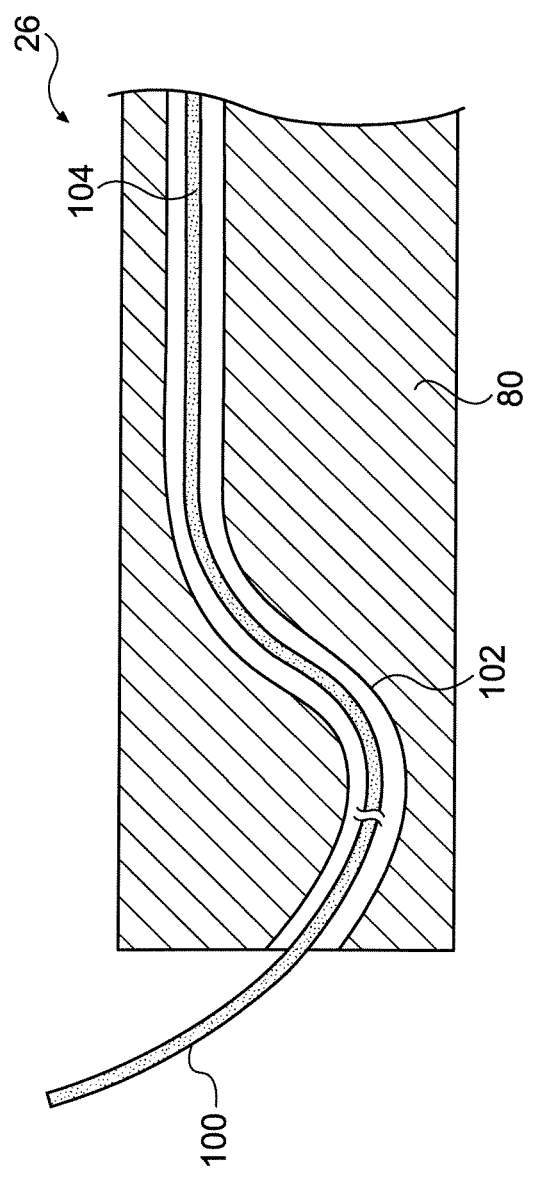

Depending on the shape and size of the channels within the guide tube, delivering a curved needle through the guide tube may be difficult. FIGS. 28A and 28B illustrate a recess 102 in which a needle 100 is stored prior to use. Instead of delivering the needle through the guide tube, the needle is housed in a distal portion of the guide tube. Recess 102 can have a curved configuration sized and shaped for storing one or more needles. The recess can be formed separately from the guide tube working and main channels or defined by a portion of one the guide tube channels. In one aspect, the distal end of at least one of the working channels is shaped and sized to house a needle. For example, the working channel can have a larger width at its distal end. To deliver the needle, a tool can be moved through the working channel and can grab the needle and/or push the needle out of the working channel.

Alternatively, recess 102 is separate from the channels of guide tube 26. To deliver the needle a pusher wire 104 can be manipulated to move the needle out of recess 102.

Figure 29A:
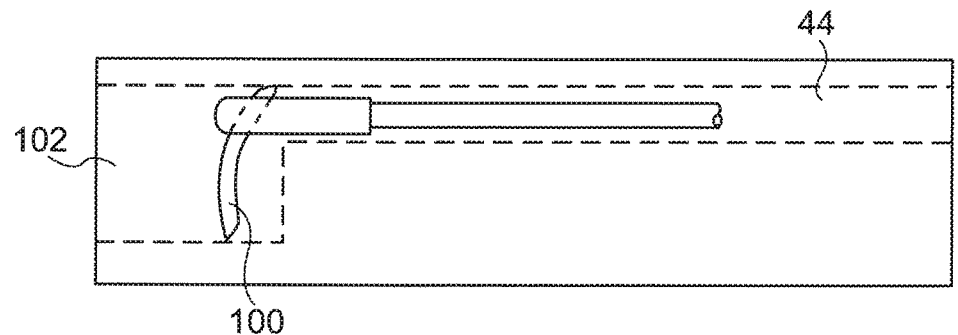
FIG. 29A is a partly transparent view of the distal end of one exemplary embodiment of a system described herein.
Figure 29B:
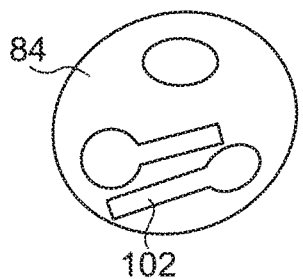
FIG. 29B is a front view of the distal end of one exemplary embodiment of a system described herein.
Figure 30:
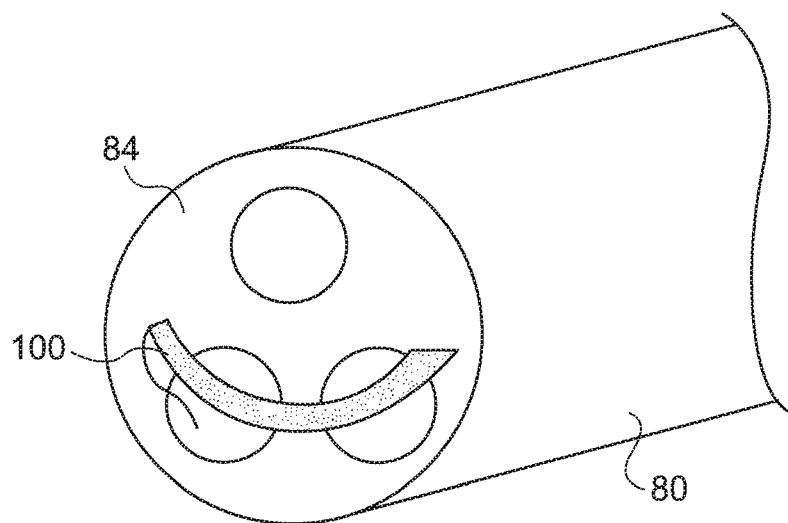
FIG. 30 is a perspective view of the distal end of one exemplary embodiment of a system described herein.
Figure 31A:
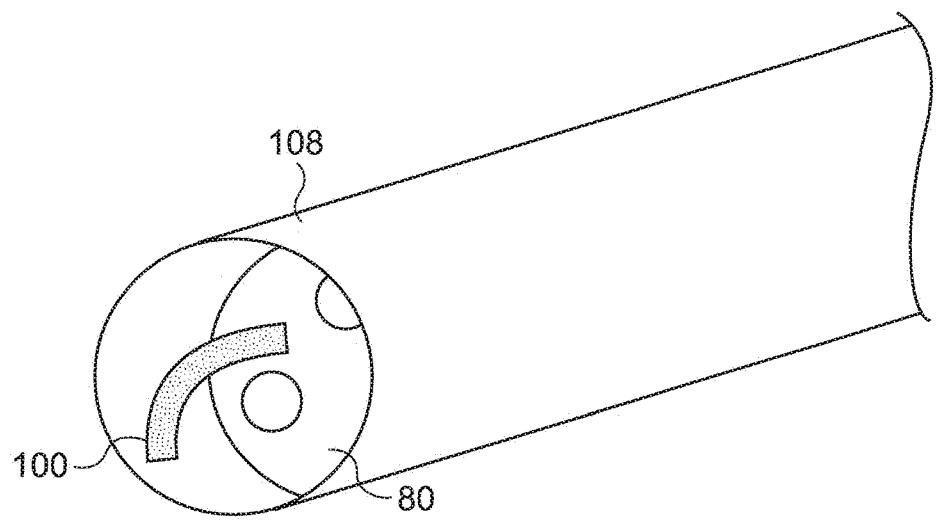
FIG. 31A is a perspective view of the distal end of one exemplary embodiment of a system described herein.
Figure 31B:
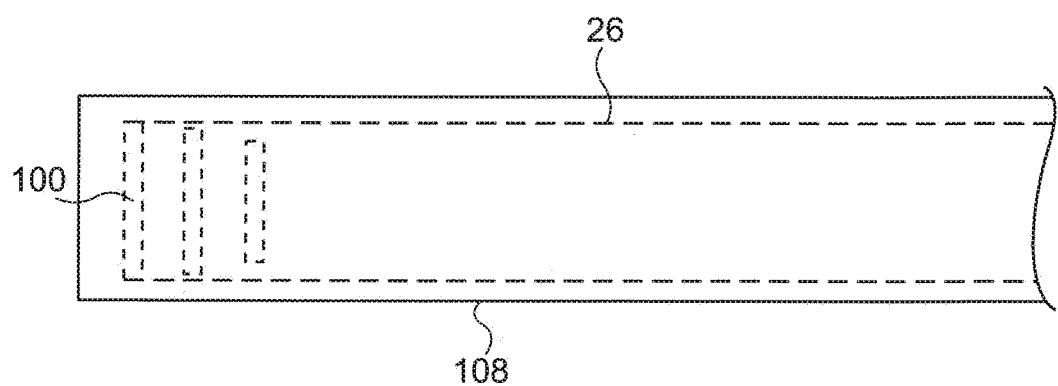
FIG. 31B is a transparent view of the distal end of one exemplary embodiment of a system described herein.
Figure 32B:
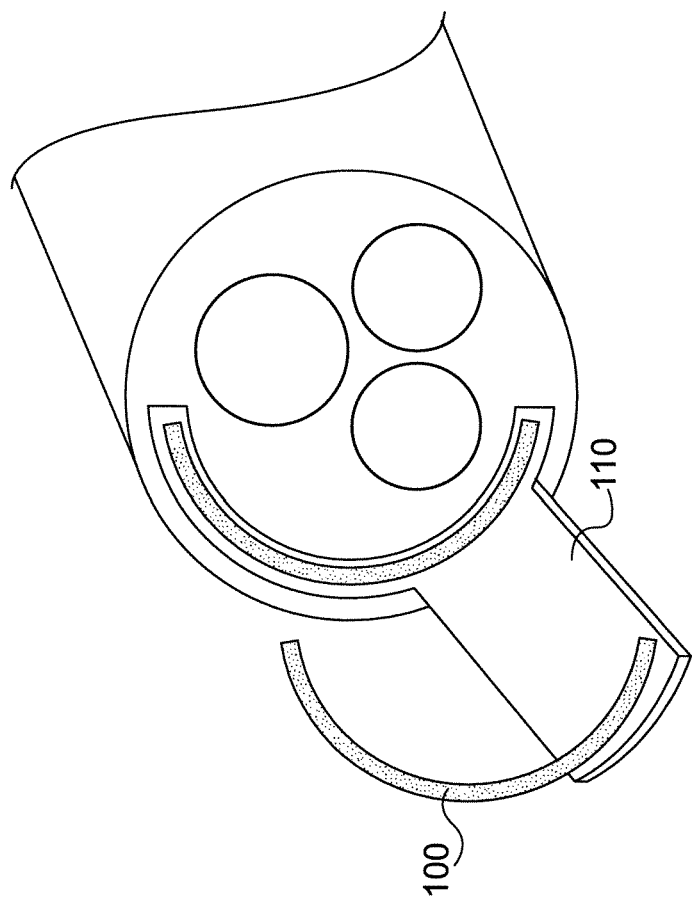
FIGS. 32A and 32B are perspective views of the distal end of one exemplary embodiment of a system described herein.
Figure 32A:
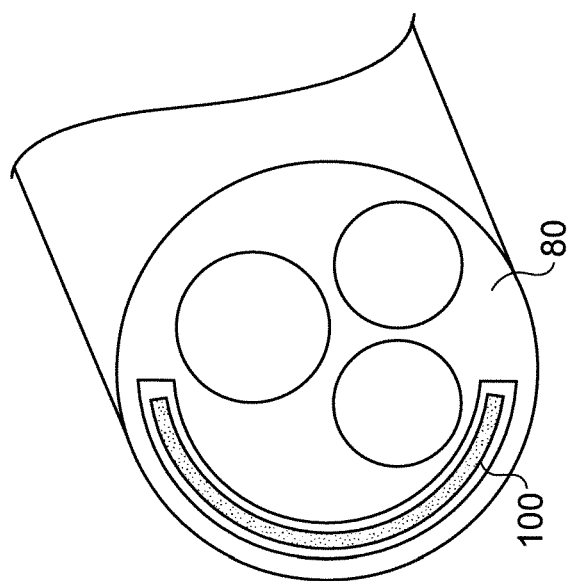

In another embodiment, illustrated in FIGS. 29A and 29B, a needle can be stored in a transverse position. For example, instead of recess 102 having a shape and size (e.g., diameter) corresponding to the width of needle 100, the recess can accommodate the length of the needle. In yet another embodiment, a needle can be clipped to the end of the guide tube. For example, FIG. 30 illustrates a needle 100 clipped to the distal surface 84 of the end cap 80. In still another embodiment, shown in FIGS. 31A and 31B, a needle or needles can be stored in a sleeve 108 that extends distally from the distal surface 84 of the end cap 80. One skilled in the art will appreciate that one or more needles can be stored at the distal portion of the guide tube. For example, as shown in FIGS. 32A and 32B, multiple needles can be placed in a needle cartridge 110 located within the end cap.

Figure 33A:
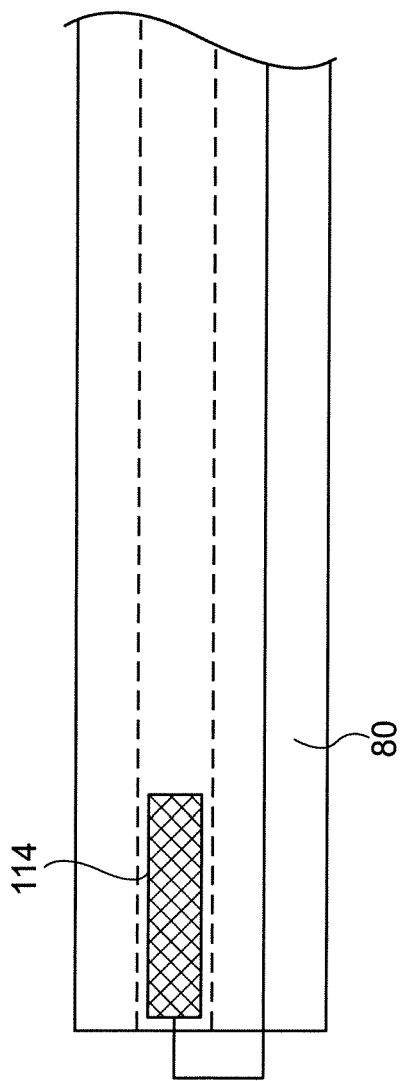
FIGS. 33A and 33B are partially transparent views of the distal end of one exemplary embodiment of a system described herein.
Figure 33B:
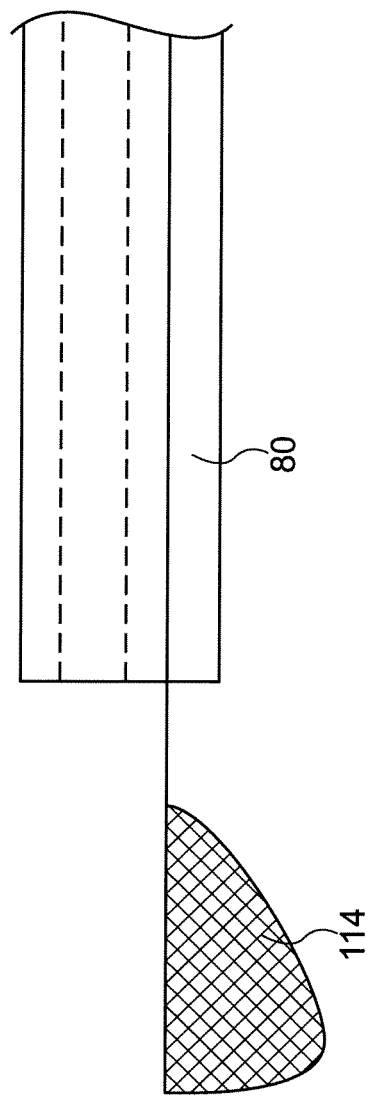
Figure 34:
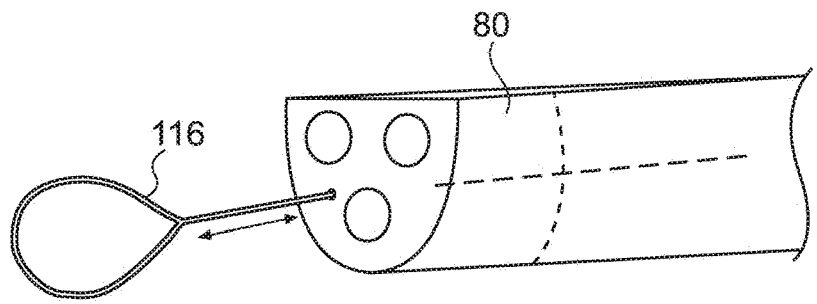
FIG. 34 is a perspective view of the distal end of one exemplary embodiment of a system described herein.
Figure 35:
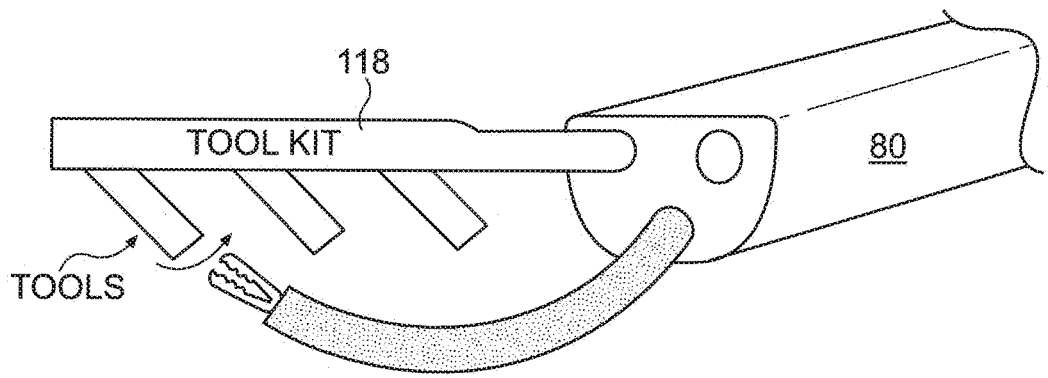
FIG. 35 is a perspective view of the distal end of one exemplary embodiment of a system described herein.

As an alternative, or in addition to a needle or needles, the end cap can contain a variety of other tools. In one aspect, as shown in FIGS. 33A and 33B, a bag 114 can be stored in, and or deployed from, the end cap. In another aspect, a snare or loop 116, as shown in FIG. 34, can be delivered from the end cap for grabbing and pulling tissue. In still another aspect, illustrated in FIG. 35, multiple tools, such as, for example, loops, needles, bags, and/or other tools, can be stored in a tool kit 118 that is delivered from end cap 80. In use, a surgeon can select amongst the tools of the tool kit without having to fully withdraw a surgical tool from the channels of the guide tube.

In another embodiment, end cap 80 and/or tools can be detachably mated with guide tube 26. A user can choose amongst several end caps and/or tools (or tool sets) and attach the desired end cap or tool to the end of the guide tube. One skilled in the art will appreciate that a variety of mechanical and/or frictional mating configurations can provide a detachable end cap or tool.

Figure 36:
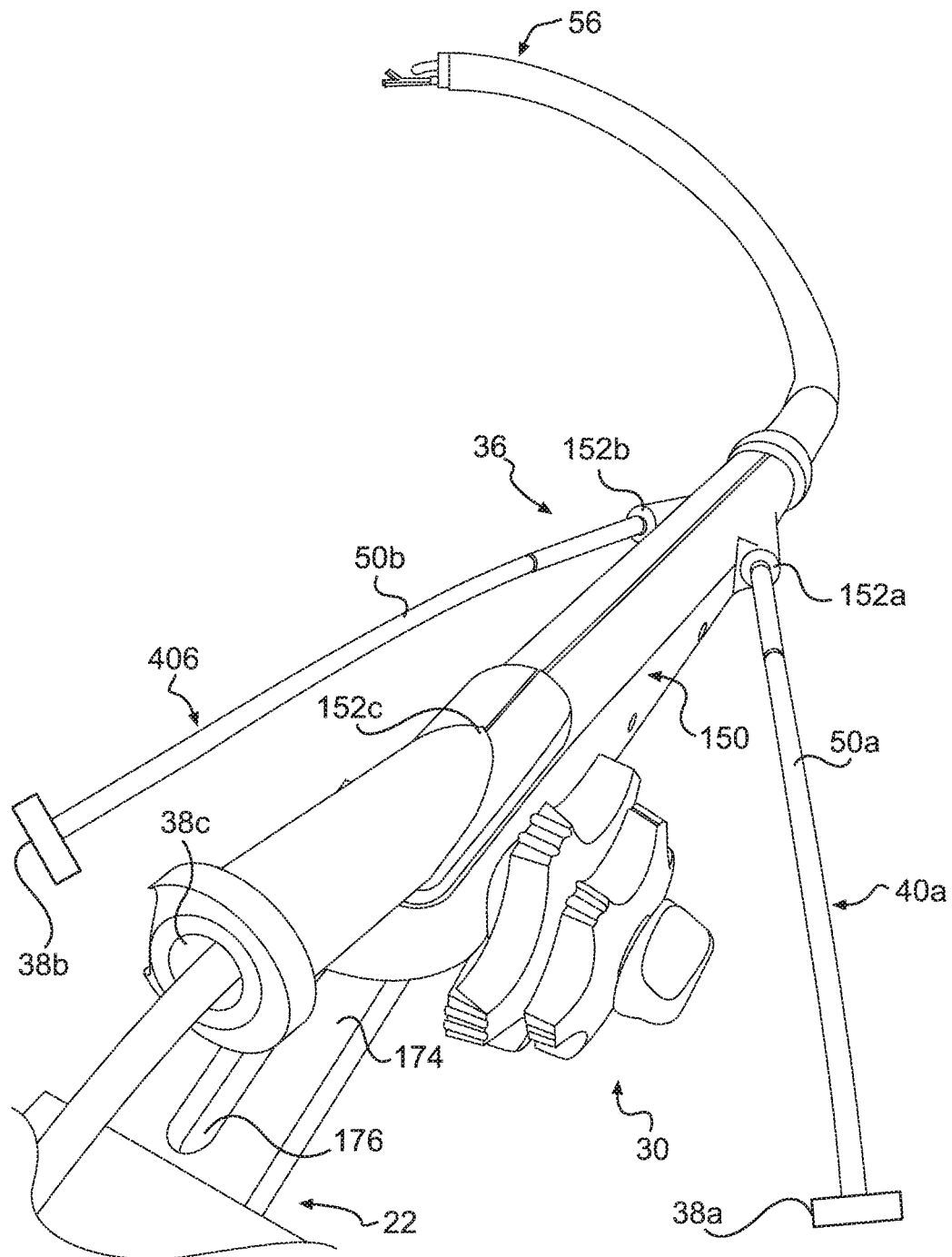
FIG. 36 is a perspective view of one exemplary embodiment of a guide tube described herein.

Referring to FIGS. 1 and 36, proximal to the mid-portion 33 of elongate body 32, guide tube 26 can include a proximal portion 36 that includes apertures for insertion of surgical tools into the channels of the guide tube and controls 30 for manipulating the articulation portion 56 of the guide tube. In addition, proximal portion 36 can be adapted for mating with frame 22.

In one aspect, proximal portion 36 includes a housing member 150 that contains the main and working channels. Housing member 150 can be formed of a rigid material that provides support for controls 30 and that mates with frame 22. With respect to FIG. 36, the main and working channels can enter the housing 150 at separate proximal apertures 152*a*, 152*b*, 152*c*. In one aspect, proximal apertures 152*a*, 152*b*, through which the working channels pass, are positioned in the housing member 150 at a location distal to the proximal end of the housing member 150 and distal to aperture 152c. In addition, working channels can exit housing member 150 on opposite lateral sides and/or can exit at an angle with respect to the longitudinal axis of the guide tube. For example, housing member 150, including apertures 152a, 152b, can direct the working channel bodies 50a, 50b (which house tools 40a, 40b) at an angle with respect to one another. The size of the angle between working channel bodies, as defined by housing 150, can be varied depending on the intended use of system 20, user ergonomics, and/or the configuration of frame 22.

Figure 37:
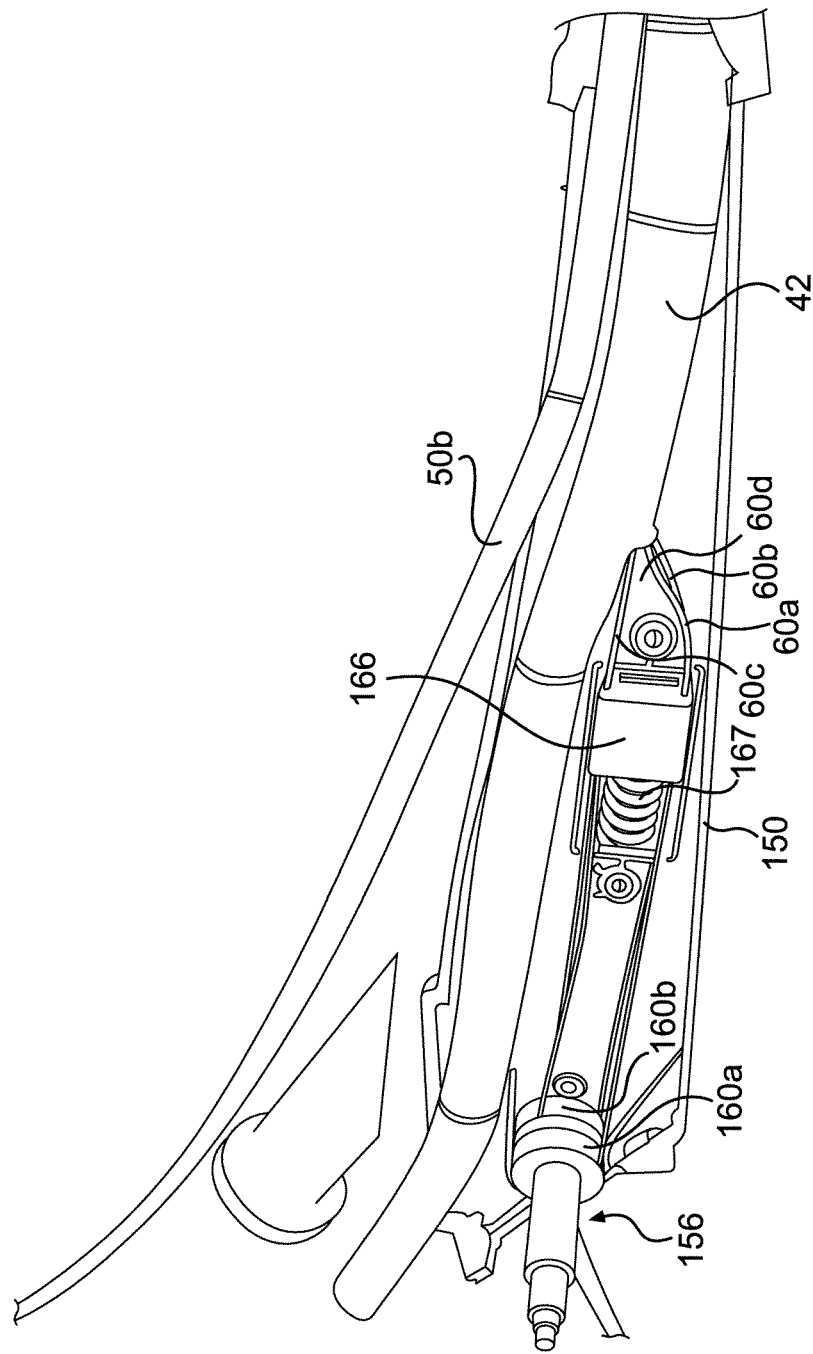
FIGS. 37 and 38 are partially disassembled views of one exemplary embodiment of a guide tube described herein.

FIG. 37 illustrates a cut-away view of housing member 150 showing main channel 42 and one of the working channel bodies 50b. Housing member 150 can also contain control mechanism 156 of controls 30. Strands 60a, 60b, 60c, 60d (for controlling the proximal articulation portion of the guide tube) can exit the outer tubular bodies (46, 48) of main channel 42 inside of housing 150. In one aspect, the strands can exit through a seal (not illustrated) to prevent liquids or gasses from exiting main channel 42 and entering the interior of housing member 150.

After exiting main channel 42, strands extend to control mechanism 156 and mate therewith. In one aspect, the strands can pass through a tensioner 166 between main channel 42 and control mechanism 156. For example, where strands are formed by bowden cables, the outer sheath of the bowden cables can extend to, but not beyond tensioner 166, while the inner filament extends to control mechanism 156. Tensioner 166 includes a spring 167 that can keep the filament taught between the tensioner and the control mechanism, while allowing the bowden cables distal to the tensioner to flex and/or translate longitudinally.

In one aspect, control mechanism 156 includes wheels 160a and 160b, where two strands (e.g., 60a, 60b) mate with one of wheels 160a, 160b to control left/right movement of the articulation portion 56 of guide tube 26 and the other two strands (e.g., 60c, 60d) mate with other of wheels 160a, 160b to control up/down movement of the articulation section. Depending on the configuration of controls 30, more or fewer than four strands can mate with more or fewer wheels. For example, while the articulation section is described as providing two degrees of freedom, fewer strands and/or wheels can be used where only a single degree of freedom is necessary. Regardless of the configuration of the control mechanism, the strands can mate with wheels via welding, adhering, mechanically interlocking, and/or frictionally engaging.

The use of two wheels 160a, 160b allows independent articulation of up/down and side-to-side movement of the articulation portion 56 of guide member 26. Thus, the control mechanism 156 allows independent control of two degrees of freedom. One skilled in the art will appreciate that depending on the desired use of guide tube 26, control mechanism 156 could alternatively be configured to control two degrees of freedom with a single movement such that the up/down and side-to-side degrees of freedom are not independent.

Figure 38:
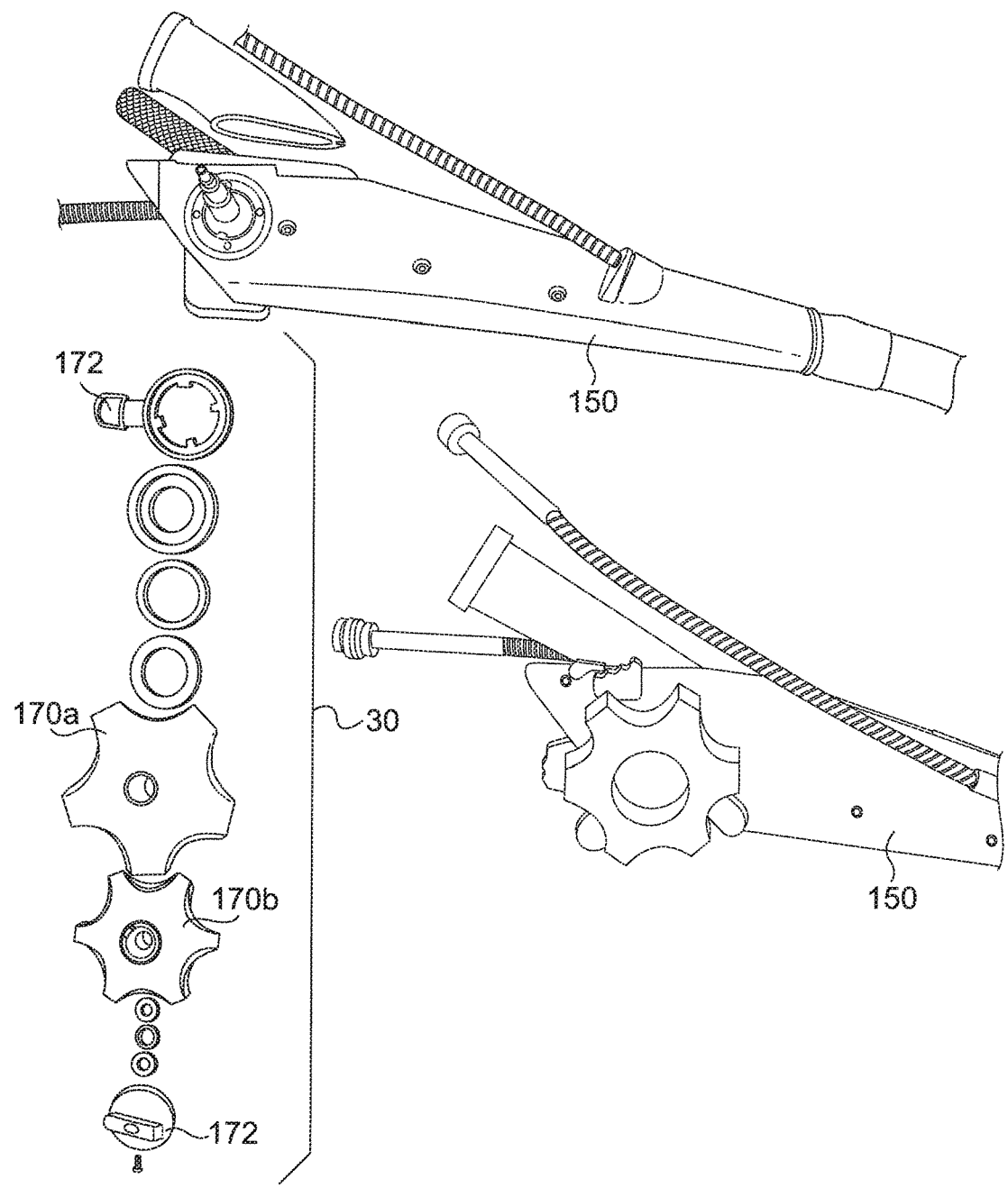

FIG. 38 illustrates a disassembled view of housing 150 showing the various components of guide tube controls 30 that are located on an outer surface of housing member 150. First and second dials 170a, 170b can be drive wheels 160a, 160b, respectively. In use, operation of first dial 170a drives one degree of freedom, while operation of second dial 170b drives a second, independent degree of freedom. However, in another aspect, controls 30 could be configured to manipulated up/down and side-to-side movement with a single movement of one mechanism. Controls 30 also include one or more switches 172 that controls a locking mechanism to lock guide tube 26 in position once a desired configuration of articulation portion 56 is reached. In one aspect, at least one of switches 172 are friction locks that when tightened, inhibits movement of dials 170a, 170b. While the illustrated embodiment is configured to independently lock each degree of freedom, in another aspect, a single switch could lock both dials at the same time. One skilled in the art will appreciate the variety of conventional endoscopic locks and steering mechanisms can be used with system 20.

Figure 39:
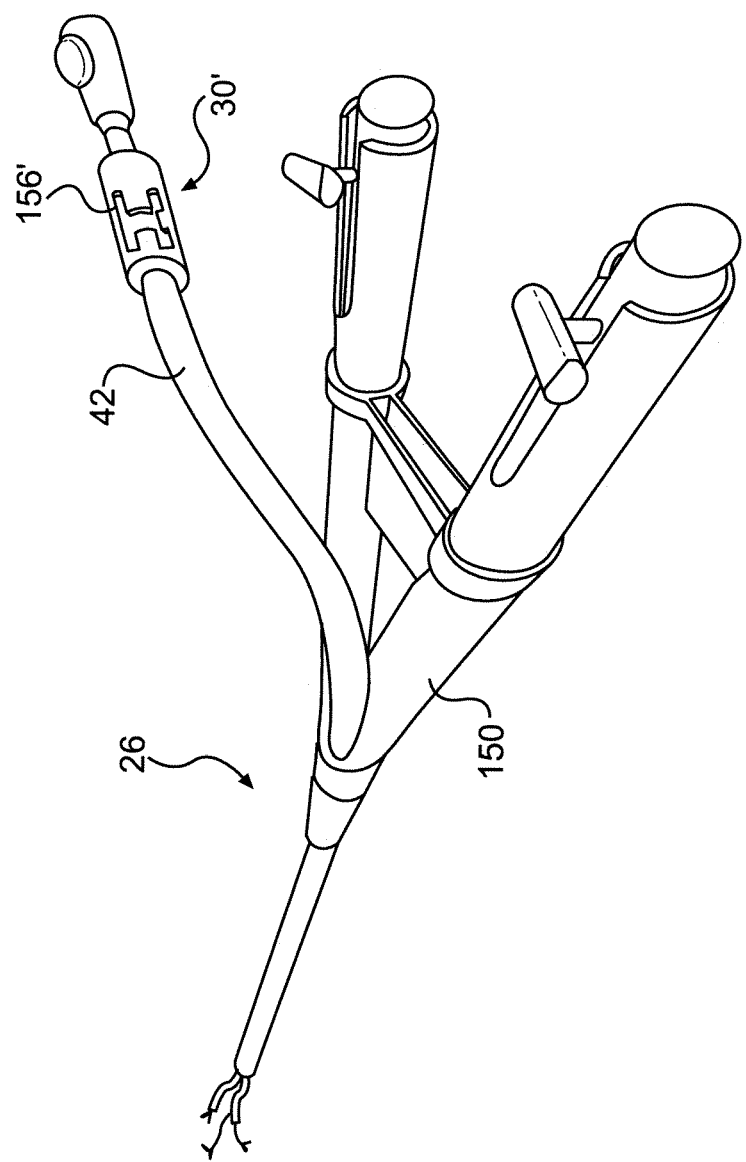
FIG. 39 is a perspective view of one exemplary embodiment of a system described herein.

In another embodiment of the guide tube described herein, the guide tube controls can be positioned remotely from housing 150. FIG. 39 illustrates a perspective view of housing 150 with the main channel extending distally from housing 150. Controls 30' are positioned on main channel 42 proximate to the controls for the optical device. Instead of the control mechanism positioned within housing 150, the strands can extend to a control mechanism 156' positioned on main channel 42. Controls 30' can include various slides, switches, levers, or other such mechanisms to control one, two, or more than two degrees of freedom with respect to guide tube 26. For example, controls 30' can include the various capabilities of controls 30 discussed above.

In one aspect, the distal portion of main channel 42 is flexible to permit the user to position control 30' at a desired location. In addition, having controls 30' located at a more distal location and/or adjacent to the controls for the optical device, can facilitate user interaction with the system.

With respect to FIGS. 1 and 36, the proximal end of housing member 150 can further include a mating member for mating the housing member to frame 22. As shown in FIG. 36, the frame can include an elongate mating bar 174 that includes a slot 208 for receiving mating member 178 of housing member 150. In one aspect, the mating member can slide within slot 208 and lock in place at a desired location. While the illustrated mating member allows longitudinal movement of the guide tube, one skilled in the art will appreciate that a variety of additional degrees of freedom can be achieved between frame 22 and guide tube 26. For example, guide tube 26 could be moved transversely with respect to the frame, could be moved up and down with respect to the frame, pivoted with respect to the frame, and/or rotated with respect to the frame. In addition, mating can be achieved via guide tube 26 or a separate mating element that connect frame 22, housing 150, and/or guide tube 26. In addition, as described in more detail below, a portion or all of the frame can be incorporated into guide tube 26.

Once the main and working channels exit housing member 150, the main and working channels can extend to proximal apertures 38a, 38b, 38c (FIG. 36) that define the proximal ends of the main channel and working channels. In one aspect, the proximal ends of the main and/or working channels can include a seal between the wall of the channels and a surgical instrument extending through the channels. The seal can reduce or inhibit the flow of fluid (e.g., solid, liquid and/or gas) to allow insufflation and/or aspiration of a body cavity and/or to prevent retrograde blood flow.

System 20 can include a variety of seals such as, for example, a wiper, septum, and/or duckbill type seal. With respect to the main channel the seal can be sized and shape for receipt in housing 150. The distal end of the seal can mate with the guide tube (e.g., with inner and/or outer tubular bodies 46, 48 that defines the main channel), while the proximal end of the seal can form a seal with the instrument passing through the main channel.

Figure 40A:
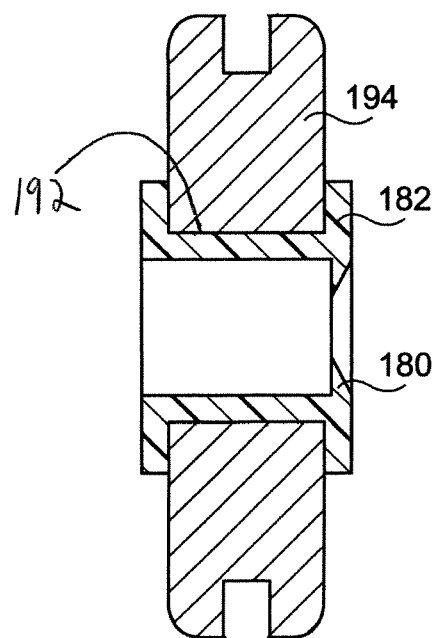
FIGS. 40A and 40B are cross-sectional views of one exemplary embodiment of the proximal end of a working channel.

FIG. 40A illustrates one exemplary embodiment of a seal 182 position at the proximal end of working channels 44a, 44b. Seal 182 includes an outer surface 192 sized and shaped to mate with a portion of frame 22 and an inner surface adapted to prevent the flow of fluid between a surgical instrument and the seal. The proximal end of seal 182 can define the opening 38a, 38b to working channels 44a, 44b, while the distal end of seal 182 can mate with the tubular body defining a portion of the working channel.

FIG. 40A illustrates a wiper-type seal positioned adjacent to the proximal end of a working channel. Blades 180 can be formed of a resilient material such that as a surgical instrument (not shown) is moved through seal 182, blades 180 form an interference fit with the outer surface of the surgical instrument. In addition, or as an alternative, the inner walls of seal 182 can have a size and shape corresponding to the outer surface of an optical device or tool to limit fluid flow between the outer surface of the surgical instrument and the inner surface of the seal.

Figure 40B:
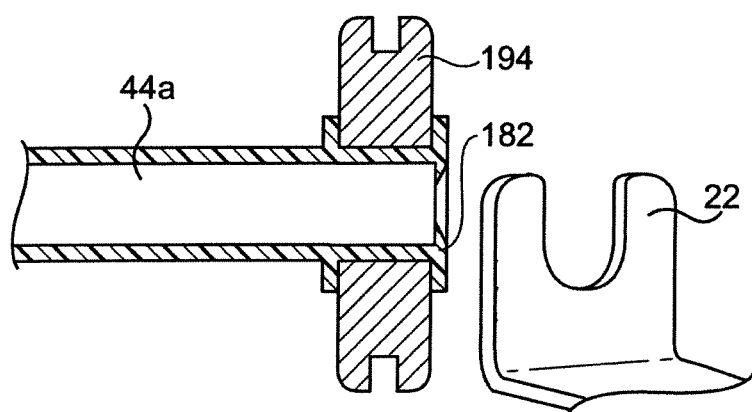

FIG. 40B illustrates seal 182 with grommet 194 for supporting seal 182 and permitting mating of seal 182 and working channel 44a with frame 22. Grommet 194 can provide a rigid structure having a surface which corresponds to a mating surface on frame 22, such as, for example, a "U" shaped bracket of frame 22. One skilled in the art will appreciate that grommet 194 can have a variety of shapes and sizes depending on the configuration of frame 22 or that grommet 194 can be defined by a portion of frame 22. In addition, working channel 44 can mate directly to frame 22 without the use of grommet 194.

In addition to apertures for the receipt of surgical instruments into working channels 44a, 44b and main channel 42, the proximal end of guide tube 26 can include at least one aperture for the delivery of a gas or liquid and/or the application of suction. In one aspect, a fluid can be delivered and/or withdrawn through one of the channels, such as, for example, the main channel. Alternatively, the fluid can be delivered and/or withdrawn through a separate channel. And in yet another embodiment, the fluid pathway can be defined by a portion of the guide tube between the inner surface of the guide tube and the outer surface of the main and working channels or delivered via an instruments that passes therethrough.

In one aspect, insufflation gas or suction can be delivered via housing 150. An aperture defined, for example by a luer fitting, can provide ingress/egress for an insufflation gas. In one aspect, the luer fitting can be placed adjacent to the entrance of working channel 44. Insufflation gas can be delivered at a variety of locations to system 20. For example, pressurized gas can be delivered via a separate lumen, through the main channel, and/or via a more proximally/distally positioned aperture.

The distal end of guide tube 26 can include apertures for delivery and/or withdrawal of a irrigation, aspiration, and/or insufflation. In addition, or in the alternative, an aperture can be provided for water jets for the delivery of a liquid for fluid dissection, raising lesions, separating tissue planes, and/or other liquid based procedures. Where the guide tube spans an anatomical wall, such as, for example, the abdominal wall, the location of insufflation, irrigation, and/or aspiration apertures can be chosen to deliver or receive fluid to or from multiple body cavities. In addition, while transfer of liquids or gasses is generally described, in an alternative aspect, solids could be delivered or withdrawn.

Figure 40C:
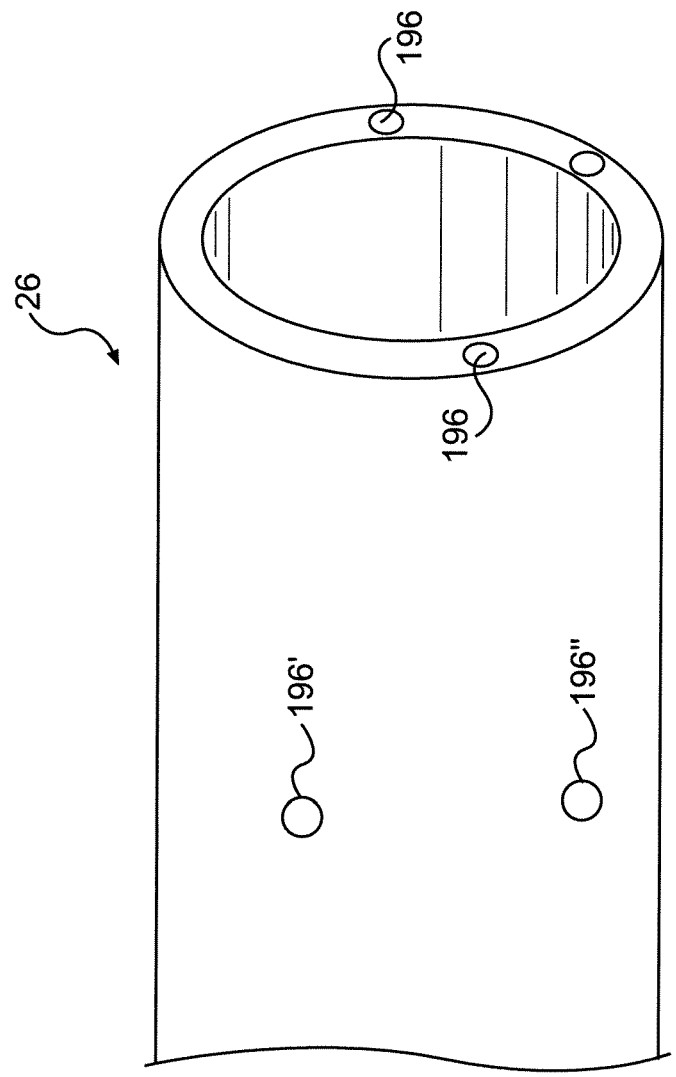
FIG. 40C is a perspective view of one exemplary embodiment of the distal end of a guide tube.

In one embodiment, at least one opening 196' for applying suction is positioned along the outer sidewall of guide tube 26. In addition, as illustrated in FIG. 40C, openings 196' are located along the distal portion of the guide tube sidewall, but are spaced from the distal-most end of guide tube 26. The location of suction openings '196 can permit withdrawal of fluids (e.g., blood) without the need to withdraw tools into guide tube 26 and/or to move guide tube 26 in the distal direction.

In another embodiment of guide tube 26, the working and/or main channel proximal openings are positioned at a location distal to the proximal-most end of the guide tube. For example, an instrument port can be positioned distal to guide tube housing 150. In one aspect, the instrument port can mate with a detachable instrument channel. In addition, a variety of other ports for delivery of tools, fluids, electrosurgical energy, or other treatment apparatus can be positioned along the mid or distal portion of the guide tube.

As mentioned above with respect to guide tube 26, the guide tube and instruments can bend or flex to allow insertion of at least a portion of system 20 along a non-linear or curved pathway. However, in another aspect, a portion of guide tube 26 and/or the instruments can be rigid. With respect to FIG. 41A guide tube 26 and/or tool 40 can comprise a rigid shaft with an articulation section at a distal end. The guide tube can have any of the properties and structures described above, but be formed at least in part of rigid materials. Alternatively, or in addition, a stiffening material can be added to guide tube 26 to increase rigidity.

In one aspect, the guide tube includes rigid links that are movably mated to one another. As illustrated in FIG. 41B, a rigid link 26a can pivot with respect to an adjoining link (26b, 26c) to allow the guide tube to bend. In one aspect, the links can be driven. For example, pull wire can drive one link with respect to another link. Alternatively, the links can move freely with respect to one another. As the guide tube is moved through a passageway, the contour of the pathway can cause the links to move relative to one another and cause the guide tube to bend.

Figure 41A:
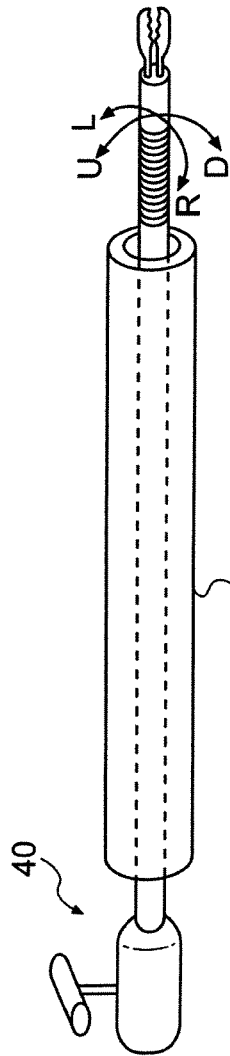
FIGS. 41A, 41B, and 41C are various exemplary embodiments of rigid or partially rigid guide tubes.
Figure 41B:
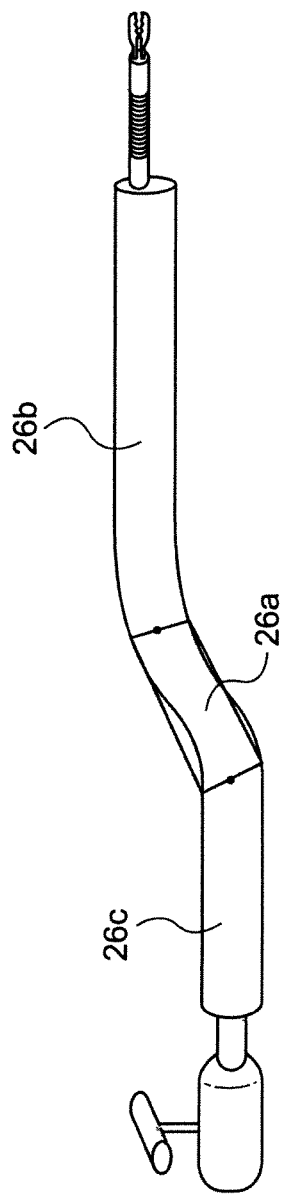
Figure 41C:
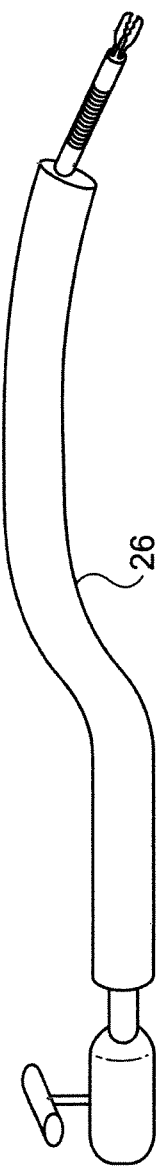

While FIG. 41A illustrates a linear, rigid guide tube, in another aspect, the guide tube curved. For example, as illustrated in FIG. 41C, the guide tube can have a rigid, pre-formed shape with at least one change in direction along its length.

In another embodiment of system 20, guide tube 26 is configured for use in a laparoscopic procedure. In one aspect, a distal portion of guide tube 26 can dock with a laparoscopic port. FIG. 42A illustrates tools 40a, 40b extending through guide tubes 26a, 26b which are mated with ports 780a, 780b. One skilled in the art will appreciate that a variety of locking structures, including mechanical interlocks and/or frictional engagements can mate system 20 with ports 780a, 780b. In one aspect, guide tubes 26a, 26b include mating features that mate with corresponding mating features on ports 780a, 780b.

Alternatively, instead of system 20 mating with laparoscopic ports, the ports are defined by a portion of the system such as, for example, guide tube (or tubes) 26. The ports can be integral with guide tube 26 and/or fixedly mated therewith.

Figure 42B:
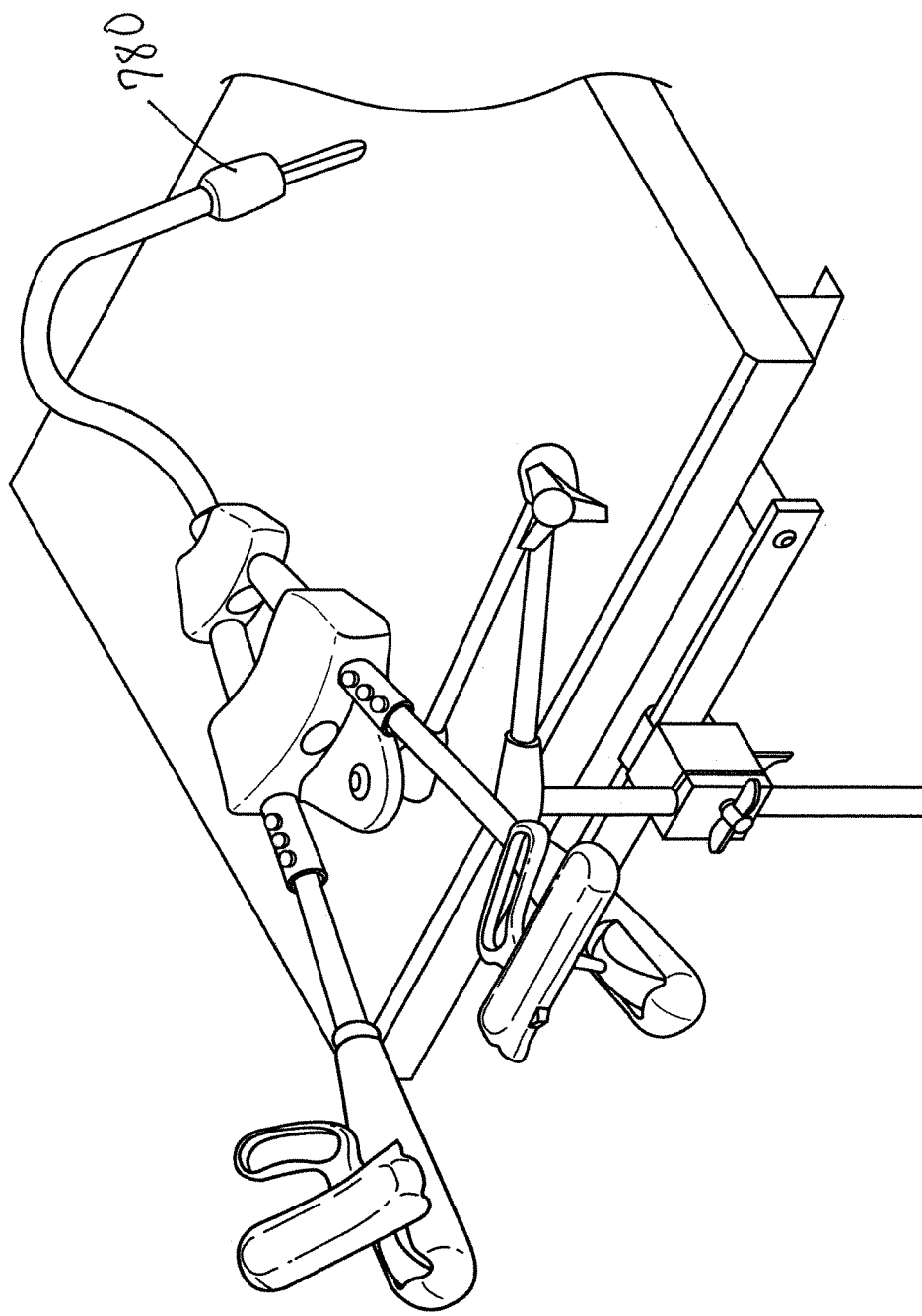
Figure 42C:
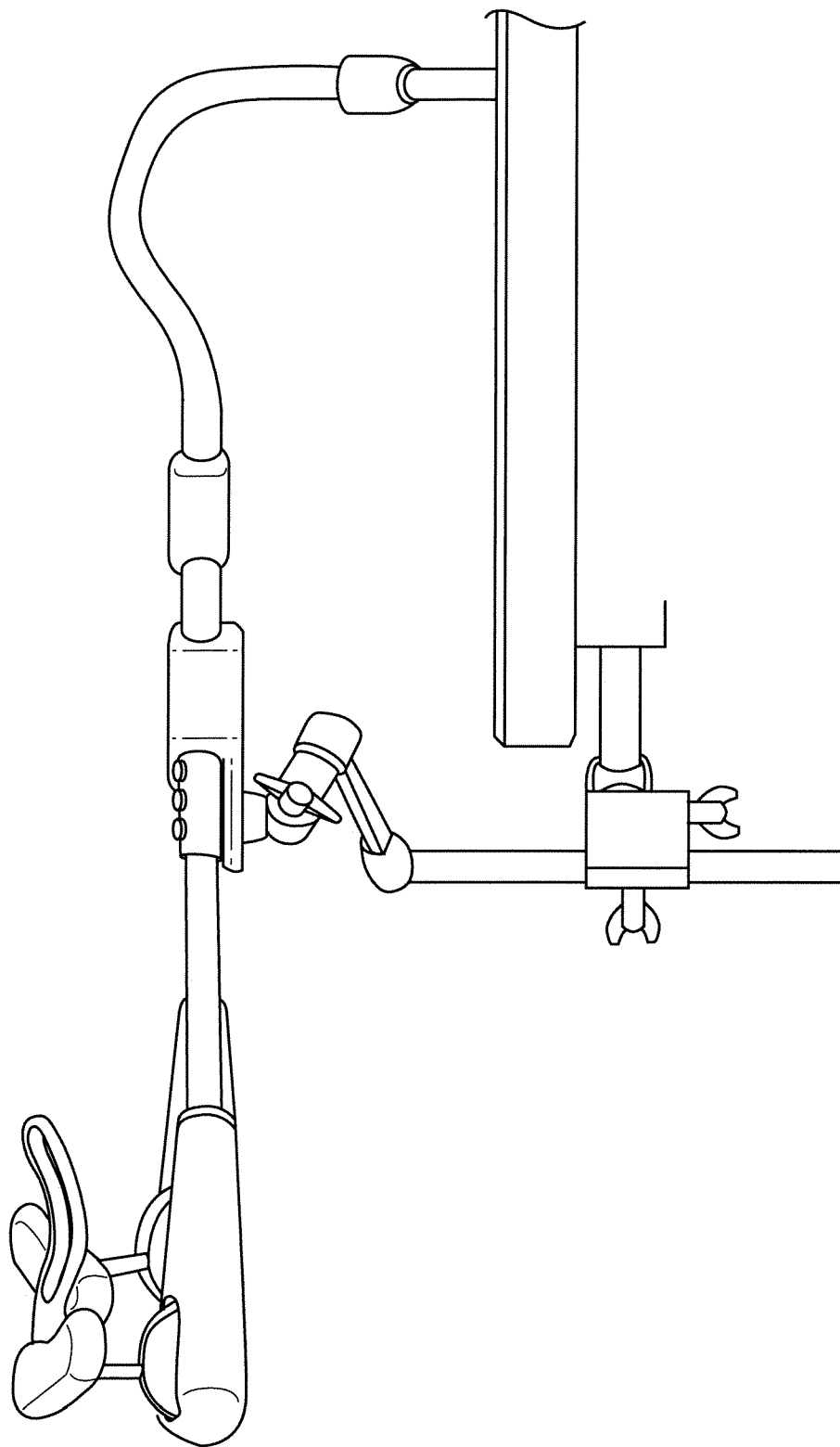

In the illustrated embodiment of FIG. 42A a single tool passes through each of ports 780a, 780b. However, multiple tools, fluid lumens, optical devices, and other instruments be delivered through a single port. In one aspect, illustrated in FIGS. 42B and 42C, tools 40a, 40b extend through a single guide tube 26 and through a single port 780.

Figure 43A:
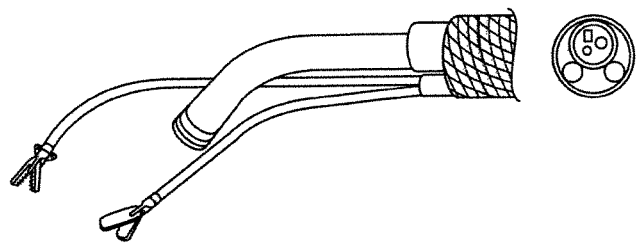
FIGS. 43A, 43B, 43C, 43D, 43E, 43F, 43G, 43H, and 43I are perspective views of various guide tube and instrument embodiments described herein.
Figure 43B:
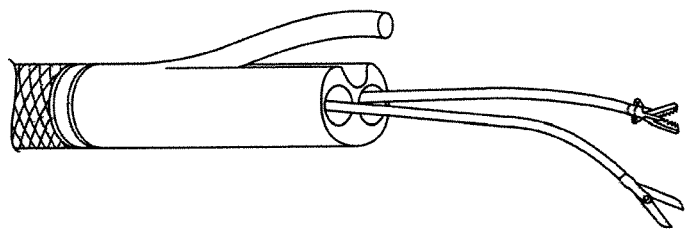
Figure 43C:
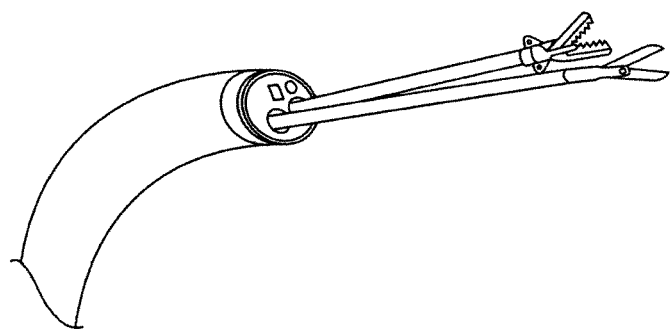
Figure 43D:
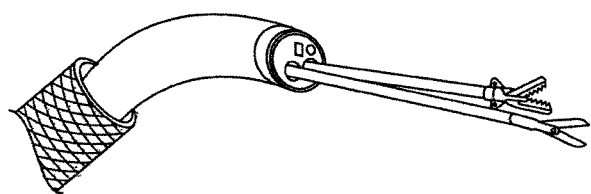
Figure 43E:
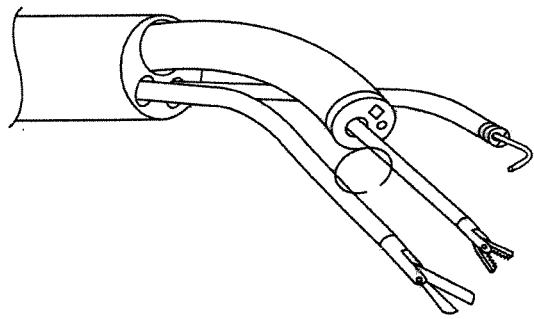

FIGS. 43A through 43I, describe other exemplary configurations of the guide tube 26, optical device 28, and tools 40a, 40b. FIG. 43A, illustrates a non-articulating guide tube. In one aspect, the guide tube can be bent or articulated into a desired configuration and instruments (e.g., optical device 28 and/or tools 40*a*, 40*b*) can be articulated to perform a procedure. The instruments in this configuration do not rely on the working channel for articulation. For example, the instruments 40*a*, 40*b* can be supported by a single working lumen 44. FIG. 43B illustrates a guide tube with a built-in optical device. The optical device body can mate with the guide tube, while the distal end of the optical device is configured to articulate with respect to the guide tube. FIG. 43C illustrates a conventional endoscope with tools 40*a*, 40*b* passing therethrough. FIG. 43D illustrates an articulating optical device with tools 40*a*, 40*b* passing therethrough. In one aspect, the guide tube of FIG. 43D does not articulate. Instead, guide tube 26, can supply supporting structure and pathway to enable a procedure at a site within a body. FIG. 43E illustrates a guide tube similar to guide tube 26 with an additional tool extending through the optical device.

Figure 43F:
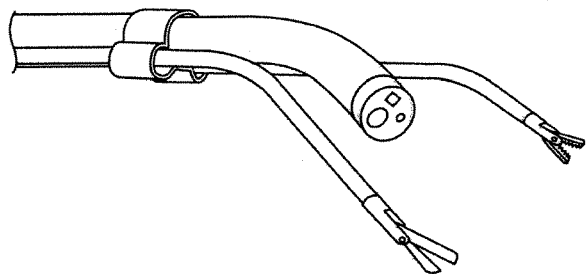
Figure 43G:
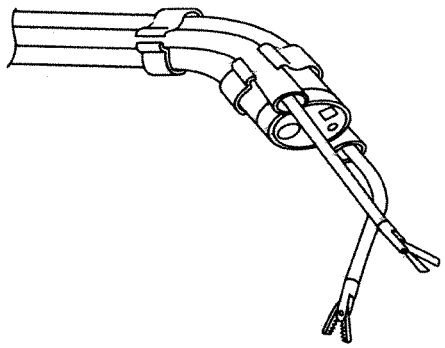
Figure 43H:
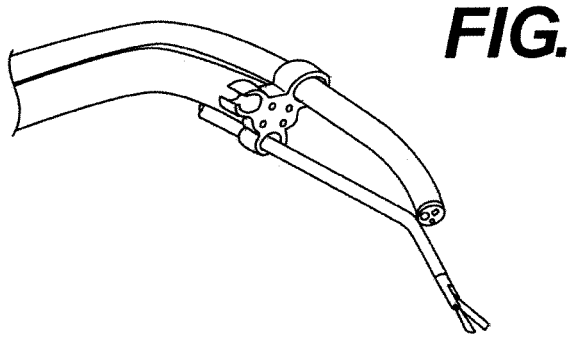
Figure 43I:
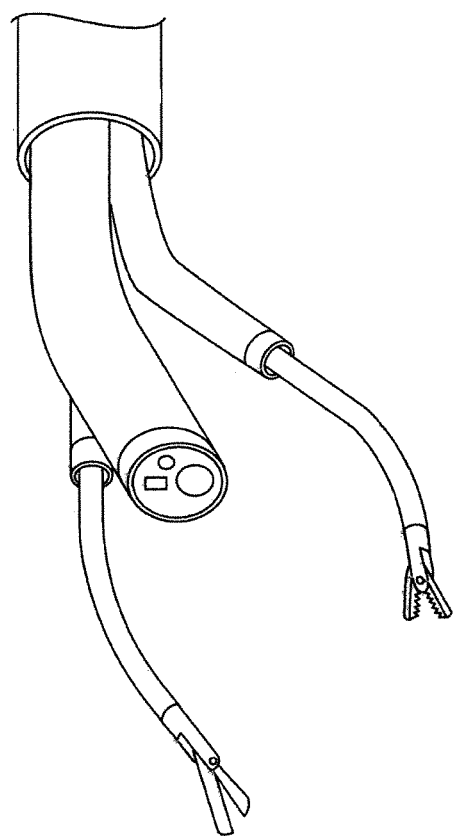

In another embodiment of system 20, FIGS. 43F and 43G illustrate a system with no guide tube. Instead, an optical device and tools are mated with one another. With respect to FIG. 43F, a clip 77 defines lumens or apertures through which tools and the optical device pass. The clip is positioned proximally from the articulation section of the optical device and tools to allow independent articulation of the instruments. FIG. 43G illustrates a clip 77' that holds an optical device and working channels relative to one another. As the optical device articulates, the working channels move with the optical device. In one aspect, the clip detachably mates the working channels and optical device. In yet another embodiment, illustrated in FIG. 43H, instead of an articulating guide tube for the passage of an optical device and tools, system 20 can include a steerable member to which tools and/or optics are attached. In still another embodiment, illustrated in FIG. 43I, additional degrees of freedom are provided to system 20 with steerable instrument channels. With regard to any of the guide tube and/or instruments discussed above or below, the guide tube and/or instruments can include more than one articulation section. For example, two independent articulation sections can provide additional degrees of freedom to the systems described herein. The additional articulation section can provide a "wrist" and/or "elbow" to the guide tube and/or instruments.

Frame

As mentioned above, the systems described herein can include a frame for mating with the guide tube and/or instruments (e.g., tools 40*a*, 40*b*, and/or an optical device 28). The frame not only can support the instruments, but can allow the user to obtain useful control of those instruments. In particular, the frame can provide a reference point for manipulating the various degrees of freedom relative to one another (and/or relative to a portion of the system and/or relative to a patient) in a manner which allows execution of complicated surgical procedures. In addition, or alternatively, the frame can permit a user to apply a force relative to the frame to control and/or move the guide tube and/or instruments.

In one aspect, the frame is connected with the instruments and/or guide tube and is defined by a separate and distinct structure. In another aspect, various portions and/or all of the frame is incorporated into the guide tube and/or instruments.

As mentioned above, and with respect to FIG. 1, system 20 can include frame 22 that is adapted to mate with surgical instruments and/or guide tube 26. In one aspect, referring now to FIG. 44, frame 22 includes an upper portion 200 having a first body 201 for mating with and supporting the various elements of system 20 and a lower portion 202 (also referred to as a second body 202) that supports the upper portion. In use, frame 22 provides a work space for a surgeon to manipulate surgical instruments (e.g., tools 40*a*, 40*b* and optical device 28). In addition, frame 22 can provide a reference between the surgical instruments and a patient.

Figure 44:
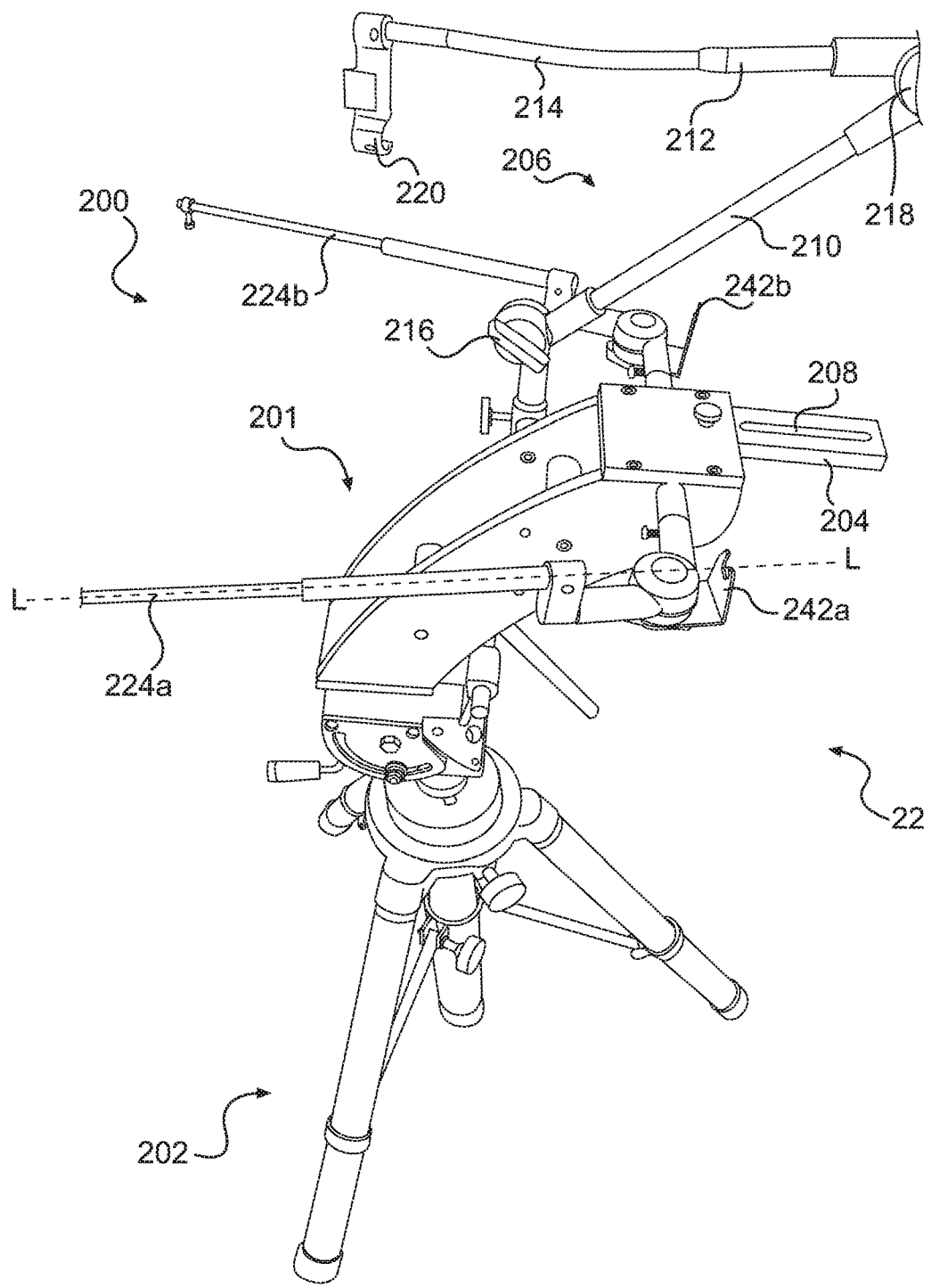
FIG. 44 is a perspective view of one exemplary embodiment of a frame for use with a system described herein.

FIG. 44 illustrates frame 22 without the surgical instruments attached. Frame 22 includes a guide tube mating surface 204, rails 224*a*, 224*b* for control members 24*a*, 24*b*, and an optical device holder 206. In one aspect, guide tube mating surface 204 allows frame 22 to detachably mate with guide tube 26 such that the guide tube can be inserted into a patient and then mated with frame 22. In use, guide tube mating surface 204 can also allow a user to adjust the position of guide tube 26 relative to the frame. In one aspect, the guide tube can be mated with an elongate slot 208 on the frame that allows longitudinal movement of the guide tube with respect to the frame. Alternatively, or additionally, guide tube mating surface can be configured to allow pivotal, up/down, transverse, and/or rotational movement of guide tube 26 relative to frame 22.

Figure 45:
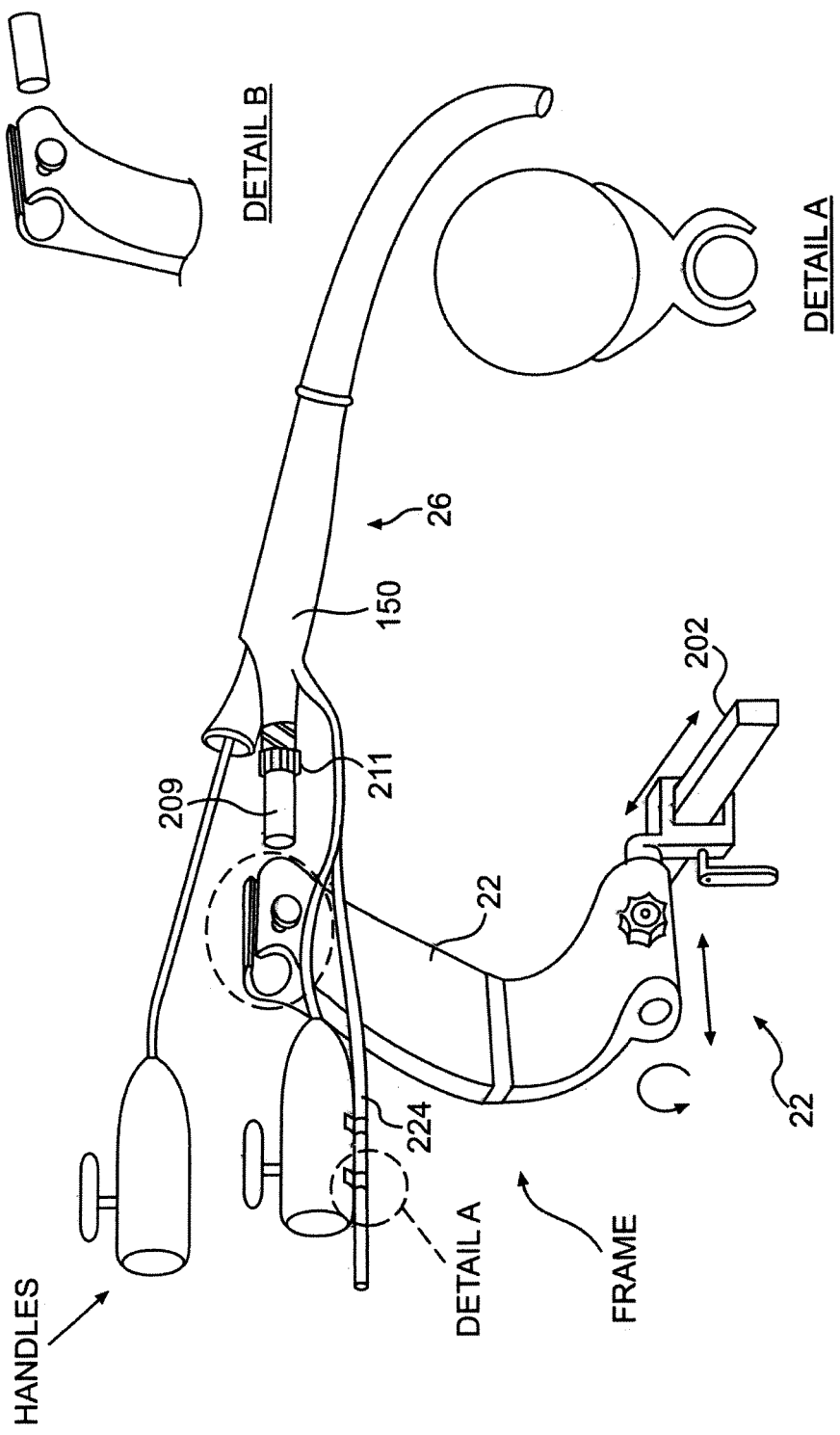
FIG. 45 is a perspective view of one exemplary embodiment of a frame and guide tube for use with a system described herein.

In another aspect, guide tube 26 could be configured for a quick disconnect from frame 22. For example, FIG. 45 illustrates a post 209 that extends from guide tube 26. The guide tube can be mated to frame 22 by sliding post 209 into a slot in frame 22. Post 209 can provide additional degrees of freedom by allowing the guide tube to move relative to a point of reference (e.g., the frame, the operating room, and/or a patient). For example, the guide tube post can rotate and/or move longitudinally in frame 22. When the guide tube is in a desired location, the guide tube can be locked in position with respect to the frame. In one aspect, a lock, such as, for example, locking collar 211 can allow a user to quickly attach/detach the guide tube and frame. Alternatively, or additionally, a locking features such as a clamp or pin 211 (Detail B) on frame 22 can frictionally or mechanically engage post 209.

Figure 46:
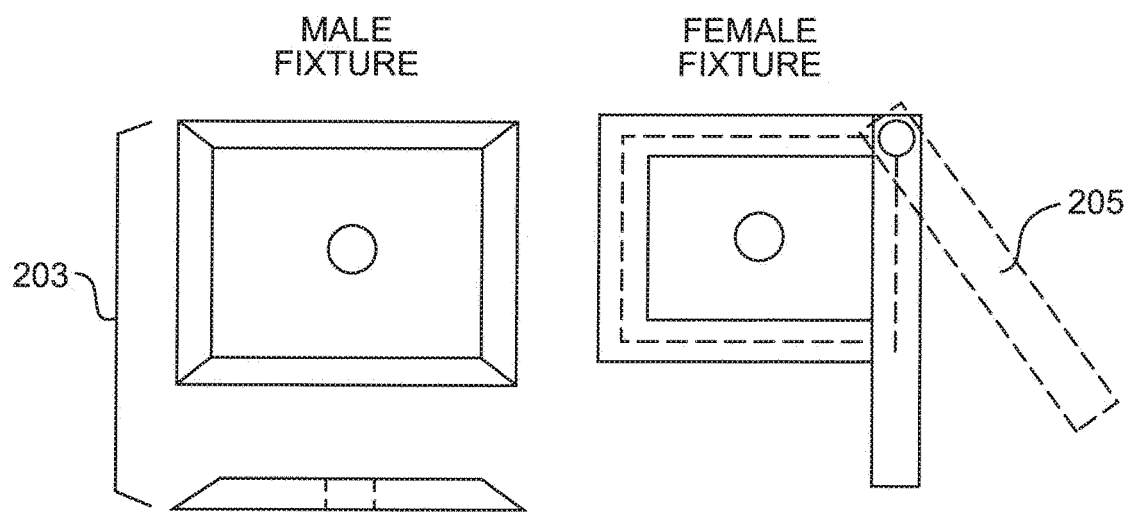
FIG. 46 is a top view of one exemplary embodiment of a quick-disconnect for use with the guide tubes and frames described herein.

FIG. 46 shows a another example of a quick release defined by a male/female interlock 203 with a switch 205 configured to lock the guide tube and frame. The male or female portion of interlock 203 can be positioned on the guide tube while the other of the male or female portion can be positioned on the frame. Seating the male portion in the female portion and closing switch 205 can lock the guide tube and frame.

In another aspect, locking guide tube 26 to frame 22 locks the rails 224 to the frame. For example, as shown in FIG. 45, rails 224 can be mated with or defined by a portion of guide tube 26. The rail and guide tube can then be attached/detached from frame 22 as a single unit.

Regardless, the ability to adjust the guide tube with respect to the frame allows a user to change the location of the working volume of the tools with respect to the frame. As mentioned above, the space in which the distal end of the tools can move adjacent to the distal end of the guide tube is the working volume. Because the tools have a limit to the amount of travel (longitudinal movement and/or articulation) relative to the guide tube, the working volume is not unlimited. However, by moving the guide tube (and therefore the tools) relative to the frame, the location of the working volume is changed.

In another aspect, moving the first body member 201 (which is attached to the guide tube) relative to the second body member 202 can change the location of the working volume. The first body member can have one, two, three, or more degrees of freedom of movement with respect to the second body member which provide one, two, three, or more degrees of freedom in which to adjust the location of the working volume. With respect to FIGS. 44 and 45 (and as discussed in more detail elsewhere), frame 22 can permit, for example, the first and second body members to pivot, rotate, and/or move forward/back, up/down, and/or side-to-side. Once the working volume is in the desired location the first body member can then be locked with respect to the second body member. Similarly, moving the whole frame relative to a point of reference (e.g., a patient) can change the location of the working volume.

In one embodiment, frame 22 can include a holder 206 upon which a surgeon can rest optical device 28. Holder 206 allows the user to steady optical device 28 before and/or after placing the optical device in a desired orientation. For example, the optical device can be placed in holder 206 and then articulated. Adjustability of the holder allows the user to rotate the optical device such that the image viewed by the user matches the user's orientation (i.e., the image is not upside down) and/or the orientation of the surgical site. The holder provide a location for the user to place the optical device so that the optical device will hold its orientation during a procedure and allow access to controls for articulation.

Figure 47:
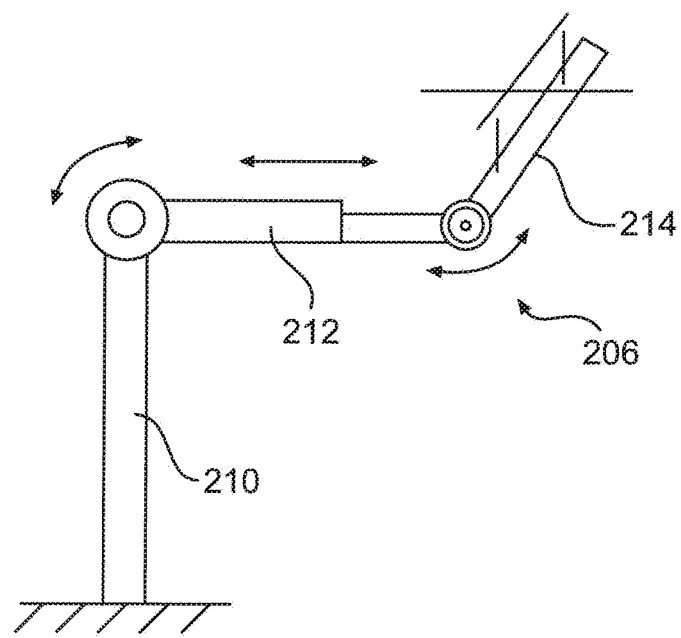
FIG. 47 is a side view of one exemplary embodiment of a frame for use with a system described herein.

In one aspect, with respect to FIG. 44, holder 206 comprises a three arm structure such that a surgeon can have a full range of motion when adjusting the position of an optical device relative to frame 22. In one aspect, a first and second arm 210, 212 are rigid and a third arm 214 is flexible. Third arm 214 can be adapted to hold its position once bent into a desired configuration by a user. For example, the force required to move third arm 214 can be greater than the force applied by the weight of optical device 28 when placed in holder 206. In another aspect, illustrated in FIG. 47, holder 206 can include a telescoping arm in addition, or as an alternative, to first, second, or third arm 210, 212, 214. The holder of FIG. 47 can allow pivoting and/or rotational movement in addition to telescoping. In yet another aspect, a single flexible arm could be used to allow articulation of holder 206.

Holder 206 can include first and second pivot points 216, 218, respectively. As shown in FIG. 44, holder 206 is mated with frame 22 via a first pivot point 216. First arm 210 can extend between first and second pivot points 216, 218, while second arm 212 extends between second pivot point 218 and third arm 214. Pivot points 216, 218 can also be designed to hold their position once place in a desired configuration. Alternatively, or additionally, holder 206 can include locks that a user can activate to prevent movement of pivot points 216, 218.

Holder 206 can mate with a variety of surgical instruments, such as, for example the illustrated optical device 28. In one aspect, holder 206 includes a clip 220 into which optical device 28 can sit. Clip 220 can have an open sided configuration which relies upon gravity and/or friction to hold optical device 28 in place. Alternatively, clip 220 can include a locking mechanism (not illustrated) to prevent movement of optical device 28 relative to clip 220.

As mentioned above, upper portion 200 can further include rails 224a, 224b that receive controls 24a, 24b for tools 40a, 40b. Rails 224a, 224b allow control members 24a, 24b to move longitudinally and/or to pivot with respect to other portions of system 20 (e.g., frame) and/or the surrounding environment (e.g., with respect to a patient). Since the rails can be defined by a portion of frame 22, by a portion of guide tube 26 (e.g., part of housing 150), and/or as a stand alone structure, the rails will be described in a separate section below.

Figure 48:
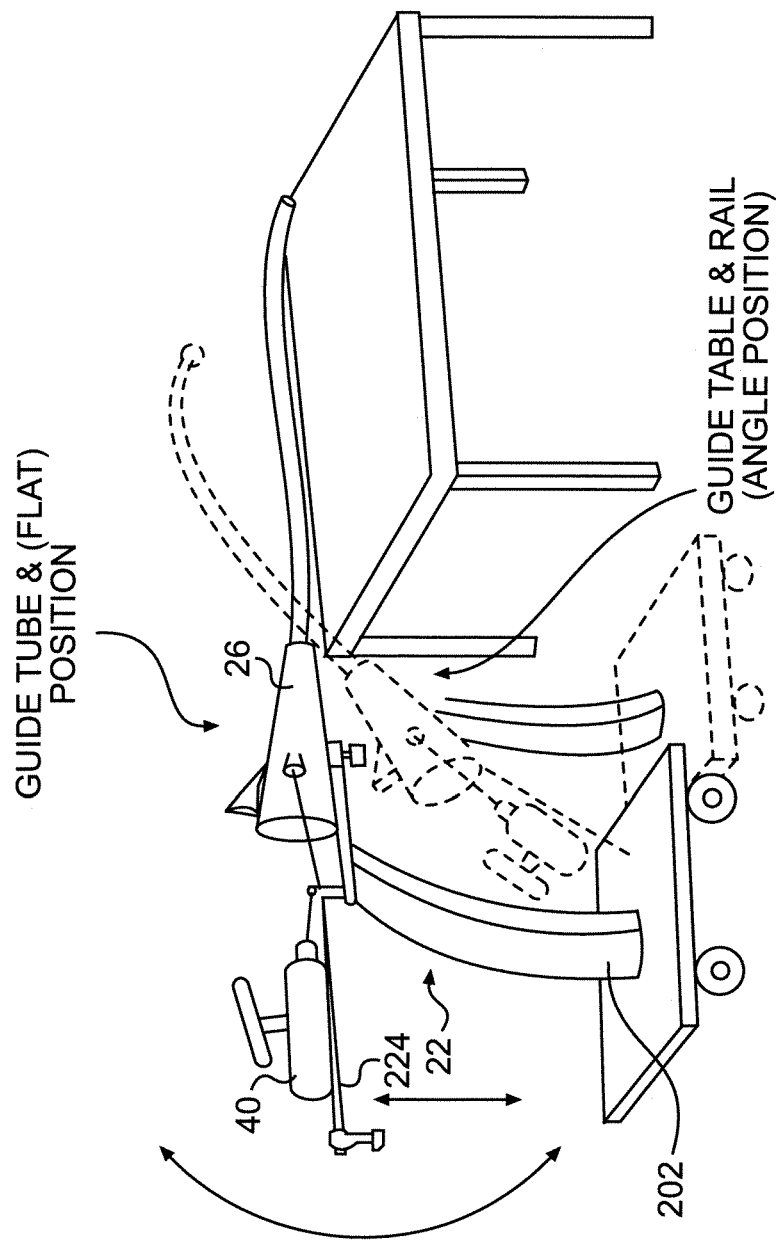
FIG. 48 is a perspective view of one exemplary embodiment of a frame for use with a system described herein.

The lower portion 202 of frame 22 can have a variety of configurations adapted to support upper portion 200 and to hold frame 22 in place relative to a patient and/or an operating table. In one aspect, lower portion 202 has a tripod configuration that rests on an operating room floor. To facilitate movement of frame 22, the frame can include wheels or sliders. For example, FIG. 48 illustrates system 20 mounted on a rollable lower portion 202. Frame 22 allows rolling or sliding of the guide tube and tool 40. In addition, the frame of FIG. 48 can allow a user to adjust the angle of rail 224, guide tube 26, and/or tool 40.

The connection between the upper and lower portions can be configured to allow upper portion 200 to move relative to the lower portion 202. As shown in FIG. 44 upper portion 200 can be pivoted and lock in position relative to upper portion 200.

Figure 49:
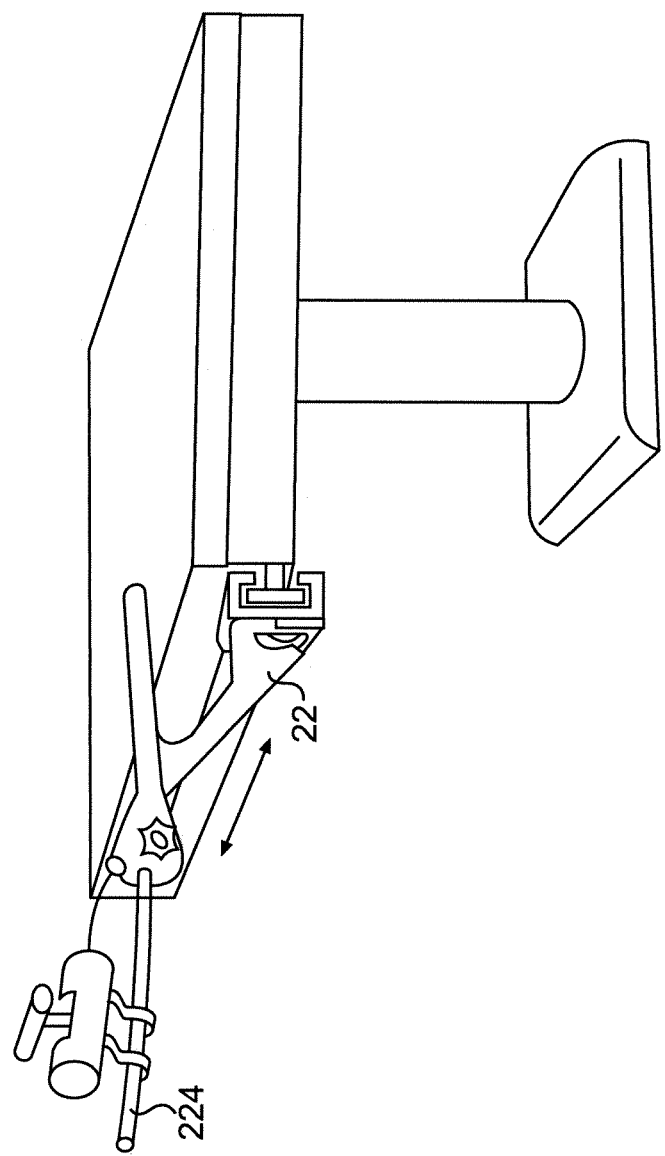
FIG. 49 is a perspective view of one exemplary embodiment of a frame for use with a system described herein.

In another aspect, lower portion 202 can mate with an operating table such that frame 22 moves with the operation table as the table and patient are moved. FIG. 49 illustrates system 20 mated to an operating table rail. In one aspect, frame 22 is adjustably mated with a frame of an operating room table.

Figure 50:
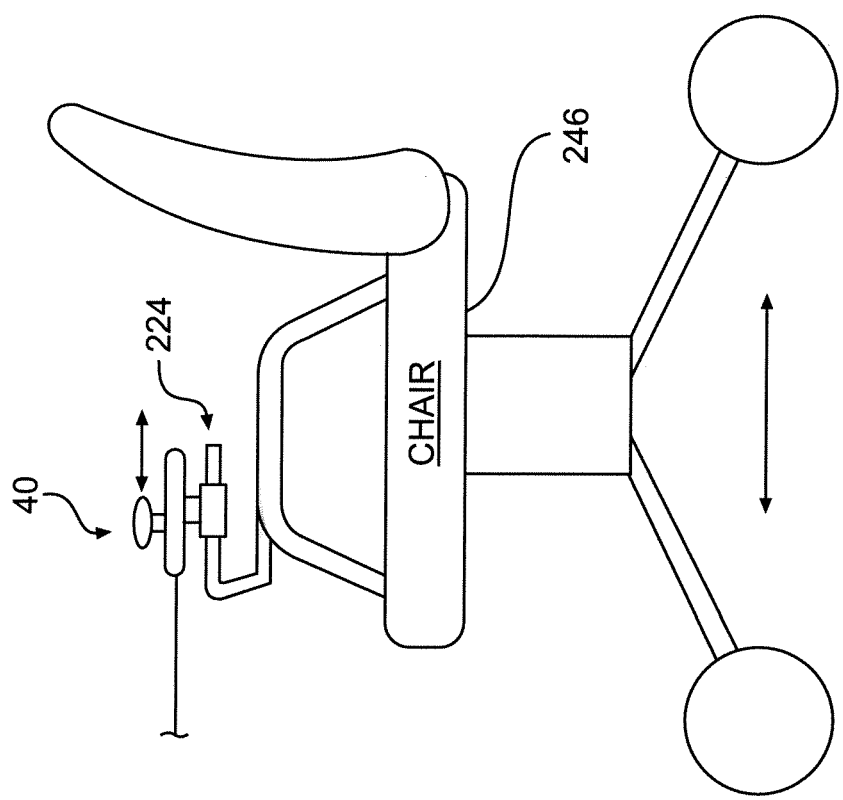
FIG. 50 is a perspective view of one exemplary embodiment of a frame for use with a system described herein.
Figure 51:
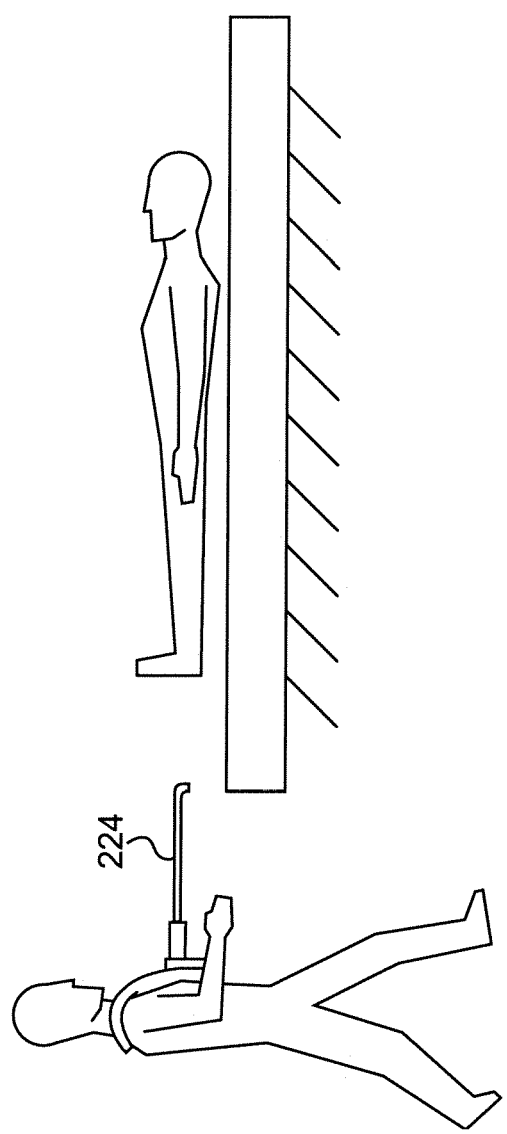
FIG. 51 is a perspective view of one exemplary embodiment of a frame for use with a system described herein.

In yet another aspect, system 20 can be mounted on a movable chair. FIG. 50 illustrates system 20 mounted on a chair 246 that can be moved via rolling. In still another aspect, as shown in FIG. 51, system 20 can be harnessed to a physician.

As mentioned above, in one aspect, the rail is movably mated with frame 22, for example, via pivoting joints. In another aspect, additional degrees of freedom can be provided to rails 224a and/or 224b with respect to frame 22, an operating room, and/or a patient. For example, FIG. 47 (discussed above) illustrates a holder 206 that can provide one, two, three, or more than three degrees of freedom to an optical instrument. In one aspect, the rails can be mounted on an adjustable frame similar to holder 206 to permit adjustment of the rails with respect to the guide tube 26 and/or to improve user ergonomics.

Figure 52:
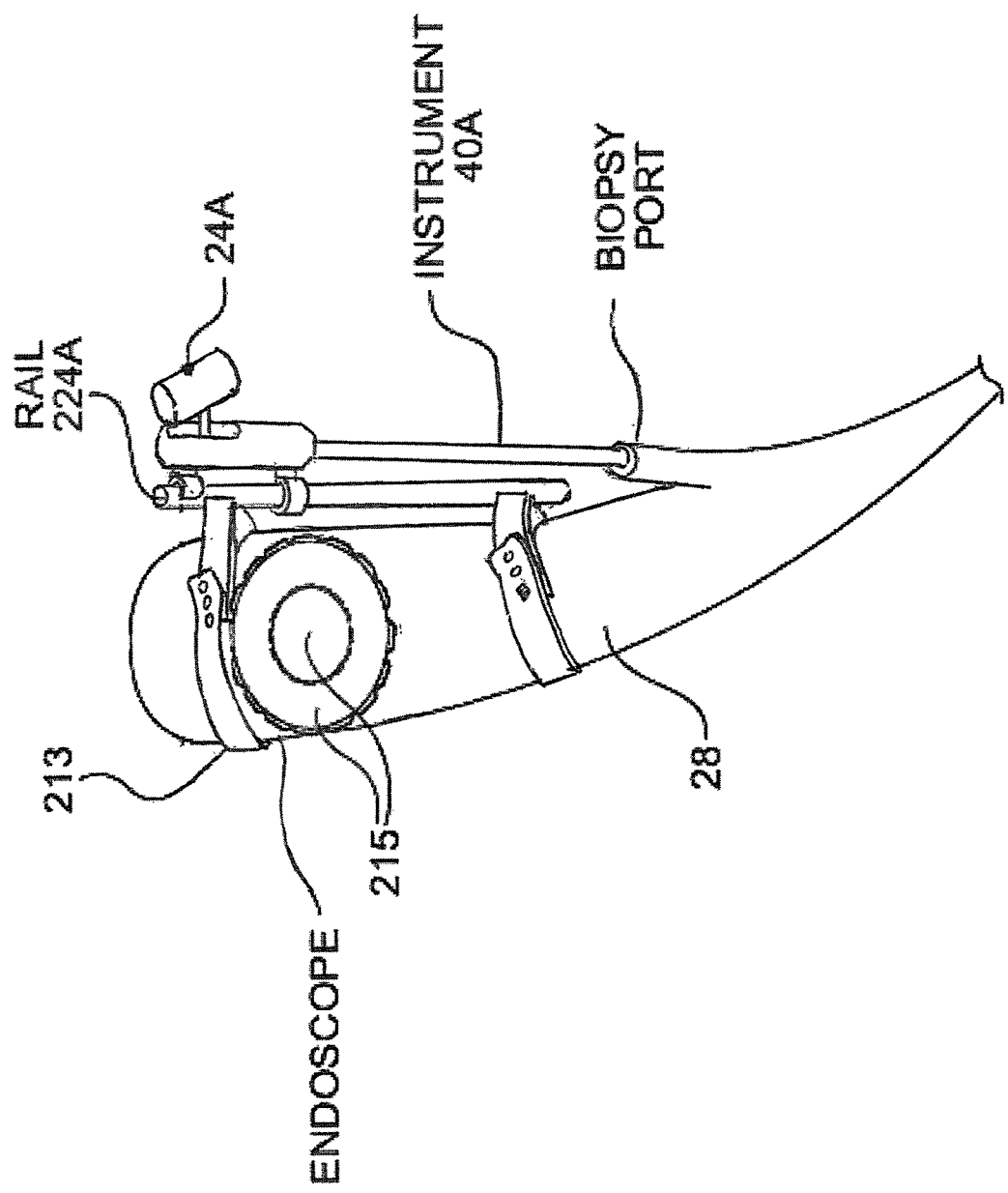
FIG. 52 is a perspective view of one exemplary embodiment of a rail mounted on an optical device.

In other embodiment, illustrated in FIG. 52, the rails can be mounted to an optical device. A user can hold the optical device 28 (e.g., endoscope) in one hand and drive the control member 24a with the other hand. As described below, the control member 24a and rails 224a can facilitate control of multiple degrees of freedom with a single hand. Mounting rail 224a to the endoscope can permit manipulation of optical controls 215 and surgical instrument handle 24a via a single user. The rail 224a can be mounted at various angles, such as, for example, parallel to the optical device control housing.

In one embodiment, the catheter body of instrument 40a has sufficient rigidity that moving handle 24a along rail 224a cause the body (and distal end) of instrument 40a to move relative to the optical device 28 (and/or relative to a frame, patient, point of reference, etc.). For example, a user can torque handle 24a and cause the body of instrument 40a to rotate. Similarly, moving the handle longitudinally along the rail can cause the body of instrument 40a to move longitudinally within a working channel in optical device 28.

In one aspect, optical device 28 acts as the frame. In another aspect a separate structure could provide support to optical device 28 and act as the frame. In one such aspect, tissue or a natural body orifice acts as a frame to support optical device 28.

With respect to FIG. 52, a strap 213 mates rail 224a with optical device 28. However a variety of other detachable or fixed mating features can be used to attach rail 224a to optical device 28.

Rails

In one aspect, control members 24a, 24b of tools 40a, 40b can mate with rails 224a, 224b. As mentioned above, rails 224a, 224b can be formed by a portion of frame 22. However, in another embodiment, the rails can be defined by or mate with another portion of system 22 and/or be used without a frame. In addition, while the discussion below generally refers to two rails, the systems described herein can include a single rail or more than two rails.

Generally, the rails and control members allow a user to manipulate (i.e., move and/or freeze) multiple degrees of freedom of the tools. For example, the tools 40a, 40b can be moved longitudinally with respect to and/or rotated with respect to the rails (or another portion of system 20) to control longitudinal and/or rotational movement of the distal ends of the tools (i.e., the end effectors). However, not only do the rails permit movement and provide a frame of reference for a user, but they can also facilitate control of multiple degrees of freedom. Thus, in addition to providing multiple degrees of freedom, the systems described herein can enable a user to make use of the multiple degrees of freedom. In one aspect, the system 20 allows a user to control multiple degrees of freedom with a single hand. In another aspect, system 20 permits simultaneous control of multiple degrees of freedom (e.g., movement of tool 40 relative to a patient while manipulating control member 24).

As described above, in one aspect, tools 40a, 40b include proximal control members 24a, 24b, elongate bodies referred to herein as catheters 25a, 25b, and distal end effectors 502. The various elements of tools 40a, 40b are described in more detail below, however for the purpose of discussing rails 224a, 224b, it should be understood that the rails mate with the proximal control members 24a, 24b and facilitate movement of the proximal control members 24a, 24b. Moving the proximal control members relative to the rails (or another portion of system 20) is one way to control the movement of catheters 25a, 25b and the end effectors 502. In one aspect described below, rotating and/or translating the proximal control members causes the catheters and end effectors to rotate and/or translate relative to the rails, frame, and/or guide tube. Thus, the rails can provide one, two, or more than two degrees of freedom to each tool.

In another aspect described below, the proximal control members can be fixedly mated with the rails and the rails can move relative to the frame, guide tube, and/or patient to provide one, two, or more than two degrees of freedom to each tool. In yet another aspect described below, the tools can be movable mated with the rails and the rails can move relative to the frame, guide tube, and/or patient. For example, movement of the rails can provide one or more degrees of freedom to the tools (e.g., rotation and/or longitudinal movement) and movement of the tools relative to the rails can provide one or more additional degrees of freedom (e.g., rotation and/or longitudinal movement of the tools with respect to the rails).

Figure 53:
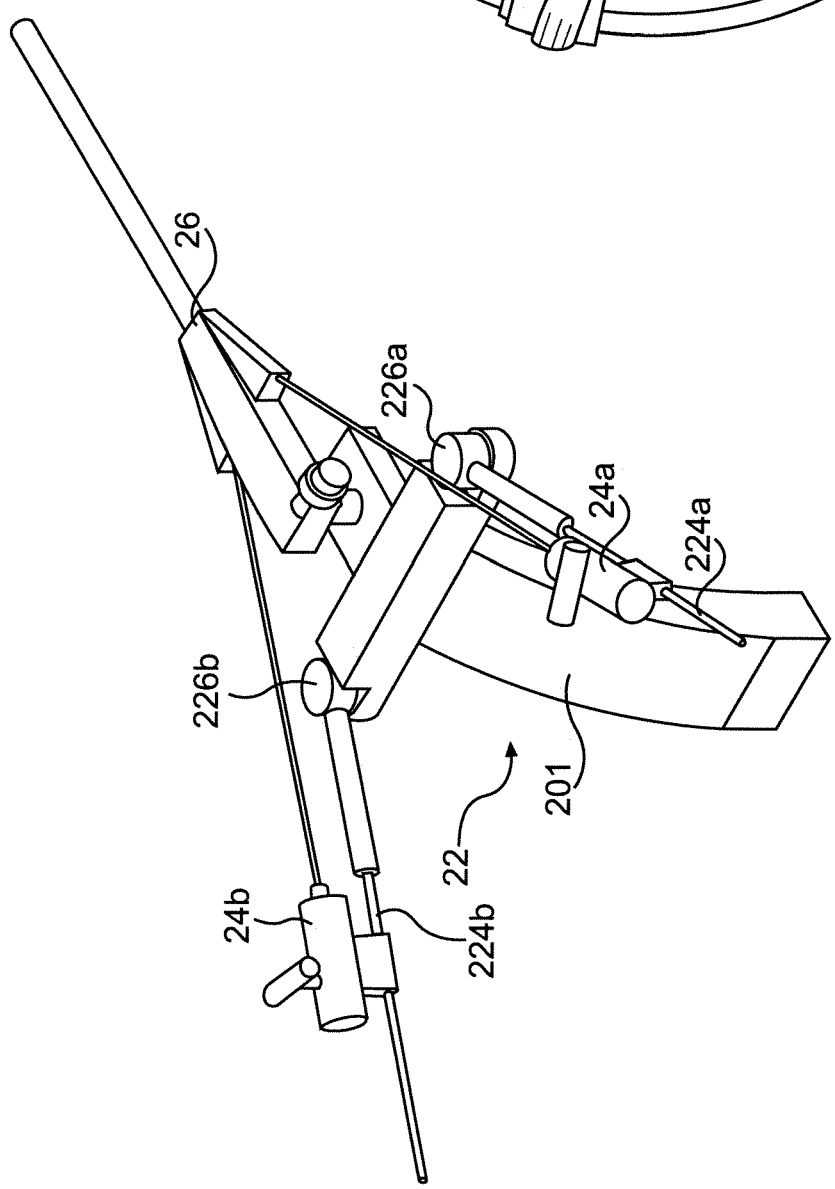
FIG. 53 is a perspective view of one exemplary embodiment of a frame for use with a system described herein.

In one embodiment, rails 224a, 224b extend proximally from frame 22. In use, a surgeon can stand or sit with control members 24a, 24b on opposites sides of his or her body. To improve ergonomics, rails 224a, 224b can be adjustable with respect to frame 22. FIG. 53 illustrates frame 22 with rails 224a, 224b attached to frame 22 at pivot points 226a, 226b. In another aspect, rails 224a, 224b, could be attached to frame 22 such that the position of the rails can be adjusted and locked with respect to frame 22. For example, the rails can be adjusted longitudinally, moved up/down, rotated, and/or moved transversely with respect to frame 22 to accommodate different users. In addition, more than two rails can be provided. In yet another aspect, two rails could be stacked on one another.

In one aspect, the rails 224a, 224b constrain movement of the control members 24a, 24b within a control member volume. The maximum travel of the control members (longitudinal movement and rotation) defines the control member volume. Adjusting the rails with respect to the frame can change the location of the control member volume. In another aspect, adjusting the frame (e.g., movement of first body member 201 relative to second body member 202) can change the location of the control member volume.

Figure 54:
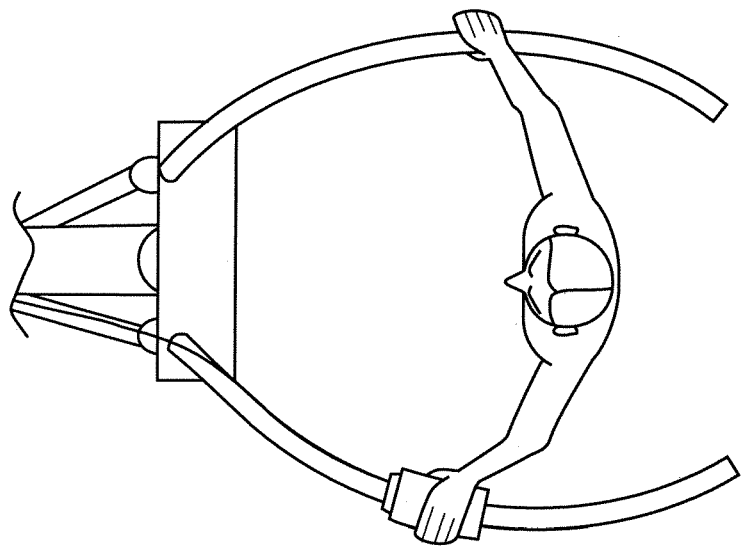
FIG. 54 is a perspective view of one exemplary embodiment of rails for use with a system described herein.

In one embodiment, the rails can extend from the system in a non-linear configuration. For example, FIG. 54 illustrates curved guide rails that arc around a user. The curved rails can improve user ergonomics and/or allow for longer rails. For example, the curved rails can provide increased control member travel while keeping the control members within reach of the user. Depending upon the user and/or the intended use of system 20, the curve of the rails can be adjustable. A user can bend the rails into a desired configuration.

FIG. 55 illustrates one embodiment of the connection between rail 224a and control member 24a. Control member 24 can include guide members 234, 235 (referred to as "clamps" in another embodiment below) extending from the surface of the control member and mating with rail 224a. Generally the guide members have an aperture or recess corresponding to the outer surface of the rail. The connection between the control member and rail allows relative translation and/or rotation between the control member and rail. While two guide members 234, 235 per control member are illustrated, one skilled in the art will appreciate that the guide members can have a variety of alternative configurations, such as, for example a control member with a single guide member.

While rails 224a, 224b are illustrated as having a generally circular cross-section shape, rail 224a and/or rail 224b could have a variety of alternative configurations. In addition, the cross-sectional shape of the rails can be chosen to control the movement of the control members relative to the rails. The rails can have a non-circular cross-sectional shape, such as, for example, a rectangular, oval, elliptical, triangular, and/or irregular shape that prevents relative rotation of the control member. In one aspect, the shape of the rails can prevent rotation of the control member relative to the rails. However, not all non-cylindrical rails prevent rotation of the control member with respect to the rails.

Figure 56:
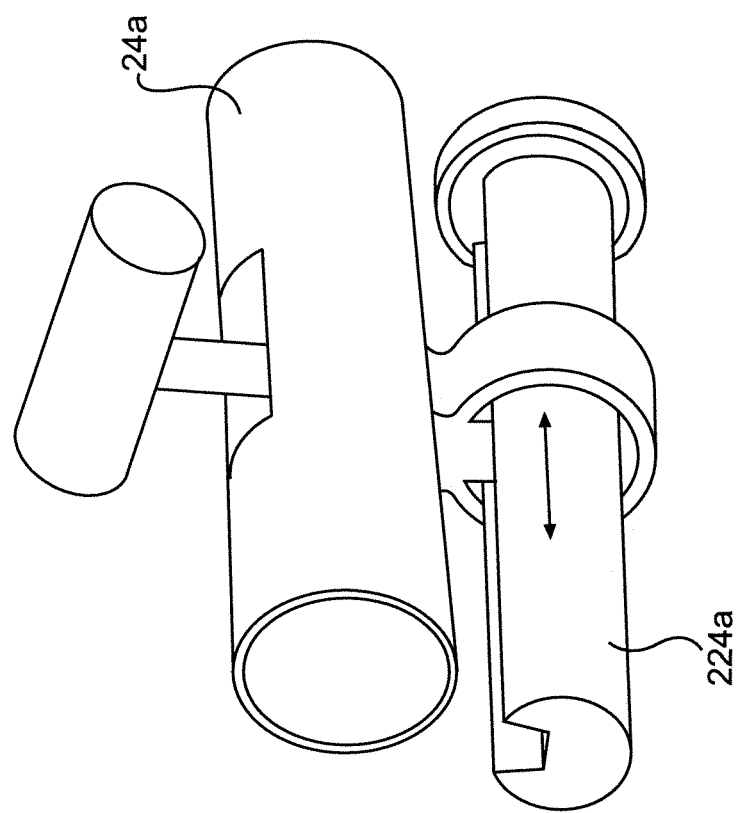
FIG. 56 is a side view of one exemplary embodiment of tool and rail for use with a system described herein.

In another aspect, the rails can have a groove or protrusion which corresponds to a groove or protrusion on the control members. FIG. 56 illustrate an exemplary configurations of rail 224a that allow translation of control members 24a, but inhibits rotation of the control member with respect to the rail. The groove/protrusion provides a "keyed" pathway that allows one degree of freedom while inhibiting another. In one aspect, the keyed pathway allows relative translational movement, but can prevent relative rotational movement of control member 24a with respect to rail 224a. If rotation of the tools is desired, the control members 24a, 24b could rotate independently of rails 224a, 224b (described in more detail below) and/or the rails could rotate together with the control members (also described below). In another aspect, the keyed pathway can limit the range of motion or travel of the control member with respect to the rail.

In one embodiment, the rails can include stops to limit the travel of the control members relative to the rails. As illustrated in FIG. 55, stops 230, 232 limit longitudinal movement of guide members 234, 235. A portion of rail 224a having a larger size than the inner diameter of guide member 235 can limit distal movement. Conversely, proximal stop 230 can be formed separately from rails 224a and mated therewith. For example, stop 230 can be defined by an adjustable locking nut that a user can lock at a desired location. In another aspect, both stops 230, 232 are adjustable. In use, a clinician can position stops 230, 232 to adjust the amount of travel of the control member.

In another aspect, at least one of the stops could be defined by a quick disconnect feature that allows rapid mating of control members 24a, 24b with rails 224a, 224b. If a user wishes to remove control member 24a from rail 224a, the quick disconnect stop can be manipulated to allow the control member to slide off of the rail. FIG. 57 illustrates one exemplary quick disconnect 230 defined by a spring loaded ball. FIGS. 58A and 58B illustrate a rail end stop that can move between a low profile configuration that (FIG. 58A) that permits passage of guide 234 and an off-center configuration (FIG. 58B) that prevents passage of guide 234. In the low profile configuration, the outer surface of stop 230 does not extend beyond the outer surface of the rail. In the off-center configuration, stop 230 pivots away from the rail and prevents passage of control member 24.

In one aspect, only the proximal stop 230 is a "quick disconnect" stop, however, both proximal and distal stops 230, 232 can have a quick disconnect configuration. In another embodiment, the connection between control member 24a and rail 224 can be a quick disconnect. For example, guide member 234 can detachably mate with rail 224a.

In one aspect, the movable connection between the control member and the rail and/or between the rail and the frame requires user input in order to move tool 40a, 40b. The amount of force required to move control member 24 can be chosen such that gravity alone does not cause the control member to move when a user removes their hand. In one aspect, the guide members 234, 235 can be configured to allow translation and/or rotation while providing some frictional resistance to movement. Thus, when a user removes a hand from the control member, the frictional resistance between the control member and rail will hold the control member in place relative to the rail, the guide tube, the frame, a patient, and/or a reference point. One skilled in the art will appreciate that the materials and/or inner dimensions of the guide members, rails, and/or frame can be chosen according to the desired frictional resistance.

In another aspect, system 20 includes a damper to increase the force required to move the tools. For example, the damper can prevent movement of a tool where the force applied by the user is below a predetermined threshold and/or can limit the maximum velocity of the tool. In addition, or alternatively, the damper can smooth the resultant tool movement from a user's input forces. If the user's inputs are jerky or inconsistent, the damper can improve the consistency and/or predictability of tool movement.

Figure 59A:
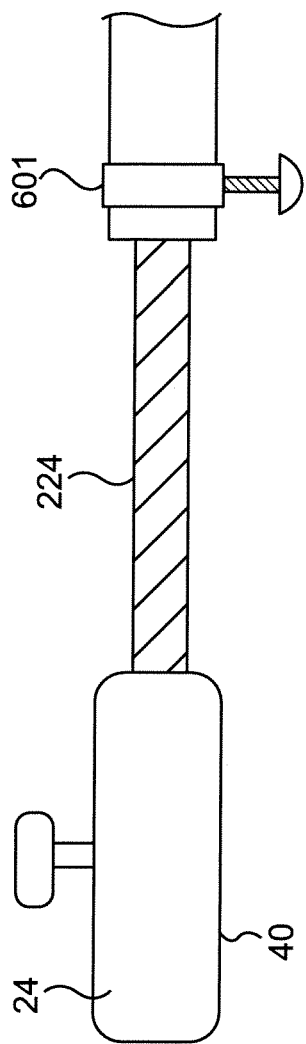
FIGS. 59A, 59B, and 59C illustrate various locking and/or damping elements for use with a system described herein.

A variety of dampers can be used with system 20. FIG. 59A illustrates an adjustable constricting ring 601 that allows a user to control the frictional resistance to movement of tool 40. In another aspect, a hydraulic damper could be incorporated into system 20. For example, where two parts of the system move with respect to one another (e.g., the control member with respect to the rail and/or the rail with respect to the frame), a hydraulic damper can damp relative movement.

In another aspect, the damper can damp one degree of freedom to increase the force required to move the tool in the one degree of freedom, but not damp another degree of freedom. In one example, the damper can increase the force required to move the tool longitudinally, but not the force required to rotate the tool and/or not the force required to manipulate the handle of the control member. Damping one degree of freedom without damping another can reduce the chance of unwanted or non-intuitive tool movements where two degrees of movement are controlled by similar user inputs.

In addition, or in the alternative, system 20 can include a brake or lock for preventing movement of control members 24a, 24b relative to the rails, guide tube, frame, patient, and/or point of reference. In one aspect, when engaged, the lock can increase resistance to movement between the rail and control member and thereby inhibit movement of the tool. While a variety of locks can be used, in one aspect, system 20 includes a lock that can independently lock different degrees of freedom, such as, for example lockable roller bearings. In use, movement of the roller bearings in one direction is inhibited to lock one degree of freedom of the control member. In another embodiment, the lock can inhibit multiple degrees of freedom and include, for example, frictionally or magnetically driven brakes. A magnetic lock can include an electromagnet positioned on the rail and/or control member and a ferrous substance positioned on or defining a portion of the control members 24a, 24b and/or rails 224a, 224b.

Figure 59B:
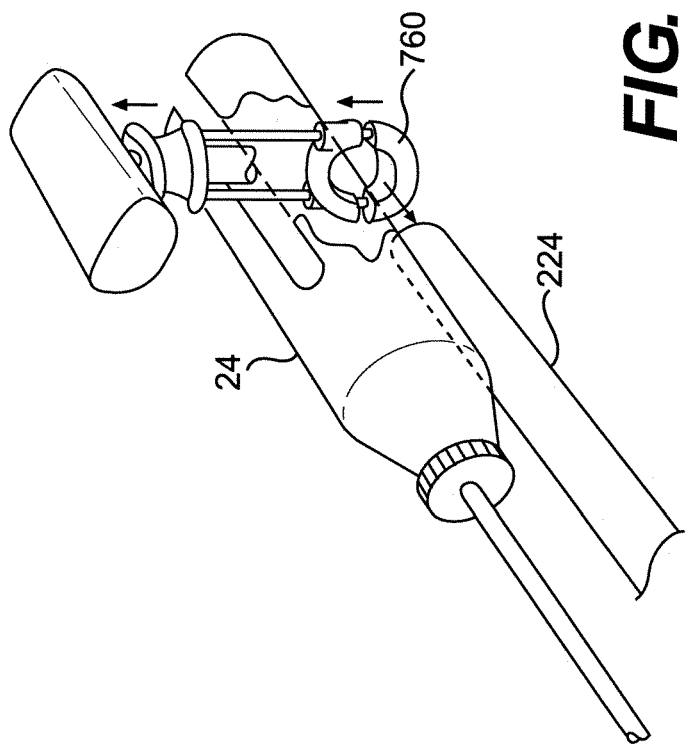

FIG. 59B illustrates another embodiment of a lock for inhibiting movement between the control member and rail. In one aspect, the a collar 760 extends at least partly around rail 224. When tightened, collar 760 can inhibit rotation and/or translation of control member 24 with respect to rail 224. Collar 760 can be used in addition to guide members 234, 235 or can be substituted for one or both the guide members. Thus, in one aspect, locking collar 760 can mate control member 24 and rail 224.

In one aspect, collar 760 can be controlled via an actuator on control member 24 to permit on-the-fly locking. For example, pull wires can extend between the control member and collar 760 to permit locking of control member 24 without a user removing his or her hand from the control member.

Figure 59C:
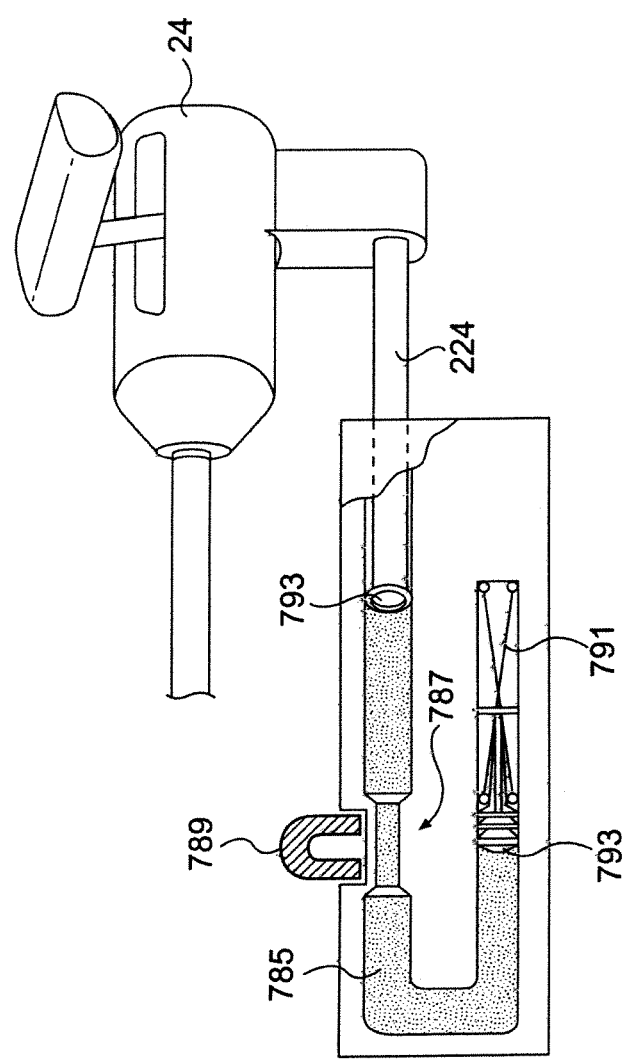

In another embodiment, the control member 24 can be locked using magnetic rheological fluid. A portion of control member, or a structure mated with the control member, can move through magnetic rheological fluid as the control member travels along the rail. To lock the control member, a magnetic field can be applied to the fluid, locking the control member in place with respect to the rail. FIG. 59C illustrates control member 24 and rail 224, with rail 224 extending into a chamber 785 containing magnetic rheological fluid. As rail 224 moves into chamber 785, the fluid flows through a constricted area 787 of chamber 785. In order to inhibit further movement of rail 224 and control member 24, a magnetic field is applied with magnet 789, causing the magnetic rheological fluid to stiffen.

Chamber 785 can include a counter force defined by springs 791. After removing the magnetic field rail 224 can be moved backwards. Springs 791 can force the magnetic rheological fluid back through constricted area 787 as rail 224 withdraws from chamber 785. The rail and springs can therefore apply opposing forces to move the magnetic fluid back and forth as the rail moves back and forth.

In one aspect, rail 224 and springs 791 can include a fluid seal 793 to prevent leaking of the fluid. In addition, the seals 793 can prevent the passage of air into passage 785 and inhibit separation of rail 224 from the magnetic rheological fluid. Thus, locking or stiffening the magnetic rheological fluid can additionally inhibit backward movement of control member 24 via suction.

In other aspect, rail 224 and/or control member 24 can be locked and/or damped directly with magnets. For example, rail 224 can be ferrous. A magnet can be moved into position and/or activated to inhibit movement of the rail. In one aspect, a portion of system 20 adjacent to rail 224 can be magnetized to inhibit movement of the rail.

As mentioned above, tools 40a, 40b can include proximal control members 24a, 24b and distal end effectors. In some cases, a user may wish to determine the distance traveled by the distal end of the tools, based on the location of the proximal control members. In one aspect, rails 224a, 224b can include visual and/or tactile feedback to assist with determining the location of and/or distance traveled by the distal end of the tools 40a, 40b. FIG. 60 illustrates one embodiment of a marking system 236 that can be positioned adjacent to rail 224 to assist the user with determining the location of and/or distance traveled by the tools. Indicia 236 on the rail, frame, tool, and/or surrounding environment can permit a user to determine tool location and/or measure tool movement. The indicia are positioned to allow measurement of the distance traveled by control member 24 relative to frame 22 and/or rail 224. In one aspect, translational movement of control member 24 relative to rail 224 and/or frame 22 can be measured with indicia. In another aspect, indicia allow measurement of rotational movement of control member 24 relative to rail 224 and/or frame 22

Figure 61:
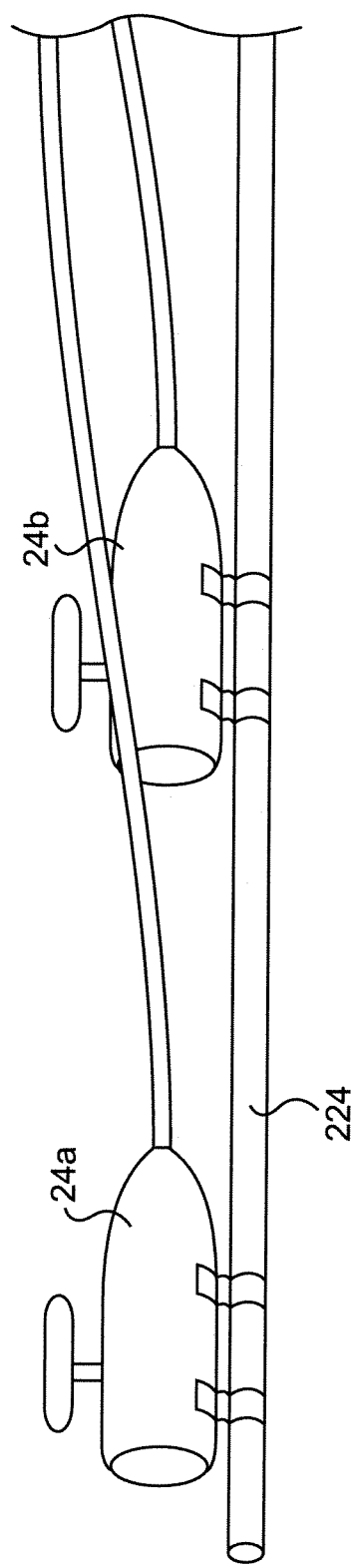

While system 20 is generally described with respect to one tool per rail, the use of more than one tool per rail is contemplated. For example, tools 40a, 40b can be positioned adjacent to each other on a single rail. In addition, or alternatively, system 20 can include more than two tools on two or more rails. FIG. 61 illustrates one example of two control member 24a, 24b positioned on a single rail 224. In another aspect, system 20 can include multiple rails with multiple tools.

The control members 24a, 24b illustrated in FIGS. 1 and 44 rotate about an axis defined by the rails, which is offset from the entrance to guide member 26 and offset from the location of catheters 25a, 25b. As a result, when the control members 24a, 24b rotate about rails 224a, 224b, the rotational movement of the control members can cause not only rotational movement of the catheters, but can also cause longitudinal movement (push/pull movement) of the catheters. In other words, where a user inputs only rotational movement to the control members, the resulting movement of catheters can include both rotational and longitudinal movement. Because one degree of movement of the control members (rotation) influences two degrees of movement of the catheters (rotation and translation), a user may find that control of tools 40a, 40b via movement of control members 24a, 24b is not intuitive.

Described herein are various embodiments of system 20 adapted to disconnect (or minimized the influence of) the rotational movement of the tools from (on) the longitudinal movement of the tools. Generally, these embodiments are referred to as "on-axis" systems.

In one embodiment, system 20 can include catheter holders 242a, 242b. The catheter holders can align at least a portion of the catheters with the rotational axis of the control members. With respect to FIGS. 1 and 44, the catheter holders 242a, 242b can align the catheters 25a, 25b with an axis L-L defined by rails 224a, 224b (the axis of rail 224a is indicated by a dashed line L-L in FIG. 44). In use, catheters 25a, 25b can extend from the control members 24a, 24b; through an aperture in the catheter holders 242a, 242b, which is coaxial with rails 224a, 224b; and into guide tube 26.

The catheter holders 242a, 242b can allow rotation and/or longitudinal movement of the catheters with respect to the catheter holders, while keeping a portion of the catheter aligned with the rotational axis of the control members 24a, 24b. In one embodiment, shown in FIG. 44, the catheter holders 242a, 242b can be defined by "U" shaped holders having an open upper surface. In use, the catheters can be quickly attached/detached from frame 22 by sliding the catheters 25a, 25b into/out of holders 242a, 242b. The catheter holders inhibit radial movement (i.e., movement in a radial direction away from the rotational axis of the control members), but allow axial and/or rotational movement of the catheters.

While the illustrated catheter holders 242a, 242b extend from a portion of frame 22, the catheter holder can be mated or defined by a different part of system 20. For example, the catheter holders can be defined by or mate with guide tube 26, with rails 224a, 224b, and/or with another frame.

In one aspect, catheter holder 224a, 224b additionally or alternatively mate with the working channels 44a, 44b. For example, the catheter holders can mate with a portion (e.g., the proximal end) of the working channel bodies. In one aspect, the catheter holders can detachably or fixedly mate with the working channel bodies. In another embodiment the catheter holders can be integral with or defined by the working channel bodies. Regardless, the catheters, in one aspect, can mate with the catheter holders by passing through the working channels while the working channels are mated with the catheter holders. The catheter holders can thereby inhibit radial (but not longitudinal and/or rotational) movement of the catheters with respect to the frame and/or working channels at the location where the catheters mate with (e.g., extend through) the catheter holders.

In another embodiment, control member 24 can rotate independently of the rail. The axis of rotation of the control member can provide independent rotation and longitudinal movement of tool 40. In one aspect, the axis of rotation corresponds to a portion of the catheter. In one example, the tools can rotate around an axis that extends through a point proximate to the interface between the control member and the catheter. In another aspect, the control member can rotate about an axis defined by, or in close proximity, to an axis defined by a portion of the catheter.

FIGS. 62A through 62C illustrate control member 24a configured to rotate about an axis co-linear with a portion of catheter 25. With respect to FIG. 62A, the control member can rotate about an axis C-C that is coaxial with a portion of catheter 25. In one aspect, axis C-C extends through catheter 25 adjacent to control member 24. In another aspect, axis C-C extends through the location at which catheter 25 mates with control member 24.

As illustrated, control member 24 can rotate independently of rail 224 while rail 224 remains fixed in position. In one aspect, control member 24 includes first and second body member. The first body member can movably mate with the rail and movably mate with the second body member. The movable connection between the first body member and the rail can provide one degree of freedom, for example, longitudinal movement. The movable connection between the first body member and an the second body member can provide another degree of freedom to the control member (with respect to the frame, rail, and/or guide tube), such as, for example, rotation. In the illustrated embodiment of FIGS. 62A through 62C, a first body member 233 is defined by guide member and a second body member 228 is defined by a portion of control member 24 that rotatably mates with the first body member.

The first body member 233 can mate with rails in a variety of ways, including, for example, via a lumen which receives rail 224a. In one aspect, first body member 233 can translate relative to rail 224a, but cannot rotate relative to rail 224a. For example, as mentioned above, rail 224a can have a non-cylindrical configuration that mates with a non-cylindrical lumen of the guide member. The first body member can include a proximal arm and a distal arm that movably mate with second body member 228. FIGS. 62B and 62C illustrate exemplary mating features that allow one degree of freedom, rotation, of the second body member 228 of control member 24 relative to the first body member 233 and rail 224. In particular, the proximal arm of the guide member can define a shaft around which control member 24 rotates. Alternatively, the proximal arm can receive a portion of the control member configured for rotation within the proximal arm (FIG. 62C). The distal arm can have a configuration similar to the proximal arm. Alternatively, as illustrated in FIG. 65A, the distal arm can define a support cradle that allows rotation of the control member relative to rail 224a.

Providing a control member that rotates around its own axis permits tool 40 to freely rotate. In particular, catheter 25 will not wrap around rail 224 as the control member 24 is rotated.

Figure 63A:
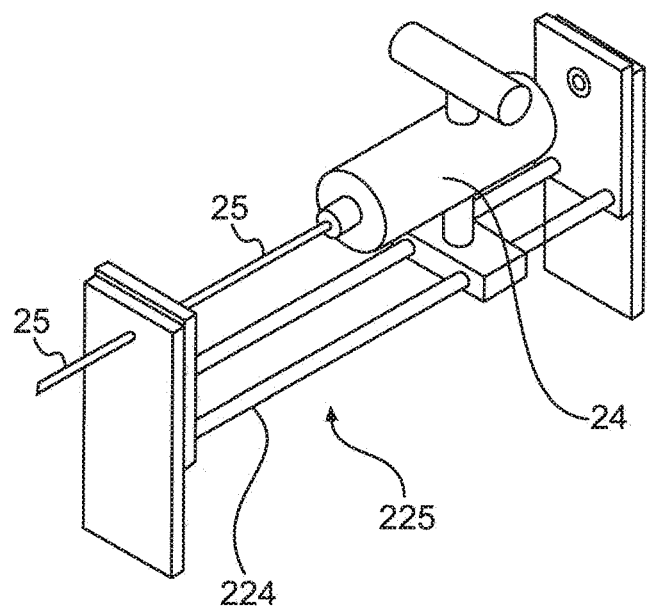
FIGS. 63A, 63B, 64A, 64B, 64C, and 65 are perspective views of various exemplary rails and tools described herein.
Figure 63B:
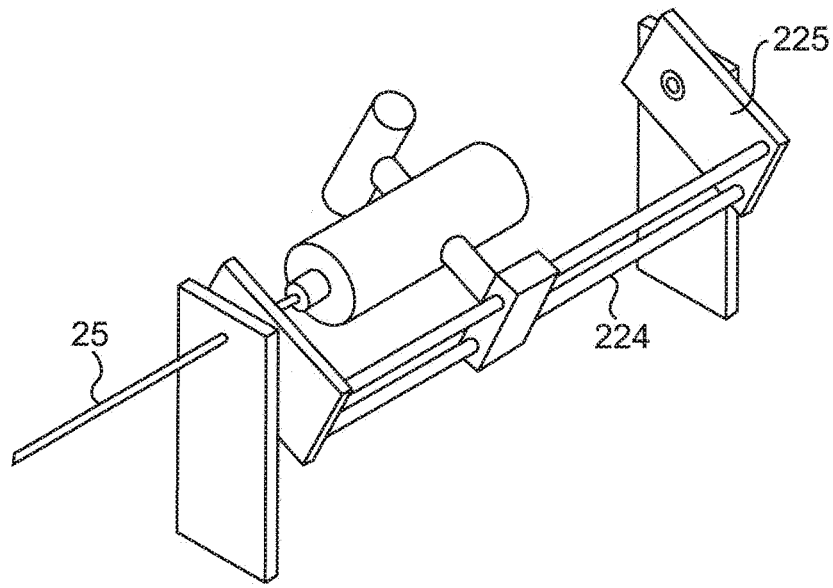

In another "on-axis" embodiment, the rails can rotate around the catheter and/or around an axis defined by, or in close proximity, to an axis defined by a portion of the catheter. FIG. 63A illustrates rotatable rail 224 defined by a cradle 225 and including first and second elongate members. Control member 24 can move longitudinally relative to rail 224, but cannot pivot or rotate about the rail. However, cradle 225 is movable mated to system 20 such that that cradle and control member can rotate together. In one aspect, the rotational axis of cradle 225 is aligned with catheter 25 such that rail 224 and control member 24 rotate around an axis co-linear with a rotational axis of the catheter. In particular, the catheter 25 can pass through the axis of rotation of cradle 225. For example, the cradle can include an aperture at the axis of rotation.

In another "on-axis" embodiment, at least a portion of the catheter is positioned within the rail. In addition, the rail can rotate about the catheter and/or the rail and catheter can rotate together. The axis of rotation can be defined by the rail and/or by the catheter within the rail. For example, rail 224 can rotate and/or move longitudinally with respect to the frame. In one such embodiment, illustrated in FIGS. 64A and 64B, instrument 40 fixed mates with rail 224, such that the control member 24 and rail 224 move together to provide one or more degrees of freedom to tool 40. The rail movably mates with the frame to allow rotation and/or longitudinal movement. When a user applies a rotation and/or translational pressure on control member 24, rail 224 can move relative to rail mount 239, frame 22, and/or guide tube 26.

Figure 64A:
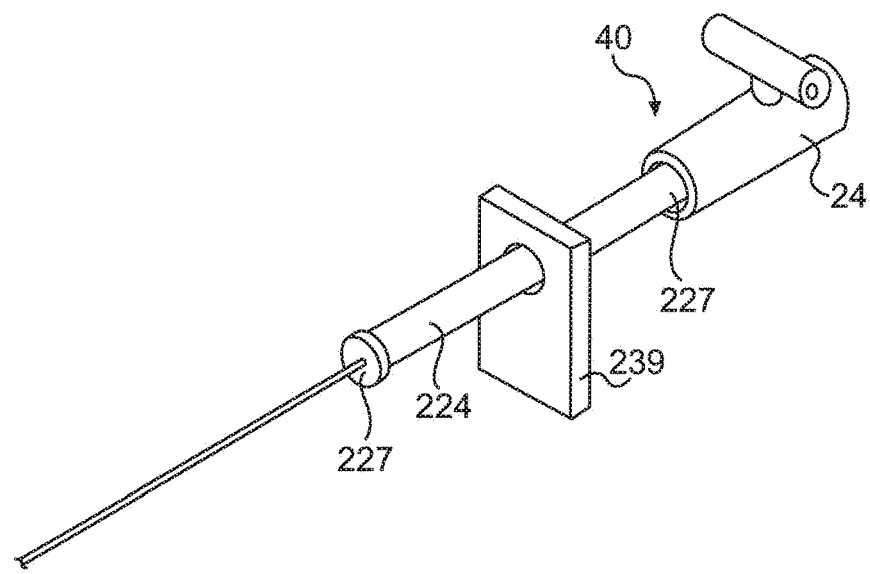
Figure 64B:
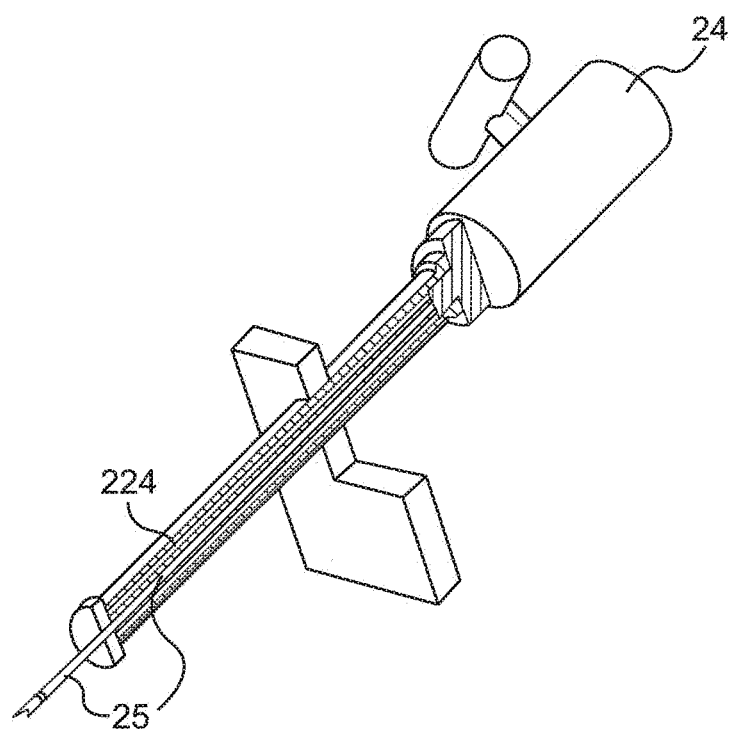

As shown in FIG. 64B, the catheter 25 of tool 40 can extend through a portion of rail 224. Having catheter 25 extend through rail 224 (and through rail mount 239) can permit co-axial rotation of the control member, rail, and catheter. In addition, tool 40 can freely rotate without the catheter entangling frame 22 or wrapping around rail 224.

Figure 64C:
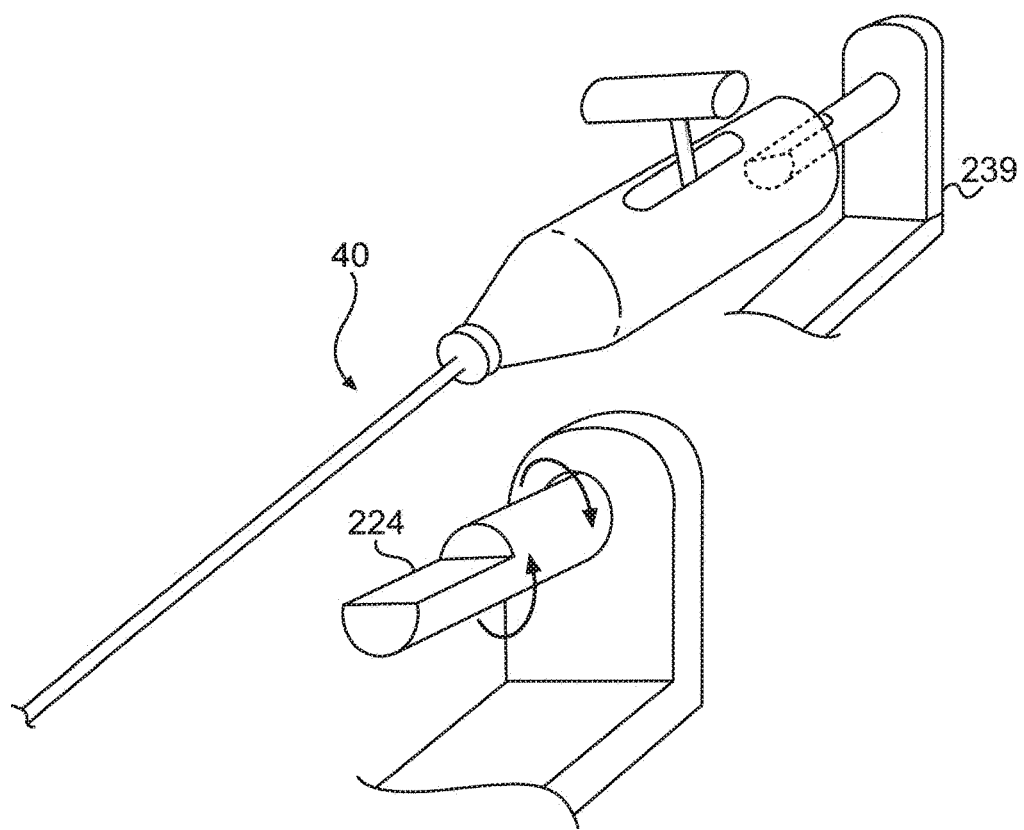

FIG. 64C illustrates another embodiment of rail 224 rotatably mated with frame 22. The rotatable connection between the rail and frame permits tool 40 to rotate relative the frame, guide tube (not illustrated), patient (not illustrated), and/or another point of reference. In order to provide longitudinal movement, rail 224 can move with respect to the frame and/or the control member can slide along rail. In one aspect, rail 224 is movably mates with the control member to allow the control member to translate with respect to the frame, guide tube, point of reference, etc. For example, a portion of the rail can be received within the control member and movably mated therewith. Regardless, unlike FIGS. 64A and 64B, the catheter need not be positioned within the rail.

In one aspect, with respect to FIGS. 64A through 64C, movement of rail 224 is limited by collar(s) 227 (FIG. 64A) positioned on either end of the rail. Contact of collar 227 with rail mount 239 can act as a stop to limit longitudinal movement of tool 40.

In yet another embodiment, a portion of catheter 25 can define the rail(not illustrated). For example, the catheter can include a generally rigid section that movably mates with a frame, such as, for example, rail mount 239. Control member 24 and catheter 25 can be moved together relative to the frame, guide tube, surrounding environment, and/or a patient to control movement of the instrument.

Figure 65:
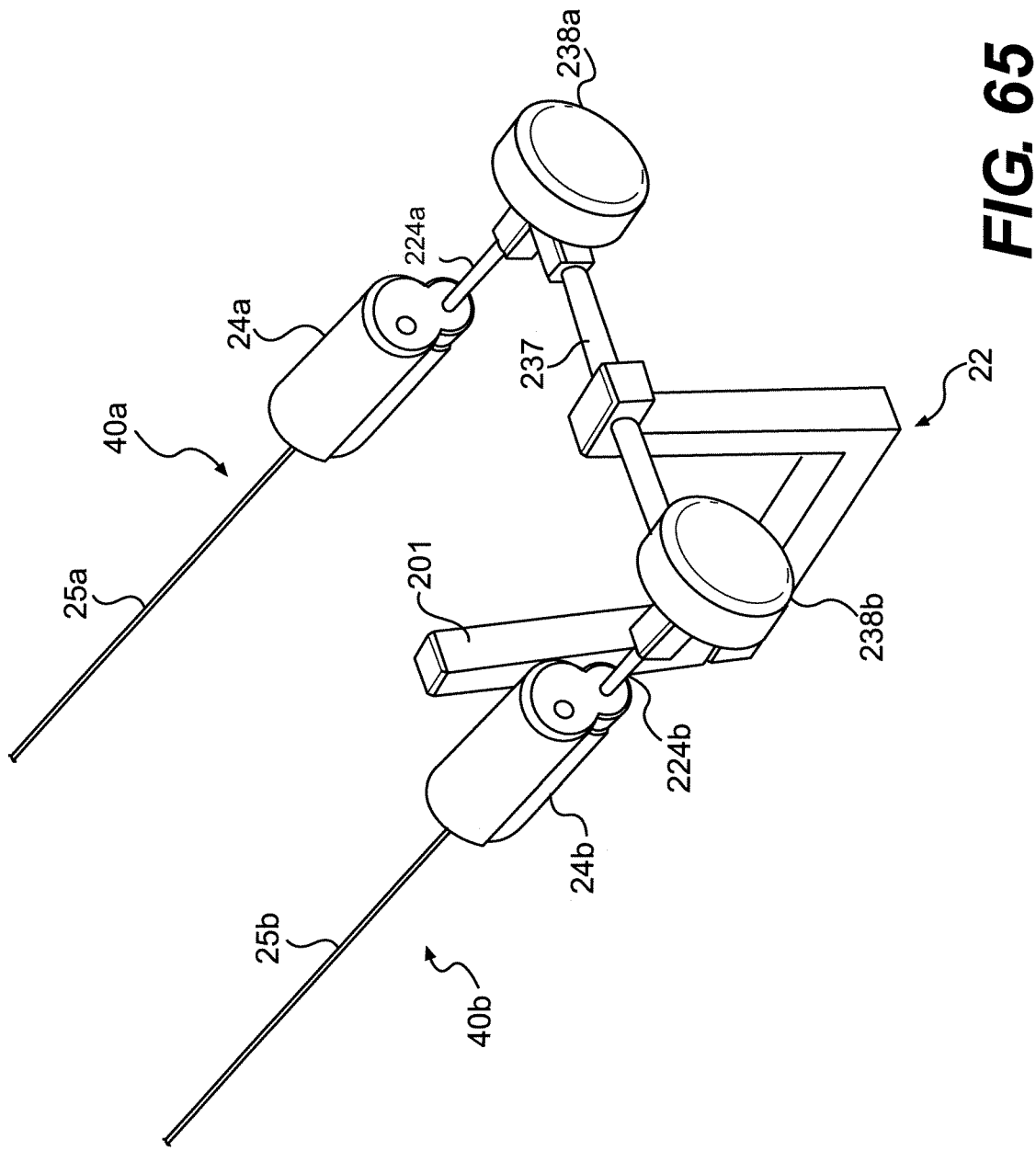

While the distal ends of the rails are described as mated with system 20, the proximal ends of the rails can alternatively mate with the system. FIG. 65 illustrates frame body 201 connected to rails 224a, 224b at the proximal end of the rails. The catheter bodies 25a, 25b of tools 40a, 40b can extend distally to guide tube 26 (not illustrated). Proximal mating of rails 224a, 224b with the frame of system 20 permits rotation of control members 24a, 24b without catheters 25a, 25b of tools 40a, 40b wrapping around or tangling with frame 22. In addition, control members 24a, 24b can be rotate 360 degrees or more.

In one aspect, the proximal ends (or a region proximate to the proximate ends) of the rails can mate with a crossbar 237 that extends from frame 22. For example, rails 224a, 224b can extend through an aperture or lumen in crossbar 237. Alternatively, each of the rails 224a, 224b can mate with separate with portions of the system or separate frames. Regardless, the connection between rails 224a, 224b and system 20 can include the various features of the control member/rail connection described above, including, for example, a locking feature to selectively inhibit movement between rails 224a, 224b and frame 22.

The control members 24a, 24b can be fixedly mated with rails 224a, 224b. Moving the rails longitudinally and/or rotationally results in a corresponding movement of tools 40a, 40b. In one embodiment, instead of a user directly manipulating the control members 24a, 24b, a user can interface with the rails or with a handle attached to the rails. For example, in FIG. 65, rails 224a, 224b can include proximal knobs 238a, 238b that allow a user to control at least one degree of freedom, and in another aspect, each knob allows a user to control two degrees of freedom of tools 40a, 40b. For example, the user can control longitudinal and/or rotational movement of tools 40a, 40b with knobs 238a, 238b. In one aspect, a user can rotate the tool 360 degrees or more without releasing the knobs. One skilled in the art will appreciate that the knobs are exemplary of the various handles or controllers that can be used to manipulate tools 40a, 40b, via rails 224a, 224b.

In another embodiment, knobs 238a, 238b can be configured to allow a user to control additional degrees of freedom. Knob 238a and/or knob 238b can include the features of handle 304 (described below) to actuate at least one degree of freedom of a distal end effector. In one example, knobs 238a, 238b can include a trigger for controlling actuation of a distal end effector.

In the illustrated embodiment of FIG. 65, control members 24a, 24b rotate around the axes of rails 224a, 224b. In one aspect, rails 224a, 224b could be co-axial with a portion of catheters 25a, 25b to permit rotation of tools 40a, 40b and/or knobs 238a, 238b around an axis corresponding to the catheters.

In still another embodiment of "on axis" rails used with the systems described herein, a rail can extend through a portion of control member 24 and/or catheter 25. FIGS. 66A and 66B illustrate control member 24 and catheter 25 with rail 224 extending through at least a portion of catheter 25. Tool 40 can rotate about rail 224 and/or move longitudinally on the rail. With rail 224 extending through a portion of catheter 25, the axis of rotation of control member 24 (or tool 40) can be co-linear or nearly co-linear with at least a portion of catheter 25. As illustrated in FIG. 66B, rail 224 can be slightly offset from the central axis of catheter 25 and still allow independent control of rotation and translation of tool 40 via control member 24.

Rail 224, of FIGS. 66A and 66B, in one aspect, is formed of a rigid or semi-rigid material. In another aspect, the rails can have varying rigidity such as a bendable or flexible segment that permits rail 224 and catheter 25 to follow a non-linear pathway and/or to articulate.

In one aspect, rail 224 mates with system 20 or the surrounding environment at a location proximal to the proximal end of the control member. Having rail 224 extend through at least a portion of the catheter can allow the rail to act as a guide wire. The rail 224 can first be directed to a target location and then used to position guide tube 26 and/or tool 40a. For example, the rail can be used in a fashion similar to a guide wire. In another aspect, rail 224 can be used to deliver electrosurgical energy. For example, the proximal end of rail 224 can be connected to an electrosurgical generator and can deliver energy to the distal end of tool 40, such as, for example to an end effector positioned at the end of tool 40.

Figure 67:
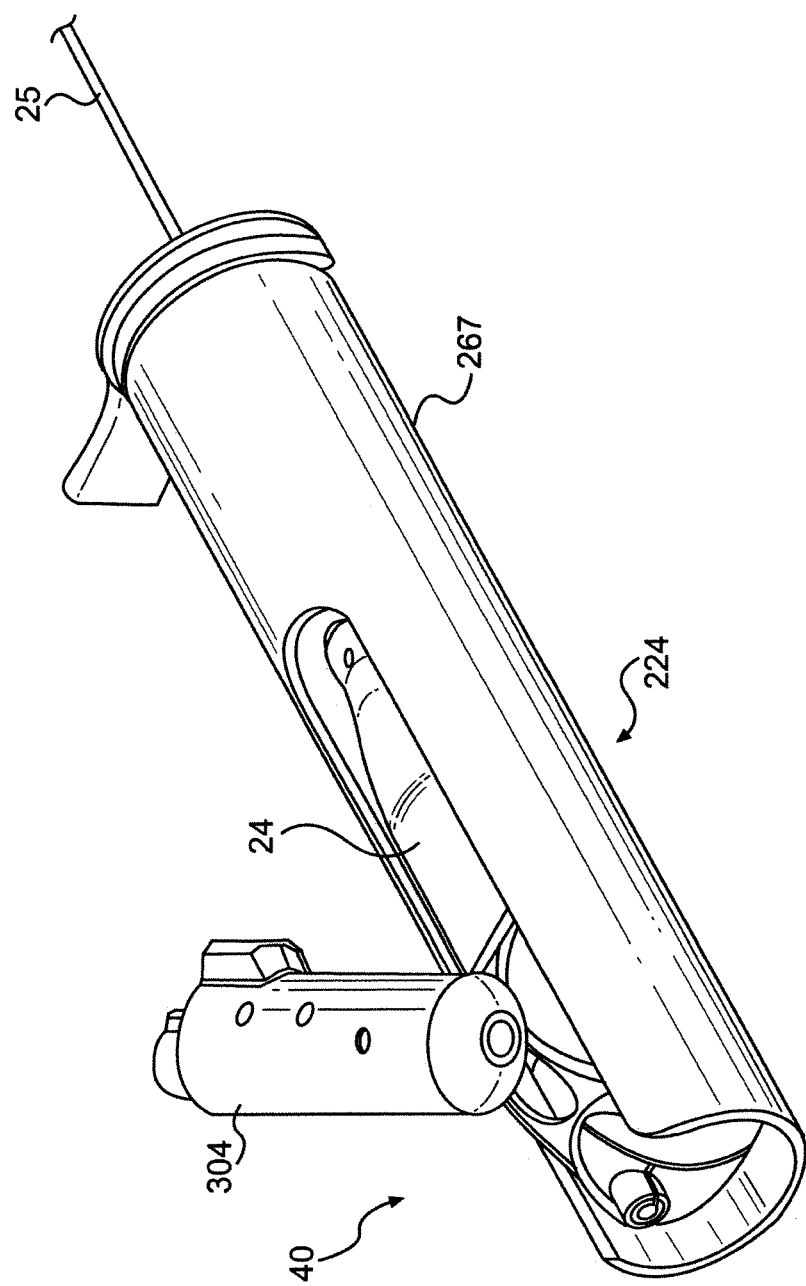
FIG. 67 is a perspective view of one exemplary embodiment of a control member and rail described herein.

In another embodiment of system 20, at least a portion of the control member 24 can be positioned within rail 224. FIG. 67 illustrates a sleeve 267 in which a portion of control member 24 sits. The control members can have at least one degree of freedom with respect to sleeves. As shown in FIG. 67 the sleeves 267 can each include an elongate slot sized and shaped to permit the passage of the control member handle 304 to permit the control members to move longitudinally with respect to the rails. To rotate tool 40, the control members 24 and sleeves 267 can rotatably mate with the frame (not illustrated). Rotating the control members 24 and sleeve together can rotate tools 40 and provide a second degree of freedom to tool 40.

In one aspect, rail 224 can house at least a portion of catheter 25 and sleeve 267 of FIG. 67 provides "on-axis" rotation of tool 40. In a further aspect, the axis of rotation of rail 224, as defined by sleeve 267, can be co-linear with a portion of the catheter. In yet a more specific aspect, the catheter can pass through the axis of rotation of sleeve 267. As a result, rotation of tool 40 is independent of translational movement of tool 40.

Figure 68A:
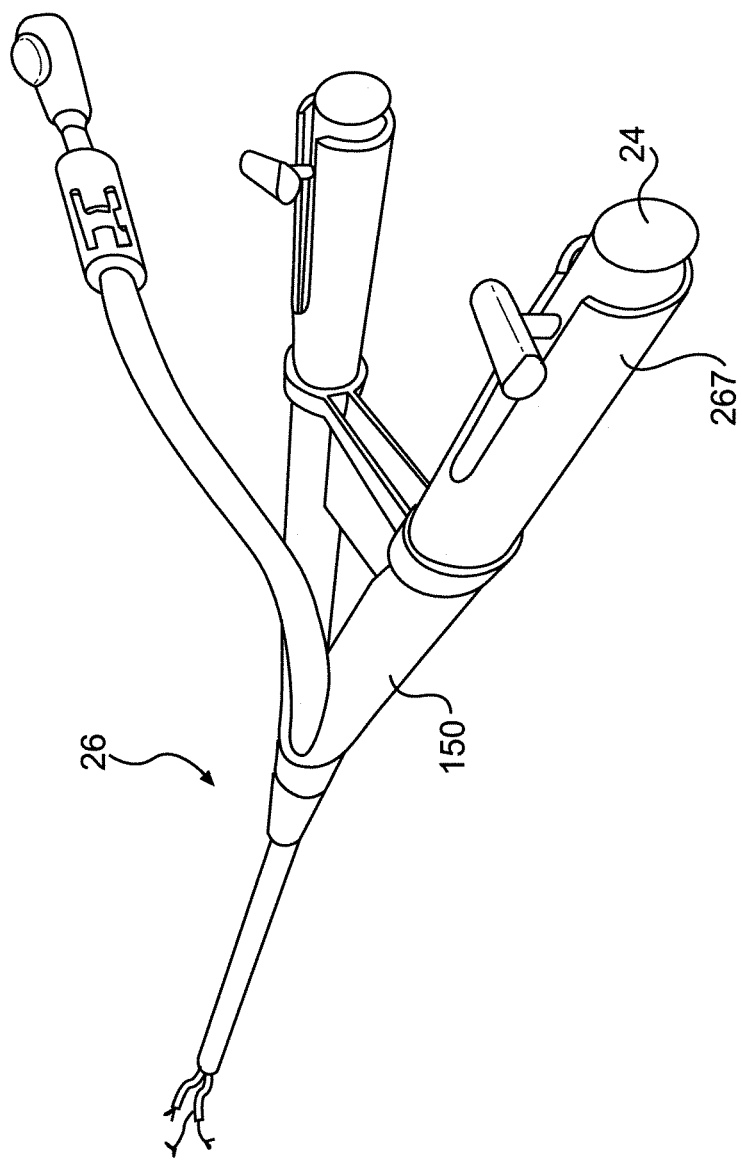
FIG. 68A is a perspective view of one exemplary embodiment of a control member and rail described herein.

As mentioned above, the rails described herein can be mated with or incorporated into other portions of system 20 besides frame 22. FIGS. 68A and 68B illustrate rails incorporated into guide tube housing 150. In one aspect, rails 224a, 224b are defined by sleeves 267 which are rotatably mated with housing 150.

Figure 69A:
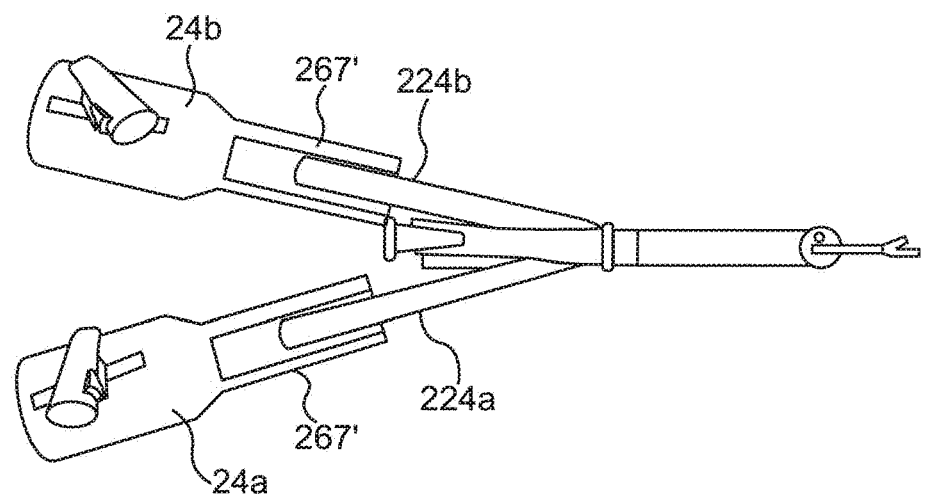
FIGS. 69A and 69B are partially transparent views of various exemplary embodiments of a control member and rail described herein.
Figure 69B:
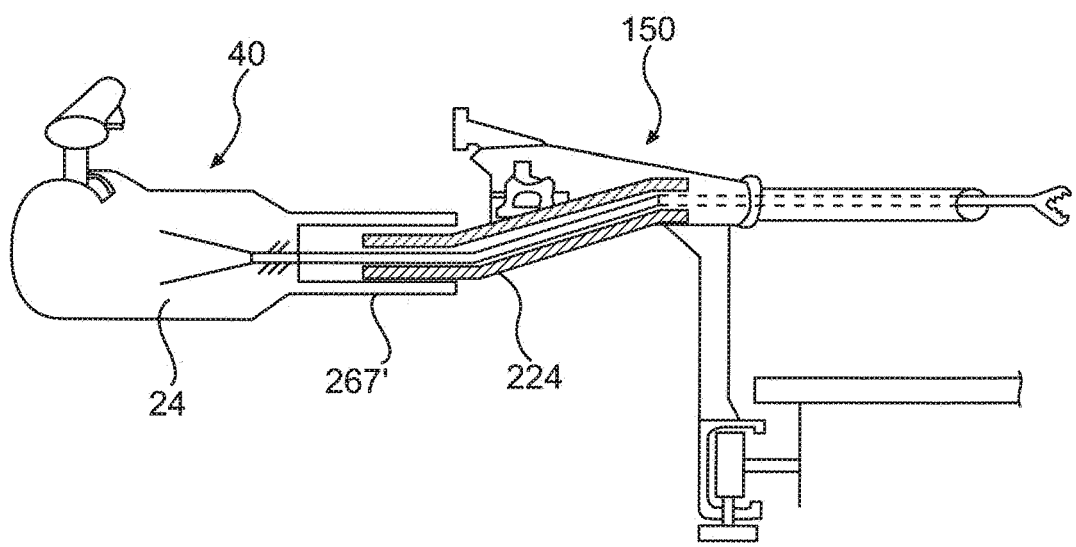

In another aspect, illustrated in FIGS. 69A and 69B, instead of the control members moving within sleeve 267, the control members include a sleeve 267' that receives a portion of rails 224 (as defined by guide tube housing 150). Sleeve 267' is configured to moveably mate with the rail and allow rotational and/or longitudinal movement of tools 40a, 40b. In addition, sleeve 267' can provide "on-axis" rotation of tool 40.

While a frame is not illustrated in FIGS. 68A through 69A, a frame could be used to support guide member 26 and/or sleeves 267. However, a separate frame device is not necessary to support the system of FIGS. 68A through 69B. For example, as shown in FIG. 69B, the guide tube housing 150 could mate with an operating table, patient, floor, ceiling, and/or other operating room structure.

In another embodiment, instead of moving the control members 24a, 24b relative to the rails (or moving the rails relative to the frame) to achieve longitudinal movement, the sleeves could have a telescoping configuration. FIG. 70 illustrates telescoping rails 224 having multiple segments 1224a, 1224b movably mated with one another. Longitudinal movement can be achieved by moving one of the segments into another segment. For example, a first segment 1224a can have a size and shape corresponding to an open channel within a second segment 1224b. Thus, pulling the control members toward the user causes telescopic expansion of rail 224. Similarly, the control members can be moved toward housing 150 by collapsing sections of the telescoping rail. While two telescoping segments are illustrated, three or more than three segments could be used.

In another aspect, the telescoping rail of FIG. 70 provides tool 40 with two degrees of freedom relative to the frame, guide tube, and/or a patient. For example, the segments 1224a, 1224b can rotate relative to one another to permit rotational movement of tool 40. Alternatively, the telescoping rail could provide only a single degree of freedom (moving longitudinally) and rotation of tool 40 could be provided by rotatably mating the telescoping rail with the control member and/or with the frame.

In one aspect, catheter 25 extend through the multiple segments of the telescoping rail to provide on-axis rotation of tool 40. In another aspect, control member 24 and telescoping rail 224 can rotate about an axis co-linear with the catheter axis.

The rails described can provide functionality in addition, or as alternative, to enabling tool articulation. In one embodiment, one or both of the rails 224a, 224b can control articulation of guide tube 26. As described above, guide tube 26 can include an articulation portion 56 that can move up/down and/or left/right. In one embodiment, the rails 224a, 224b can control at one degree of freedom of the guide tube 26, and in another embodiment, the rails can control two, or more than two degrees of freedom of guide tube 26.

Figure 71A:
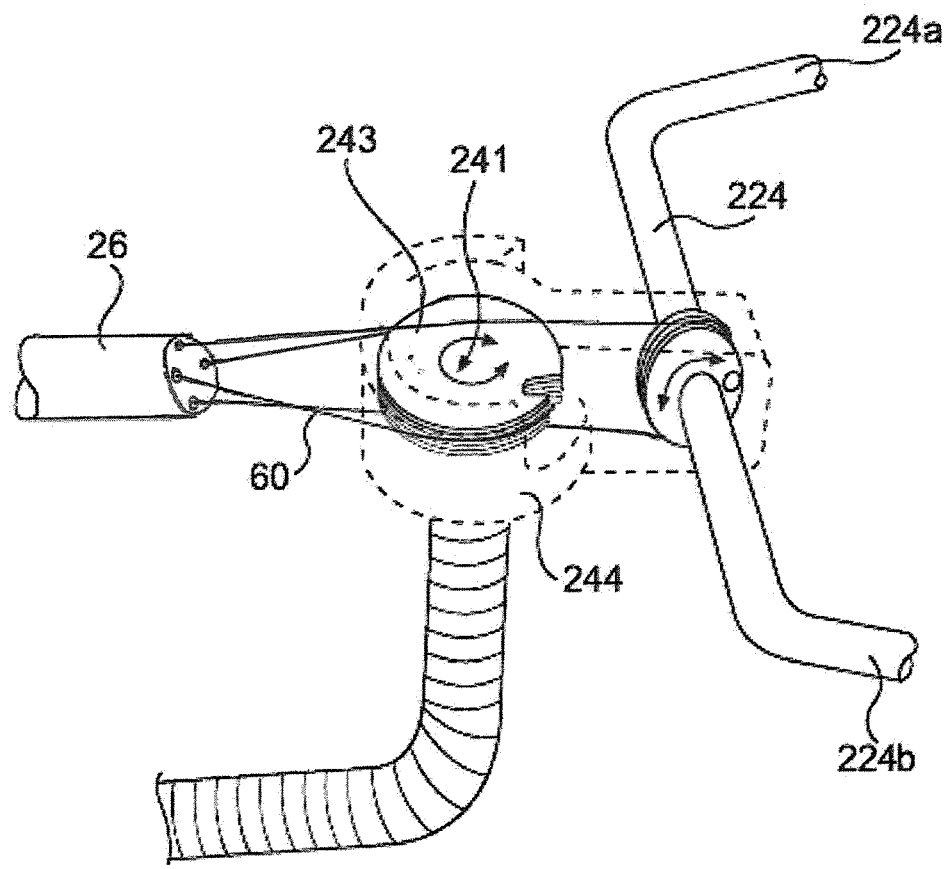
FIGS. 71A, 71B, 72, and 73 are various exemplary embodiments of a rail and guide tube described herein.
Figure 71B:
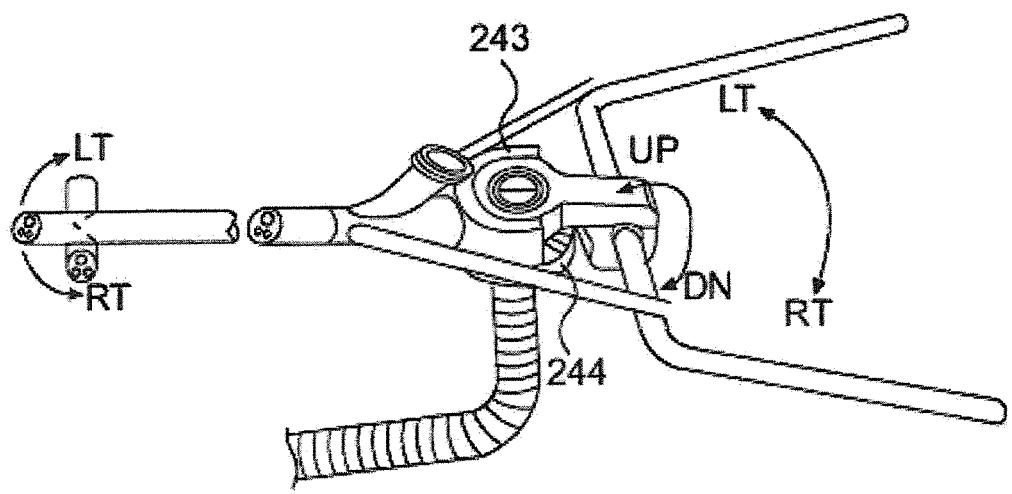

In one aspect, described above, the guide tube is controlled via strands 60 that extend from the distal articulation section of the guide tube to a proximal controller. As shown in FIGS. 71A and 7B, the strands can extend to rail 224 or to a location proximate to rail 224. In one aspect, rail 224 can movably mate with guide tube 26 to permit rotation of the rail with respect to the guide tube. Strands 60 can extend to rail 224 and mate therewith, such that rotating rail 224 pulls (and/or pushes) on strands 60. Thus, moving rail up and down with respect to the guide tube can control at least one degree of freedom of guide tube 26, and in particular, can control up and down movement of the articulation section of the guide tube. Similarly, rail 224 can be configured to pivot in a left/right configuration. When rail 224 is pivoted, strands 60 can be pulled (and/or pushed) to control at least one degree of freedom of the guide tube, and in particular, left/right movement of the articulation segment of the guide tube.

Thus, movement of rails 224a, 224b relative to guide tube 26 can drive movement of the guide tube. Alternatively, the guide tube housing can include a first and second body member. Movement of the first body member relative to the second body member can articulate the guide tube. In one aspect, the first body member can be fixedly mated with a rail or rails such that movement of rails moves the first body member with respect to the second body member and articulates the guide tube.

Figure 72:
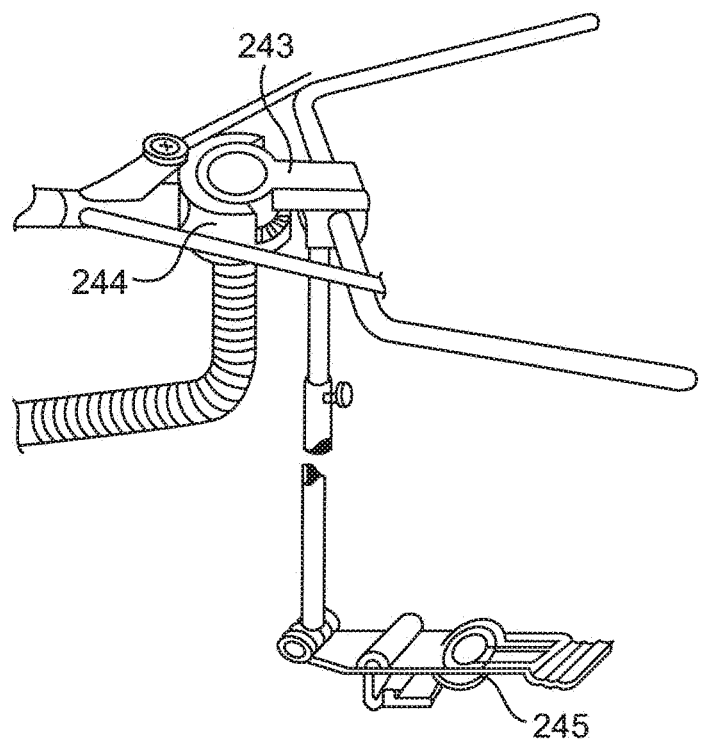

In one embodiment, the guide tube includes a joint 241, movement of which can drive a articulation of the guide tube. Joint 241 can mate with strands 60 such that pivoting joint 241 pulls (and/or pushes) on strands 60. Joint 241 can also be configured to allow locking of rail 224. For example, joint 241 can be comprised of an upper segment 243 and a lower segment 244. Upper segment 243, when unlocked, can pivot to control movement of strands 60, and conversely, when the upper and lower segments are locked to one another pivoting of the rail is inhibited. The upper and lower segments 243, 244 can include mating surfaces with corresponding surface features such that when the mating surfaces of the upper and lower segments are in contact with one another, the mating surfaces can engage one another and prevent movement of joint 241. One skilled in the art will appreciate that a variety of mating features, such as corresponding protrusions and grooves, can inhibit movement of the upper and lower segments 243, 244 when the mating surfaces are in contact. To unlock joint 241, a controller, such as foot pedal 245 (FIG. 72), can be activated to lift the upper segment 243 away from lower segment 244 and allow relative movement between the upper and lower segments.

Figure 73:
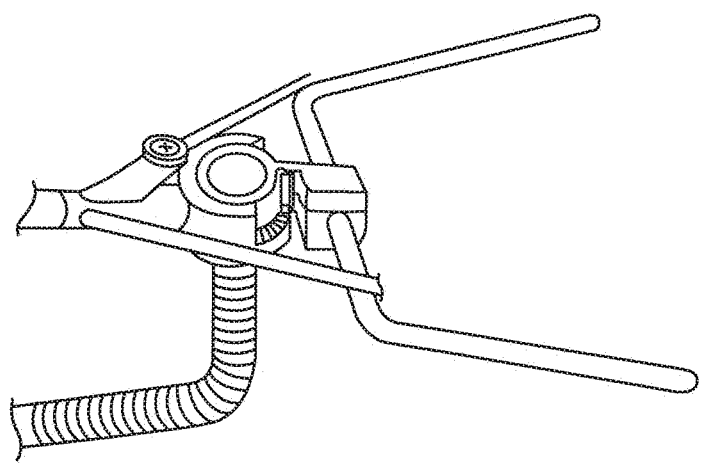
Figure 74:
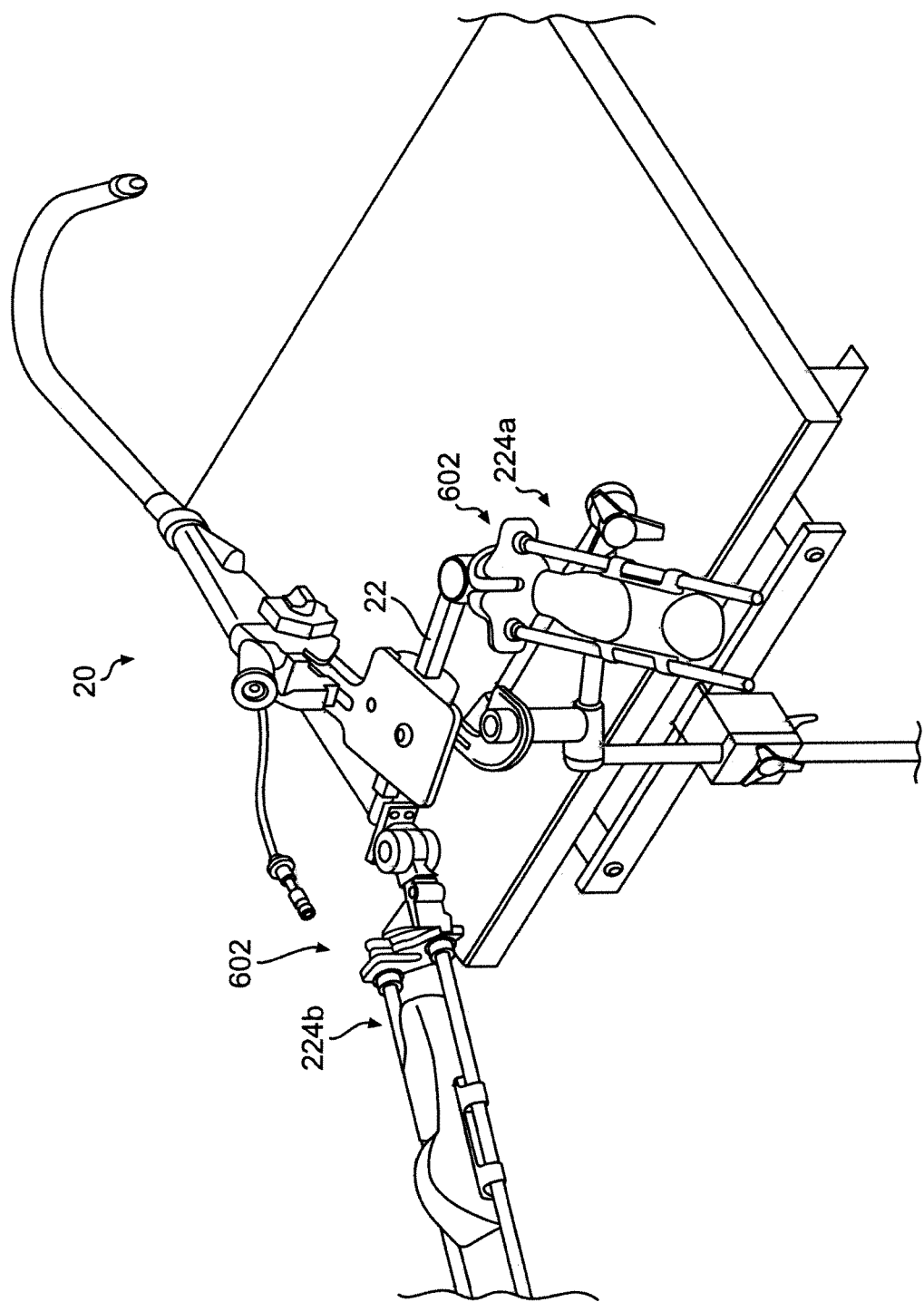
FIG. 74 is a perspective view of one exemplary embodiment of a system described herein.

The upper and lower segments of joint 241 can lock in a variety of alternative ways. For example, instead of mating protrusions/grooves, joint 241 can include a ball and detent system. FIG. 73 illustrates a spring loaded ball positioned on upper segment 243, that when activated, will engage detents on the lower segment 244. In one aspect, the ball and detent arrangement does not prevent articulation, but inhibits unwanted movement of the guide tube. After a user positions the guide tube in the desired configuration, the ball/detent lock can prevent unwanted movement of the rails. In another aspect, the force (i.e., spring) on the ball can be removed or reduced to allow movement of joint 241. One skilled in the art will appreciate that a variety of other locking features can be used to prevent unwanted movement of the guide tube articulation segment. In one exemplary embodiment a friction lock or mechanical lock prevent articulation of guide tube 26.

Figure 77:
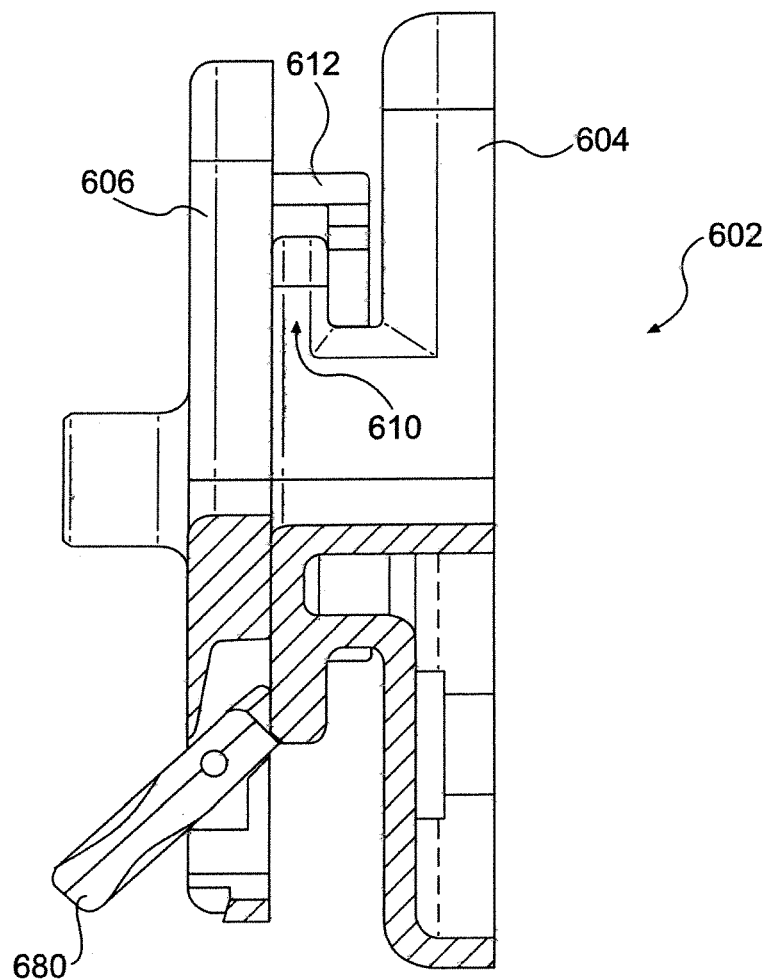

FIGS. 74 through 79 illustrate yet another embodiment of system 20 and rails 224a, 224b comprising a movable and detachable connection between rails 224a, 224b and frame 22. In one aspect, illustrated in FIG. 75, connection 602 comprises a first mating plate 604 and a second mating plate 606. When mated, the first and second mating plate include a passage 608 for catheter 25. In one aspect, passage 608 is co-linear or nearly co-linear with the axis of rotation of control member 24 to permit "on-axis" rotation of tool 40. FIGS. 76A and 76B illustrate front views two embodiments of first mating plate 604, 604'. First mating plate 604, 604' can include an offset lip 610 having a curved perimeter which can interlock with a corresponding hook 612 or hooks 612 on second mating plate 606. FIG. 77 illustrates first and second mating plates 604, 606 mated with one another. In user, hooks 612 can slide around the perimeter of offset lip 610 to permit rotation of second mating plate 606 with respect to first mating plate 604.

In one aspect, hooks 612 are disposed toward the upper surface of second mating plate 606 such that that second mating plate hangs on the first mating plate. The mating features (lip 610 and hooks 612) of the detachable connection 602 are sized and shaped to allow sliding therebetween. When a user torques tool 40, hooks 612 can slide over the top surface of lip 612 and permit rotation.

In one aspect, rotation beyond a predetermined angle will result in detachment of the first and second mating plates. As hooks 612 slide around lip 610, the hooks can fall of the side of lip 610. The detachable connection 602 can further include a lock to prevent unwanted detachment of the first and second plates. In one aspect, second mating plate 606 includes a pivotable latch 680 (FIG. 77) that can interlock with a corresponding feature on first mating plate 604. When second mating plate 606 is rotated beyond a predetermined distance, a portion of latch 680 can contact the surface of the first mating plate 604. Contact of latch 680 with first mating plate 604 can prevent further rotation of the second mating plate with respect to the first mating plate. To detach first and second mating plates 604, 606, latch 680 can be can be pivoted into a non-locking configuration. One skilled in the art will appreciate that other locking mechanisms, including various mechanical interlocks and frictional engagements can be substituted for the latch locking mechanism.

Figure 78:
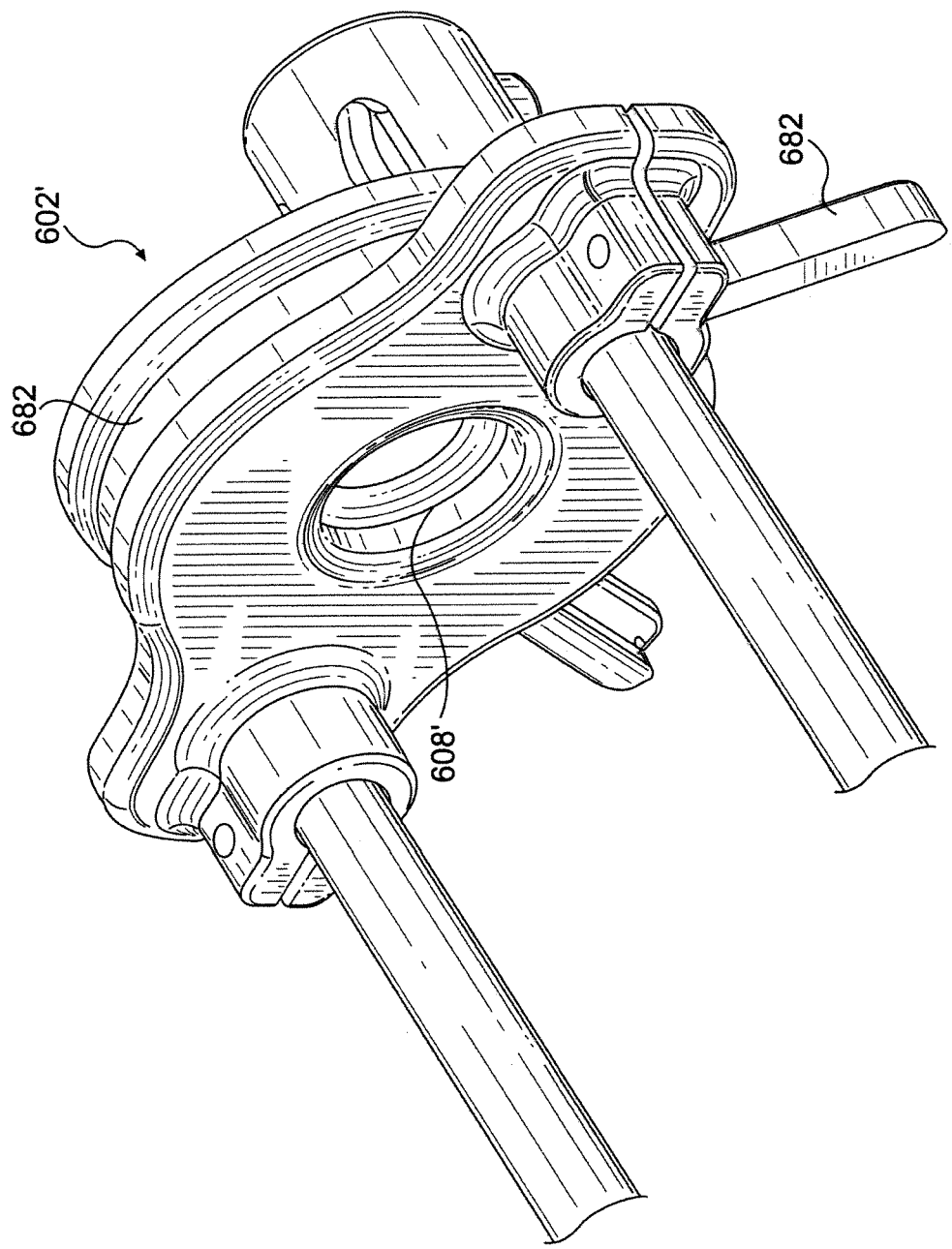
Figure 79:
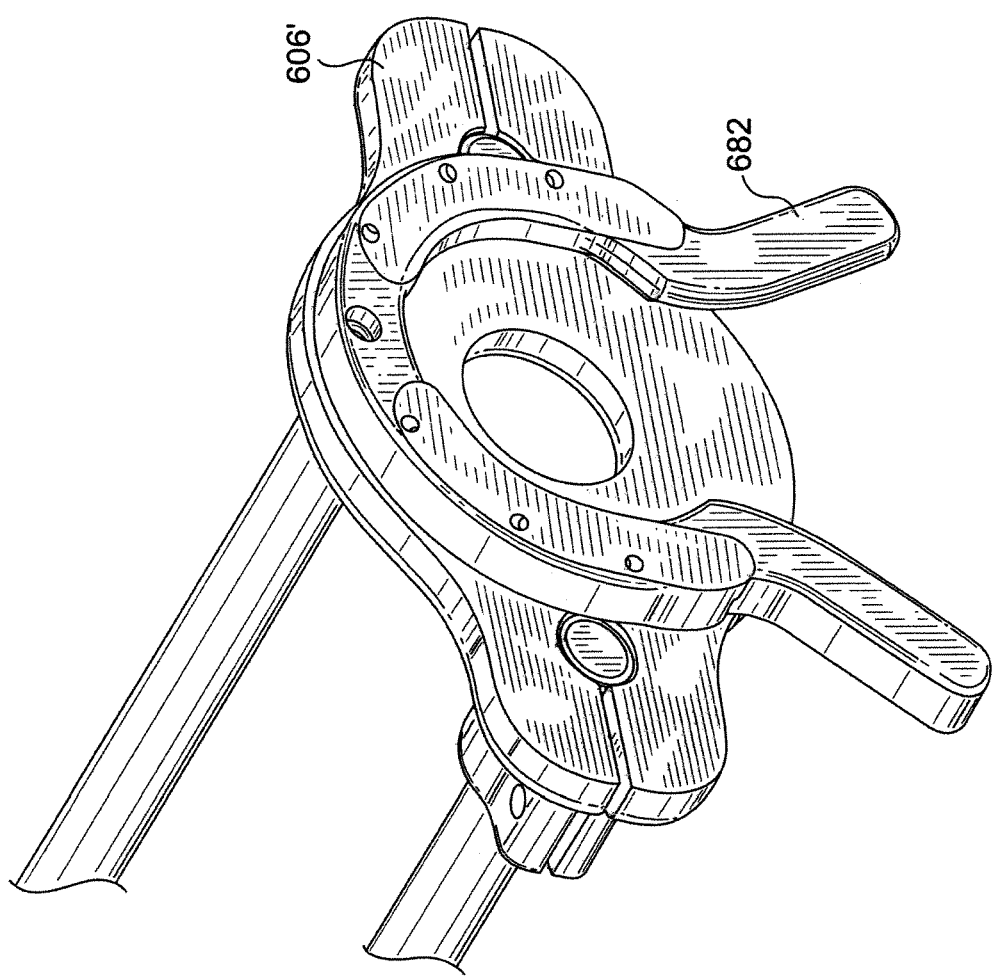

In another embodiment, a snap-ring can mate the first and second mating plates. FIGS. 78 and 79 illustrates detachable connection 602' including a snap ring 682 that mates with second mating plate 606' and corresponds to lip 610 of first mating plate 604, 604'. When the first and second plates are mated, snap ring 682 surrounds lip 610 to prevent accidental detachment of the first and second mating plates.

Figure 75:
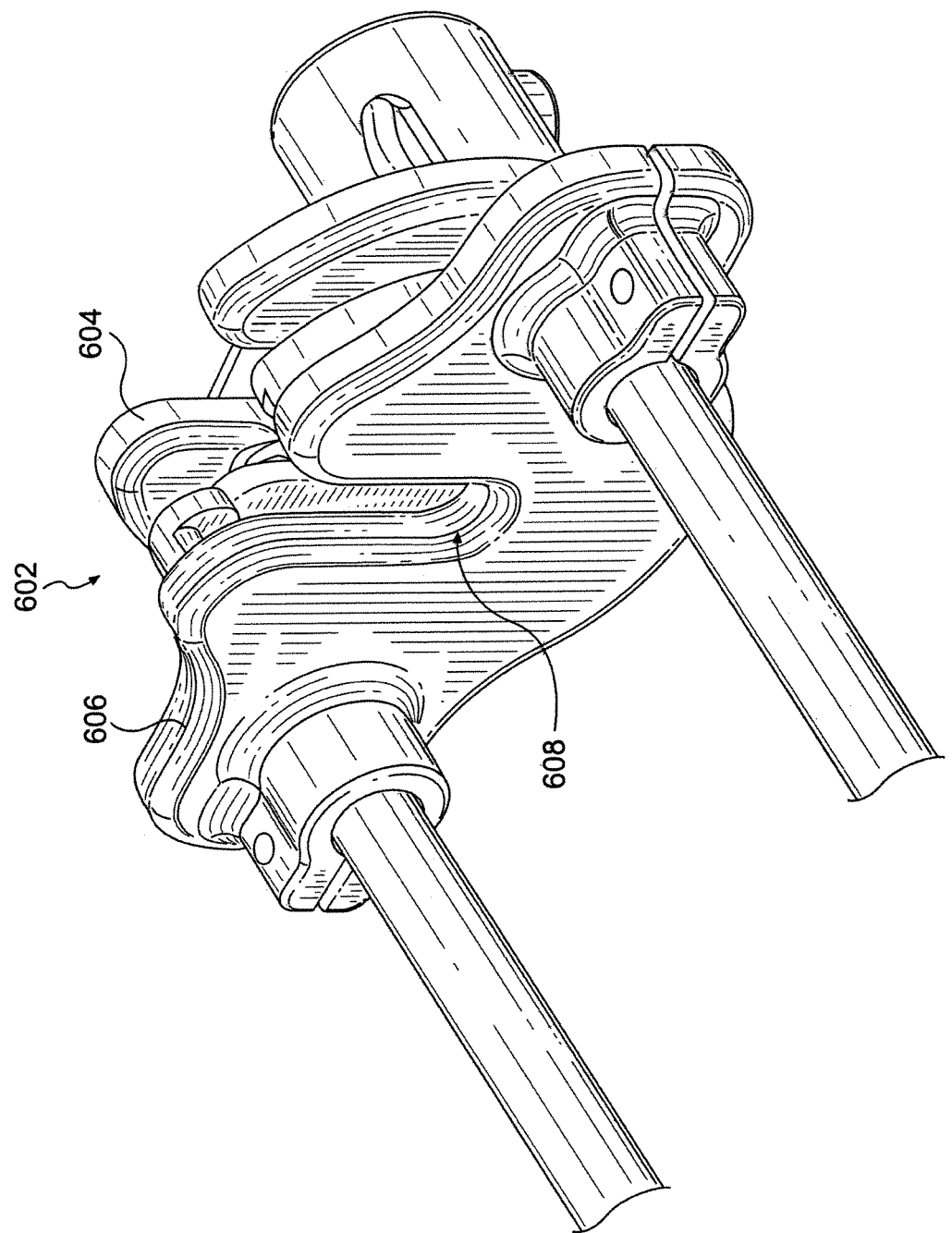
FIGS. 75, 76A, 76B, 77, 78, and 79 are views of various exemplary features of the system of FIG. 74.
Figure 76A:
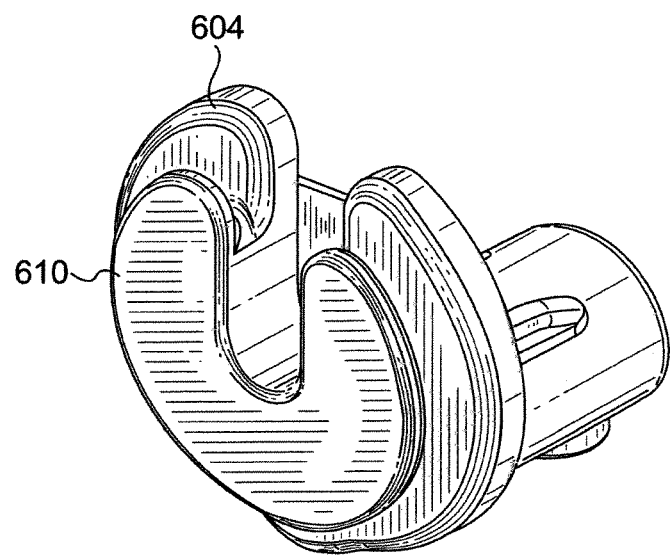
Figure 76B:
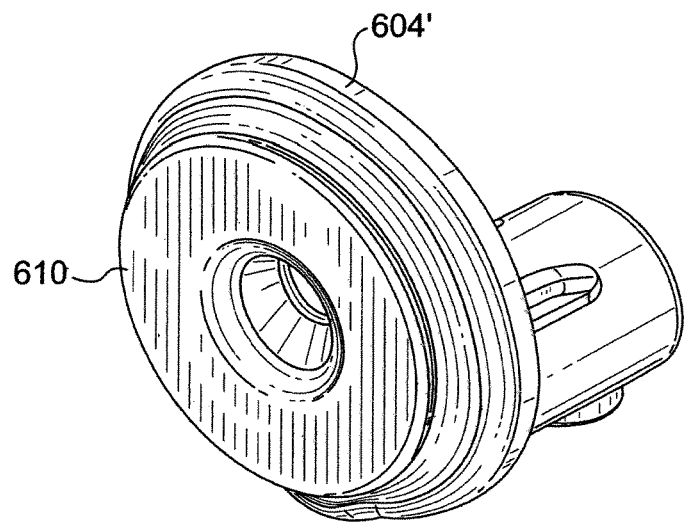

As mentioned above, the first and second mating plates can include passageway 608 for receiving a portion of tool 40 and for allowing movement of at least a portion of the tool through the passageway. In one aspect, passageway 608 includes on open upper surface to allow a user to place tool 40 in passageway 608. For example, passageway 608 can have a "U" shape as illustrated in FIG. 75. In another embodiment passageway 608' can be enclosed by the walls of the first and/or second mating plates 604, 606. For example, as illustrated in FIG. 78, a circular opening in the first and second plates allows passage of at least a portion of tool 40.

While several of the rail configuration described with respect to system 20 constrain movement of the tools along a linear pathway or pathways, frames and/or rails with different constraints are also contemplated. In one aspect, a frame and/or rail can constrain a control member to movement within a plane. For example, the control member can be mated with a surface that allows side-to-side movement in addition to forward-back movement. In another aspect, the control member can mate with a frame with a frame that permits movement in three dimension with respect to the frame, guidet tube, patient, and/or point of reference. For example, the control member can be moved side-to-side, forward-back, and up-down. Alternatively, or additionally, the control member can be rotated. In one aspect, the up-down and/or side-to-side movement of the control member controls articulation and/or actuation of the catheter. For example, moving the control member up-down and/or side-to-side can control up-down and/or side-to-side movement of a distal portion of the catheter.

Instruments

Further disclosed herein are various tools for use with the systems described herein. In addition to one or more degrees of freedom provided by moving the tools relative the guide tube, frame, and/or rails, the tools themselves can enable additional degrees of freedom. For example, the tools can include a distal articulation section that can move up/down, left/right, and/or end effectors that actuate. As used herein, the term "articulation" refers to a degree of freedom provided by moving the body of the tool and does not require a particular tool structure. In other words, the articulation section is not necessarily comprised of linked segments that move relative to one another to provide tool movement. Instead, for example, a flexible shaft can be bent to provide articulation. Described below are exemplary embodiments of the controls members, catheters, and/or end effectors that can comprise tools 40a, 40b.

As discussed above, control members 24a, 24b articulate catheters 25a, 25b, and/or end effectors. FIGS. 80A through 80E illustrate one such embodiment of a control member 24 including an actuator handle 304 that allows a user to control the orientation of a distal tip of tool 40 as will be explained below. The handle further includes a trigger 306 that allows a user to actuate an end effector.

In one embodiment, control member 24, is coupled to the rail with one or more U-shaped clamps 300 and 302. As shown in FIG. 80B, Each of the U-shaped clamps includes a pair of spaced-apart arms 308 that are connected to a pair of side rails 310a, 310b that extend for the length of the control member and form a frame to which additional components of the control member can be secured.

While control member 24 is described as including side rails 310a, 310b as supporting structure for the various elements of the control member, other control member configurations are contemplated. For example, the outer walls or shell of the control member can provide an anchor or frame to which various portion of the control member mechanisms can be mated. However, with respect to FIGS. 80A through 80E and the accompanying description below, rails 310a, 310b are illustrated and described.

In one aspect, actuator handle 304 is rotatably coupled to the side rails 310a, 310b such that the handle is able to move forward and aft relative to the control member 24. In addition, the handle 304 can rotate about a longitudinal axis of a shaft 314. Movement of the handle back and forth causes the distal tip of the tool 40 to move in one plane while rotation of the actuator handle 304 about the longitudinal axis of the shaft 314 causes movement of the distal tip of the tool 40 in another plane.

In one aspect, the amount of force required to move the control member relative to rail 224 can be chosen such that movement of handle 304 relative to the body of control member 24 does not accidentally cause articulation or actuation of the tool 40. In one aspect, the force required to translate or move control member 24 in a proximal and/or distal direction is greater than or equal to the force required to push handle 304 forward and/or pull handle 304 back (i.e., move handle 304 in a proximal/distal direction). The force required to move control member 24 can be adjusted by increasing the amount of friction between the contact surfaces of the control member and rail. In another aspect a damper can increase the force required to move control member 24. In yet another aspect, the amount of force required to move control member 24 is adjustable.

Handle 304 can be secured to the pair of side rails 310a, 310b with a trunnion 316. Trunnion 316 includes a pair of outwardly extending posts 318a, 318b that fit in corresponding holes formed in the side rails 310a, 310b. A locking mechanism such as a snap ring or other fastener can secure the posts 318a, 318b into the side rails. Alternatively, or additionally, the post can be secured by sandwiching between the side rails.

The handle 304 can be rotatably secured to the trunnion 316 with a shaft 320. Shaft 320 can mate with a collar 324 that provides a stop for a bowden cable as will be described in further detail below. Although the stop is illustrated on collar 324, in another aspect, the stop can be located inside handle 304. The trunnion 316 further includes a stop plate 326 that provides an anchor for the ends of the bowden cable housings. The stop plate 326 pivots back and forth with the posts 318a, 318b as the handle 304 is moved back and forth in the control. The trunnion 316 further includes a slot in the center of the trunnion in which a cable guide plate or disk 328 is located.

Figure 80A:
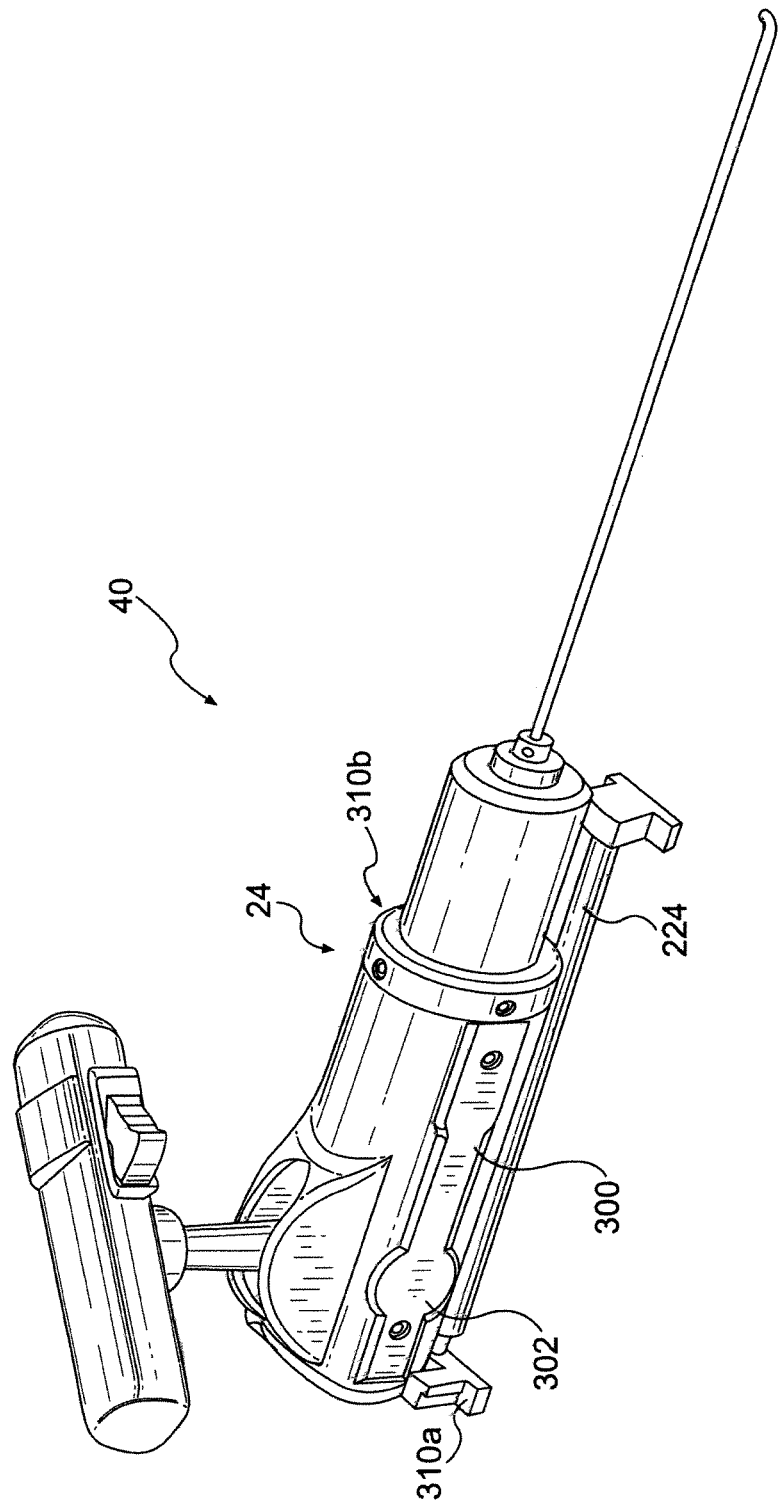
FIG. 80A is a perspective view of one exemplary tool described herein.
Figure 80C:
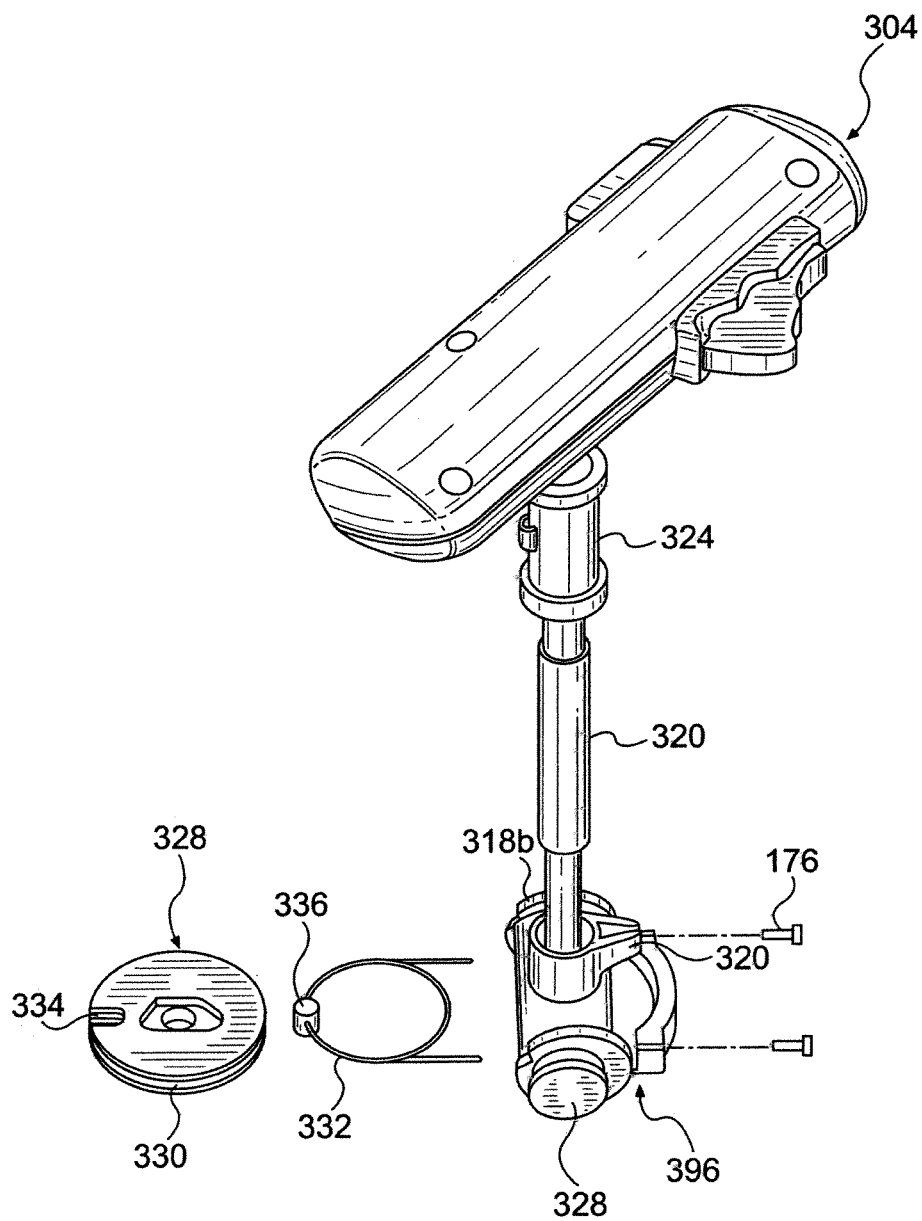
Figure 80E:
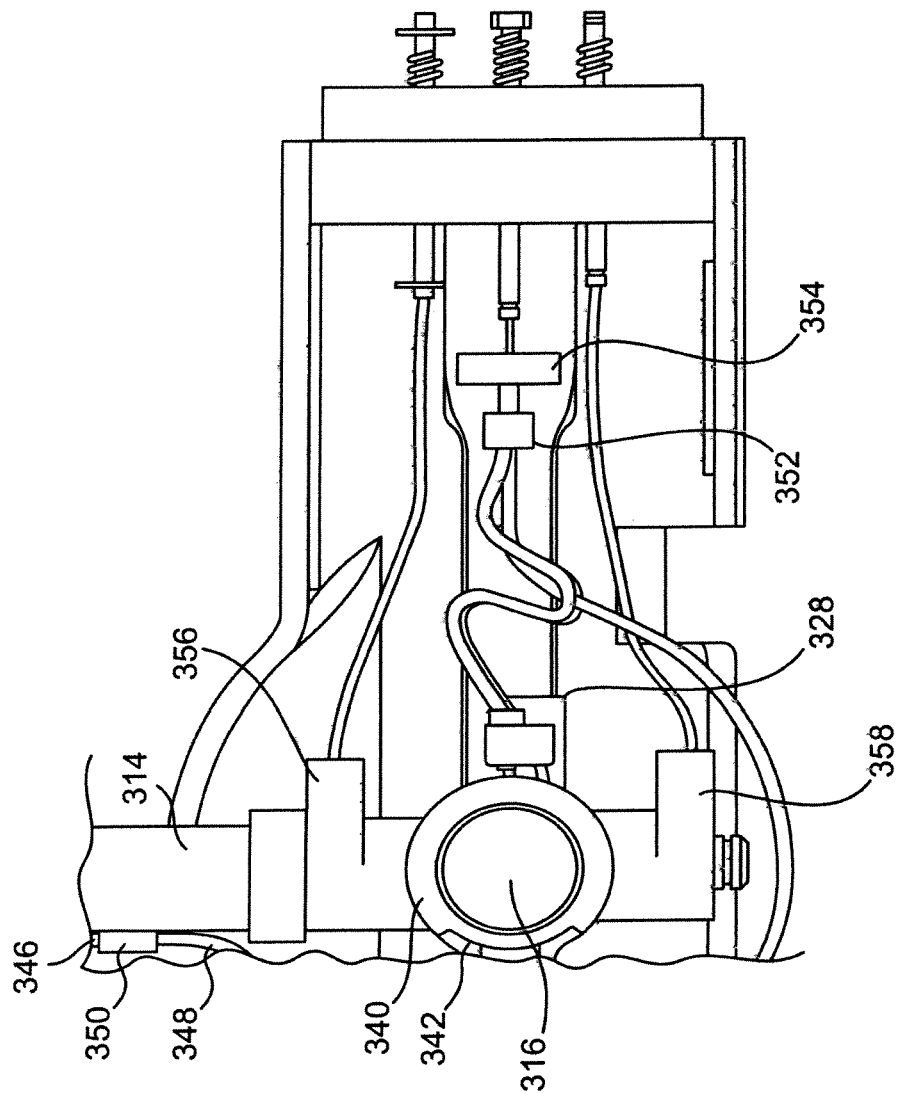

In the illustrated embodiment of FIGS. 80C, 80D, and 80E, the cable guide plate 328 is generally circular and includes a groove 330 therein in which an actuating cable 332 is fitted. The cable guide plate 328 includes a notch 334 that receives a corresponding cable stop 336 that is secured to the cable 332 (while a single notch/stop is illustrated, additional notches/stops are contemplated). The cable is wrapped around the cable guide plate 328 and includes a pair of legs (or wires) that are coupled directly and indirectly to the distal end of the tool. Movement of the cable guide plate causes corresponding tension or relaxing of the legs of the cable 336. The cable guide plate 328 is fitted into a slot within the trunnion such that it lies behind the stop plate 326. The shaft 320 fits through a corresponding hole in the cable guide plate 328 and a snap ring or other fastening mechanism secures the components together. Rotation of the handle 304 causes a corresponding rotation of the shaft 314 which in turn is coupled to the cable guide plate 328 to tension or release the legs of the actuating cable 332.

Cable 332 is illustrated as wrapped around disk 328 more than 360 degrees. In another aspect, cable 336 can be wrapped around the disk more than about 180 degrees, and in another aspect more than about 270 degrees. In yet another aspect, cable 332 mates to disk 328 without wrapping around a portion of the disc.

FIGS. 80D and 80E illustrate further detail of the trunnion 316 within the control member 24. The cable guide plate 328 is fitted within the slot of the trunnion 316 and rotates back and forth within the slot by rotation of the actuator handle 304. To limit the amount of forward and aft movement of the handle 304 in the control member, a ring 340 fitted over the posts of the trunnion 316 can have a notch 342 therein. A pin 344 secured in the side rail (not shown) limits how far the handle can travel by engaging the end of the notch 342. While the FIGS. illustrate a ring/pin configuration, one skilled in the art will appreciate that a variety of alternative mechanisms can be used to limit motion of the cable guide plate. In addition, the illustrated configuration could be reversed such that the notch could be located on the side rail and the pin could be located on the trunnion.

Also shown in FIGS. 80D and 80E is a cable 346 that is actuated by the trigger mechanism 306 on the handle. Depressing the trigger 306 causes a tensioning of the cable 346 to actuate the distal end of the tool. In the illustrated embodiment, the cable 346 is a bowden-type cable having an outer sheath 348 with one end secured to a cable stop 350 positioned on the collar 324 that is fitted over the shaft 314. The other end of the bowden cable housing extends through a cross bar 354 and joins a stop at the distal end of the catheter. The crossbar 354 also includes stops for the bowden cable housings that are driven by rotation of the handle as described above.

As shown in FIGS. 80D and 80E, the trunnion also includes a shaft that extends in a direction perpendicular to the posts that are coupled to the side rails. The shaft includes a pair of cable receivers 356, 358 having a slot or other receptacle therein that secures an end of an articulation cable. One of the cable receivers 358 is below the pivot point of the trunnion 316, and the other is above the pivot point. Upon tilting the trunnion 316 in the control member, the cable receivers 356, 358 selectively tension or release control cables that move the distal tip of tool 40 in a plane.

Further detail of one embodiment of a trigger mechanism 306 is shown in FIG. 81. In this embodiment, the trigger 306 is rotatably received within the handle 304 such that squeezing the trigger 306 causes it to rotate about a pivot point. The trigger 306 includes an arm 360 to which an end of the actuation cable 346 is secured. As the arm 360 is moved by pressing the trigger, tension on the control cable 346 is increased to actuate the tool at the end of the medical device. A roller or pulley 362 changes the direction of the control cable 346 from within the handle to a direction that extends along the shaft 320.

Figure 82A:
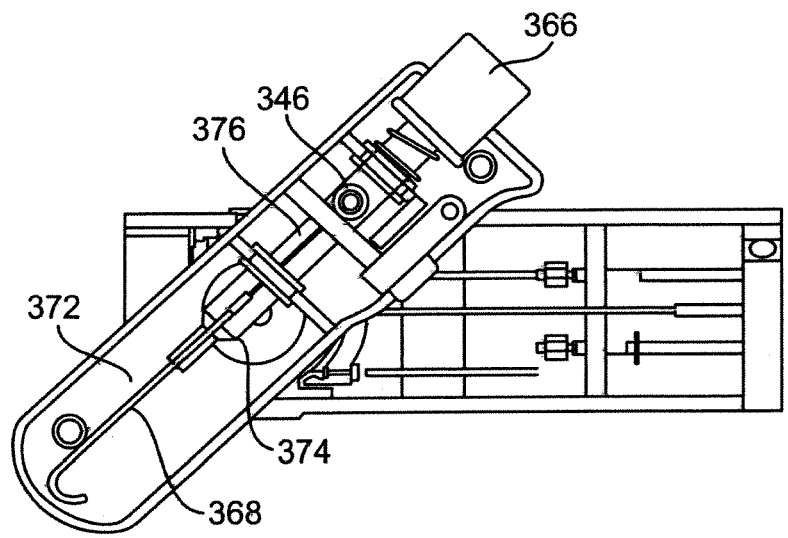
Figure 82B:
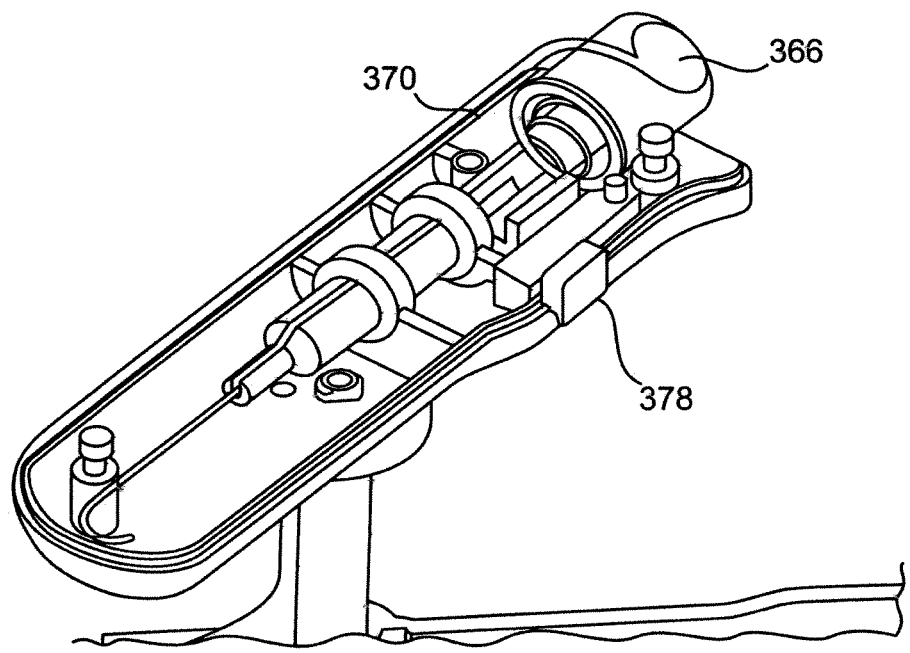

FIGS. 82A and 82B illustrate another embodiment of trigger mechanism 370 that includes a button 366 for activating the distal end of tool 40. A bowden cable 368 can extend into handle 304 to trigger mechanism 370. The second end of the outer sheath 372 of the bowden cable extends in clearance through crossbar 354 and through the body of surgical tool where it terminates proximate to end effector. The outer sheath 372 of the bowden cable 368 can mate with a stop 374 in the trigger mechanism while the inner filament 376 extends into trigger mechanism 370. When button 366 is depressed, trigger mechanism 370 tensions inner filament 376. In one aspect, trigger mechanism 370 include a ratchet-type lock that prevents the release of inner filament 376 once tensioned. A button 378 can be depressed to release inner filament 376 and allow the distal end of tool 40 to return to its original configuration.

While the various control cables or control wires in the control member 24 are illustrated as bowden-type cables, other cables, filaments, and wires can be substituted. In one exemplary embodiment, unsheathed pull wires are substituted for at least some of the bowden cables. As used herein, "control cables" can refer to any wire, filament, or cable that transmits actuating and/or articulating forces along the body to tool 40.

Figure 83A:
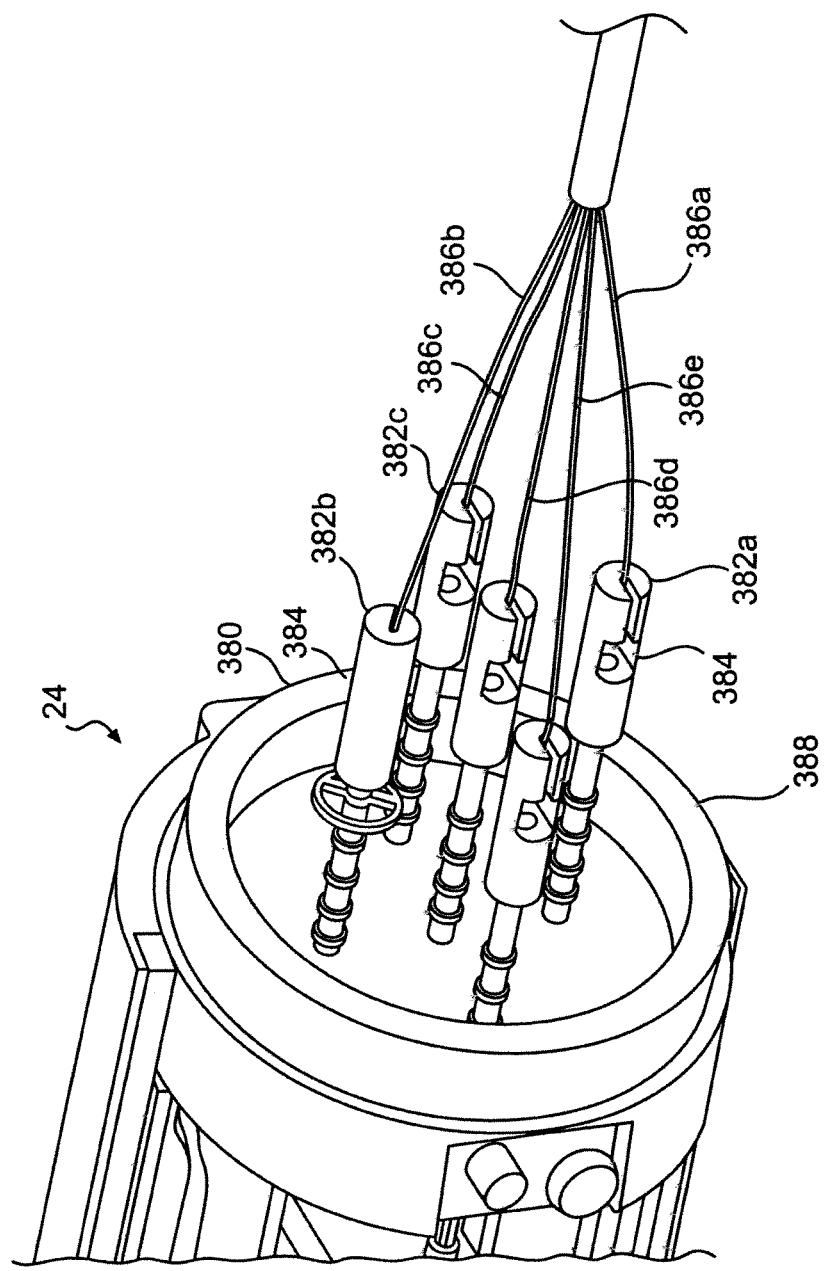
Figure 83B:
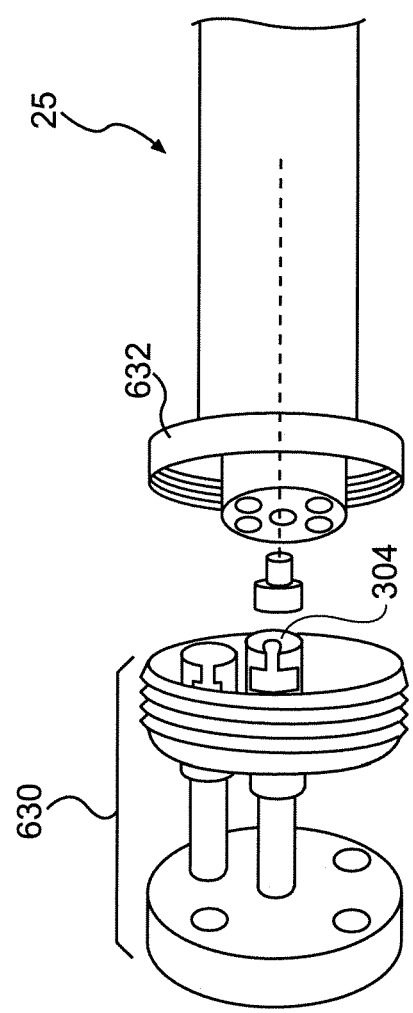

In one embodiment, the control cables extending between the control member and the distal end of the tool include a detachable connection that permits detachment of catheter 25 from control member 24. FIGS. 83A and 83B illustrate one embodiment of a coupling mechanism that can be used to selectively couple one or more of the control cables of control member 24 to one or more control cables within catheter 25 of tool 40. The coupler 380 forms an end-wall that is positioned within the control member housing between the support rails 310a, 310b. Coupler 380 has a number of spring loaded pins 382a, 382b, 382c, etc., positioned therethrough. The proximal end of pins 382a, 382b, 382c, etc., is connected to a control cable that is manipulated by handle 304 or the trigger mechanisms as described above. In addition, each pin includes a distal cable receiving notch or slot 384 therein that receives a cable terminal or stop of a corresponding control cable 386a, 386b, 386c, etc. extending through catheter 25. Securing the cable terminals in the slots 384 of each pin mates cables 386a, 386b, 386c, etc. with corresponding control cables in control member 24.

In the embodiment shown, each of the pins 382a, 382b, 382c, etc. includes a spring 388a, 388b, 388c that biases the pin in the locked position. Compressing the spring allows removal or insertion of the cable terminals into slots 384. In addition, or alternatively, springs 388 can tension the control cables within the body of the control member. When the control handle is released by a user, the springs can bias the control handle in a home position.

In one aspect, the various cables within control member 24 can be adjustably tensioned. For example, in one embodiment spring loaded pins 382 can have a threaded connection with coupler 380. Rotating pins 382 can move pins laterally to control the tension on control wires mated to pins 382. For example, rotating the pins 382 can compress or relax springs 388 to adjust tension on the control wires.

Coupler 380 can comprise a variety of different mechanical connections for detachably mating the control cables of control member 24 and catheter 25. In one aspect, instead of notch 384 and cable terminal, coupler 380 can include a threaded connection, snap fit, and/or other mechanical interlock.

FIG. 83B illustrates an exemplary quick disconnect 422 for disconnecting the control cables of catheter 25 from the control member 24. The quick disconnect can directly mate the control cables of control member 24 with the control cables of catheter 25. In one aspect, the direct connection includes a wire terminal and corresponding terminal receivers defined by slot 384. The terminal receivers can be mounted in and housed by a support base 630 (illustrated in an exploded view). After mating the terminals with the terminal receivers, a ring 632 on catheter can mate with the support base. The support base 630 and ring 632 can enclose the mated control cables and prevent unwanted control cable disconnection by limiting the freedom of movement of the mated terminals/terminal receivers.

Figure 84:
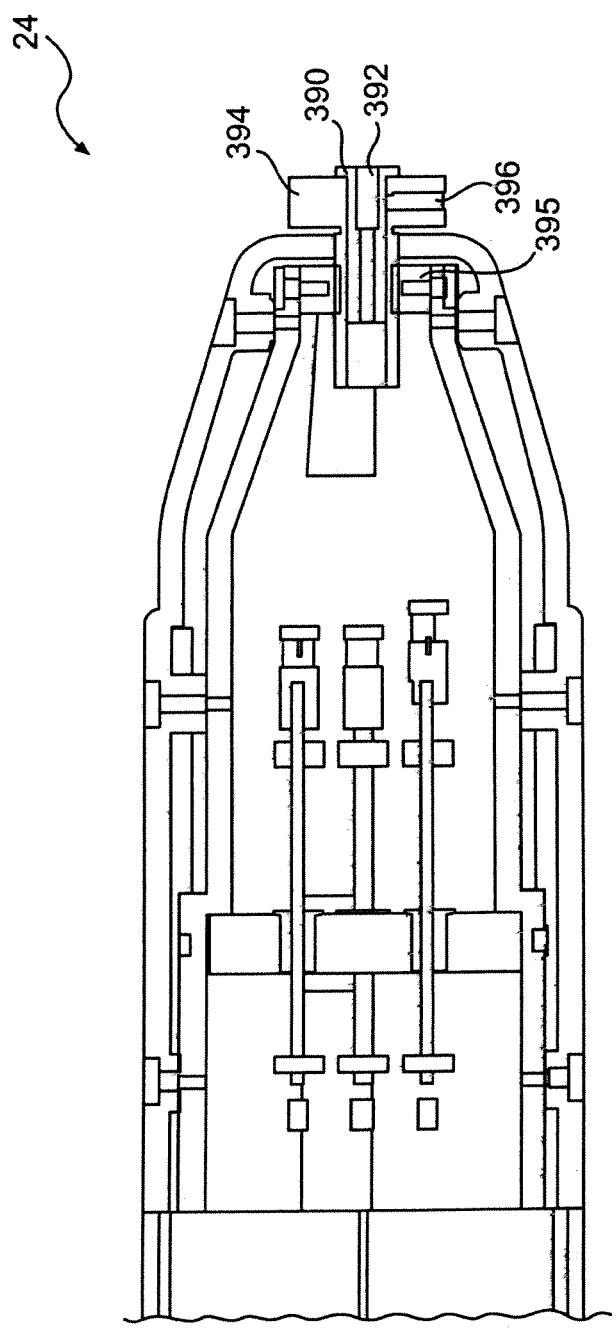

In another embodiment of control mechanism 24, system 20 can include a orientation adjuster. In use, the orientation adjuster can allow a user to rotate the elongate catheter body and distal end of a tool relative to control mechanism 24. FIG. 84 illustrates a cross-section of the distal end of control mechanism 24 with adjuster 394. Adjuster 394, in one aspect, can include an inner member 390 having a passageway 392. The passageway 392 can receive the elongate catheter body of tool 40 (not illustrated). In one embodiment, the catheter body of tool 40 includes an outer sheath that fixedly mates to the inner surface of passageway 392. One skilled in the art will appreciate that a variety of mating mechanisms, such as, for example an adhesive, mechanical interlock, and/or frictional engagement can be used. In addition, the inner member 390 can mate with the inner surface of adjuster 394. For example, as illustrated in FIG. 84, adjuster 394 includes an aperture 396 for a set screw for mating adjuster and inner member 390. In another aspect, adjuster and 394 and inner member 390 can be fixedly mate via, for example, an adhesive. In addition, the adjuster and the inner member can alternatively be formed as a single body.

To change the rotational orientation of tool 40, adjuster 394 can be rotated within control member 24. In one aspect, a locking collar 395 can be tensioned to control the amount of friction between the control member and orientation adjuster 394. For example, the locking collar 395 can be set to inhibit, but not prevent rotation of the adjuster, or set to prevent rotation until adjustment is desired. Since adjuster 394 is mated to inner member 390, and inner member 390 is mated to the body of tool 40, rotating adjuster 394 causes catheter 25 to rotate relative to control member 24.

In one aspect, tool 40 can include indicia to facilitate alignment of the catheter with the control member. For example, markings on the catheter proximate to the control member can correspond to the orientation of the distal end effector at the distal end of catheter 25. In use, a clinician can use the indicia to align the catheter and control member.

In another aspect, the amount of rotation of the catheter with respect to the control member is limited with a stop. For example, a surface feature on the orientation adjuster (not illustrated) can contact a corresponding surface feature (not illustrated) on the control member body to inhibit rotation more than a predetermined distance. Because control wires extend from catheter 25 into control member 24, rotation greater than about 360 degrees can significantly increase the forces required to articulate catheter 25 and/or can cause tangling of the control wires. In one aspect, stops can prevent rotation more than about 360 degrees, and in another aspect, can prevent rotation more than about 180 degrees in either direction (clockwise/counterclockwise).

As mention above, passageway 392 can receive catheter 25. In one aspect, passageway 392 can include a distal region sized and shaped to receive the outer surface of the catheter 25. In addition, passageway 392 can include a proximal region adapted to prevent proximal movement of the catheter. In one aspect, the proximal region of passageway 392 can have a cross-section that is smaller, in at least one dimension, than the outer surface of the catheter, but large enough to allow passage of control cables therethrough. The proximal region can thereby prevent proximal movement of the catheter beyond passageway 392 and into (or deeper into) control member 24.

In one aspect, the proximal region acts as a counter force when the control cables are tensioned or pulled. The proximal region can hold the catheter body in place to allow the control cables to move relative to the elongate catheter body.

Figure 85:
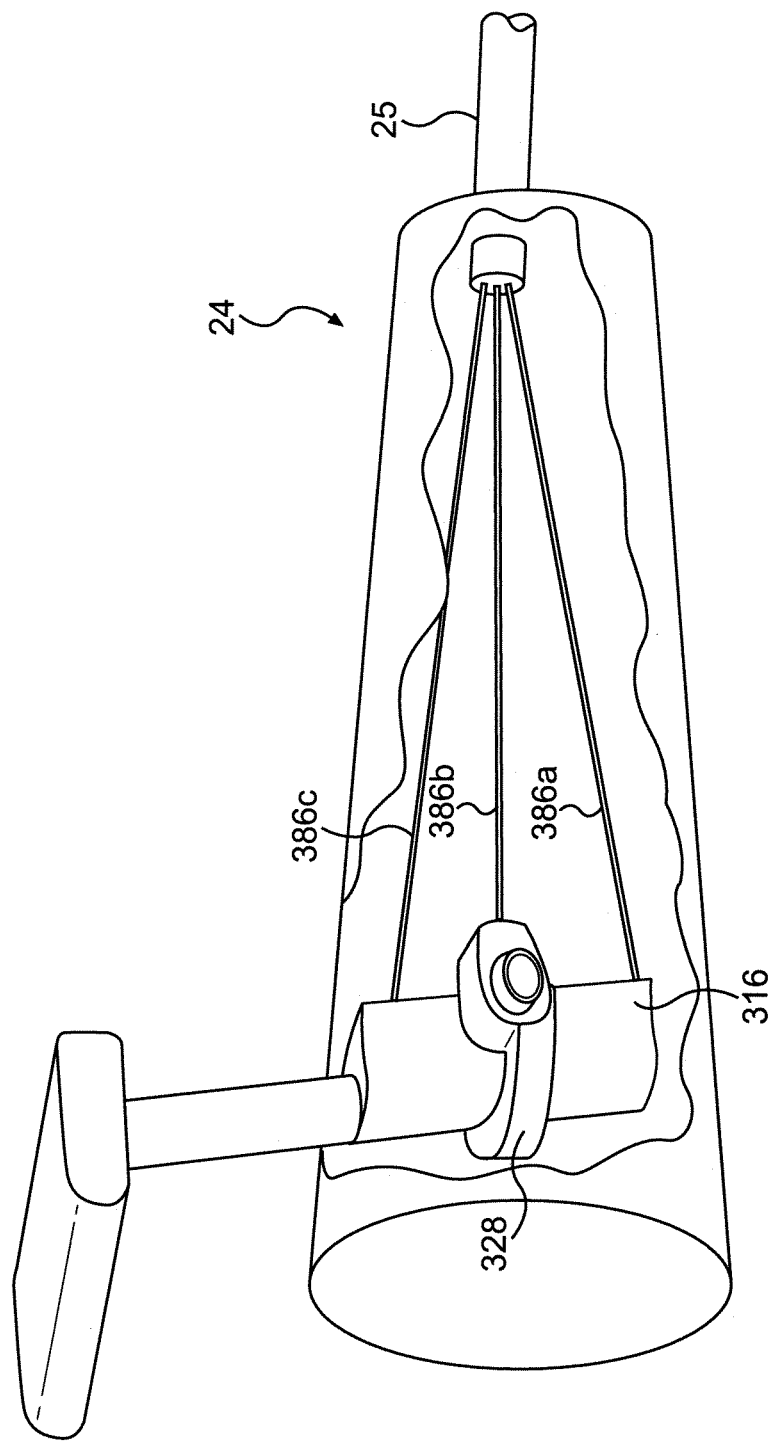
FIGS. 85, 86, 87, 88, 89A, and 89B are various partially transparent views of exemplary control mechanism for use with a control member described herein.

In the exemplary control members described above, the control cables extending from trunnion 316, plate 318, and/or trigger 306 extend to and mate with a firewall or coupler 380. Different control cables then extend through catheter 25 and mate with a distal articulation section and/or distal end effector. In another embodiment, control cables can extend directly from the control mechanism (e.g., trunnion 316, disk 328, trigger 307) of control member 24 to the distal articulation section and/or distal end effector. FIG. 85 illustrates control cables 386*a*, 386*b*, 386*c* extending into catheter 25 without the user of a firewall, coupler, or detachable connection.

A variety of alternative control members, which allow a distal end of tool 40 to be actuated in the up/down, right/left, forward/backward, and rotational directions, can be used with system 20. Such alternative control mechanisms are disclosed, for example, in U.S. patent application Ser. No. 11/165,593, entitled "Medical Device Control System" and U.S. patent application Ser. No. 11/474,114, entitled "Medical Device Control System," both of which are hereby incorporated by reference in their entirety.

Figure 86:
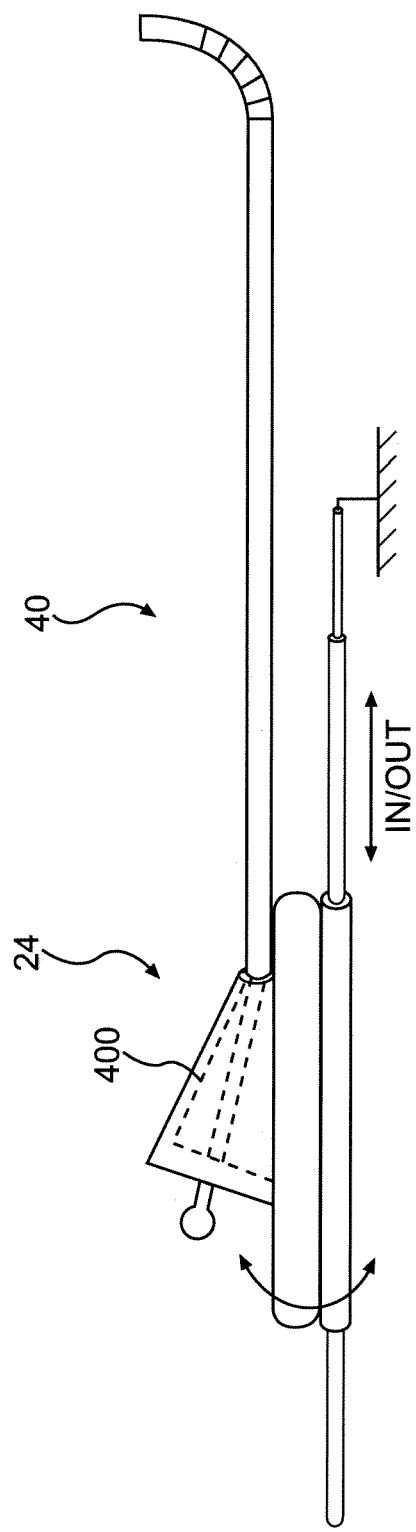

In addition, described below are a variety of alternative embodiments of control member 24 and alternative control mechanisms that can be substituted for the trunnion 316, disk 328, and trigger 307 described above. FIG. 86 illustrates a swash plate 400 that allows a user to control multiple degree of freedom with a single handle. One such exemplary control member is described in U.S. Pat. No. 3,605,725. The swash plate can work with a "joystick" type handle to control two degrees of freedom.

Figure 87:
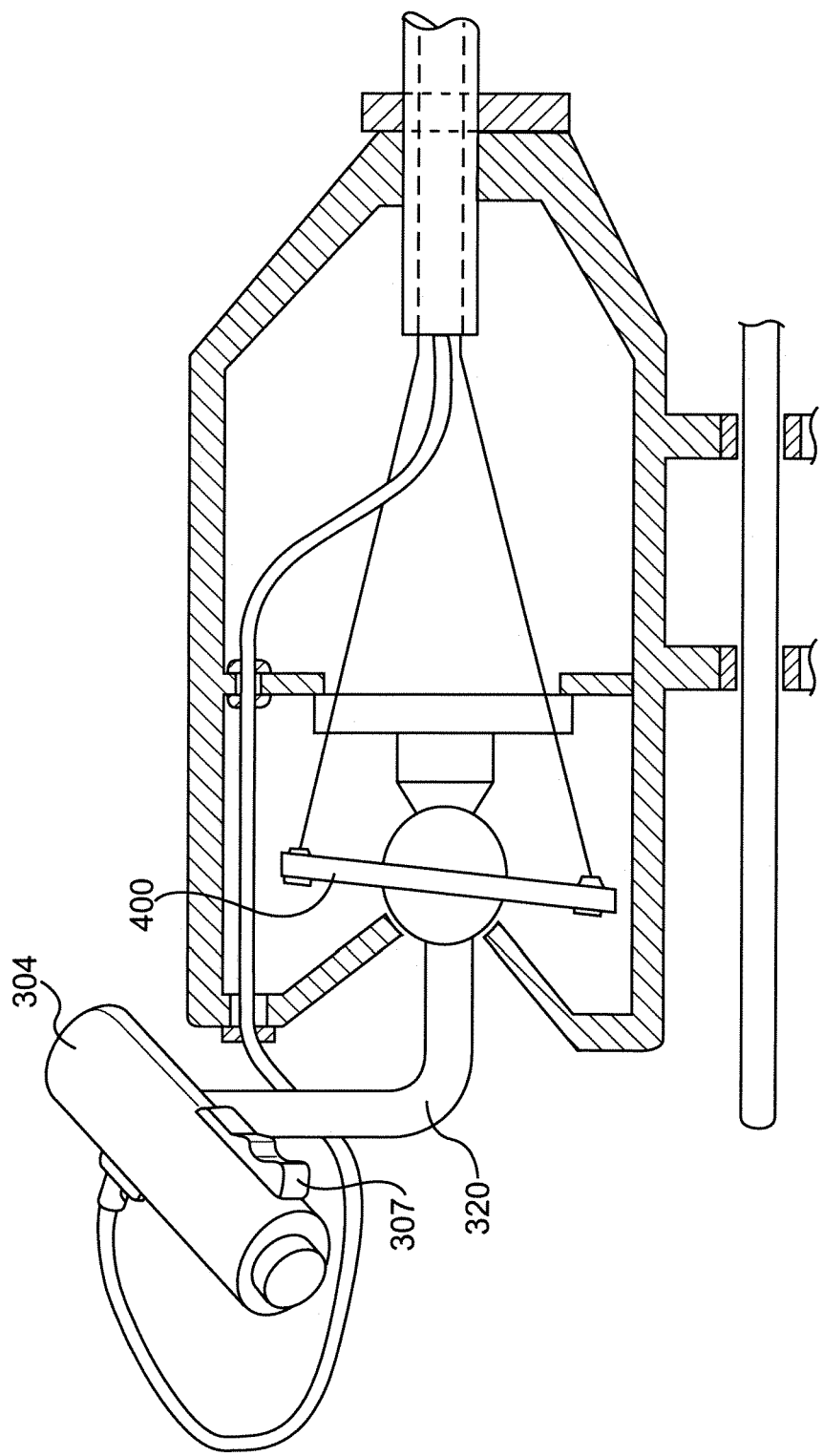

FIG. 87 provides a transparent view of another embodiment of a swash plate control member. In one aspect, the shaft 320 of swash plate control member 24 can have a bend, such as, for example, a 90 degree bend that allows use of handle 304 instead of a joystick. In addition, handle 304 can provides an additional degree of freedom via trigger 307. For example, handle 304 can include a button or trigger for controlling actuation of the distal end effector.

Figure 88:
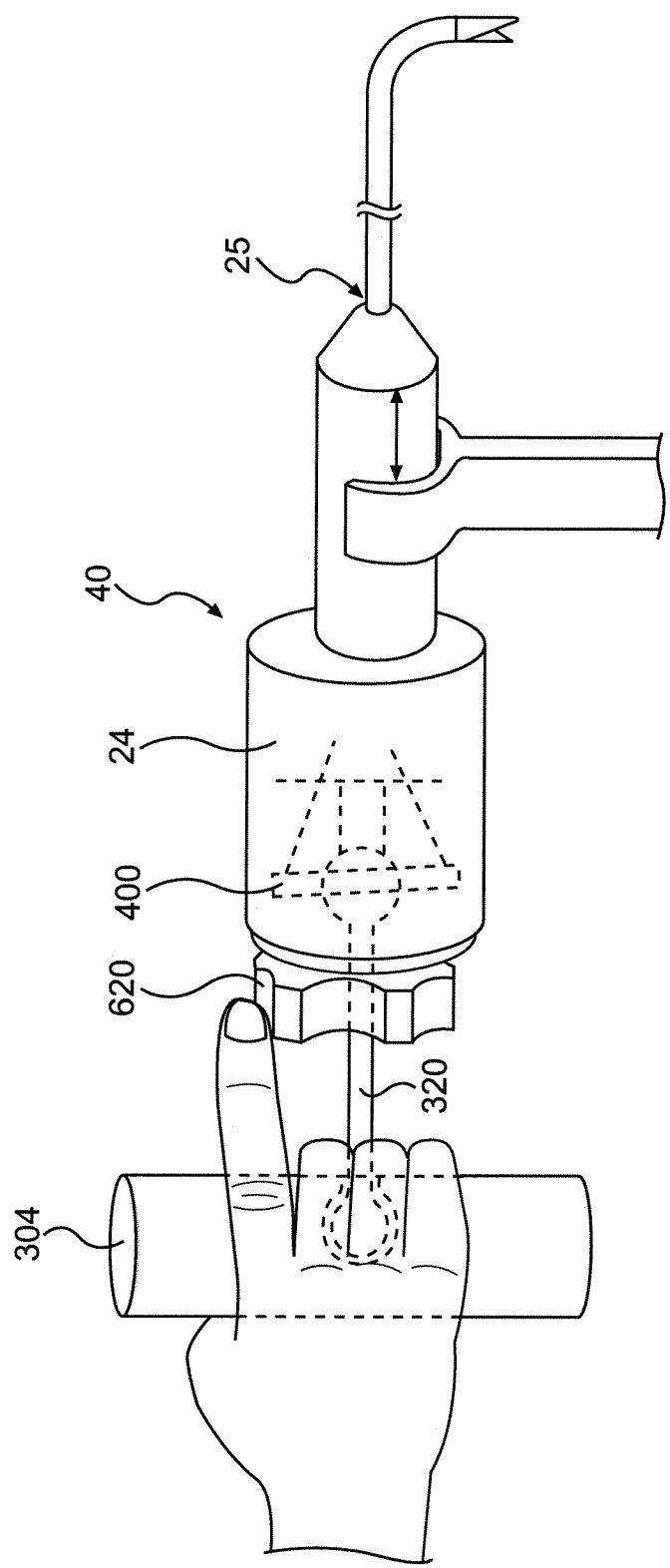

In yet another embodiment of a swash plate control member, illustrated in FIG. 88, rotation of tool 40 can be provided by rotating control member 24. For example, a handle can be rotatably fixed to a shaft that controls a swash plate. While the user interfaces with the handle, with the palm of his or her hand, the user can simultaneously interface a control knob with a digit (e.g., thumb or pointer) to achieve rotation of tool 40. FIG. 88 illustrates control member 24 mated with handle 304 via a rotatable connection such that handle 304 can rotate with respect to the control member. To rotate tool 40, a user can turn control member 24 and catheter 25 independently of handle 304. In addition, a user can move the control member relative to a rail, frame, guide tube, or other reference point by pushing/pulling on handle 304 to provide longitudinal motion.

While handle 304 can rotate with respect to control member 24 and catheter 25, the rotatable connection between handle 304 and shaft 320 can allow a user to drive other degrees of freedom. When a user moves handle 304 up/down and/or side-to-side, user input forces can drive swash plate 400. Movement of swash plate 400 can drive various degrees of freedom of tool 40 including, for example, articulation of catheter 25. In addition, longitudinal user input forces, such as pushing/pulling along an axis parallel to tool 40, can also be delivered through shaft 320 to drive tool 40.

Figure 89A:
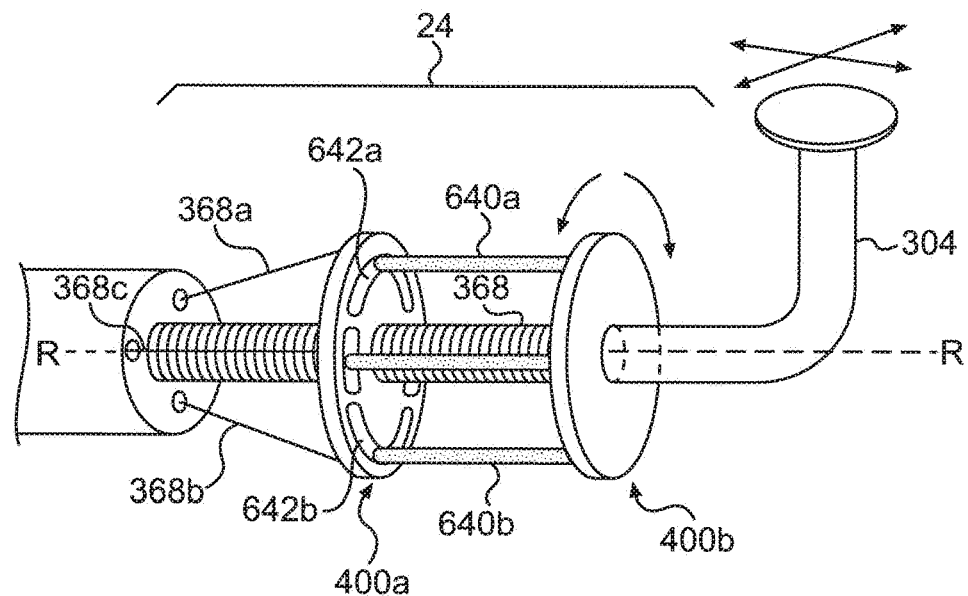
Figure 89B:
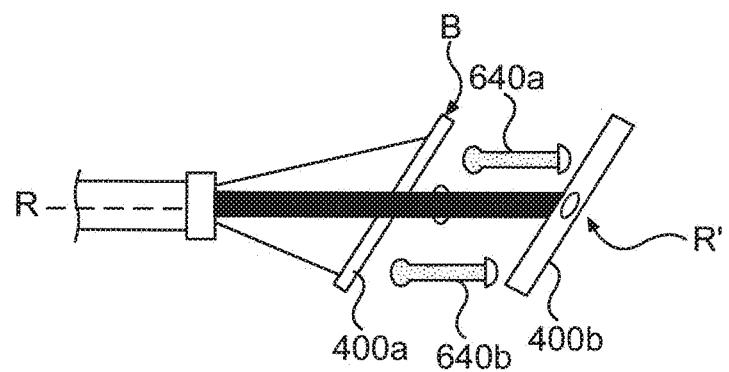

In yet another aspect, control member 24 can permit independent rotation of the end effector with respect to catheter 25 and/or with respect to control member 24. FIGS. 89A and 89B illustrate one embodiment of a control mechanism that permits independent rotation of the end effector. Control cable 368 extends from control member 24, through catheter 25, to a distal end effector (not shown). Rotating control cable 368 independently of catheter 25 and control member 24 can drive rotation of the end effector with respect to catheter 25.

In one embodiment the use of a first and second swash plate 400*a*, 400*b* can permit independent rotation of control cable 368. Second swash plate 400*b* can be mated with control cable 368 such that rotation of handle 304 cause control cable 368 to rotate. Conversely, control cable 368 can rotate independently of first swash plate 400*a*. In one aspect, control cable 368 extends through an aperture within first swash plate 400*a* that allows relative rotation between control cable 368 and first swash plate 400*a*.

Control cable 368 can be a torquable, flexible filament, coil, cable, or wire that transmits torque to the distal end effector. In one aspect, control cable 368 can additionally drive actuation of the end effector as described herein. For example, where distal end effector actuation is desired, handle 304 can include a trigger or similar mechanism to actuate the distal end effector.

Rotational movement of second swash plate 400*b* is disconnected from first swash plate 400*a*. In one aspect, cross bars 640*a*, 640*b* extend from second swash plate 400*b* and movably mate with first swash plate 400*a* via slots 642*a*, 642*b*. While two cross bars are illustrated, three, four, or more than four cross bars could extend between the first and second swash plates. As second swash plate 400*b* rotates, cross bars 640a, 640b move along slots 642a, 642b to allow independent rotation of second swash plate 400b with respect to first swash plate 400a.

Additional degrees of freedom can be provided to drive catheter articulation via side-to-side and/or up-down movement of handle 304. As handle 304 is moved up/down or side-to-side, cross bars 640a, 640b can transmit forces from second swash plate 400b to first swash plate 400a. For example, cross bars 640a, 640b can transmit forces parallel to a longitudinal axis of the cross bars and/forces parallel to the rotational axis of control cable 368. Thus, tilting second swash plate 400b on an axis orthogonal to the rotational axis R-R can drive the first swash plate and transmit user inputs to control cables 368a, 368b, 368c, and/or 368d mated with first swash plate 400a.

FIG. 89B illustrates swash plate 400b rotated about an axis R'-R' that is orthogonal to the rotational axis of control cable 368 to drive articulation of catheter 25. Note that cross bars 640a, 640b transmit push/pull forces from the second swash plate to the first swash plate and cause first swash plate 400a to pivot in a fashion corresponding to second swash plate 400b. In one aspect, swash plates 400a, 400b remain parallel to one another as they pivot.

FIG. 90 illustrates a pistol grip 402 handle that include controls knobs 404 on the grip of the handle. Knobs 404 (similar to the control knobs described above with respect to the guide tube controls 30) can substitute for a trigger control, or be used in addition to trigger control.

Figure 91:
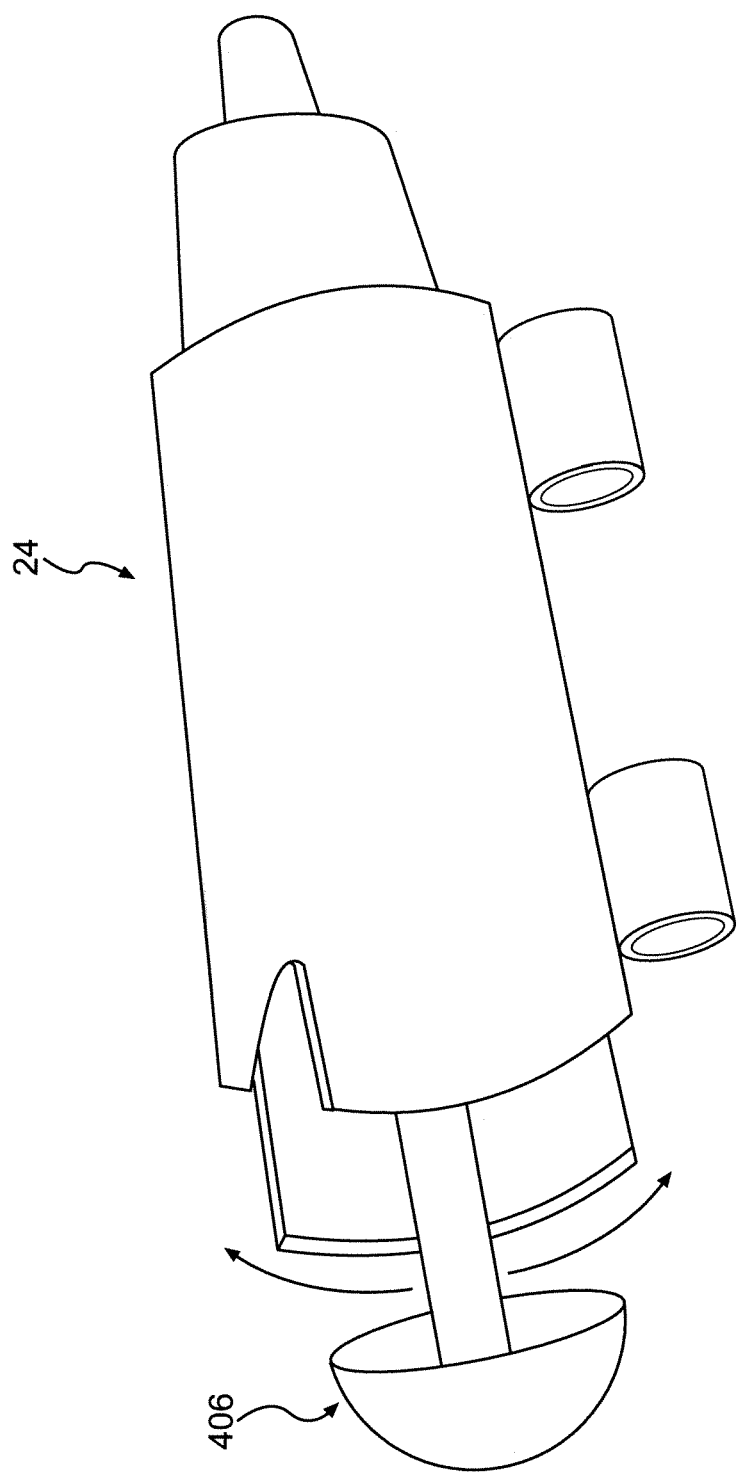

FIG. 91 illustrates a control knob 406 positioned on the proximal end of the control member 24. In one aspect, moving control knob 406 can articulate an end effector. The proximal location of control knob 406 facilitates control of tool 40 as the tool rotates with respect to the frame, rails, guide tube, and/or point of reference. As control member 24 rotates 180 degrees or more, a user may have to switch hands or adjust their grip on a standard handle. Having knob 406 positioned on the proximal end of control member 24 can facilitate control of tool 40 while control member 24 rotates around rail 224.

In one aspect, control knob 406 is rotatably mated with control member 46. A user can rotate control member 24 to control rotational movement of tool 40. In another aspect, knob cannot rotate with respect to control member 24 and rotation of knob 406 can drive tool rotation.

Figure 92:
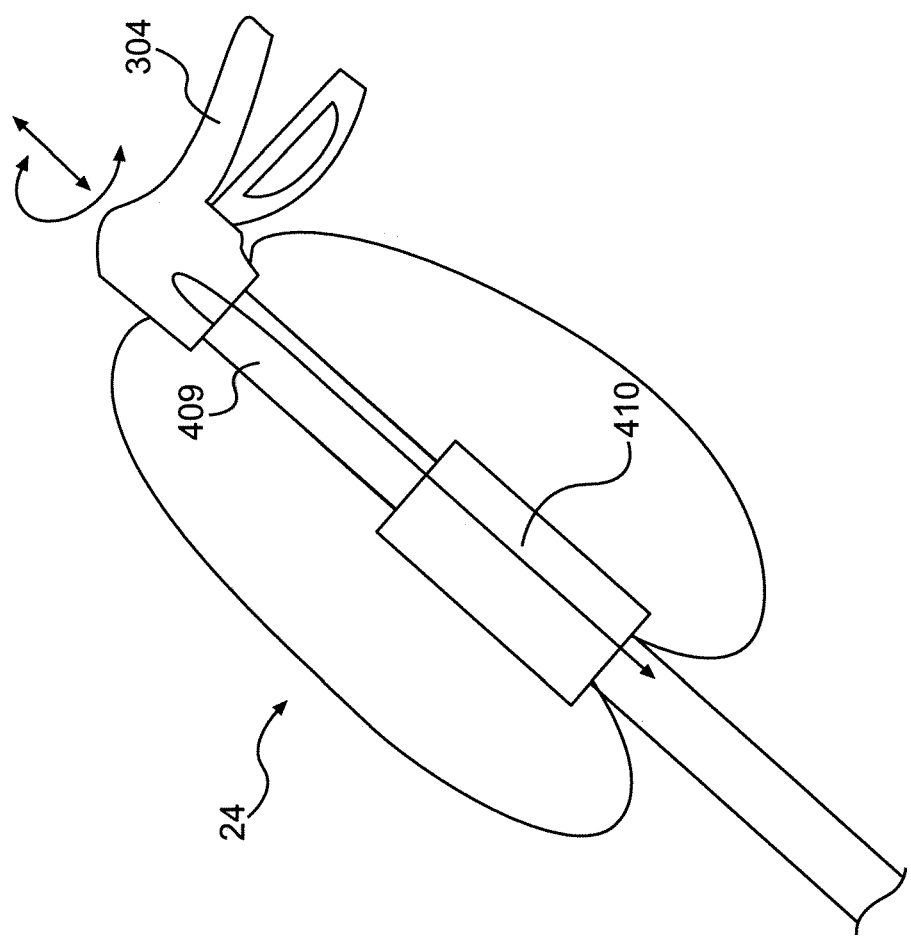

FIG. 92 illustrates a control member including a flexible body 409 mated with pull wires. Moving the flexible body 409 results in actuation of the distal end of the tool. The control member of FIG. 92 can also include a sliding sleeve 410 for and/or a handle 304 for controlling additional degrees of freedom.

Figure 93:
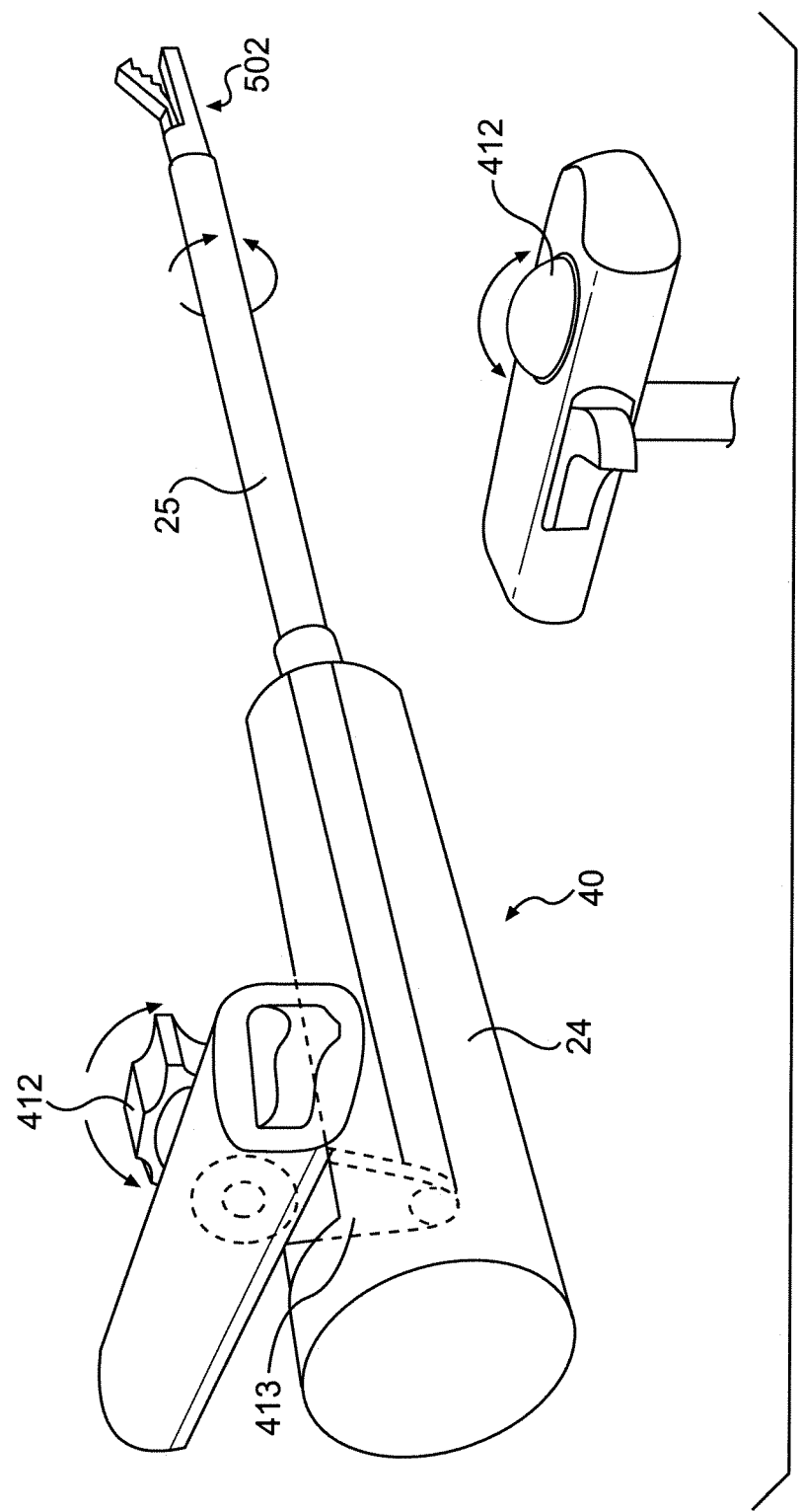

FIG. 93 illustrates a control member including a knob or ball 412 for controlling a degree of freedom. In one aspect, rotating the knob 412 can drive rotation of catheter 25 with respect to the body of control member 24. For example, the catheter 25 can be configured to rotate independently of control member 24. Rotating knob 412 can drive gears or pulleys 413 (or other such mechanism) and rotate catheter 25. In another aspect, a lever or moment arm of tool 40 (not illustrated) can rotate the catheter. For example, a lever could be mated with a torque coil extending through catheter 25. Movement of the lever could drive the torque coil and rotate the catheter and/or distal end effector 502.

Figure 94:
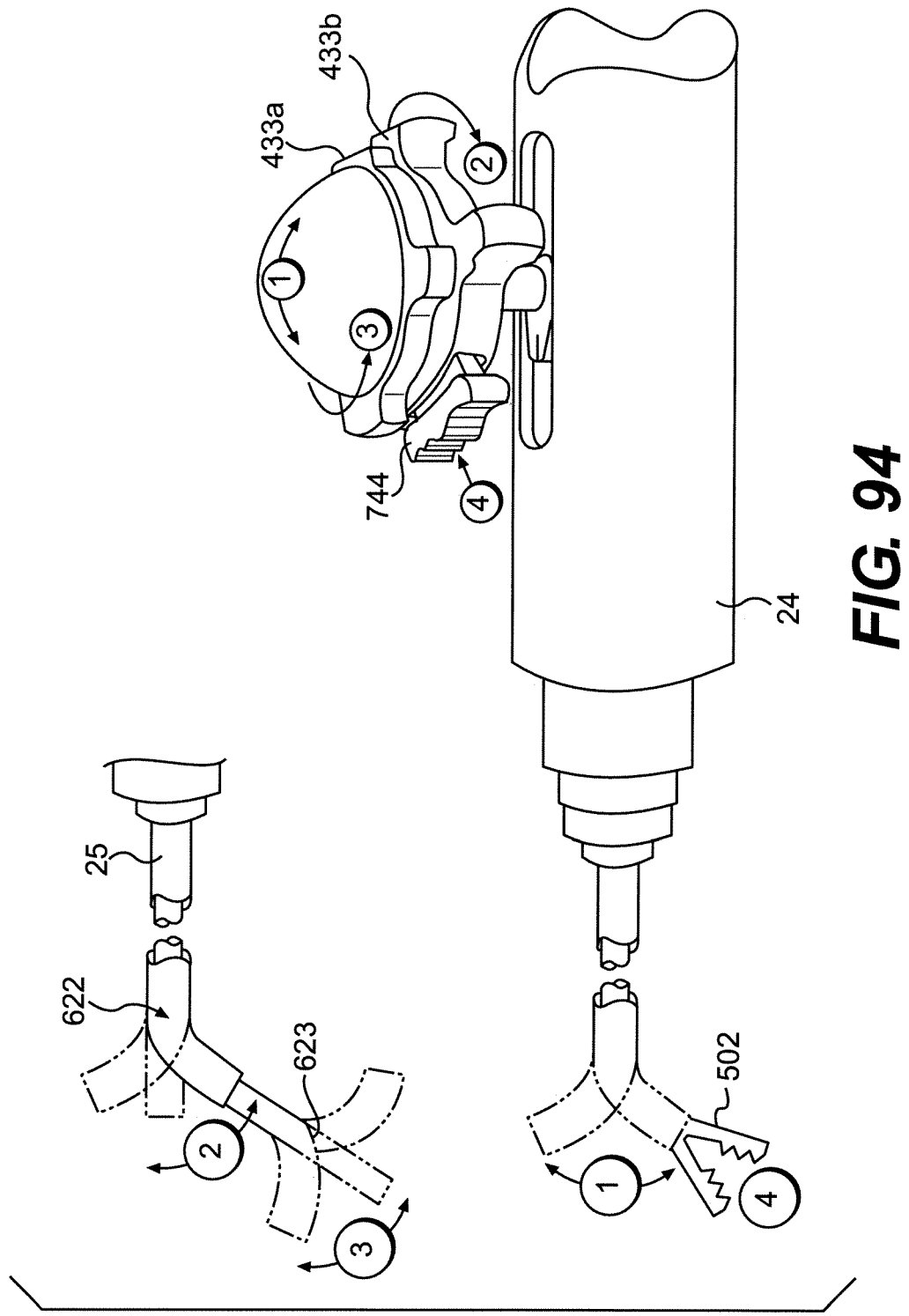

FIG. 94 illustrates another embodiment of the control member 24 including handle 304 for controlling additional degrees of freedom. While similar to the control members discussed above having a control handle that drives two degrees of freedom, the control member of FIG. 94 includes a second rotational actuator (e.g., knob) driving an additional degree of freedom of catheter 25. In one aspect, rotational actuators 433a, 433b can rotate with respect to one another and with respect to the housing of control member 24. Rotational actuator 433b can drive a disk within control member 24 via a shaft extending from handle 304 into control member 24. Similarly, rotational actuator 433a can drive a second rotating disk.

The additional degree of freedom controlled by the second rotational actuator 433a can include a second articulation section 622 in addition to first articulation section 623 driven by the first rotational actuator 433b. In one aspect, articulation section 622 can be placed proximally to the first articulation section 623, giving a "wrist" and an "elbow" to catheter 25. This additional degree of freedom can allow instruments to converge and/or diverge with another tool. Additionally, the control mechanism can include an trigger 744 to actuate end effector 502. The control handle of FIG. 94 can provide four degrees of freedom, which when used with the rails described above, can provide an instrument with six degrees of freedom. In one aspect, all six degrees of freedom can be controlled with a single hand.

Figure 95:
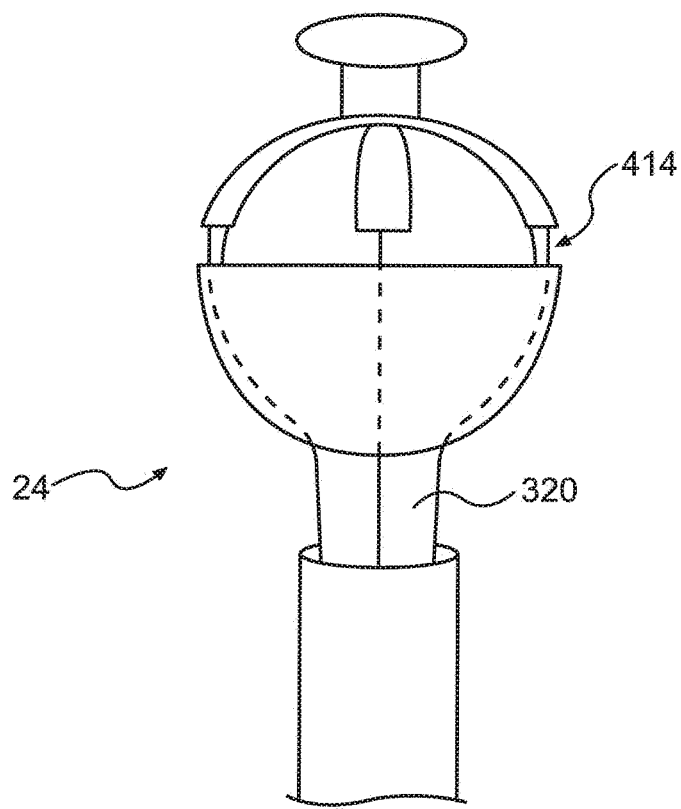

FIG. 95 illustrates a control member 24 having a "ball-type" handle 414. Moving the ball mechanically drives the distal end of the tool. In one aspect, ball handle 414 includes control wires wrapped around the curvature of the handle. Pivoting handle 414 with respect to shaft pulls (or pushes) on control wires and drives movement of tool 40.

Figure 96:
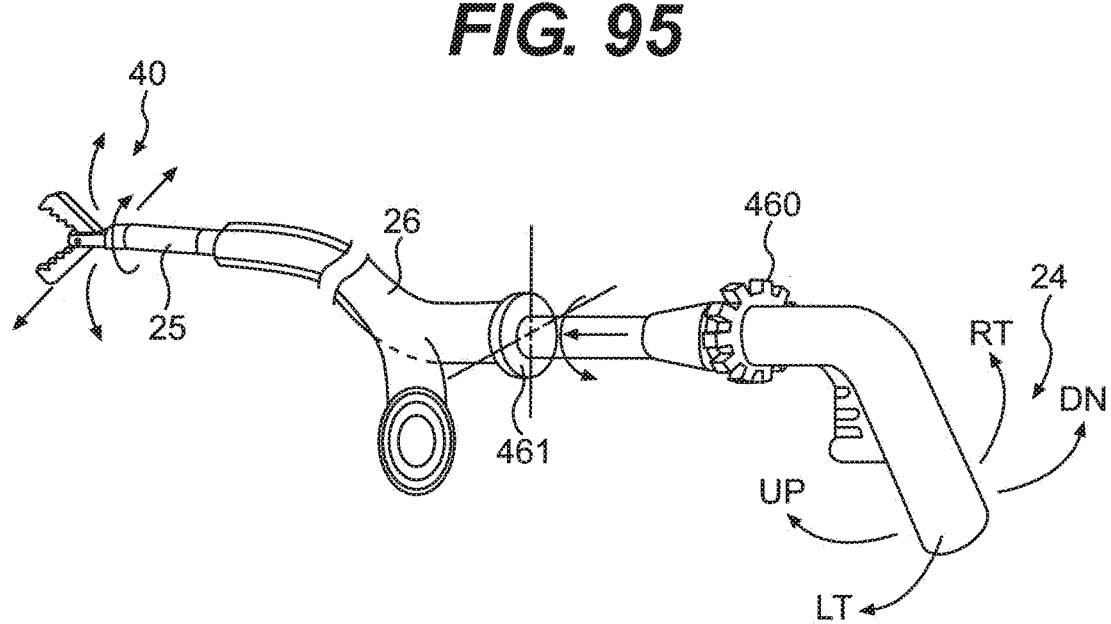

In yet another embodiment, FIG. 96 illustrates a control member having a trigger grip configuration that provides "on-axis" rotation. Articulation of the tool can be controlled by, for example, by movement about a pivot or swash plate. Rotation of tool 40 can be controlled by rotating a rotational actuator (knob) 460. In one aspect, rotational actuator 460 can control rotation of an end effector and/or catheter independently of the control member. The control member, in one aspect, can be supported by the guide tube 26 that acts as the frame. For example, a portion of guide tube 26, including ring 461 can support control member 24 and allow relative rotational and/or longitudinal movement of tool 40 (or catheter 25). Ring 461 can also act as a stop to limit distal movement of tool 40. In another aspect, ring 461 can be defined by a bite block or other apparatus mated with a patient.

Figure 97:
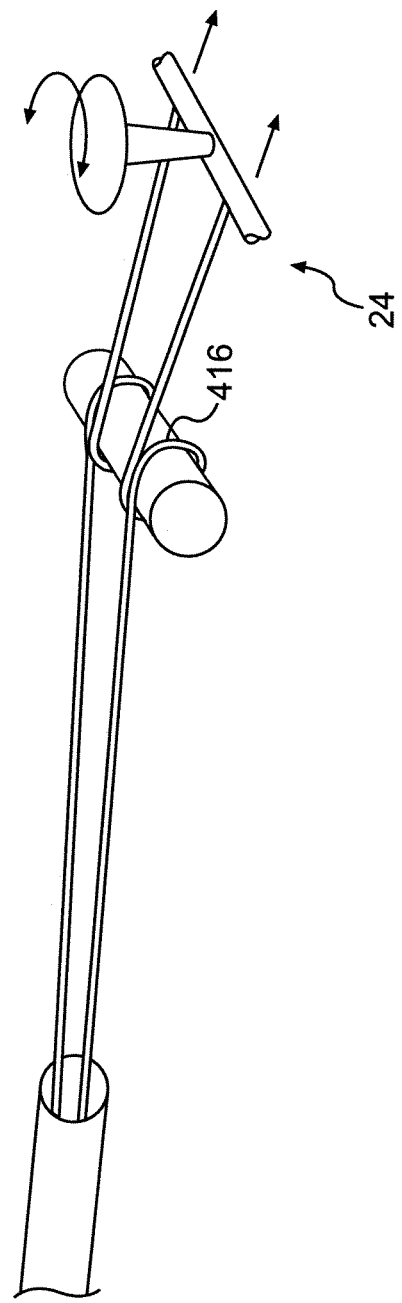
FIG. 97 is a perspective view of an exemplary embodiment of a capstan for use with a tool described herein.

FIG. 97 illustrates a capstan 416 for driving or assisting with driving one or more degrees of freedom of tool 40. For example, when a user drives a handle, the control wires can tighten around capstan 416 and rotation of the capstan can augment force applied by the user. In particular, catheter actuation and/or articulation can be controlled with or facilitated by the capstan. A variety of other mechanical force or pull length multipliers could additionally or alternatively used, including, for example, pulleys, cams, and/or gears.

Figure 98A:
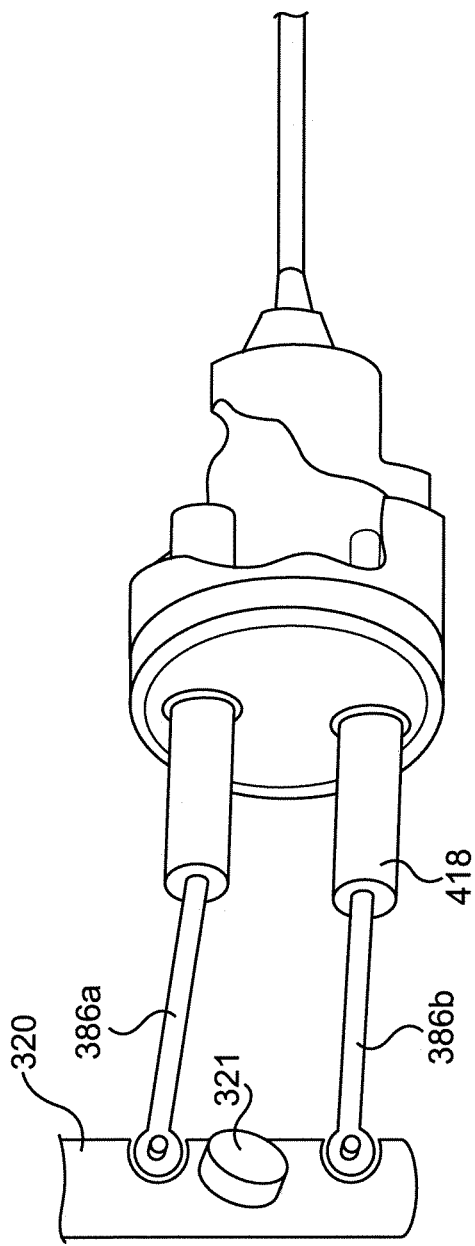
FIG. 98A is a perspective view of an exemplary control mechanism described herein.
Figure 98C:
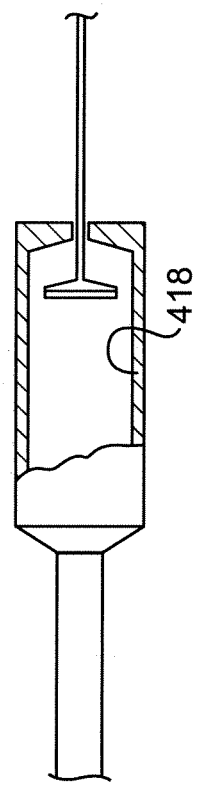
FIGS. 98B and 98C are cross sectional views of one exemplary element of the control mechanism of FIG. 98A.
Figure 98B:
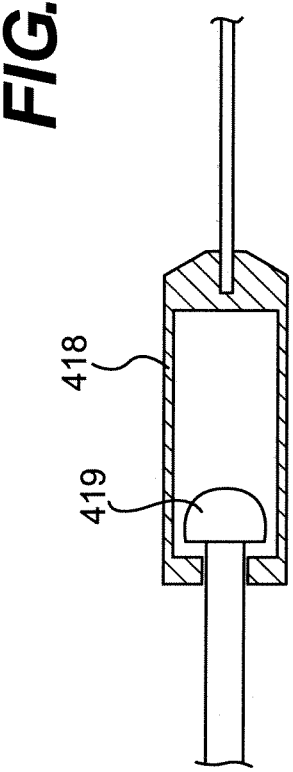

FIGS. 98A through 98C illustrates a drive link 418 that can reduce stress on control cables or wires. In certain embodiments, when a first control wire is pulled, an opposing second control wire is compressed or pushed. Applying compressive forces on control wires can cause buckling and/or wire fatigue. FIG. 98A illustrates an exemplary drive mechanism within control member 24 where pivoting of shaft 320 around axis 321 in a first direction applies compressive forces on one of control cables 368a, 368b and a tensioning forces on the other of control cables 386a, 368b. Similarly, rotating shaft 320 in a second, opposite direction tensions and compresses the other of cables 368a, 368b.

Drive link 418 allows control cables to engage only when pulled. Thus, the drive link can transmit force in one direction, but not in an opposite direction. In one aspect, the drive link mates with at least one control wire, and in another aspect mates with first and second control wires. At least one of the first and second control wires can movably mate with the drive link. In one exemplary aspect, the drive link includes a channel that receives a cable terminal 419. When a compressive force is applied on a control wire, the cable terminal can move within the channel. Conversely, then the first or second control wire is pulled, the cable terminal of the first or second control wire can engage the inner surface of the drive link and transmit forces to the second of the first and second control wire.

In another aspect, the drive link can mate with a control wire at a first end and mate with another portion of the control system at the other end. For example, the drive link can connect a shaft of the control mechanism with a control wire.

Figure 100:
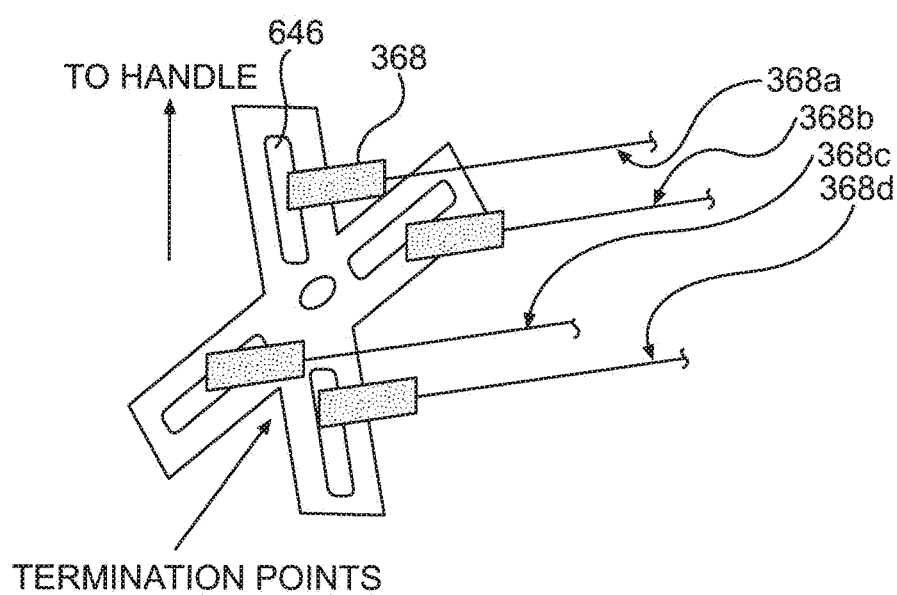

FIGS. 99 and 100 illustrate mechanisms for adjusting the mechanical advantage of control member 24. In one aspect, mechanical advantage is adjusted by changing the location wherein control cables mate with a control mechanism. Where control cables are driven via movement of a shaft or a disk (as described above) the location of where the control cables mate with the shaft or disk can be adjustable. Illustrated in FIG. 99, is a gear mechanism 420*a* which engages cable mounting points. Rotating an adjustment knob can move a control cable toward or away from a pivot point or an axis of rotation of a control mechanism. For example, as described above (e.g., FIG. 44C), rotating disk 328 drives control cables 368. The gear mechanism of FIG. 99 can be incorporated into the control member to move the location where control cables 368 mate with disk 328. In another aspect, the ratio of input to output motion can be adjusted by adjusting the position of the cables toward and away from the center line or pivot point of a drive shaft or swash plate. FIG. 100 illustrates a control member that has an adjustable mechanical advantage that can be changed by moving termination points of control cables 368 along a slot 648.

Figure 101:
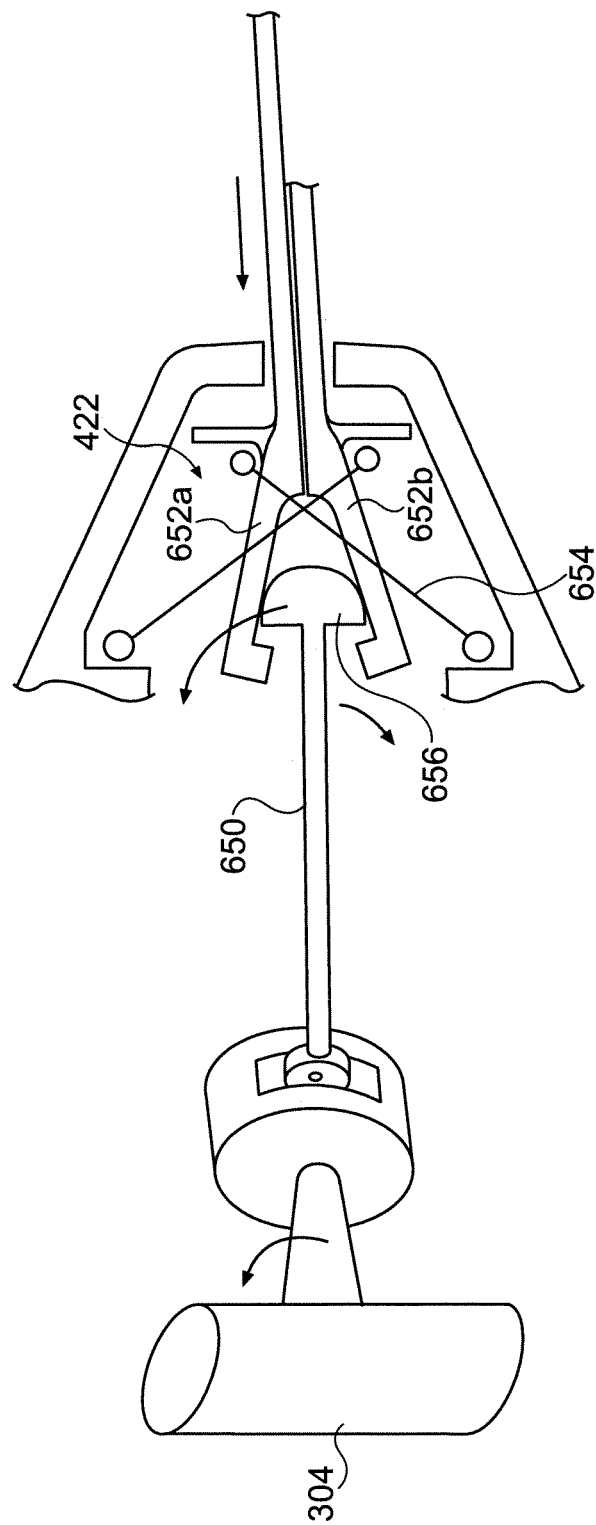

FIG. 101 illustrates control member 24 with a control mechanism 422 for controlling multiple degrees of freedom via a single rod 650. The control mechanism consists of multiple, independently driven links 652*a*, 652*b* that are manipulated via rod 650. While two links 652*a*, 652*b* are illustrated, three, four, or more than four links can surround a distal portion of rod 650. In the illustrated embodiment, rotation of handle 304 can pull rod 650 toward handle 304 and to the side (in the direction of rotation). The transverse component of the rod's movement causes rod 650 to engage one of links 652*a*, 652*b* without engaging the other of links 652*a*, 652*b*. Movement of link 652*a* or 652*b* causes corresponding movement of a control cable connected with the link.

In one aspect, control mechanism 422 is biased in the home position. When a user turns the control handle in the opposite direction or releases the control handle, springs 654 can pull engaged link 652*a* or 652*b* back towards its original position. Continued rotation of control handle 304 can engage opposing link 652*b* or 652*a* and drive a different control cable.

Rod 650 can include a distal driver 656 having a proximal surface shaped and sized to engage a corresponding surface on links 652*a*, 652*b*. When rod 650 is pulled, the proximal surface of distal driver 656 can inhibit slipping of driver 656 with respect to link 652*a* or 652*b*. The distal surface of driver 656 can be configured to slip with respect to link 652*a*, 652*b*. For example, the distal surface of driver 656 can include a tapered or spherical shape that does not engage links 652*a*, 652*b*.

In another aspect, more than two links 652 surround driver 656. Where more than two links 652*a*, 652*b* are provided, rod 650 can drive two adjacent links simultaneously to drive two degrees of freedom simultaneously.

In another aspect, control mechanism 422 allows detachment of rod 650 from drive mechanism 422. In use, the springs 654 can hold the links in contact with ball 656 and prevent detachment of rod 650 from control mechanism 422. To detach rod 650, a user can pull the links away from one another (against the force of springs 654) and/or remove springs 654. Rod 650, including driver 656, can then be detached from links 652. In one aspect, detaching rod 650 allow detachment of catheter 25 from a portion of control member 24.

Figure 102:
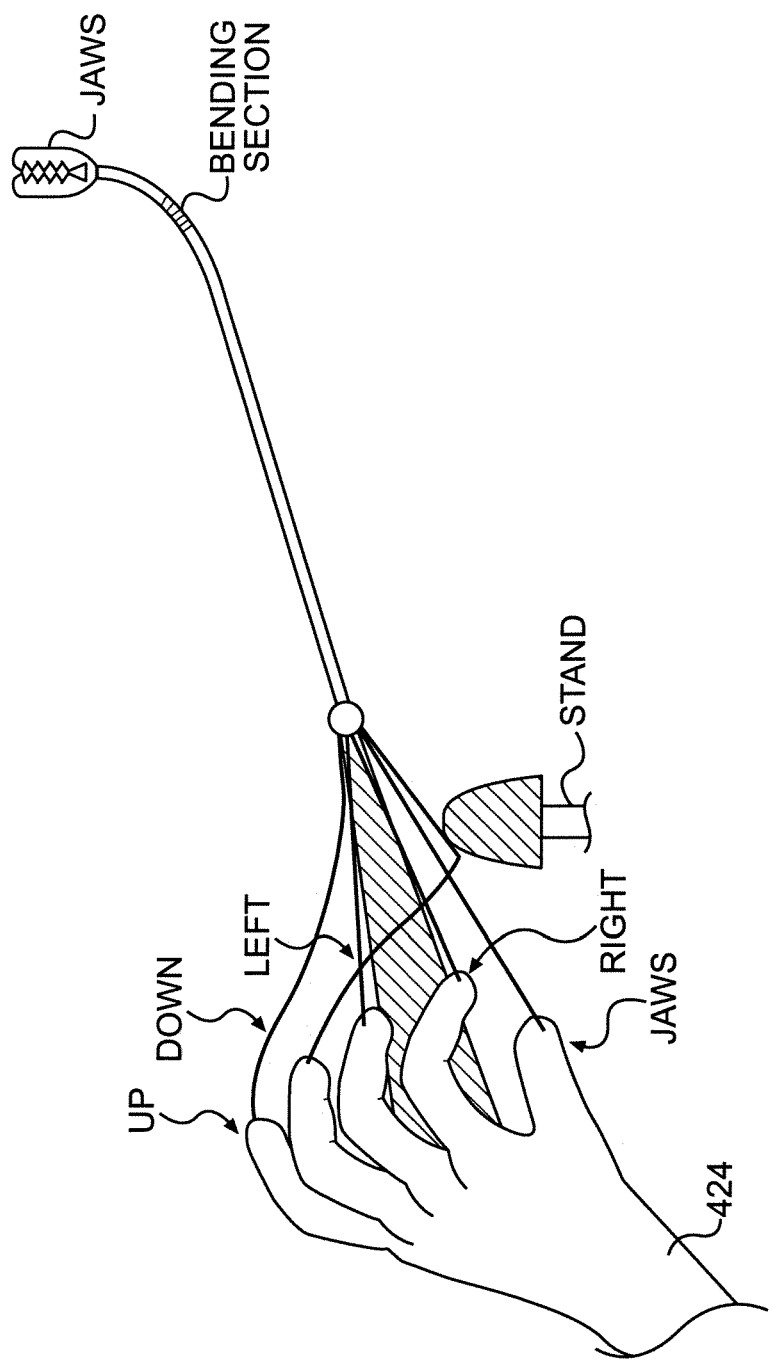
FIG. 102 is a perspective view of an exemplary control member for use with a system described herein.
Figure 103:
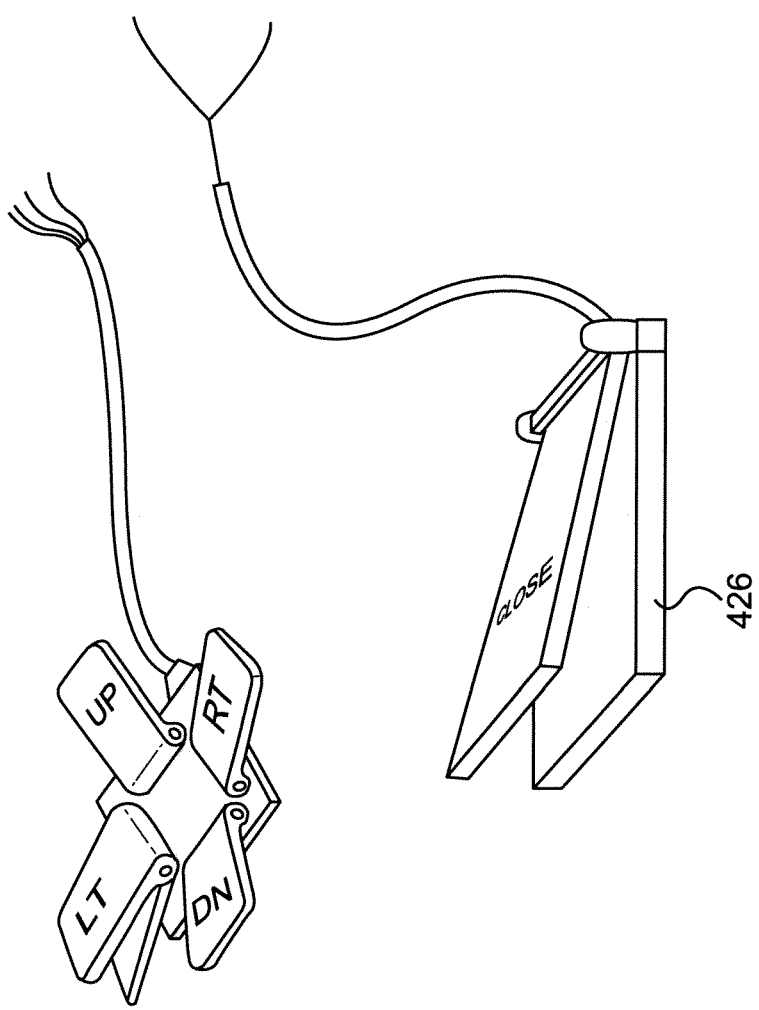
FIG. 103 is a perspective view of foot pedals for use with a system described herein.

FIG. 102 illustrates a control member where instrument cables are directly attached to a user. For example, a user can manipulate a tool via a glove 424. FIG. 103 illustrates a foot pedal 426 that can be used in addition to, or as an alternative to, a hand controlled control member. For example, the foot pedal can control an additional degree of freedom of tool 40.

In some of the embodiments described herein, control member 24 is biased in a home position. For example, resilient members (e.g., springs) within the control member can bias handle 304 in a neutral position. When a user releases the handle, springs apply forces to move the handle toward a home or neutral position. In another embodiment, control member 24 can be configured to hold tool 40 in position after a user releases handle 304. For example, frictional resistance to movement or springs can prevent movement of handle 304 after a user moves and releases the handle.

In another embodiment, tool 40 can be driven with mechanisms other than control cables. For example, system 20 can employ a hydraulic-based control system. Alternatively, system 20 can employ muscle wires where electric current controls actuation of the surgical instruments.

Figure 104:
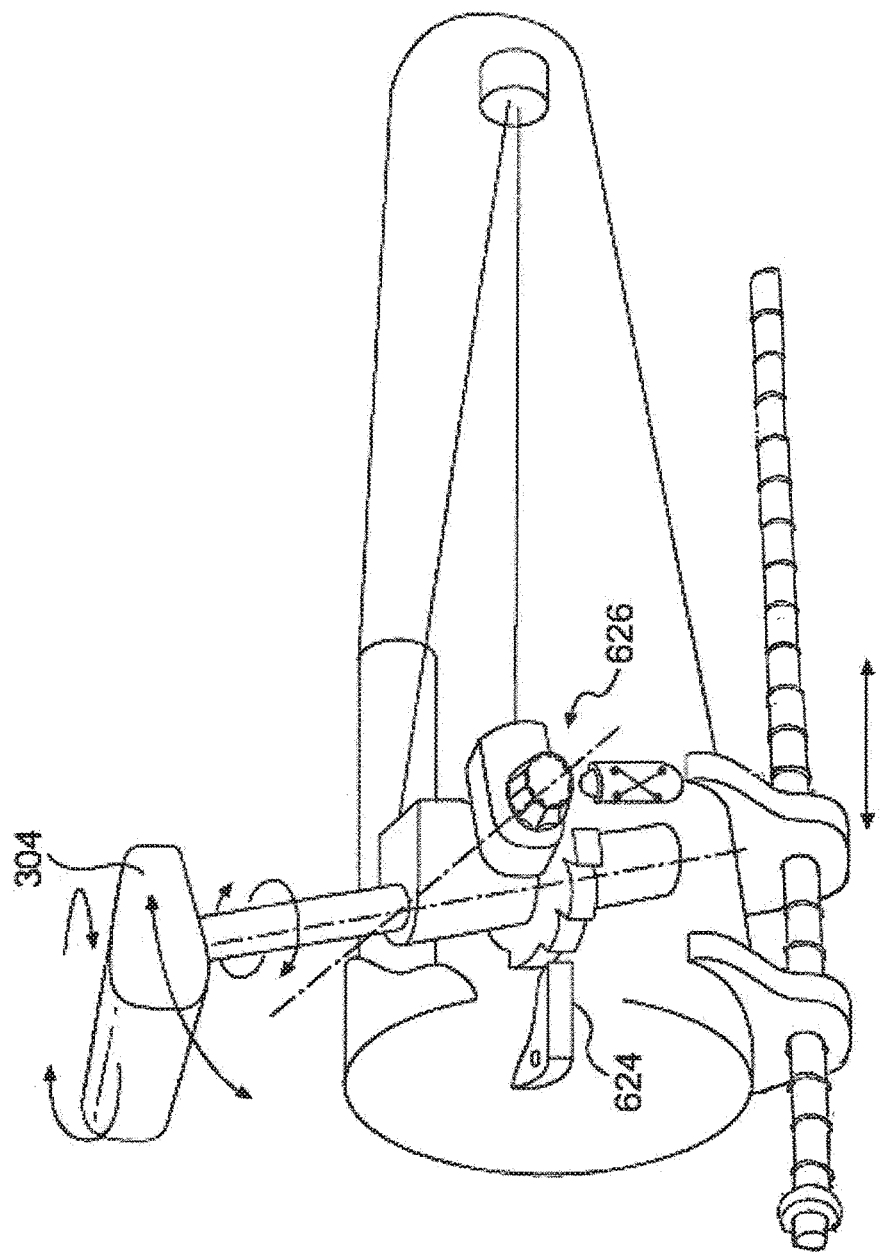
FIG. 104 is a partially transparent view of a control mechanism having exemplary locking and/or damping mechanisms.

FIG. 104 illustrates various locks for freezing or inhibiting movement of various degrees of freedom for system 20. In one aspect, (discussed above) rail 224 and control member 24 can be locked to one another to prevent relative movement. In another aspect, as shown in FIG. 104, grooves on rail 224 can inhibit relative movement. When seated in the grooves, longitudinal movement of control member 24 is inhibited with respect to rail 224. In one aspect, the control member can be lifted to allow relative movement. Alternatively, the grooves can have a small profile and/or a shape that inhibits movement until a user applies sufficient force. Regardless, surface features on rail 224 can inhibit one degree of freedom (longitudinal movement) while permitting another degree of movement (rotation).

In another embodiment, control member 24 can include locks that prevent movement of catheter 25 and/or the distal end effector. As shown in FIG. 104, a ratchet mechanism 624 or ball and detent mechanism 626 can inhibit and/or prevent movement of at least one degree of freedom of the control member. In one aspect, the locking mechanisms can prevent movement of handle 304. In another aspect, the locking mechanisms can selectively lock at least one degree of freedom of catheter actuation. In yet another aspect, the locking mechanisms can lock one degree of freedom while allowing movement and control of other degrees of freedom via control member 24.

Figure 105:
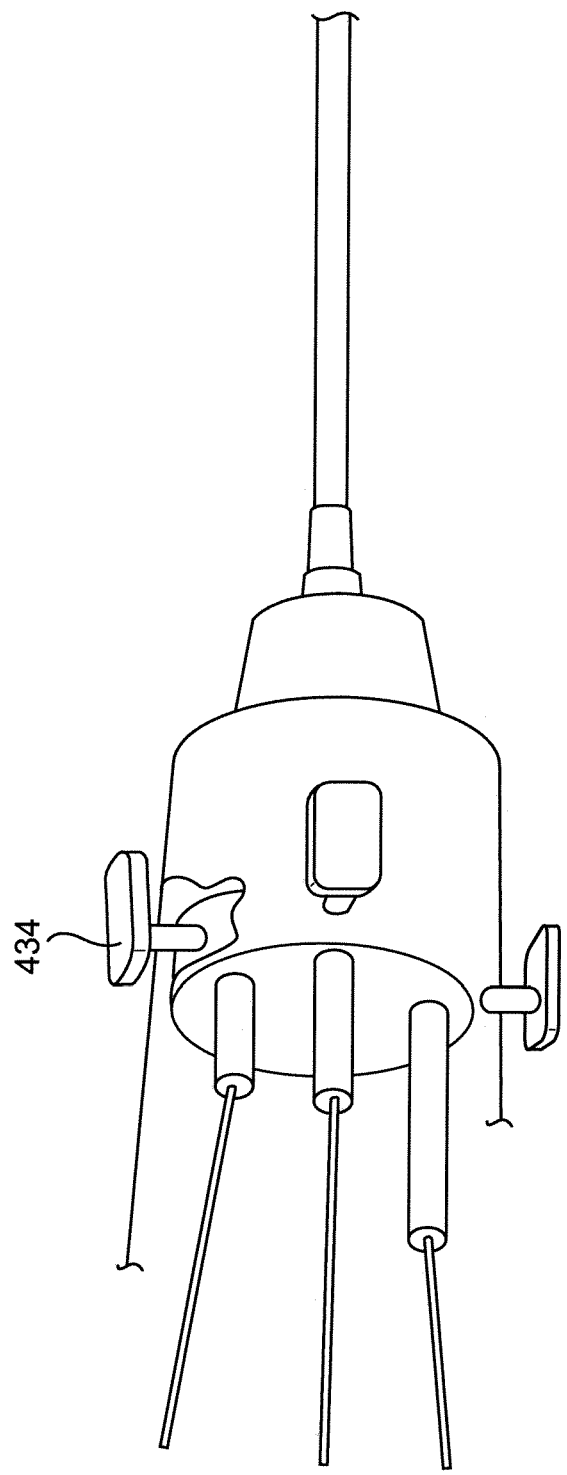
FIG. 105 is a partially transparent view of a control mechanism having an exemplary locking and/or damping mechanism.

FIG. 105 illustrates another embodiment of control member 24 with a locking mechanism 434 that can tension control wires to prevent unwanted movement of tool 40. In one aspect, locking mechanism 434 can prevent movement of control wires within the control member and thereby lock at least one degree of freedom. In another aspect, locking mechanism 434 can increase the force required to move at least one of the control wires for articulating and/or actuating tool 40.

In another aspect, the control member can include a damping mechanism to reduce unwanted movement of tool 40 during manipulation of the control member. The damping can be passive and/or active on one or more degrees of freedom. In one aspect, a hydraulic damper or dash-pot can be mated with at least one control wire within the control member to damp movement of tool 40.

In another embodiment, a position or force sensor can be incorporated into system 20 to assist a user with controlling surgical instruments. In one aspect, a force gauge can measure the amount of force applied by a user for at least one degree of freedom. Maximum or current force can be displayed for a user and/or tool movement can be restrained when a threshold force is reached.

As discussed above, system 20 can be a direct drive system such that a user's inputs to, or applied forces on, control member 24 are transmitted to the distal end of tool 40. In one embodiment, system 20 also provides a user with actual force feedback. As tool 40 contacts a structure, such as an anatomical structure, the user can feel the tool making contact with the structure and receive force and/or tactile feedback. In one aspect, system 20 is adapted to maximize actual force feedback by minimizing unwanted damping. Exemplary structures for minimizing unwanted damping include friction reducing elements such as, for example, pulley bearings; low friction washers, bearings, brushings, liners, and coatings; minimizing bends in the working channels; increased stiffness in catheters; and gradual transitions between passages within the guide tube. A stable ergonomic platform or frame can also assist with force feedback by enabling deliberate movement/control of tools 40 and minimizing distractive losses of energy. As an example, energy required to support a tool can result in distractive losses. Thus, the use of a frame to support tool 40 can reduce distractive losses.

Figure 106:
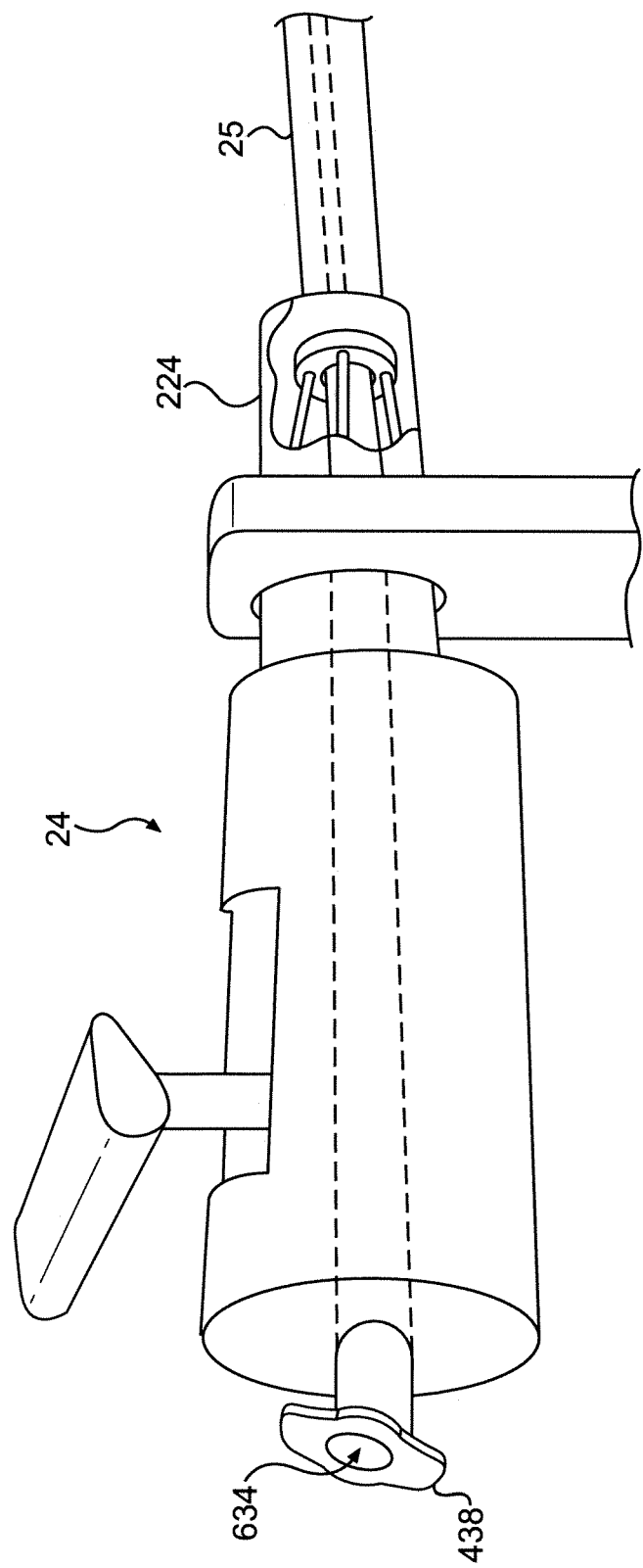
FIG. 106 is a partially transparent view of one exemplary embodiment of a tool and rail described herein.

As mentioned above, a gas or liquid can be delivered to a body cavity via guide tube 26. In one embodiment, the fluid is passed though a lumen within the control member and/or at least one of rails 224a, 224b. As shown in FIG. 106, a opening 438 (e.g., luer fitting) can be positioned on the control member to provide an ingress and/or egress for fluid or solids. The fluids or solids travel through a passageway 634 in control member 24 and into the guide tube and/or catheter 25 for egress proximate to the distal end of system 20. The luer fitting can also, or alternatively, be use to deliver a gas for insufflation or deflation. In another aspect, this lumen can be used to pass instruments to a surgical site.

Passageway 634 can extend through rail 224 in addition to, or as an alternative to control member 24. For example, as illustrated in FIG. 106, the passageway can extend through both control member 24 and rail 224. In another aspect, rail 224 is spaced from control member 24 and the rail includes a fitting for receiving ingress and/or egress of fluid.

Figure 107:
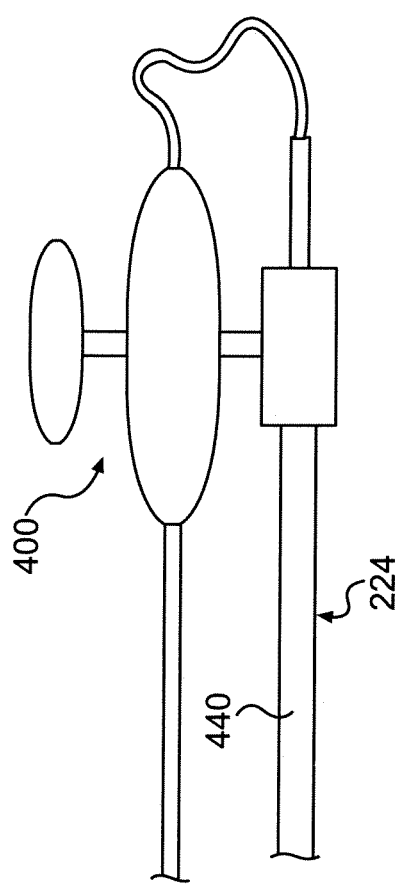
FIG. 107 is a side view of one exemplary embodiment of a tool and rail described herein.

In another aspect, an electric current can be delivered to system 20 through control member 24, guide tube 26, and/or rail 224. FIG. 107 illustrates an electrified rail 440 for delivering power to a RF surgical device. The rail can comprise an electrified pathway defined by an electrically conductive portion of the rail and/or defined by a wire housed within a portion of the rail. In one aspect, energy can be transmitted from rail 244 to tool 40 via direct contact (electrified surface of rail in electrical communication with electrical contact on control member 24); via a wire extending between rail 224 and tool 40; and/or wirelessly (e.g., induction coil).

As mentioned above, system 20 can include an optical device, such as, optical device 28, for viewing a surgical site. The optical device can include a distal lens, a flexible elongate body, and proximal controls for articulating the distal end of the elongate body. In one aspect, optical device 28 includes controls and an articulating section. Alternatively, guide tube 26 is articulated to move the optical device. Regardless, a variety of optical devices, such as an endoscope, pediatric endoscope, and/or fiber-optic based device, can be used with system 20. In addition, the optical device can comprise a variety of chips, such as, for example, CMOS and CCD based chips. In yet another aspect, optics can be incorporated into tools 40a and/or 40b. And in still another aspect, optics can be additionally, or alternatively, integrated into other system components, such as, for example, the guide tube.

Catheter and End Effector

Figure 108:
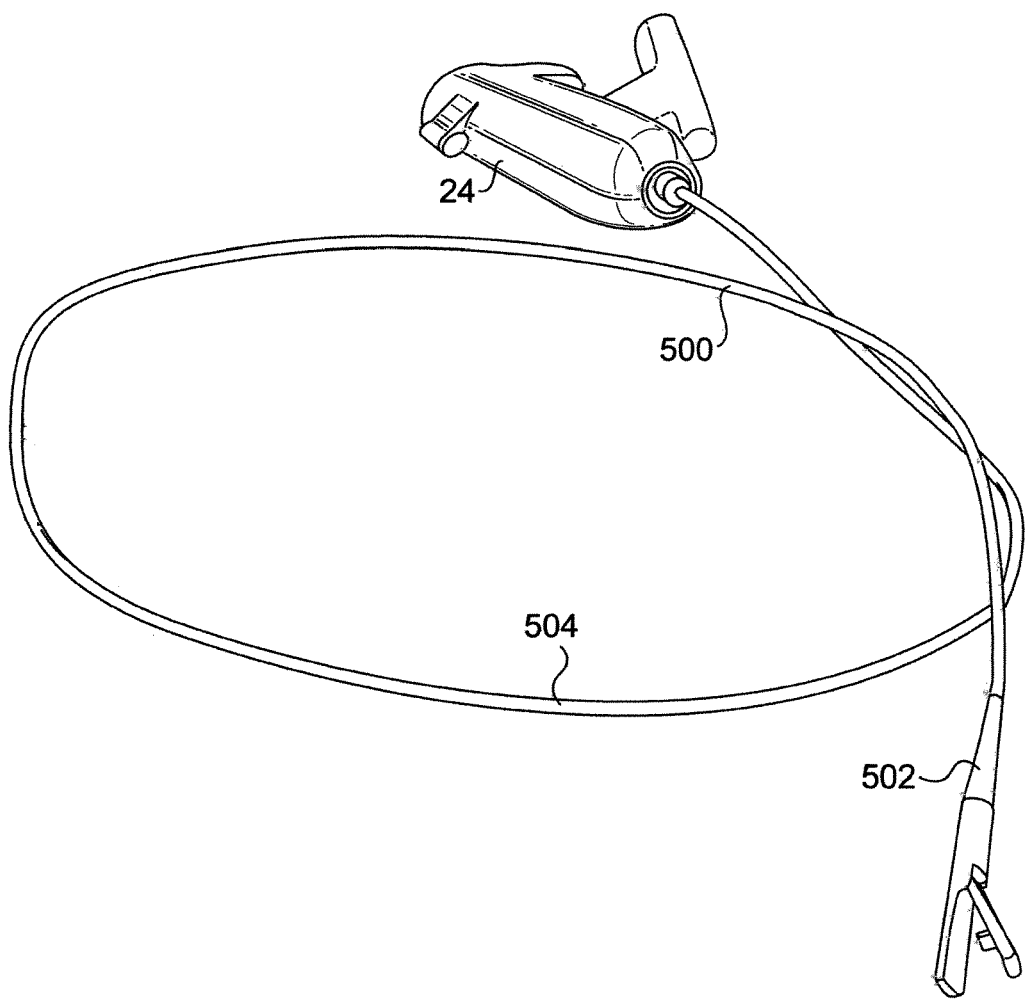
FIG. 108 is a perspective view of one exemplary embodiment of an instrument described herein.
Figure 109:
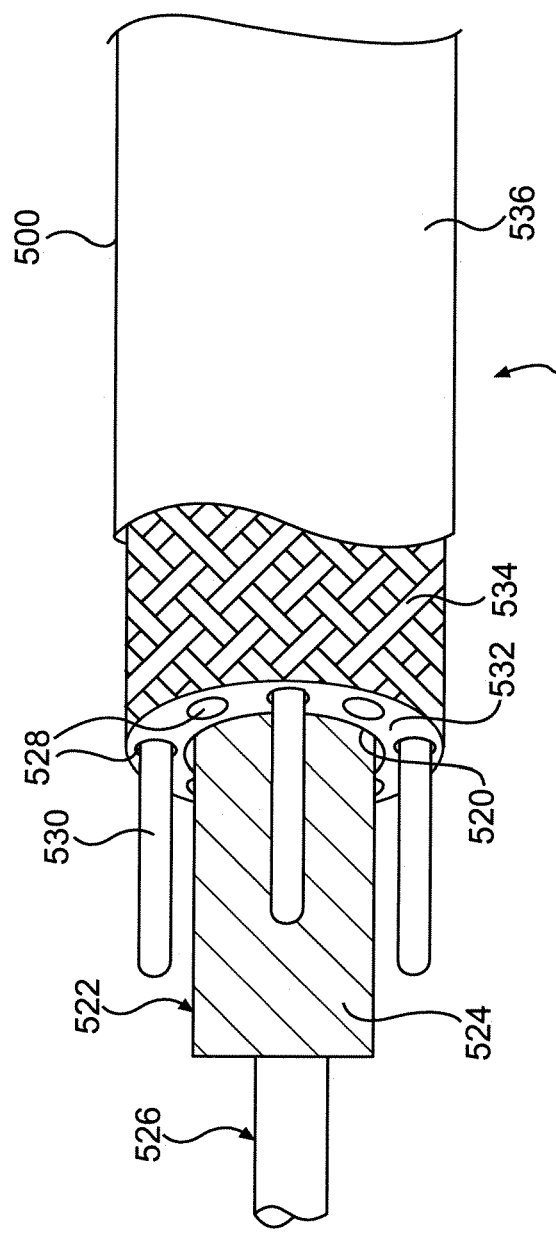
FIG. 109 is a cut-away view of one exemplary embodiment of a tool described herein.

As shown in FIG. 108, tool 40 generally includes a proximal control member 24, an elongate catheter body 25, and an end effector 502. FIG. 109 illustrate a cut-away view of the mid-portion of catheter 25 including an inner channel 520 for a bowden cable 522, which can include an outer sheath 524 and inner filament 526. In one aspect, more than one inner channel 520 and/or one or more than one bowden cable 522 can extend through catheter 25 for control of end effector(s) 502. In yet another embodiment, the bowden sheath is replaced with an insulated material (e.g., liner or insulated composite) and houses an electrically conductive wire for transmitting electrosurgical energy.

Catheter 25 can further include tubular body 532 defining control wire lumens 528. Tubular body 532 can include the various features of working channel bodies 50 and/or inner and outer tubular bodies 46, 48, discussed above. In another aspect, tubular body 532 is a single, unitary body defining multiple control wire lumens 528. In one aspect, control wire lumens 528 can house control wires 530 for manipulating an articulation section of tool 40. The number of control wires 530 and control wire lumens 528 can be varied depending on the desired degrees of freedom of the tool 40 and the intended use of system 20.

Elongate body 500 can further comprise a wire or mesh layer 534 positioned around tubular body 532. The properties of mesh layer 534 can be varied to adjust the stiffness and/or strength of elongate body 500. The elongate body 500 can also include an outer sheath 536 to prevent the ingress of biological materials into tool 40. Outer sheath 536, in one aspect, is formed of a fluid impervious elastomeric or polymeric material.

In one aspect, tool 40 can be configured to provide at least one degree of freedom, and in another aspect, can provide two, or more than two, degrees of freedom. For example, at least a portion tool 40 can controllably move up/down, side-to-side, laterally along the axis of the guide tube, rotationally around the axis of the guide tube, and/or can actuate the end effector. In one aspect, control cables extending through catheter body 25 can move the end effector up/down, side-to-side, and can actuate end effector 502.

Figure 110:
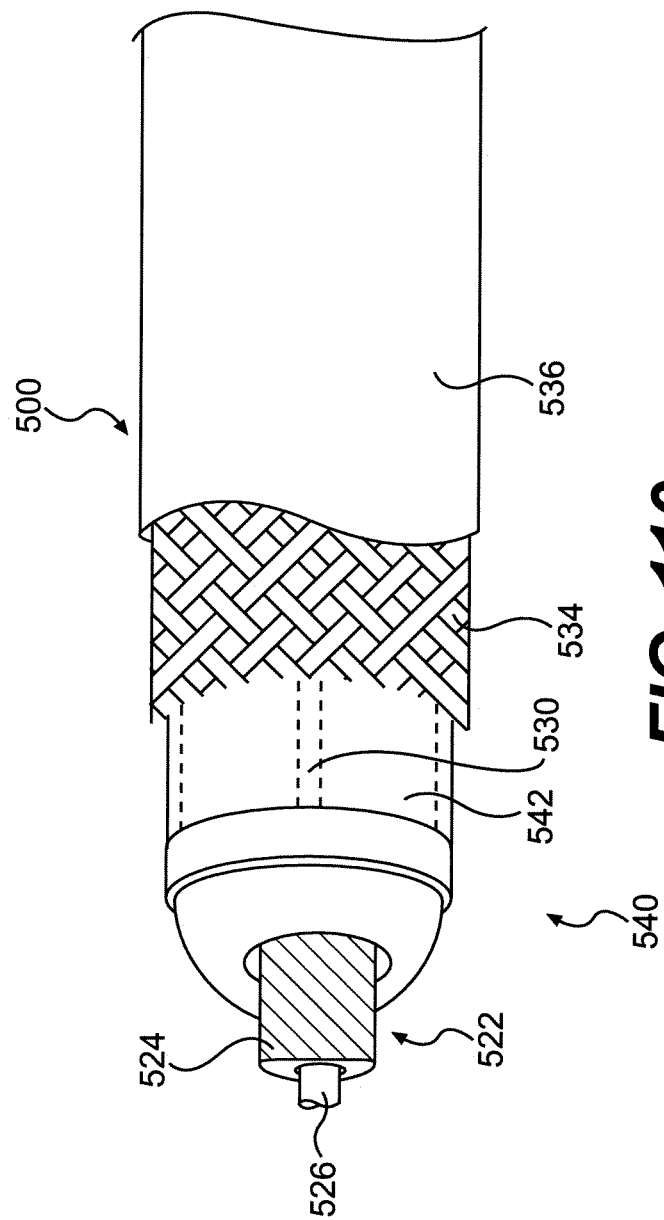
FIG. 110 is a cut-away view of another exemplary embodiment of a tool described herein.

The distal end of tool 40 can, for example, include an articulating section 540 which provides an up/down and/or side-to-side articulation. As illustrated in FIG. 110, articulation section 540 can include mesh layer 534 and/or outer sheath 536 as discussed above with respect to the mid-portion of elongate body 500. Within mesh layer 534, articulation section 540 can comprise an articulating body 542 formed of a series of tube segments or rings (not illustrated). Control wires 530 can be mated to articulating body 542 to control movement of the articulating body 542.

In addition, tool 40 can include a variety of alternative end effectors, for example, a grasper, scissors, tissue cutter, clamp, forcep, dissector, and/or other surgical tool that can open and close. In another aspect, the end effector is not configured to actuate. In still another aspect, the end effector is defined by a portion of the catheter body and includes, for example, a blunt end or open lumen.

Figure 111A:
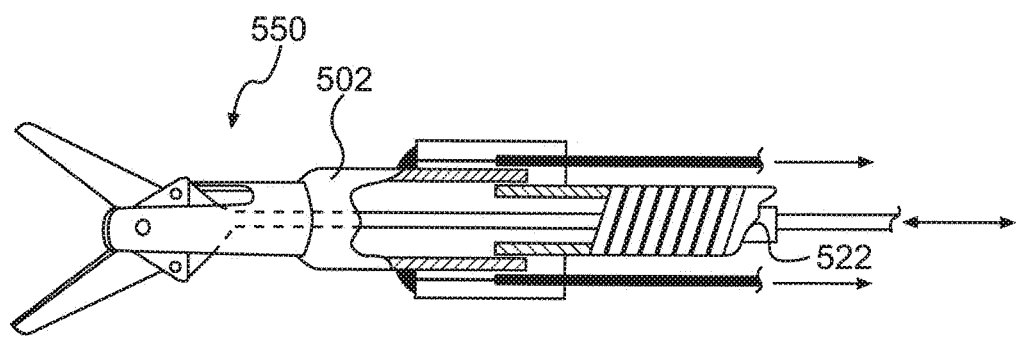
FIGS. 111A, 111B, and 111C are partially transparent views of exemplary end effectors described herein.
Figure 111B:
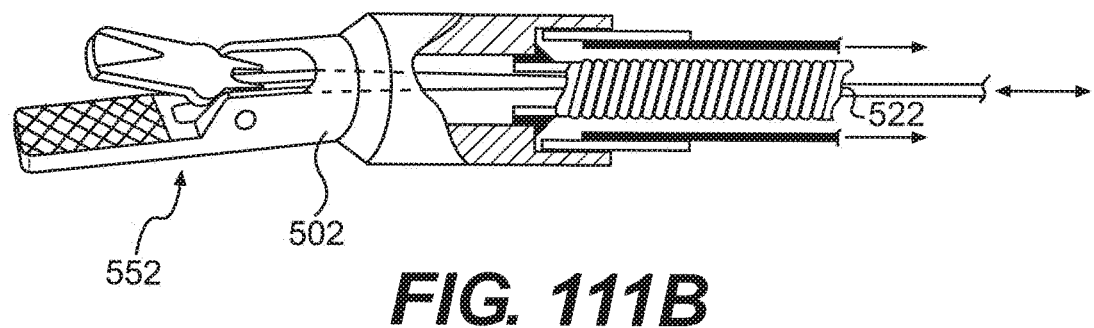
Figure 111C:
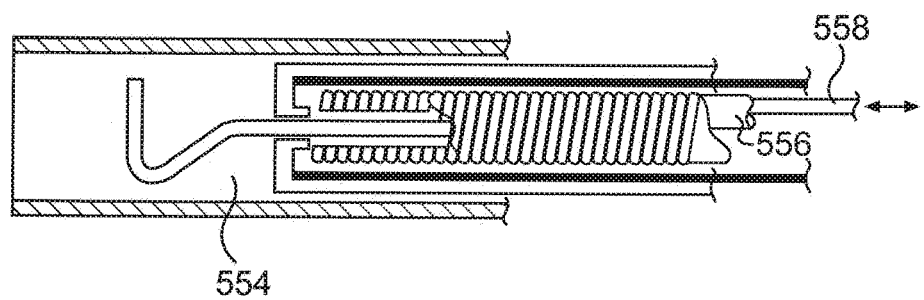

FIG. 111A illustrates one exemplary embodiment of end effector 502. As shown, bowden cable 522 can be tensioned to close grasper 550. Similarly, FIG. 111B illustrates one exemplary embodiment of a needle driver 552 controlled by bowden cable 522. In yet another embodiment, a cautery device can be used in place of the end effector. For example, FIG. 111C illustrates a hook cautery device 554. An energy source can coupled to tool 40. For example, control member 24, frame 22, and/or rail 224, and can transmit energy to the distal hook cautery device 554. The variety of monpolar and bipolar cautery devices can be used with system 20. System 20 can include insulating materials to reduce the chance of stray electrical currents injuring the user and/or patient. In one aspect, an insulating sheath 556 is positioned around an energy delivery wire 558.

Additional end effectors are also contemplated in addition to those illustrated in FIGS. 111A through 111C. For example, the end effector can include closure mechanisms such as clips, staples, loops and/or ligator suturing devices. In addition, retrieval means, such as, for example, snares, baskets, and/or loops can also be mated with system 20. In still another aspect, the end effector can be an exploration or tissue sampling device, such as, for example, optics, cytology brushes, forceps, coring devices, and/or fluid extraction and/or delivery devices. In yet another aspect, instruments that aid in the patency of a lumen or dilate an opening are contemplated. For example, the end effector can be a balloon, patency brush, stent, fan retractor, and/or wire structures.

In yet another embodiment, tool 40 does not include an end effector. For example, the tool can include a blunt tip for exploration and/or for assisting another surgical instrument or end effector. In still another embodiment, tool 40 can include an open distal end for the delivery of a treatment fluid or solid and/or for collection of a bodily fluid or tissue sample. In one such aspect, catheter 25 can include an open lumen that extends to the distal opening for delivery and/or collection of a substance.

Described below are several alternative embodiments of tool 40.

Figure 112:
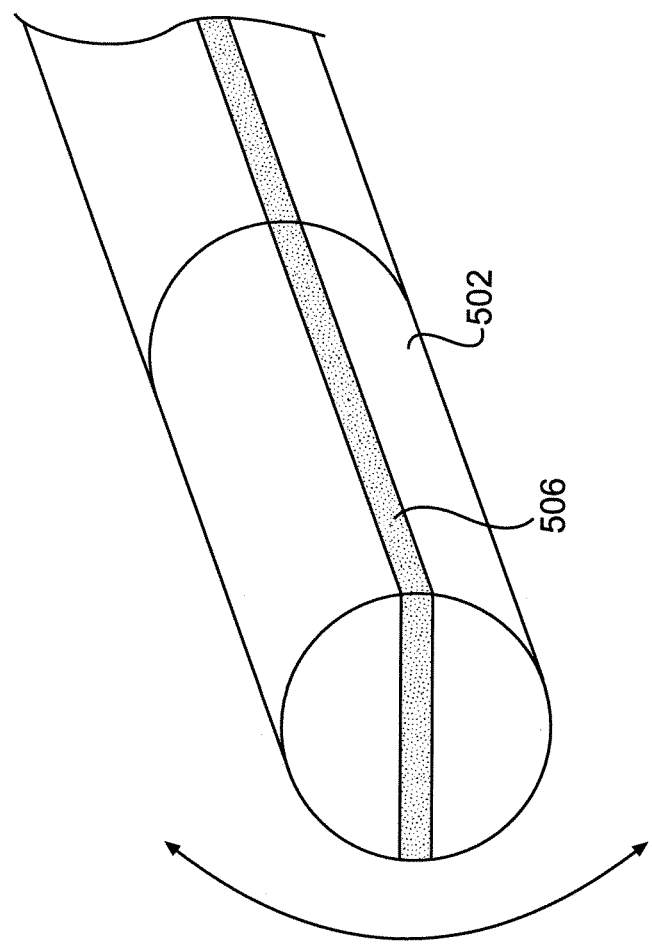
FIG. 112 is perspective view of the distal end of one exemplary embodiment of a tool described herein.

FIG. 112 illustrates one aspect of an end effector 502 that includes a leaf spring 506 adapted to restrict motion of the end effector. In one aspect, leaf spring 506, when position in end effector 502, prevents at least one degree of freedom, such as, for example, motion in a direction parallel to a plane of the leaf spring. Leaf spring can be moved in and out of position via a pusher wire (not illustrated). While leaf spring 506 is discussed with respect to an end effector, a leaf spring or springs can be used throughout catheter 25 to inhibit movement of a degree of freedom.

FIG. 113 illustrates a mating plate 508 positioned proximate to the interface of the catheter body 25 and end effector 502 of tool 40. As describe above with respect to plate 63, mating plate 508 can facilitated mating of control cables 510 with end effector 502.

As mentioned above, tool 40 can include control cables. In one aspect, at least one of the cables is a bowden-type cable. For example, a bowden-type cable 512 can drive end effector 502, while the other degrees of freedom are manipulated by non-bowden-type wires. Alternatively, more than one degree of freedom could be controlled with bowden cables.

Figure 114:
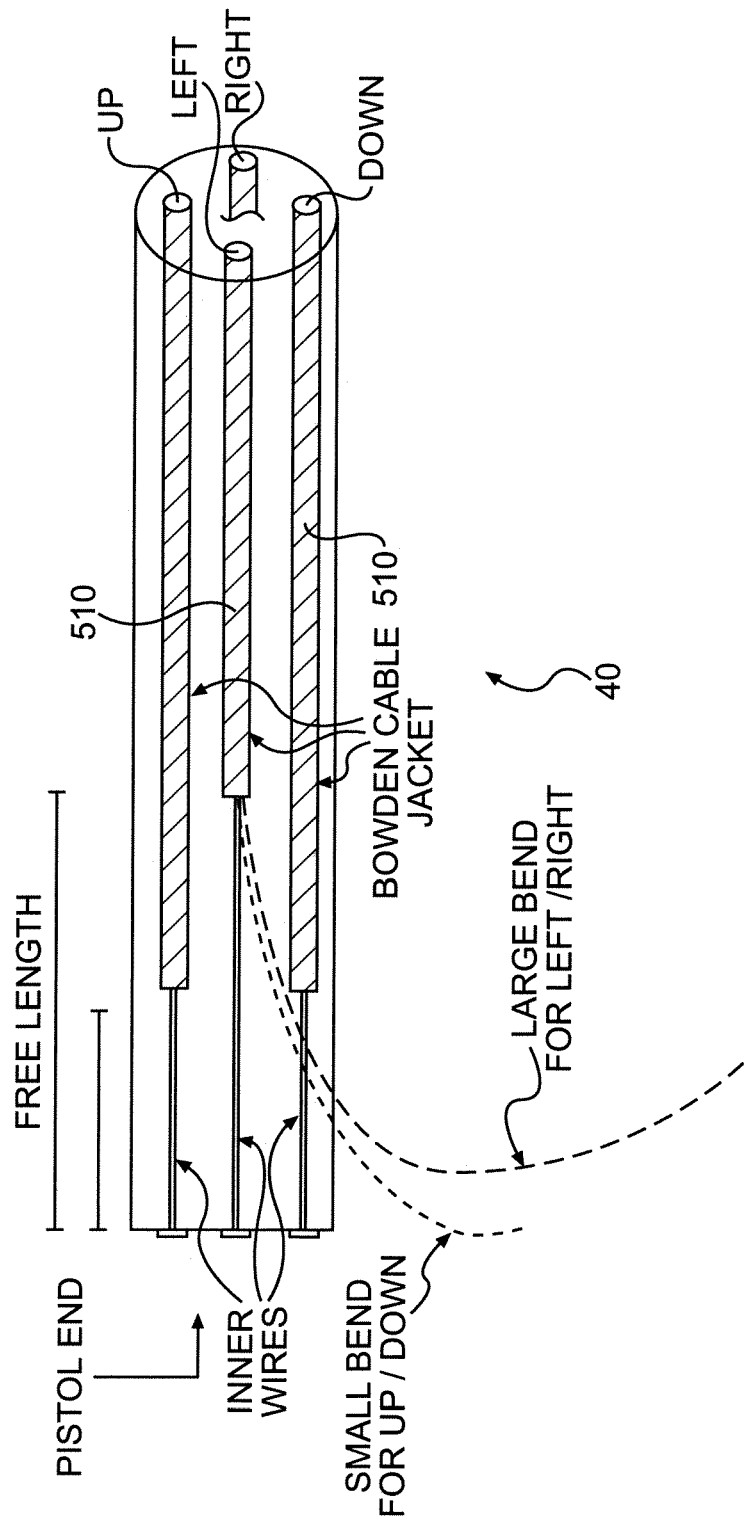
FIGS. 114, 115, 116A, and 116B are partially transparent views of exemplary embodiments of tools described herein.

In another embodiment, tool 40 can have a variable length articulation section. For example, as shown in FIG. 114, the length and/or position of control cables 510 can be adjusted to control the length of the articulation section of tool 40. In one aspect, cables 510 can be bowden-type cables and the length or position of the bowden cable sheath is adjusted to change the length of the articulation section.

Figure 115:
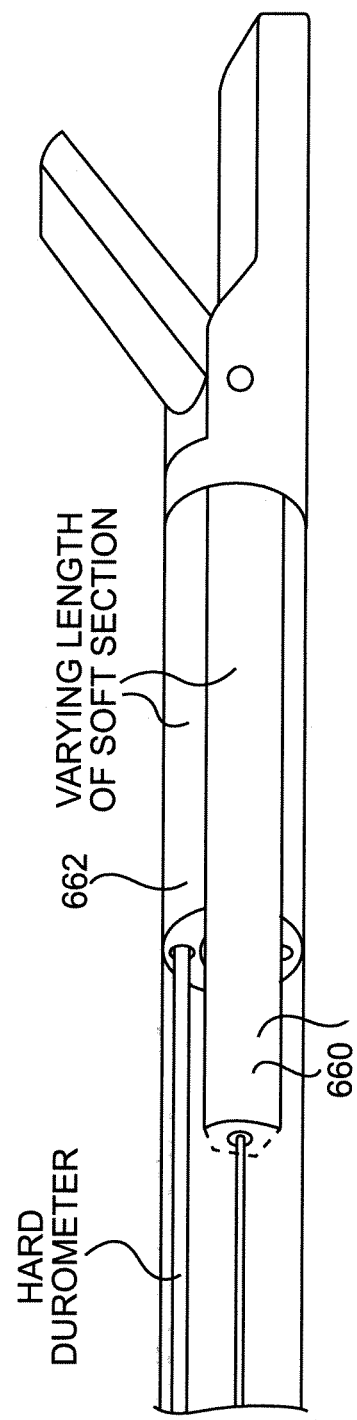

Cather body 25 can have a variety of alternative configurations. In one aspect, the catheter body includes different properties along its axial length. For example, elongate body 500 can have materials with different hardness along the length of the elongate body. In one example, catheter hardness varies along the length of the catheter. In another aspect, catheter hardness can vary in a transverse direction. FIG. 115 illustrates a softer durometer section 660 that extends parallel to a harder durometer section 662. Variations in hardness can be chosen to provide different bending characteristics.

Figure 116A:
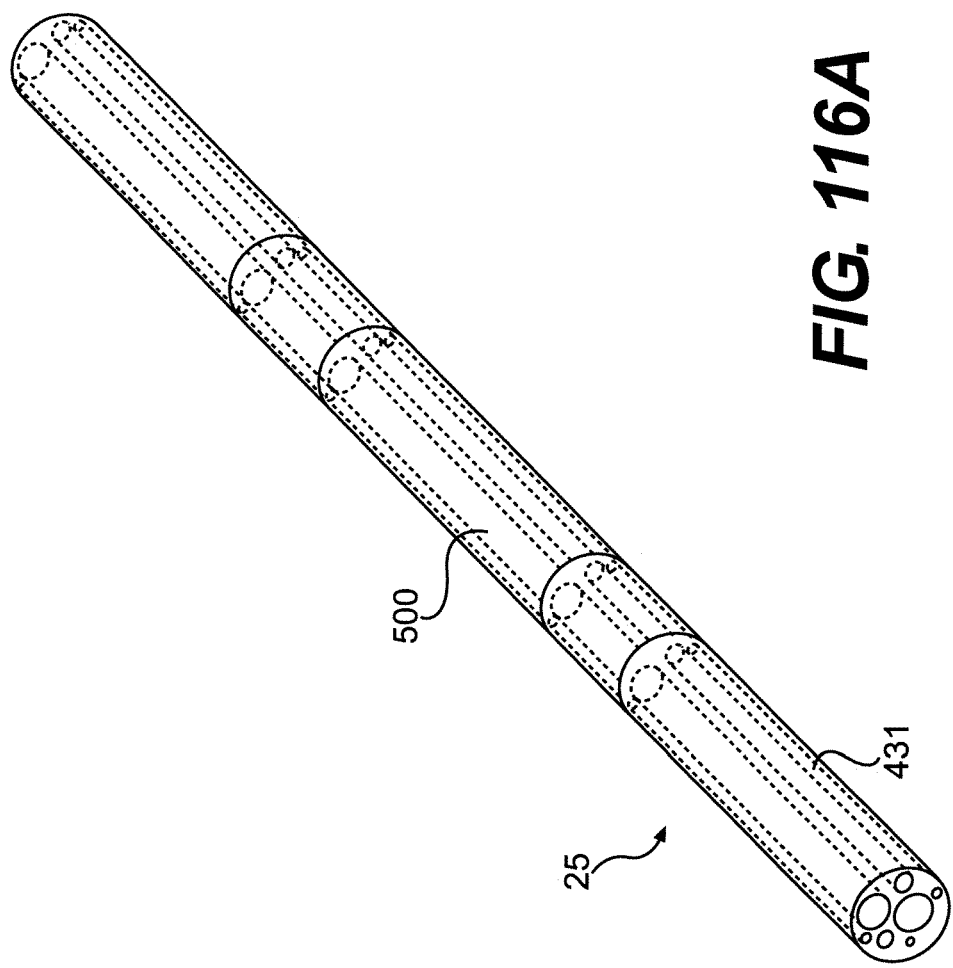
Figure 116B:
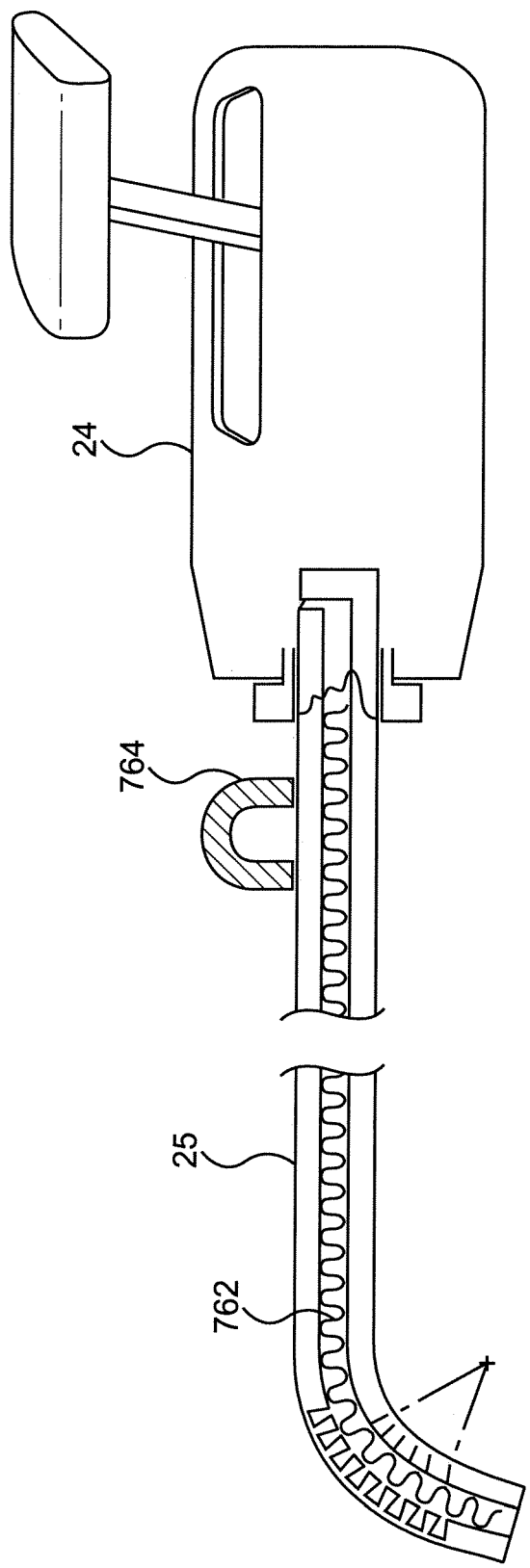

In another aspect, a user can vary the hardness of catheter 25. FIG. 116A illustrates catheter 25 having control wire lumens and stiffening lumens 431. The stiffness of catheter 25 can be adjusted by injecting or removing a material (e.g., a fluid) into the stiffening lumens 431. In one aspect, catheter 25 includes opposed stiffening lumens 431 that permit a user to adjust the bending characteristics of the catheter. For example, one side of the catheter can be increased in stiffness. In another aspect, different segment of the catheter along its length can have different stiffening lumens to allow stiffness variability along the length of the catheter.

In one aspect, a user can inject a stiffening fluid. In another aspect, the stiffening lumens can receive a stiffening rod or rods. For example, catheter 25 can be provided with a set of stiffening rods having different stiffness. A user can select a stiffening rod of a desired stiffness and insert the selected rod to adjust catheter properties. The stiffening rods can also have different lengths or varying stiffness along their length to allow adjustment of stiffness along the length of the catheter.

In another embodiment, a magnetic rheological fluid within catheter 25 can stiffen and/or lock the catheter. FIG. 1166 illustrates a chamber 762 for receiving magnetic rheological fluid and a magnet 764 that can apply a magnetic field on the fluid within chamber 762 to stiffen the catheter. In one aspect, chamber 762 extends along a length of catheter 25. When a magnetic field is applied, the stiffened fluid can prevent side-to-side and/or up/down movement of the catheter.

Figure 117:
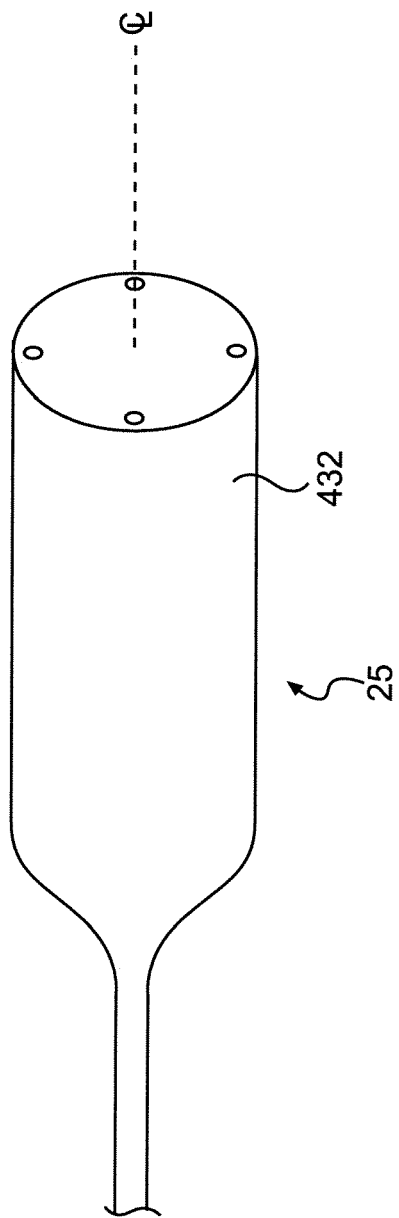
FIG. 117 is perspective view of the distal end of one exemplary embodiment of a tool described herein.

FIG. 117 illustrates catheter tips have a tip wider 432 than the body of catheter 25. The wide tip can provide greater bend strength by allowing increased separation of pull wires. In one aspect, catheter 25 of FIG. 117 is used with a guide tube having a working lumen with increased diameter in a distal portion thereof. The distal section of the working channel can be sized and shaped for receipt of the wide tip. In one aspect, the wide tip is larger than a proximal portion of the working lumen. The catheter can be placed within the working lumen prior to insertion of the guide tube into a patient.

Figure 118:
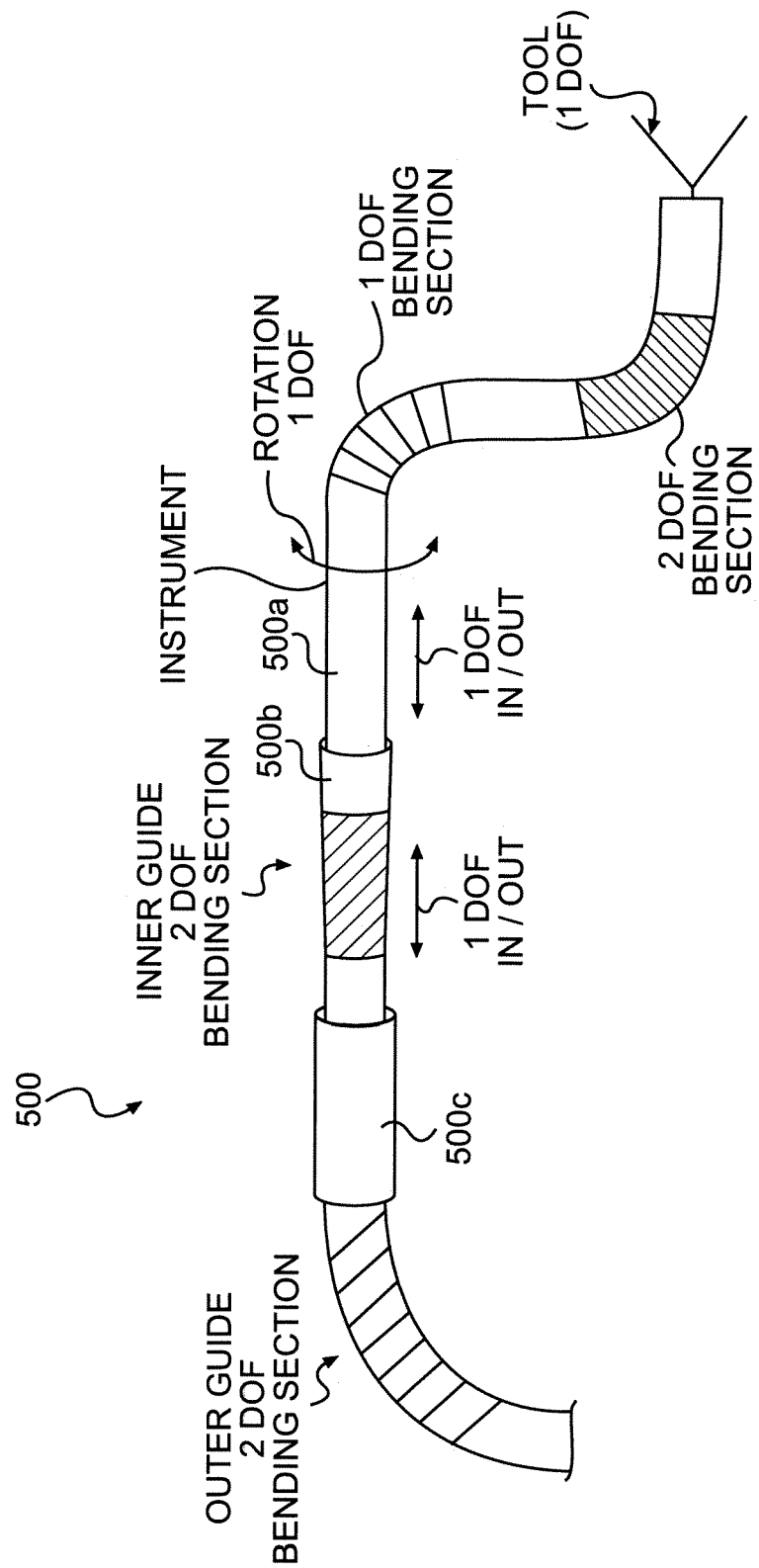
FIG. 118 is perspective view of the distal end of one exemplary embodiment of a tool described herein.

In still another embodiment, the elongate body 500 of tool 40 can have more than three degrees of freedom. FIG. 118 illustrates body 500 having multiple body segments and multiple degrees of freedom, including, for example additional rotation, longitudinal, pivotal, and bending degrees of freedom. In one aspect, tool 40 can include more than one articulating or bending section along its length. In another aspect a first catheter segment 500a can rotate with respect to a second catheter segment 500b. In another aspect, catheter body 500 can include telescoping segments. For example, catheter segments 500a, 500b, 500c can be telescoping.

In another example of a catheter having additional degrees of freedom, catheter 25 can have two longitudinally separated articulation sections. Thus, the catheter can have a "wrist" and an "elbow." The wrist and elbow can permit the tool to form a s-curve.

To assist with determining the location of, or degree of movement of, the end effector 502, a portion of tool 40 can include markings. FIG. 119 illustrates tool 40 having markings 516 for determining the amount of relative movement between tool 40 and another portion of system 20. In one aspect, the indicia allow a user to determine the rotational and/or longitudinal position of the catheter with respect to the guide tube, frame, rails, patient, and/or another point of reference.

A variety of catheter body structures can be used with system 20. FIGS. 120A and 120B illustrate one exemplary embodiment of tool 40 having a main body 700 and a distal articulating section 702. Main body 700 can be comprised of a semi-flexible extrusion 704 such as nylon, PTFE, or the equivalent. In one aspect, the main body can include at least one lumen for a bowden cable. For example, a bowden cable can extend through a central lumen within main body 700. Additional control cables, such as bowden cables or pull wires, can extend through the central lumen and/or be housed in separate lumens. In one aspect, multiple lumens, such as, for example, four lumens, are provided for multiple bowden cables, such as, for example, four bowden cables.

Alternatively, or additionally, the catheter body can have a variety of different configurations depending on the intended use of tool 40. For example, instead of mating with an end effector, body 700 can have an open lumen for delivering a separate instrument or therapeutic substance. In another aspect, the body can be formed of an electrically insulative material and/or include an insulative liner to allow the transmission of electrosurgical energy to an end effector.

The articulation section 702 can include a softer or lower durometer extrusion. The articulation-section extrusion can have a similar arrangement of lumens as the body extrusion. For example, the articulation section 702 can include a central longitudinal opening for receiving a bowden cable.

Tool 40 can include a transition region where the catheter stiffness changes between harder and softer sections. As shown in FIG. 120A, a portion of main body 700 can extend into the articulation section. In particular, a extension member 710 of the main body can extend into a lumen of the articulation section. Extension member 710 can have a size and shape corresponding to the inner lumen of the articulation section. In use, the extension member can stiffen the proximal end of the articulation section to provide a gradual transition between the harder main body and softer articulation section. In one aspect, the extension portion has varying flexibility such that at its proximal end the extension portion has a stiffer configuration and less stiff configuration at its distal end.

As shown in FIGS. 120A, 121A, and 121B, tool 40 can include a thrust plate 706 positioned between the main body and articulation section. In one aspect, the thrust plate can include holes or slots 708 for strands to extend through. The holes can be sized to allow the inner strand of a bowden cable to pass therethrough. Conversely, the outer casing of the bowden cables are prevented from extending distally beyond the thrust plate. For example, the outer casings can mate with the thrust plate and/or the thrust plate holes can be sized to prevent the passage of the bowden casings therethrough. In one aspect, as shown in FIG. 121B, the thrust plate can include recessed areas around the holes 708 to receive the bowden cable casings.

In one aspect, the thrust plate can be formed by a single-piece thrust plate body. In another aspect, thrust plate 706 is defined by a multiple piece structure. For example, FIG. 120A illustrates a two-piece thrust plate. Together, the two-pieces define the desired shape of thrust plate 706.

In another aspect, thrust plate 706 includes a central opening 711 sized and shaped to receive extension member 710 of main body 700. The extension member can pass through central opening 711 and into a corresponding lumen within articulation section 702.

Figure 122A:
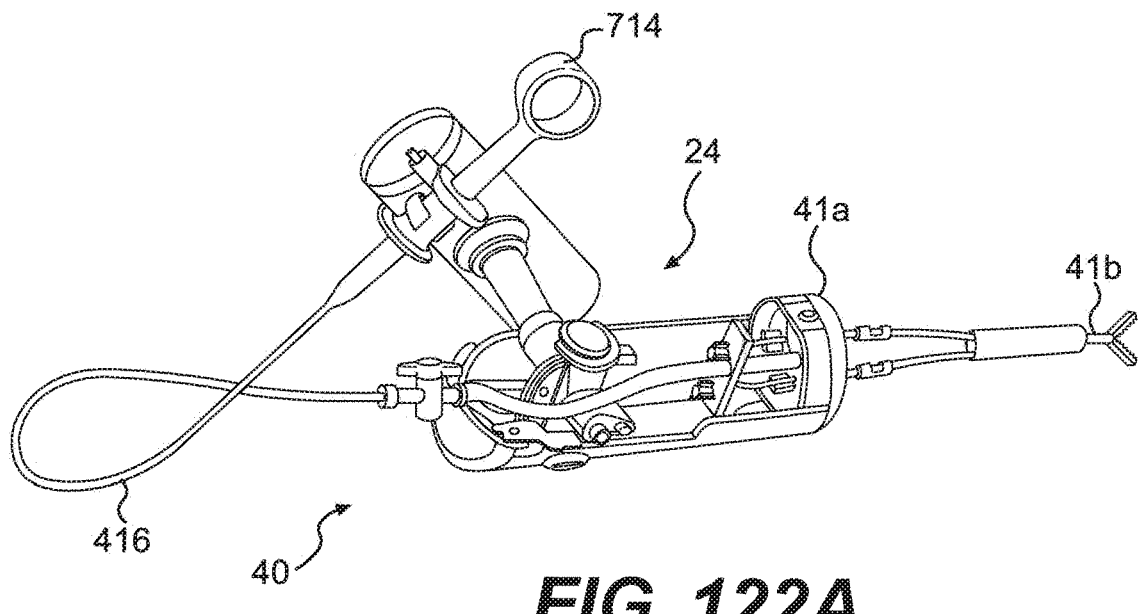
FIG. 122A is a cut-away view of one exemplary embodiment of a two-part tool described herein.

FIGS. 122A through 126 illustrate yet another embodiment of a tool for use with the systems described herein. Instead of an end effector mated with tool 40 as described above, in another embodiment tool 40 is composed of two independent bodies. As illustrated in FIG. 122A, tool 40 can include a first tool member 41a and a second tool member 41b. Together, tool members 41a and 41b can provide the same functionality as tool 40 described above. However, two-part tool 40 allows a user to removed and replace tool member 41b to change distal end effectors. In addition, the two-part tool can provide additional degrees of freedom.

Figure 123A:
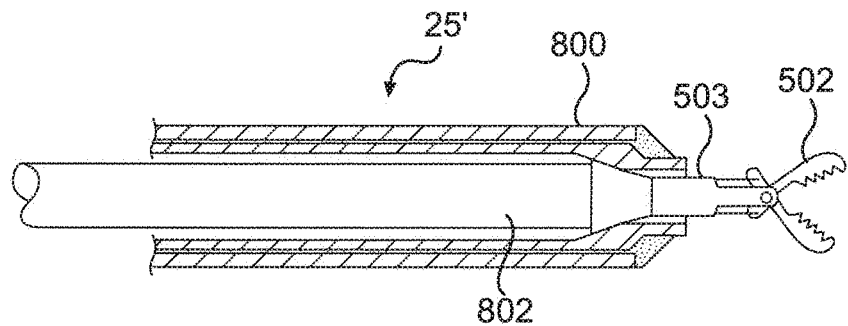
Figure 123B:
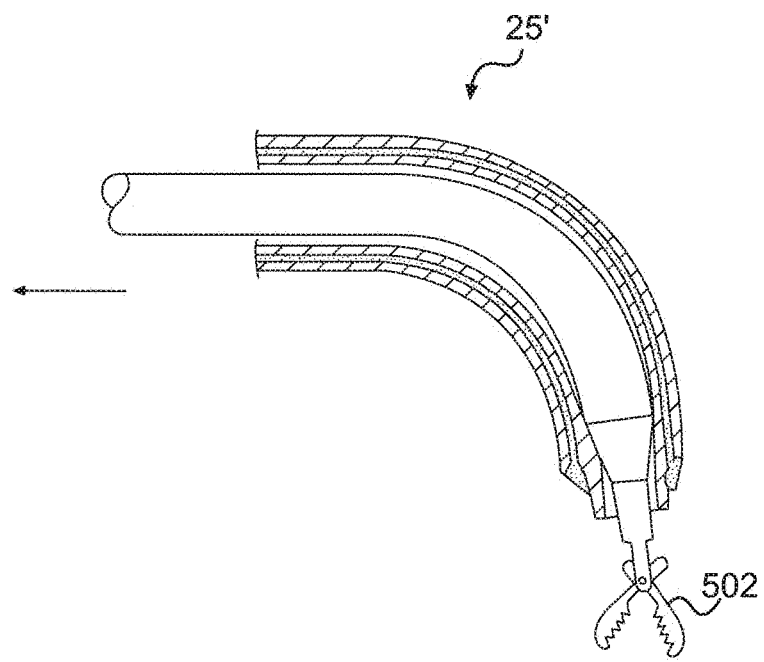

FIGS. 123A and 123B illustrate catheter body 25' defined by a first outer body 800 of tool member 41a and a second inner body 802 of tool member 41b. The outer body 800 can have an open inner lumen that extends from control member 24 to the distal end of the tool. Second inner body 802 can include an elongate member and end effector configured to pass through the outer body. In use, the inner body can be directed through the outer body so that the end effector of the inner body extends out of the distal end of the outer body. The inner and outer bodies can work together and act as a single-body tool.

The outer body can control up to four degrees of freedom, while the inner body can have at least one degree of freedom. For example, the outer body can control left/right, up/down, longitudinal movement, and/or rotational movement as described above with respect to tools 40. The additional degree of freedom provided by the inner body can be actuation of the end effector.

In one aspect, the inner and outer bodies 800, 802 can mate with each other with such that inner body 802 and end effector 502 move in unison with outer body 800. When the inner and outer bodies are mated with one another, bending or articulating outer body 800 can cause the inner body 802 to bend without end effector 502 of the inner body moving longitudinally with respect to the outer body. Additionally, or alternatively, when the inner and outer bodies are mated, rotational movement of the outer and/or inner body is transmitted to the other of the outer and inner body. For example, when the outer body rotates, the end effector 502 of inner body 802 can move in unison with the outer body.

In one aspect, the distal ends of the inner and outer bodies can mate with an interference fit when the inner body is positioned within the outer body. In addition, or alternatively, the inner and outer bodies can mate with a threaded connection, twist lock, snap-fit, taper lock, or other mechanical or frictional engagement. In one aspect, the inner and outer bodies mate at the distal end of tool 40 proximate to end effector 502. In another aspect, the inner and outer body can mate a several locations along the length of tool 40. In one aspect, mating the inner and outer bodies 800, 802 prevents relative translational and/or rotational movement of the distal ends of the inner and outer bodies.

In another embodiment, the inner and outer bodies can include mating features that allow one of rotational and translational movement while preventing the other of rotational and translational movement. For example, longitudinal grooves and corresponding recess on the inner and outer bodies can inhibit relative rotational movement while allowing relative longitudinal movement. In another aspect, the mating features of the inner and outer body can be adapted to allow rotation while preventing longitudinal movement. For example, a rotatable snap fit can inhibit relative longitudinal movement of the first and second bodies.

The mating features of tool 40 can act as a stop so that when the inner and outer bodies are mated, distal movement to the inner body, with respect to the outer body, is prevented. The mating features can therefore control the distance which the inner body (and particularly the end effector) extends beyond the outer body. In one aspect, the distal end of inner body 802 includes a first diameter and a second, larger diameter. The outer body 800 can have stop defined by an inner diameter that allows passage of the first diameter by prevents passage of the second, larger diameter. In one aspect, the stop is positioned to such that further distal movement of the inner body is prevented after end effector 502 passes through a distal opening 503.

Figure 123C:
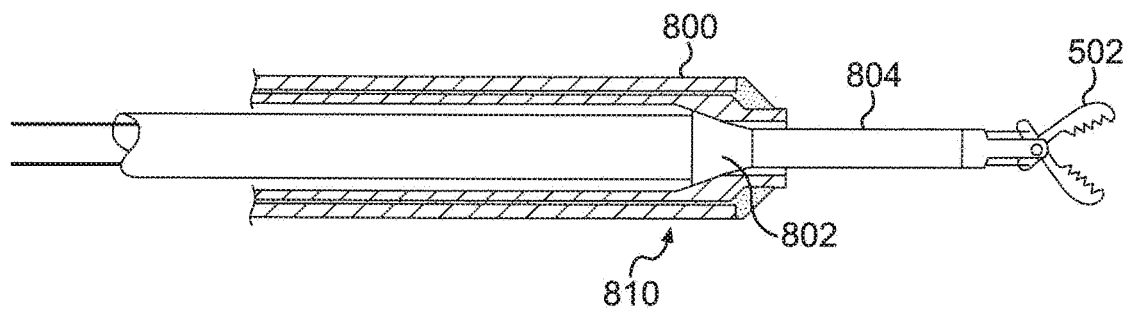
Figure 123D:
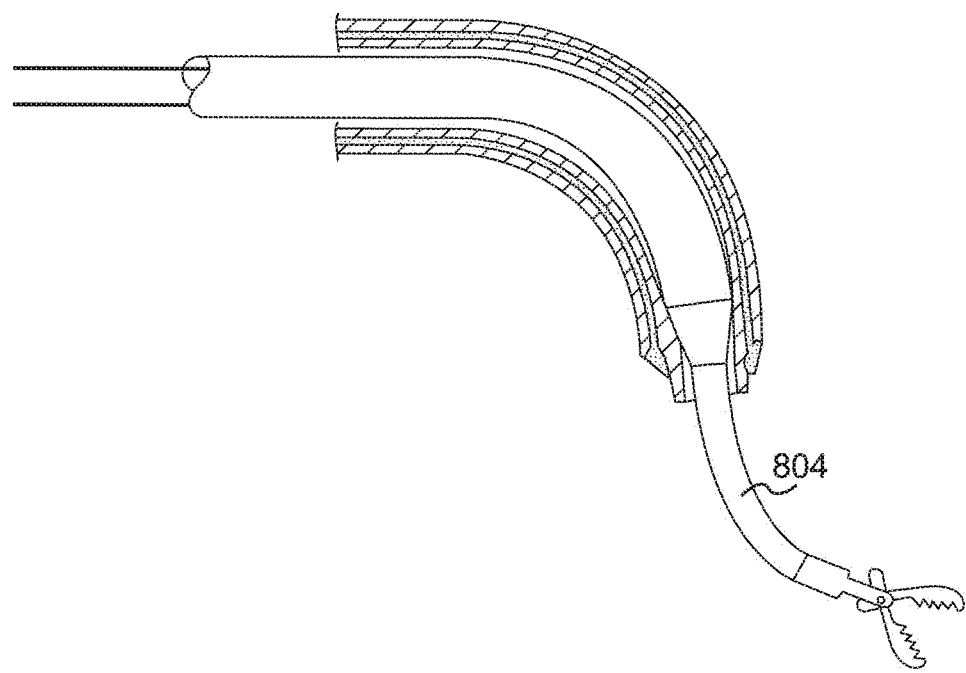

In another aspect, illustrated in FIGS. 123C and 123D, a portion of inner body 802 comprising an articulation section 804, can extend beyond a distal end 810 of outer body 800. Articulation section 804 can provide one or more than one additional degree of freedom to tool 40 and allow, for example, left/right and/or up/down movement. Other additional, or alternative degrees of freedom for the inner body with respect o the outer body can include longitudinal movement and/or a pre-curved body.

In another aspect, the end effector can rotate with respect to outer body 800 of tool 41*a*. For example, the inner body can be fixedly mated with the end effector and rotation of the end effector can be driven by rotating the inner body. Alternatively, the end effector can be rotated independently of the inner and outer bodies. In another aspect, rotation of the end effector can be controllably locked with respect to the outer body. For example, after rotating the end effector into a desired configuration via rotation of the inner body, the end effector can be locked with respect to the inner a With respect to FIG. 122A, the inner body 802 can extend to a proximal controller 714 for controlling end effector 502 and/or articulation section 804. In one aspect, inner body 802 passes through proximal controller 24 of tool member 41*a*. For example, control member 24 can include a proximal aperture for receiving inner body 802.

Figure 122B:
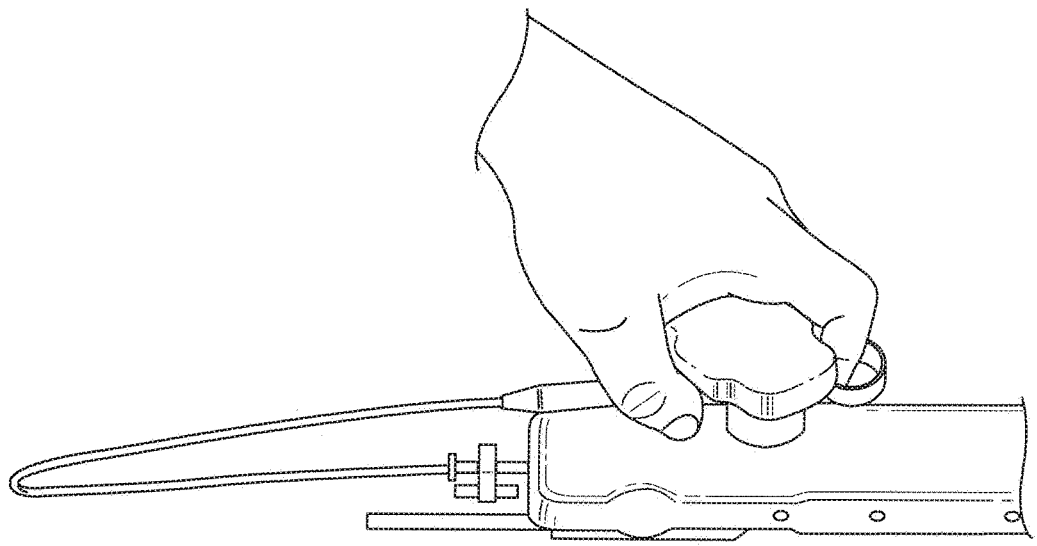
FIG. 122B is a perspective view of the tool of FIG. 122A.

Proximal controller 714 can, in one aspect, mate with a portion of control member 24. As illustrated in FIGS. 122A and 122B, controller 714 can be a pull or push ring for manipulating with a user's finger. The proximal controller 714 can mate with handle 304 of tool member 41*a* to allow a user to control both the inner and outer bodies 802, 800 with a single hand.

In another embodiment, a user can articulate the inner body via manipulation of outer body control member 24. As illustrated in FIG. 124, the inner body, and particularly controller 714 of tool member 41*b*, can mate with control member 24 of tool member 41*a*. A user can drive controller 714 via manipulation of control member handle 304. In one exemplary aspect, the proximal end of the inner body 802 can mate with a spool mount 812 on control member 24 which is articulated via the trigger on the handle 304 of the control member. It should be appreciated that the spool and/or thumb ring can be driven via movement of handle 304 or trigger 306.

In one embodiment, the outer body can work with a variety of different inner bodies to allow a clinician to quickly change the end effector associated with tool 40. When a new end effector is desired, a user can remove and replace the inner body with a different inner body having a different end effector.

In another embodiment of a two-part tool, the outer body can include an end effector while the inner body drives articulation of the combined inner and outer bodies. FIGS. 125A through 125C illustrate exemplary aspects of this configuration. As illustrated in FIG. 125A, outer body 800 includes a lumen 770 sized and shaped to receive the inner body. In one aspect, lumen 770 has a closed distal end and outer body 800 includes end effector 502. Inner body 802 can have a size and shape corresponding to at least a portion of lumen 770. In addition, inner body 802 can have an articulation section 772 for driving articulation of tool 40. For example, pull wires 774 can extend to articulation section 772 for driving the inner body. When positioned within the outer body, articulation of the inner body drives the outer body.

In one aspect, illustrated in FIG. 125A, the inner body can include a control wire 776 for driving the end effector of the outer body. Control wire 776 can mate with an end effector control wire 778 when the inner and outer bodies are mated. When force is applied on control wire 776, the force can be transmitted to control wire 778 for actuating end effector 502. One skilled in the art will appreciate that a variety of mechanical interlocks and/or frictional engagements can be used to mate control wires 776, 778. In one aspect, the distal end of control wire 776 can include a mating feature for receipt within a control wire 778. Control wire 776 is first advanced into control wire 778. The proximal end of control wire 778 can then be squeezed or compressed to prevent withdrawal of control wire 776 from control wire 778. In one aspect, moving control wire 778 of outer body 800 into inner body 802 can compress control wire 778 and lock control wire 778 with inner body 802.

In another aspect, instead of control wires for end effector 502 extending through inner body 802, a control wire or wires can extending through or along the outer body 800. As illustrated in FIG. 125B, control wires 778*a*, 778*b* extend through lumen 770. Alternatively, a lumen within the wall of outer body member 800 can house control wires 778*a*, 778*b*.

In one aspect, two control wires 778*a*, 778*b* are provided for actuating end effector 502. In use, wires 778*a*, 778*b* are pulled in unison to avoid unwanted articulation of tool 40. In one aspect, control wires 778*a*, 778*b* mate with a shaft 782. User input forces can be delivered through control wires 778*a*, 778*b* to shaft 782 such that pulling on control wires 778a, 778b actuates end effector 502. Outer body member 800 can include a chamber 784 that permits movement of shaft 782 therein.

While articulation of tool 40 is illustrated a articulated via control wires, other articulating mechanisms are also contemplated. In one aspect, illustrated in FIG. 125C, the inner body 802 can include a pre-shaped body. When the inner and outer body members exit a guide tube 26, and are not longer constrained by the guide tube, the pre-shaped inner body 802 can bend tool 40. In one aspect, the inner body 802 can be rotated within the outer body to allow tool 40 to bend in different directions.

The inner and outer bodies 802, 800 illustrated in FIGS. 125A through 125C can mate or dock with one another when inner body 802 is positioned within lumen 770 within the outer body. In one aspect, illustrated in FIG. 125B, the inner and outer bodies can mate with a snap-fit. When the inner body is mated the snap fit can provide a user with tactile feedback and indicate proper docking of the inner and outer bodies. One skilled in the art will appreciate that a variety of additional or alternative mating mechanisms can permit docking of the inner and outer bodies.

Figure 126:
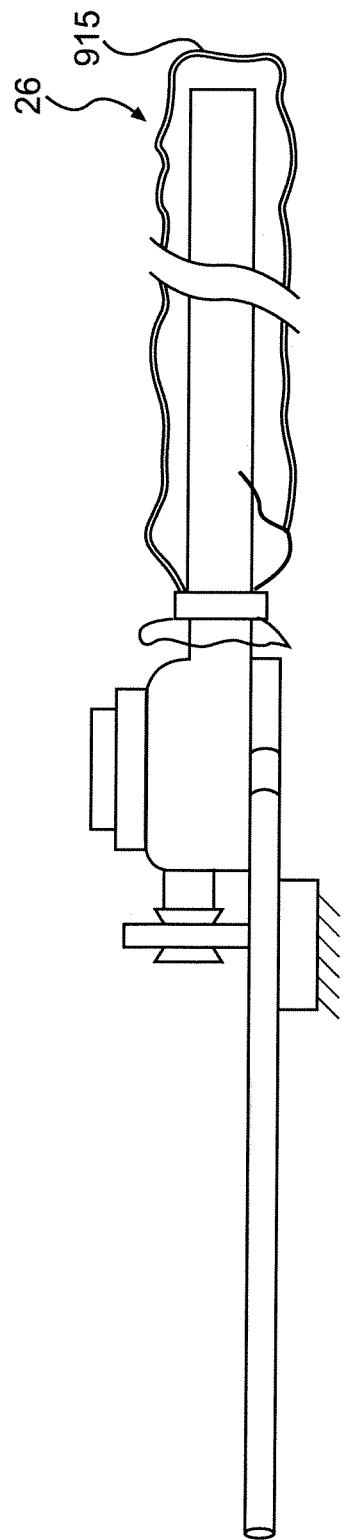
Figure 127:
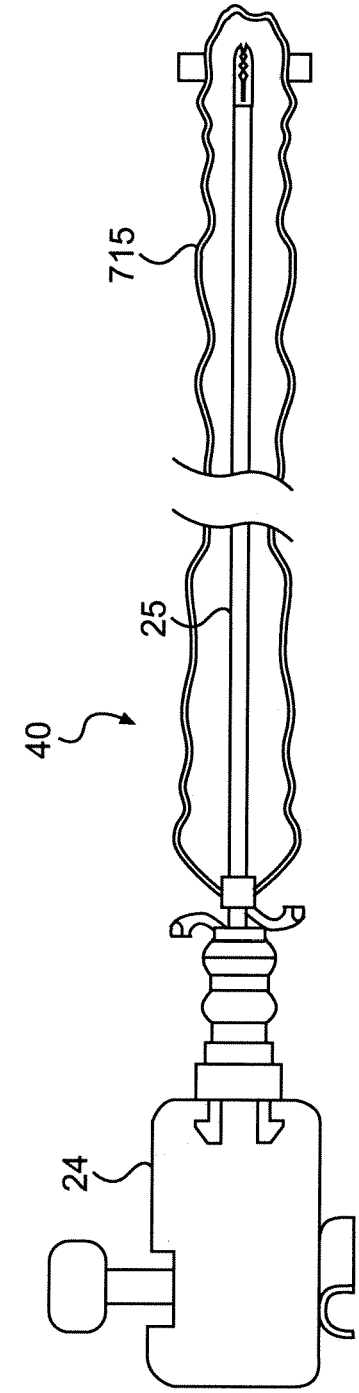
Figure 128:
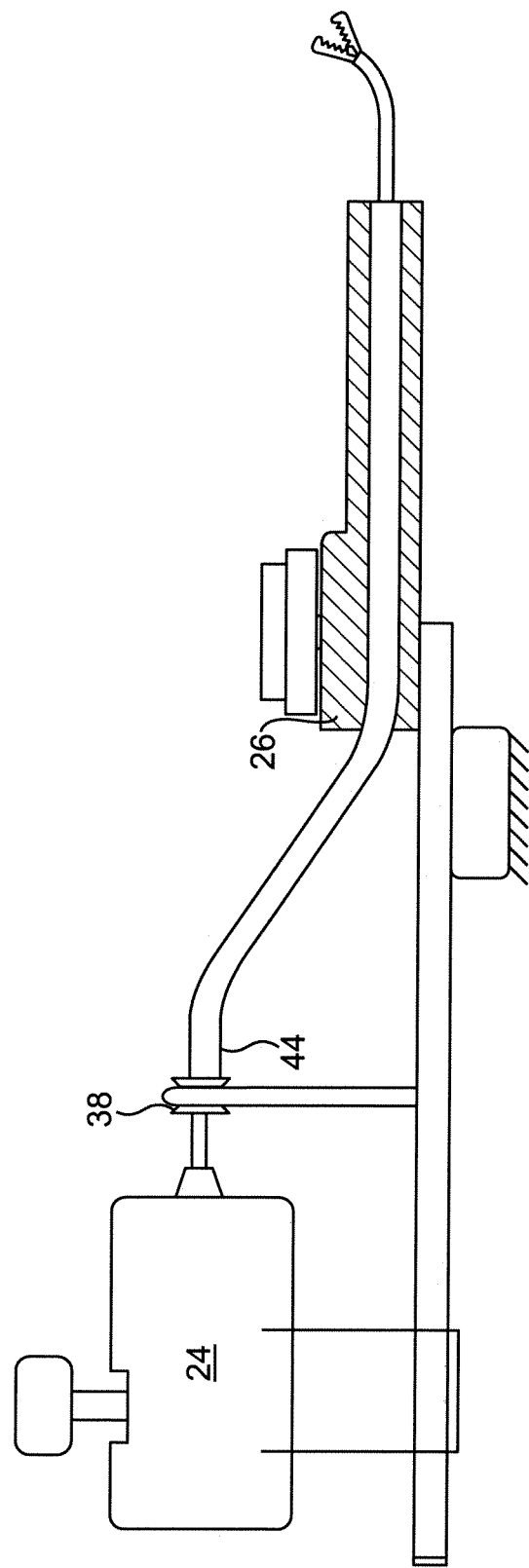
Figure 129:
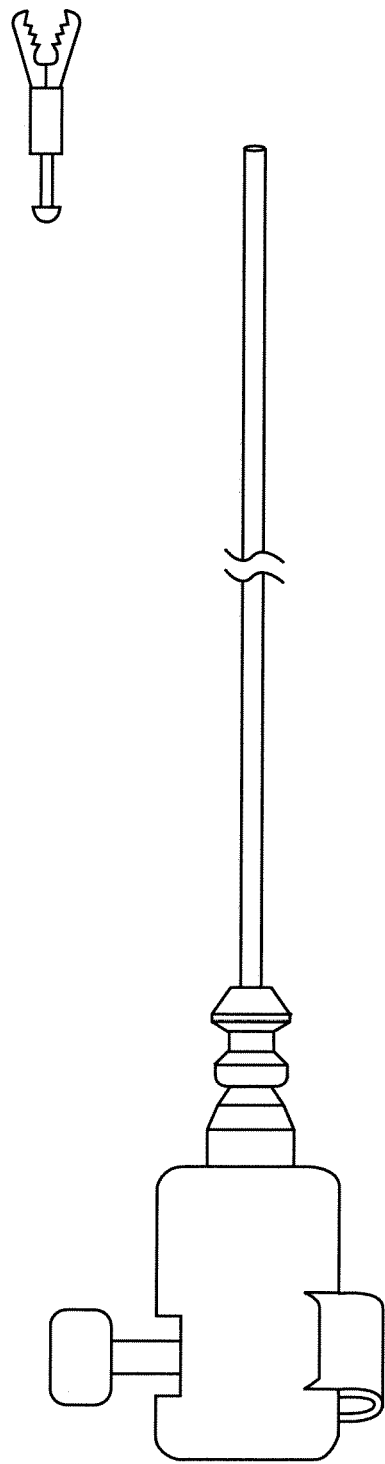
Figure 130:
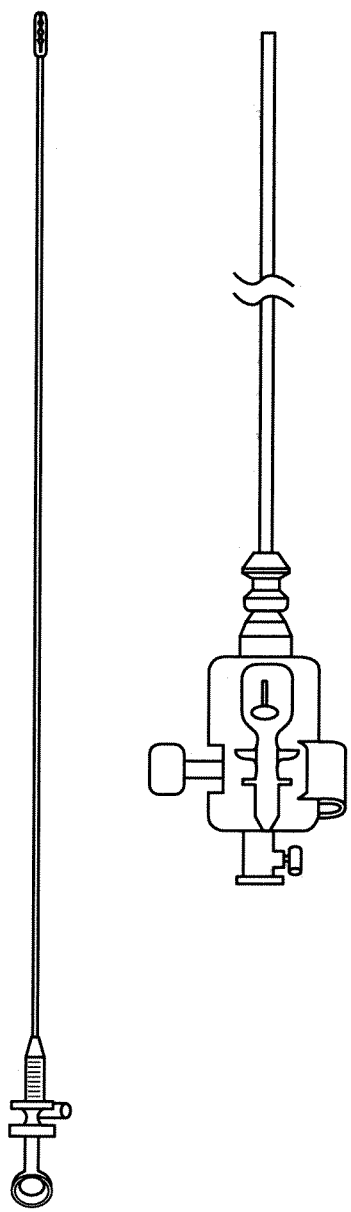

The various embodiments and the various components of system 20 described herein can be disposable or reusable. In one embodiment, at least some of the components of system 20 designed for contact with tissue can be disposable. For example, guide tube 26 and/or tools 40a, 40b can be disposable. In another aspect, a portion of tools 40a, 40b, such as catheter 25a, 25b and/or end effectors 502 can be disposable. In yet another embodiment, for example, where rails 224a, 224b are fixedly mated with control members 24a, 24b, the rails can also be disposable. Conversely, components such as frame 22 and/or rails 224a, 224b can be reusable.

Where sterile system components are necessary or desired, the system can include seals, shrouds, drapes, and/or bags to protect sterility. For example, where the working and/or main lumen of the guide tube is maintained is a sterile condition, a shroud, drape, and/or seal could be placed at the distal and/or proximal entrances to the guide tube passageways. FIG. 126 illustrates a bag or sheath 715 placed over the distal portion of tool 40 to maintain sterility. As described above, a portion of the tool, such as catheter 25, can be detachably mated with tool 40. In use, the sterile catheter can be attached to the reusable or non-sterile control member 24. Similarly, as illustrated in FIG. 127, a bag or sheath can be mated with the distal portion of guide tube 26. The non-sterile and sterile portions of the guide tube can be mated prior to use. FIG. 128 illustrates a shroud 660 at the entrance 38 to working lumen 44 to help protect the sterility of guide tube 26. FIG. 129 illustrates a reusable control member and catheter with a detachable, end effector. FIG. 130 illustrates tool 40 with a disposable inner body and a reusable outer body.

Further described herein are methods of using system 20. In one embodiment, guide tube 26 is delivered through a natural body orifice to a surgical site. At least one optical device, such as a pediatric endoscope, is then delivered through working channel 42. In addition, at least one tool 40 is delivered through one of the working channels. The proximal end of tool 40, e.g., control member 24, can be attached to frame 22. In one aspect, control member 24 is mated with rail 224 such that the tool 40 can be moved longitudinally on rail 224 and/or rotated about rail 224.

In one aspect, system 20 provides at least two degrees of freedom to the distal end of tool 40 which is controlled by moving control member 24 on rail 224. For example, a end effector can be rotated and moved longitudinally by manipulating control member 24.

In another aspect, additional degrees of freedom are provided by an articulation section of guide tube 26. For example, guide tube 26 can by moved up/down and/or side-to-side via controls 30. Thus, system 20 can provide three or more than three degrees of freedom to the end effector.

In another aspect additional degrees of freedom are provided by tool 40. For example, control member 24 can move the distal end of tool 40 up/down and/or side-to-side by manipulating handle 304. In addition, handle 304 can control actuation of end effector to grasp and/or cut tissue. Further degrees of freedom can be added to the tool and/or guide tube with the use of additional articulation sections and/or pre-curved segments.

In one embodiment, the various degrees of freedom provided by control member 24, rails 224, and/or guide tube 26 allow a surgeon to move tissue, grasp tissue, cut tissue, suture tissue, and/or explore an anatomical structure. In another embodiment, system 20 includes two tools 40 each having multiple degrees of freedom. In particular, system 20 can provide sufficient freedom of movement to allow tools 40 to work together while viewed by a surgeon. Thus, unlike conventional systems, the system described herein allows surgeons to perform procedures that require at least partially independent control of two tools and sufficient freedom of movement to allow the tools to work together.

In one embodiment, the degrees of freedom system 20 provides to the end effectors and the ability to simultaneously control those degrees of freedom, allows a clinician to tie knots and/or suture at a distance. Further described herein is a method of knot tying at a distance. In one aspect, knot tying is performed via a system including a flexible guide tube and/or flexible tools. Such a system can allow knot tying at a distance where system 20 is inserted through a natural orifice.

Figure 131A:
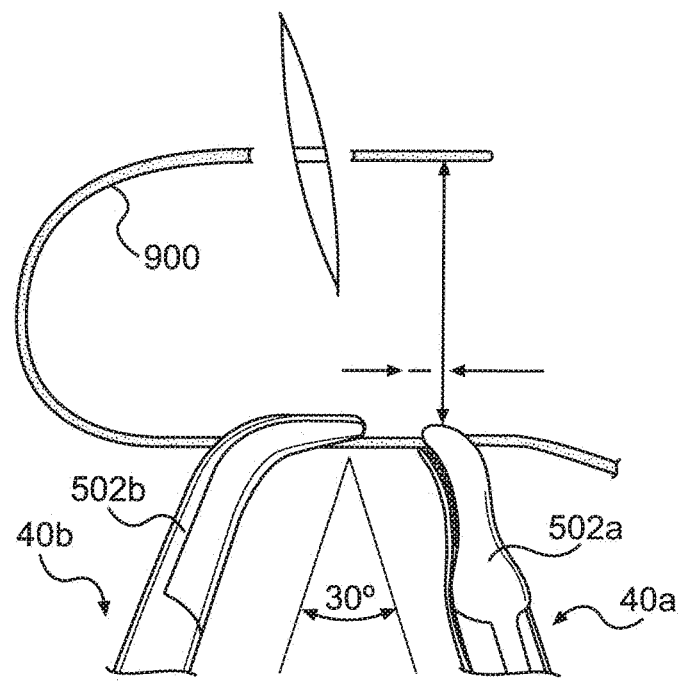

A system 20 having any or all of the various features described above can be provided. In one aspect, as illustrated in FIG. 131A, a first and second tool 40a, 40b a placed proximate to a target site, such as, for example, a surgical site. In one aspect, knot tying is part of a suturing or tissue apposition procedure. A suture, wire, or filament 900 is grasped with a first tool. A variety of end effectors can be mated with tool 40a, 40b for grasping and/or manipulating the suture. In one aspect, at least one of the end effectors is a forceps.

Figure 131B:
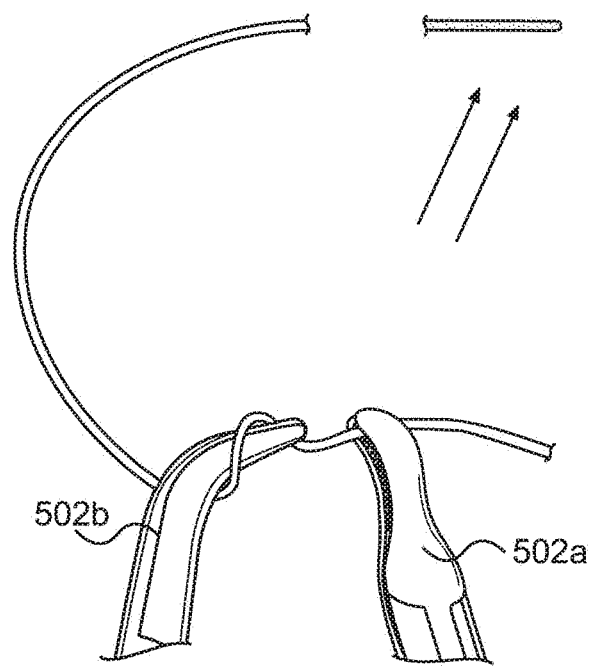

With the suture held with a first end effector 502a, the first and second tools are manipulated, via first and second proximal controllers, to wrap the suture around the second tool 40b (i.e., around a second distal end effector 502b). In one aspect, first distal end effector 502a remains stationary and the second distal end effector 502b is moved around the suture to form a loop. For example, as shown in FIG. 131B, the tip of second distal end effector 502b is maneuvered around the suture. Alternatively, the second distal end effector can remain stationary and the suture can be wrapped around the second distal end effector by movement of the first distal end effector. In yet another aspect, the user can move by the first and second distal end effector relative to one another to form a loop around the second distal end effector.

Figure 131C:
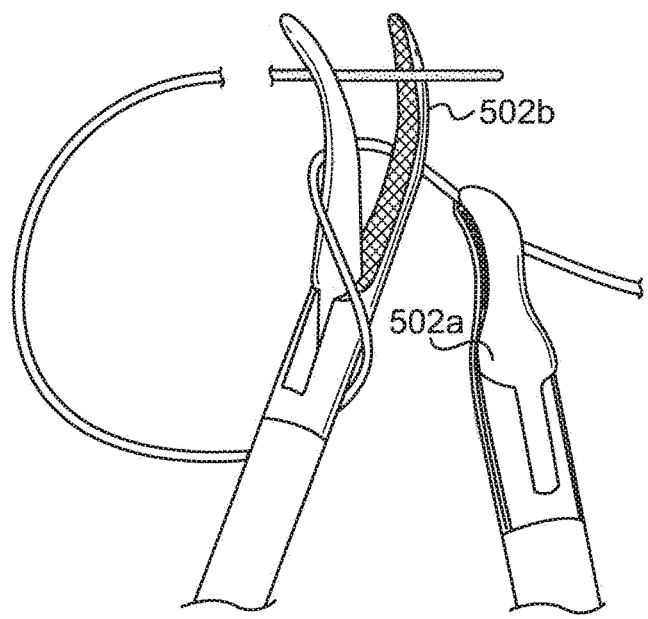
Figure 131D:
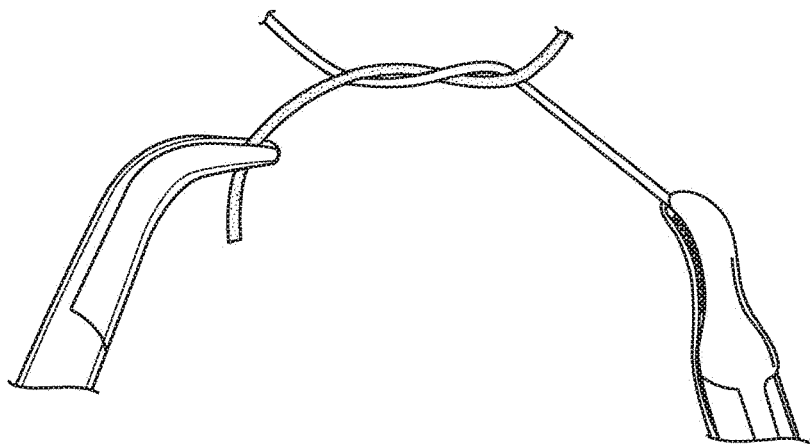
Figure 131E:
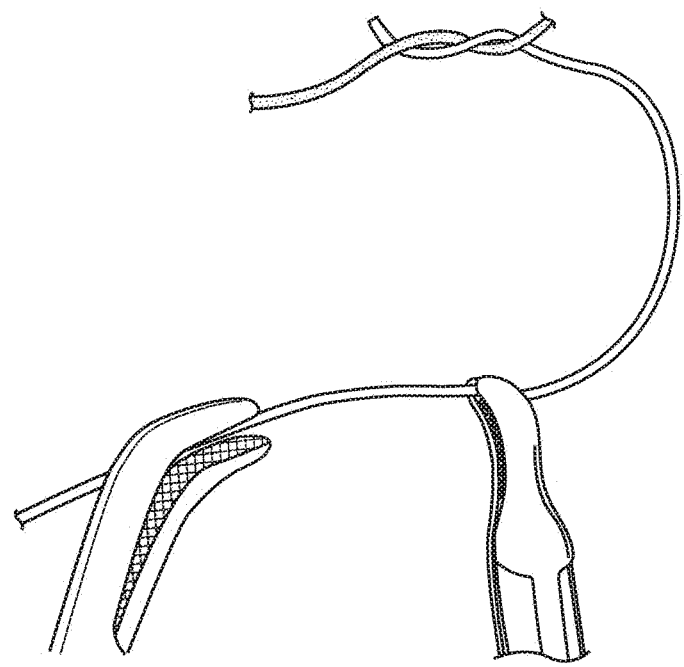
Figure 131F:
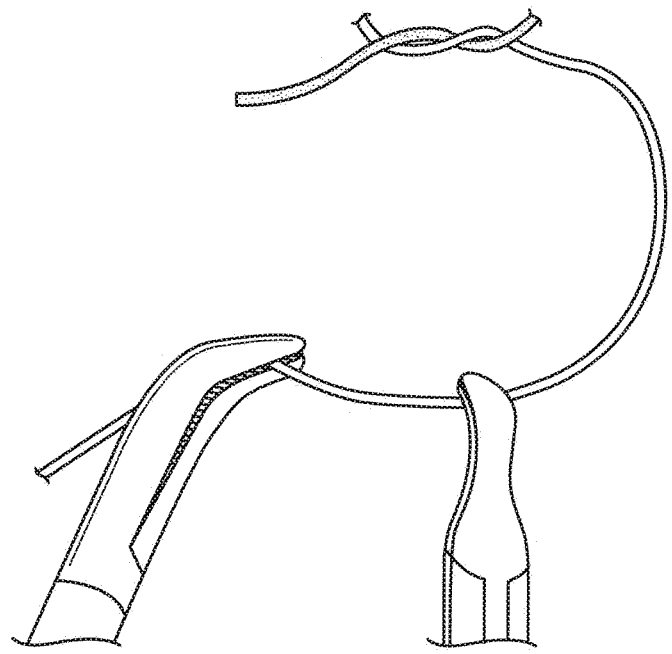
Figure 131G:
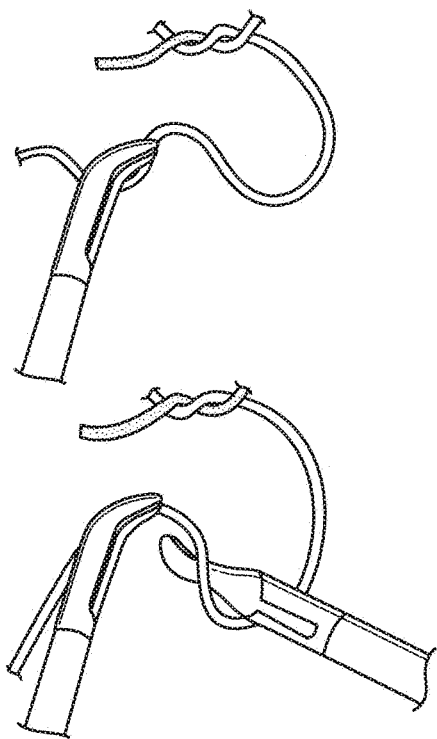
Figure 131H:
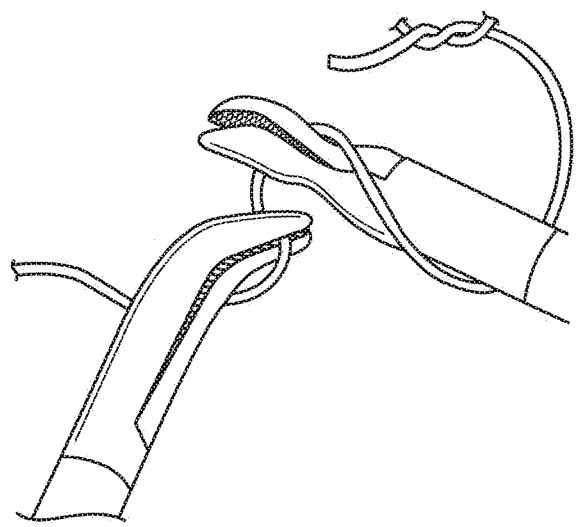
Figure 131I:
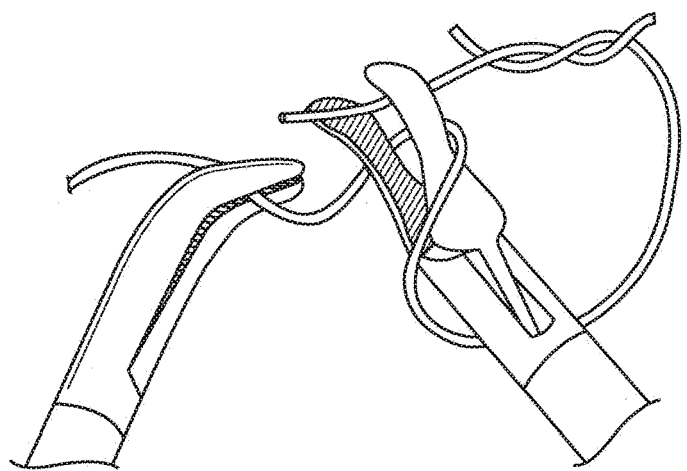
Figure 131J:
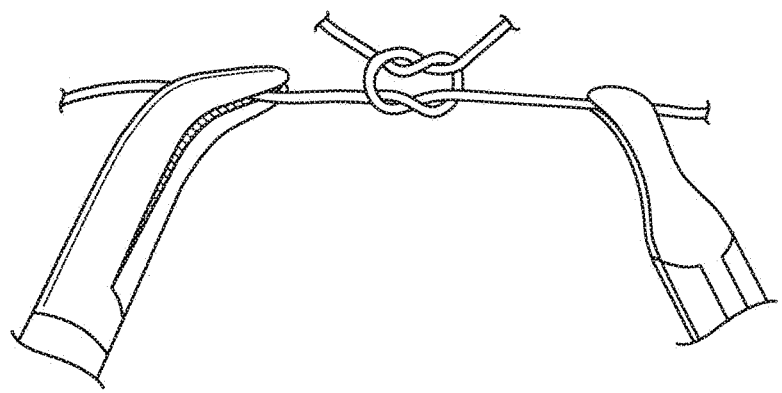

Once a loop is formed about second distal end effector 502b, a user can move the second tool 40b into position to grasp the suture with the second distal end effector 502b. As shown in FIG. 131C, second distal end effector 502b can be translated to move forward and actuated to open the forceps. With the suture grasped by the first and second end effectors, the user can translate (pull on) the second tool to move the second distal end effector through the loop and form a single flat knot as shown in FIG. 131D.

With the first flat knot in place, a second knot can be formed to complete a square knot. As illustrated in FIGS. 131E through 131J, the procedure describe above can be repeated with the first and second distal end effectors taking opposite roles and the loop of suture being wrapped in the opposite direction.

As part of the knot tying procedure, tools 40a, 40b allow a user to independently control movement or hold the position of the first and second distal end effectors. In one aspect, the first and second tools, via first and second proximal control members, are translated (moved forward/back), rotated (torqued), articulated (moved up/down and/or left/right), and actuated (forceps are opened closed). Each of these movements can be performed independently for the first and second tools. In addition, a user can control two or more of these movements simultaneously.

Provided below are exemplary classes of procedures and specific procedures which the system described herein can perform.

Cardiovascular
  Revascularization
  Drilling
  Bypass
  Shunts
  Valves(replacement & repair)
  Left Atrial Appendage (closure, occlusion or removal for stroke prevention)
  Left Ventricular Reduction
  Atrial and Septal Defects
  Aneurysm Repair
  Vascular Grafting
  Endarterectomy
  Percutaneous Transluminal Coronary Angioplasty (PTCA)
  Percutaneous Transluminal Angioplasty (PTA)
  Vascular Stenting
  Primary Placement
  Restenosis Therapy
  Vessel Harvest
  Saphenous Vein Graft
  Internal Mammary Artery
  Cardiac Assist Devices
  Electrophysiology (mapping & ablation)
  Intraluminal
  Extraluminal
Radiology
  Non-Vascular Radiology
Pulmonary/ENT
  Lung Volume Reduction
  Lung Cancer Therapy
  Esphagectomy
  Larynx Surgery
  Tonsils
  Apnea
  Nasal/Sinuses
  Otolaryngology
Neurology
  Tumor Therapy
  Hydrocephalus
Orthopedics
Gynecology
  Hysteroscopy
  Hysterectomy
  Fertility
  Improvement
  Sterilization
  Myomectomy
  Endometriosis
General Surgery
  Cholecystectomy
  Hernia
  Abdominal
  Diaphragm
  Adhesions
Gastrointestinal
  Bleeding
  Tissue Resection
  GERD
  Barret's Esophagus
  Obesity
  Colon Surgery
Urology
  Kidney Stones
  Bladder Cancer
  Incontinence
  Ureteral Reimplantation
  Prostate Provided below is an exemplary list of access points for the systems described herein Trans-oral
Trans-anal
Trans-vaginal
Percutaneous
  Laparoscopic
  Thorascopic
  To the circulatory system
Trans-nasal
Trans-uretheral

What is claimed is:

1. A medical system comprising:
a guide tube including a body extending from a proximal end to a distal end, the body including:
a first working channel that terminates at a first distal opening;
a second working channel that terminates at a second distal opening;
a third working channel that terminates at a third distal opening;
an end cap at the distal end, the end cap including a cover configured to selectively close and open at least one of the first distal opening or the second distal opening;
an articulation portion proximate the distal end; and
a housing member at the proximal end with controls coupled to the articulation portion via a plurality of control wires, wherein proximal portions of the first working channel and the third working channel pass through respective apertures on opposite lateral sides of the housing member, and wherein the proximal portion of the first working channel extends outside of the housing member such that a first proximal opening of the first working channel is proximal to its respective aperture;
wherein the guide tube includes a diverging mechanism that adjusts an amount of divergence between the first working channel and the third working channel distal to the articulation portion, the first and third working channels being closer to each other at a middle portion of the guide tube than at either the proximal end or the distal end of the guide tube.

2. The medical system of claim 1, wherein the first working channel extends from the first proximal opening to the first distal opening, and the medical system further comprises a first instrument insertable into the first proximal opening.

3. The medical system of claim 2, wherein the first instrument includes a first end effector slidable along the first working channel to exit the first distal opening.

4. The medical system of claim 3, wherein the medical system further comprises a second instrument that includes a second end effector, the second instrument being slidable along the third working channel to allow the second end effector to exit the third distal opening.

5. The medical system of claim 1, wherein the controls include a first actuator configured to move the articulation portion along a first plane and a second actuator configured to move the articulation portion along a second plane independent of moving the articulation portion along the first plane.

6. The medical system of claim 1, wherein the articulation portion includes a plurality of segments movable relative to one another along at least a part of the articulation portion.

7. The medical system of claim 1, wherein the second working channel extends from a second proximal opening to the second distal opening, and wherein the second proximal opening is proximal to the controls.

8. The medical system of claim 1, wherein at least one of the first distal opening or the third distal opening is proximal to the distal end of the guide tube.

9. The medical system of claim 1, wherein the body further comprises a fourth working channel.

10. The medical system of claim 1, wherein the diverging mechanism adjusts divergence between the first working channel and the third working channel without engaging the second working channel.

11. The medical system of claim 1, wherein a distal portion of the first working channel is angled relative to a longitudinal axis of the guide tube.

12. A medical system comprising:
a guide tube including a body extending from a proximal end to a distal end, the body including:
a first working channel extending from a first proximal opening to a first distal opening;
a second working channel extending from a second proximal opening to a second distal opening;
a third working channel extending from a third proximal opening to a third distal opening;
an end cap at the distal end;
an articulation portion proximate the distal end, the articulation portion including a plurality of articulation segments movable relative to one another along at least a part of the articulation portion; and
a housing member at the proximal end with controls coupled to the articulation portion via a plurality of control wires, wherein proximal portions of the first working channel and the third working channel pass through respective apertures on opposite lateral sides of the housing member, and wherein the proximal portion of the first working channel extends outside of the housing member such that the first proximal opening of the first working channel is proximal to its respective aperture;
wherein the guide tube includes a diverging mechanism that adjusts an amount of divergence between the first working channel and the third working channel distal to the articulation portion, the first and third working channels being closer to each other at a middle portion of the guide tube than at either the proximal end or the distal end of the guide tube; and
wherein a distal portion of the first working channel is angled relative to a longitudinal axis of the guide tube.

13. The medical system of claim 12, wherein the end cap includes a cover configured to selectively close and open at least one of the first distal opening or the second distal opening.

14. The medical system of claim 12, wherein the second proximal opening is distal to each of the first proximal opening and the third proximal opening.

15. The medical system of claim 12, wherein the medical system further comprises a first instrument and a rail, the first instrument including a first end effector, and the first instrument being disposed in the first working channel and slidable along at least a portion of the rail to move the first end effector through the first distal opening.

16. A medical system comprising:
a guide tube including a body extending from a proximal end to a distal end, the body including:
a first working channel that terminates at a first distal opening;
a second working channel that terminates at a second distal opening;
a third working channel that terminates at a third distal opening;
an end cap at the distal end, the end cap including a cover configured to selectively close and open at least one of the first distal opening or the second distal opening;
an articulation portion proximate the distal end, the articulation portion including a plurality of articulation segments movable relative to one another along at least a part of the articulation portion; and
a housing member at the proximal end, the housing member including controls coupled to the distal end via a plurality of control wires, wherein proximal portions of the first working channel and the third working channel pass through respective apertures on opposite lateral sides of the housing member, and wherein the controls include a first actuator configured to move the articulation portion along a first plane and a second actuator configured to move the articulation portion along a second plane independent of moving the articulation portion along the first plane;
wherein at least a portion of each of the first distal opening and the third distal opening is proximal to the distal end of the guide tube, and
wherein the guide tube includes a diverging mechanism that adjusts an amount of divergence between the first working channel and the third working channel distal to the articulation portion.

17. The medical system of claim 16, wherein the medical system further comprises a first instrument disposed within the first working channel, the first instrument including a first end effector slidable along the first working channel to exit the first distal opening.

18. The medical system of claim 16, wherein the aperture through which the first working channel passes is distal to at least a portion of the controls of the housing member.

19. The medical system of claim 16, wherein the first proximal opening is proximal to at least a portion of the controls of the housing member.

20. The medical system of claim 16, wherein the end cap is tapered.

* * * * *